United States Patent
Cristau et al.

(10) Patent No.: US 8,501,781 B2
(45) Date of Patent: Aug. 6, 2013

(54) HETEROARYLPIPERIDINE AND -PIPERAZINE DERIVATIVES

(75) Inventors: Pierre Cristau, Lyons (FR); Nicola Rahn, Düsseldorf (DE); Tomoki Tsuchiya, Düsseldorf (DE); Joachim Kluth, Langenfeld (DE); Pierre Wasnaire, Düsseldorf (DE); Sebastian Hoffmann, Neuss (DE); Jürgen Benting, Leichlingen (DE); Ulrike Wachendorff-Neumann, Neuwied (DE); Thomas Seitz, Langenfeld (DE)

(73) Assignee: Bayer Cropscience AG, Monheim (DE)

(*) Notice: Subject to any disclaimer, the term of this patent is extended or adjusted under 35 U.S.C. 154(b) by 38 days.

(21) Appl. No.: 12/913,437

(22) Filed: Oct. 27, 2010

(65) Prior Publication Data

US 2011/0306620 A1    Dec. 15, 2011

Related U.S. Application Data

(60) Provisional application No. 61/257,243, filed on Nov. 2, 2009.

(30) Foreign Application Priority Data

Oct. 30, 2009  (EP) .................... 09174614

(51) Int. Cl.
*A01N 43/00* (2006.01)
*A61K 31/445* (2006.01)

(52) U.S. Cl.
USPC .......... 514/326; 514/254.04; 514/254.01; 514/254.02; 514/254.03; 514/254.05; 546/209; 546/210; 546/211; 546/208; 544/366; 544/370; 544/371; 544/367; 544/369

(58) Field of Classification Search
USPC ... 514/254.04, 326, 254.01, 254.05; 546/209, 546/210, 208; 544/366, 370, 371, 367, 369
See application file for complete search history.

(56) References Cited

U.S. PATENT DOCUMENTS

2005/0234033 A1  10/2005  Anandan et al.
2007/0072908 A1  3/2007  Yamamoto et al.
2010/0010219 A1  1/2010  Harada et al.
2010/0137245 A1  6/2010  Cristau et al.
2011/0105429 A1  5/2011  Cristau et al.

FOREIGN PATENT DOCUMENTS

| WO | WO 2004/058750 A1 | 7/2004 |
|---|---|---|
| WO | WO 2004/058751 A1 | 7/2004 |
| WO | WO 2005/003128 A1 | 1/2005 |
| WO | WO 2005/116653 A2 | 12/2005 |
| WO | WO 2007/014290 A2 | 2/2007 |
| WO | WO 2007/027777 A2 | 3/2007 |
| WO | WO 2008/013622 A2 | 1/2008 |
| WO | WO 2008/013925 A2 | 1/2008 |
| WO | WO 2008/091580 A2 | 7/2008 |
| WO | WO 2008/091594 A2 | 7/2008 |
| WO | WO 2009/055514 A2 | 4/2009 |
| WO | WO 2009/094407 A2 | 7/2009 |
| WO | WO 2009/094445 A2 | 7/2009 |
| WO | WO 2009/132785 A1 | 11/2009 |

OTHER PUBLICATIONS

Mellor et al, Pestic Sci 55 : 326-330 (1999).*
International Search Report for International Application No. PCT/EP2010/066098, European Patent Office, Netherlands, mailed on Feb. 8, 2011.

* cited by examiner

*Primary Examiner* — Brandon Fetterolf
*Assistant Examiner* — Jean Cornet
(74) *Attorney, Agent, or Firm* — Sterne, Kessler, Goldstein & Fox P.L.L.C.

(57) ABSTRACT

Heteroarylpiperidine and -piperazine derivatives of the formula (I),

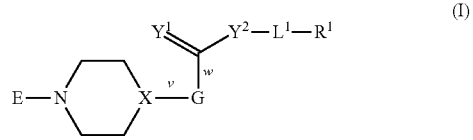

in which the symbols have the meanings given in the description and agrochemically active salts thereof and their use for controlling phytopathogenic harmful fungi and also processes for preparing compounds of the formula (I).

8 Claims, No Drawings

HETEROARYLPIPERIDINE AND -PIPERAZINE DERIVATIVES

This application claims benefit under 35 U.S.C. §119(e) to U.S. Provisional Application No. 61/257,243, filed Nov. 2, 2009, the entirety of which is incorporated by reference herein.

The present invention relates to novel heteroarylpiperidine and -piperazine derivatives, to processes for preparing these compounds, to compositions comprising these compounds and to their use as biologically active compounds, in particular for controlling harmful microorganisms in crop protection and in the protection of materials.

It is already known that certain heteroarylpiperidine and -piperazine derivatives, for example piperidinyl-substituted thiazole-4-carboxamides, can be used as fungicidal crop protection agents (see WO-A-2007/014290, WO-A-2008/091594, WO-A-2008/013925, WO-A-2008/013622, WO-A-2008/091580, WO-A-2009/055514, WO-A-2009/094407, WO-A-2009/094445, WO-A-2009/132785, WO-A-2010/037479). However, in particular at relatively low application rates, the fungicidal activity of these compounds is not always sufficient. Furthermore, in many cases the activity spectrum of these amides is insufficient.

WO-A-2004/058750, WO-A-2004/058751, U.S. Pat. No. 0,234,033, WO-A-2005/003128, WO-A-2005/116653, FR-A-2856685, WO-A-2006/132436 and WO-A-2008/069313 describe further heteroarylpiperidine and -piperazine derivatives, which can also be used medicinally. However, an effect on fungal pathogens is not described.

Since the ecological and economical demands made on modern active compounds, for example fungicides, are increasing constantly, for example with respect to activity spectrum, toxicity, selectivity, application rate, formation of residues and favourable manufacture, and there can furthermore be problems, for example, with resistances, there is a constant need to develop novel fungicidal compositions which, at least in some areas, have advantages over the known ones.

The invention relates to compounds of the formula (I)

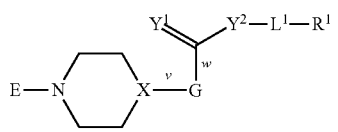

in which the symbols have the following meanings:

E represents

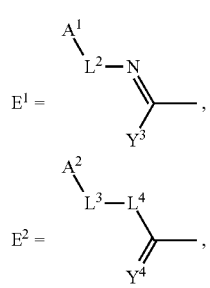

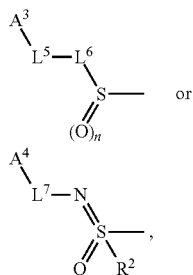

$A^1$, $A^2$, $A^3$, $A^4$ represent cyano, $C_1$-$C_8$-alkyl, $C_1$-$C_8$-haloalkyl, $C_3$-$C_8$-cycloalkyl, $C_5$-$C_8$-cycloalkenyl, $C_3$-$C_8$-halocycloalkyl, $C_4$-$C_{10}$-cycloalkylalkyl, $C_4$-$C_{10}$-halocycloalkylalkyl, $C_4$-$C_{10}$-alkylcycloalkyl, $C_5$-$C_{10}$-alkylcycloalkylalkyl, $C_2$-$C_8$-alkenyl, $C_2$-$C_8$-haloalkenyl, $C_2$-$C_8$-alkynyl, $C_2$-$C_8$-haloalkynyl, $C_2$-$C_8$-alkoxyalkyl, $C_2$-$C_8$-haloalkoxyalkyl, $C_4$-$C_{10}$-cycloalkoxyalkyl, $C_3$-$C_{10}$-alkoxyalkoxyalkyl, $C_2$-$C_8$-alkylthioalkyl, $C_2$-$C_8$-haloalkylthioalkyl, $C_2$-$C_8$-alkylsulphinylalkyl, $C_2$-$C_8$-alkylsulphonylalkyl, $C_2$-$C_8$-alkoxycarbonyl, $C_3$-$C_8$-alkoxycarbonylalkyl, $C_3$-$C_8$-haloalkoxycarbonylalkyl, $C_2$-$C_8$-alkylaminoalkyl, $C_3$-$C_{10}$-dialkylaminoalkyl, $C_2$-$C_8$-haloalkylaminoalkyl, $C_4$-$C_{10}$-cycloalkylaminoalkyl, $C_1$-$C_8$-alkoxy, $C_1$-$C_8$-haloalkoxy, $C_3$-$C_8$-cycloalkoxy, $C_3$-$C_8$-halocycloalkoxy, $C_4$-$C_{10}$-cycloalkylalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_2$-$C_8$-alkoxyalkoxy, $C_2$-$C_8$-alkylcarbonyloxy, $C_2$-$C_8$-haloalkylcarbonyloxy, $C_1$-$C_8$-alkylthio, $C_1$-$C_8$-haloalkylthio, $C_3$-$C_8$-cycloalkylthio, tri($C_1$-$C_4$-alkyl)silyl, $C_1$-$C_8$-alkylamino, $C_2$-$C_8$-dialkylamino, $C_1$-$C_8$-haloalkylamino, $C_2$-$C_8$-halodialkylamino, $C_3$-$C_8$-cycloalkylamino, $C_2$-$C_8$-alkylcarbonylamino, $C_2$-$C_8$-haloalkylcarbonylamino, $C_1$-$C_8$-alkylsulphonylamino or $C_1$-$C_8$-haloalkylsulphonylamino, or $A^1$, $A^2$, $A^3$, $A^4$ represent phenyl which may contain up to three substituents, where the substituents independently of one another are selected from the list below:

halogen, cyano, hydroxyl, SH, amino, nitro, $C_1$-$C_6$-alkyl, $C_2$-$C_6$-alkenyl, $C_2$-$C_6$-alkynyl, $C_3$-$C_{10}$-cycloalkyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, $C_2$-$C_8$-dialkylamino, $C_3$-$C_6$-cycloalkylamino, $C_4$-$C_{10}$-cycloalkylalkoxy, $C_2$-$C_4$-alkoxyalkyl, $C_2$-$C_6$-alkoxyalkoxy, $C_1$-$C_4$-hydroxyalkyl, $C_2$-$C_4$-alkylcarbonyl, $C_2$-$C_6$-alkoxycarbonyl, $C_2$-$C_6$-alkylcarbonyloxy, $C_2$-$C_6$-alkylcarbonylthio, $C_2$-$C_6$-alkylaminocarbonyl, $C_3$-$C_8$-dialkylaminocarbonyl, C(=O)H, CR$^3$=NOR$^4$, phenyl or benzyl or $A^1$, $A^2$, $A^3$, $A^4$ represent a heteroaromatic radical selected from the group below: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl which may contain up to three substituents, where the substituents independently of one another are selected from the list below:

substituents at carbon:
halogen, cyano, hydroxyl, SH, amino, nitro, $C_1$-$C_6$-alkyl, $C_2$-$C_6$-alkenyl, $C_2$-$C_6$-alkynyl, $C_3$-$C_{10}$-cycloalkyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, haloalkylsulphinyl, $C_1$-$C_4$-haloalkylsulphonyl, $C_1$-$C_4$-alkylamino, $C_2$-$C_8$-dialkylamino, $C_3$-$C_6$-cycloalkylamino, $C_4$-$C_{10}$-cycloalkylalkoxy, $C_2$-$C_4$-alkoxyalkyl, $C_2$-$C_6$-alkoxyalkoxy, $C_1$-$C_4$-hydroxyalkyl, $C_2$-$C_4$-alkylcarbonyl, $C_2$-$C_6$-alkoxycarbonyl, $C_2$-$C_6$-alkylcarbonyloxy, $C_2$-$C_6$-alkylcarbonylthio, $C_2$-$C_6$-alkylaminocarbonyl, $C_3$-$C_8$-dialkylaminocarbonyl, tri($C_1$-$C_4$-alkyl)silyl, $CR^3$=$NOR^4$, phenyl or benzyl substituents at nitrogen:
$C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkylsulphonyl, C(=O)H, C(=O)Me, C(=O)OMe or $C_2$-$C_4$-alkoxyalkyl, $L^1$ represents $(C(R^{15})_2)_p$,
p represents 0, 1 or 2,
$L^2$, $L^5$, $L^7$ represent a direct bond, C(=O) or S(=O)$_2$,
$L^3$ represents a direct bond,
$L^4$ represents oxygen, $CHR^5$, $NR^6$ or C(=O),
$L^6$ represents $CHR^5$ or $NR^6$,
$L^8$ represents a direct bond, —O, —C(=O), —S(O)$_m$, —$CHR^{16}$ or —$NR^{17}$,
$Y^1$, $Y^2$, $Y^4$ independently of one another represent sulphur or oxygen,
$Y^3$ represents $OR^7$, $SR^8$, $NR^9R^{10}$ or $R^{11}$,
m represents 0, 1 or 2,
n represents 0, 1 or 2,
X represents $CR^{12}$ or nitrogen,
G represents

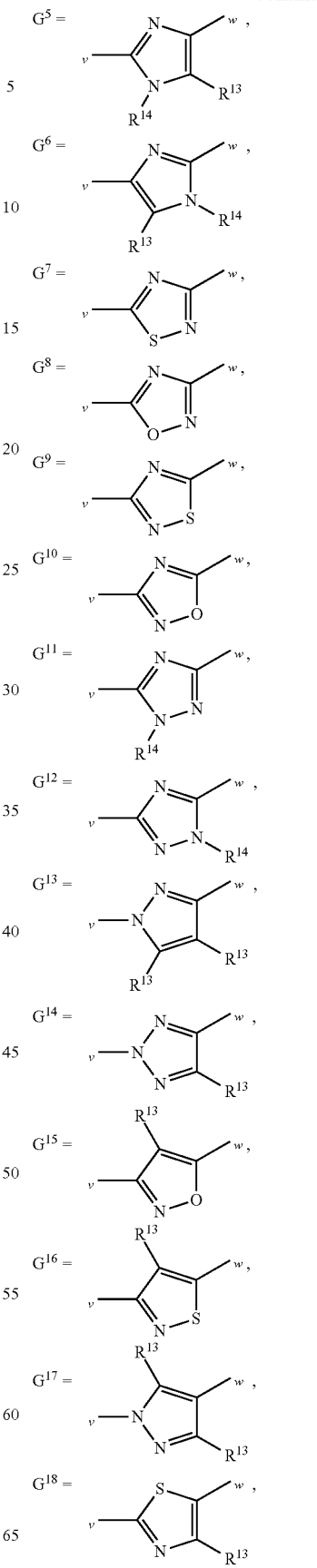

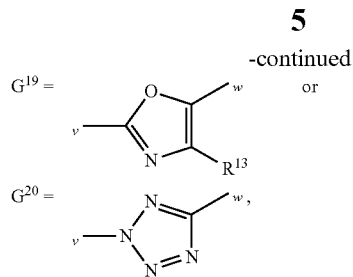

G¹⁹ = [structure shown]

G²⁰ = [structure shown]

where the bond identified by "v" is attached directly to X and where the bond identified by "w" is attached directly to C(=Y¹)Y²L¹R¹, R¹ represents $C_3$-$C_6$-alkyl, $C_3$-$C_6$-haloalkyl, $C_2$-$C_6$-alkenyl, $C_2$-$C_6$-alkynyl, $C_3$-$C_8$-alkoxyalkyl or $C_5$-$C_6$-cycloalkoxyalkyl, or R¹ represents unsubstituted or substituted $C_3$-$C_{10}$-cycloalkyl, where the substituents independently of one another are selected from the list below:
  cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, phenoxy, hydroxyl, oxo, $C_2$-$C_6$-alkoxycarbonyl, $C_1$-$C_6$-alkylcarbonyloxy, $C_1$-$C_6$-alkylcarbonyl, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio, $C_1$-$C_6$-haloalkylthio or -Q, or R¹ represents unsubstituted or substituted $C_5$-$C_{10}$-cycloalkenyl, where the substituents independently of one another are selected from the list below:
  cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, phenyl, hydroxyl, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, or R¹ represents unsubstituted or substituted phenyl, where the substituents independently of one another are selected from the list below:
  halogen, cyano, hydroxyl, SH, amino, nitro, C(=O)H, C(=O)OH, CONR³R⁴, NR³R⁴, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkylaminoalkyl, $C_2$-$C_6$-haloalkylaminoalkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxyalkyl, $C_1$-$C_6$-alkoxy, $C_1$-$C_6$-haloalkoxy, $C_3$-$C_8$-cycloalkoxy, $C_3$-$C_8$-halocycloalkoxy, $C_4$-$C_{10}$-cycloalkylalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_8$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, $C_1$-$C_6$-alkylsulphonylamino, $C_1$-$C_6$-haloalkylsulphonylamino or -L⁸Q, or R¹ represents saturated or partially or fully unsaturated unsubstituted or substituted naphthyl or indenyl, where the substituents independently of one another are selected from the list below:
  cyano, nitro, halogen, $C_1$-$C_6$-alkyl, $C_1$-$C_4$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, benzyl, phenyl, hydroxyl, SH, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, or R¹ represents an unsubstituted or substituted 5- or 6-membered heteroaryl radical where L¹ is attached to a carbon of the heteroaryl radical and where the substituents independently of one another are selected from the list below:
  substituents at carbon: halogen, cyano, hydroxyl, SH, amino, nitro, NR³R⁴, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or -L⁸Q,
  substituents at nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C(=O)Me, C(=O)OMe, benzyl or phenyl, or R¹ represents benzo-fused unsubstituted or substituted 5- or 6-membered heteroaryl where L¹ is attached to a carbon of the heteroaryl radical and where the substituents independently of one another are selected from the list below:
  substituents at carbon: halogen, cyano, hydroxyl, SH, amino, nitro, NR³R⁴, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$haloalkylsulphinyl, $C_1$-$C_4$-alkylsulphonyl, $C_1$-$C_4$-haloalkylsulphonyl, tri($C_1$-$C_4$-alkyl)silyl or phenyl,
  substituents at nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C(=O)Me, C(=O)OMe, benzyl or phenyl, or $R^1$ represents unsubstituted or substituted $C_5$-$C_{15}$-heterocyclyl where $L^1$ is attached to a carbon of the heterocyclyl radical and possible substituents independently of one another are selected from the list below:

substituents at carbon: halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl, substituents at nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C(=O)Me, C(=O)OMe, benzyl or phenyl, Q represents phenyl which may contain up to two substituents, where the substituents independently of one another are selected from the list below:

halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl, or Q represents a 5- or 6-membered heteroaryl radical which may contain up to two substituents, where the substituents independently of one another are selected from the list below:

substituents at carbon: halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl, substituents at nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C(=O)Me, C(=O)OMe or phenyl, $R^2$ represents $C_1$-$C_4$-alkyl, $C_1$-$C_4$-haloalkyl or $C_2$-$C_4$-alkoxyalkyl, $R^3$, $R^4$ independently of one another represent hydrogen, $C_1$-$C_4$-alkyl, $C_2$-$C_6$-alkenyl, $C_2$-$C_6$-alkynyl, $C_1$-$C_3$-haloalkyl, $C_3$-$C_6$-cycloalkyl, benzyl or phenyl, $R^5$ represents hydrogen, halogen, cyano, hydroxyl, C(=O)H, OC(=O)H, OC(=O)Me, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_2$-$C_4$-alkoxyalkyl, $C_2$-$C_4$-alkylthioalkyl, $C_2$-$C_4$-alkylsulphinylalkyl, $C_2$-$C_4$-alkylsulphonylalkyl, $C_2$-$C_4$-alkylcarbonyl, $C_2$-$C_4$-haloalkylcarbonyl, $C_2$-$C_5$-alkoxycarbonyl, $C_3$-$C_5$-alkoxycarbonylalkyl, $C_2$-$C_5$-alkylaminocarbonyl, $C_3$-$C_5$-dialkylaminocarbonyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$ alkylsulphinyl, $C_1$-$C_4$-haloalkylsulphinyl, $C_1$-$C_4$-alkylsulphonyl or $C_1$-$C_4$-haloalkylsulphonyl, $R^6$ represents hydrogen, C(=O)H, $C_1$-$C_4$ alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_2$-$C_4$-alkoxyalkyl, $C_2$-$C_4$-alkylthioalkyl, $C_2$-$C_4$-alkylsulphinylalkyl, $C_2$-$C_4$-alkylsulphonylalkyl, $C_2$-$C_4$-alkylcarbonyl, $C_2$-$C_4$-haloalkylcarbonyl, $C_2$-$C_5$-alkoxycarbonyl, $C_3$-$C_5$-alkoxycarbonylalkyl, $C_2$-$C_5$-alkylaminocarbonyl, $C_3$-$C_5$-dialkylaminocarbonyl, $C_1$-$C_4$-alkylsulphonyl or $C_1$-$C_4$-haloalkylsulphonyl, $R^7$, $R^8$ independently of one another are selected from the list below:

$C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_3$-$C_6$-cycloalkyl, $C_3$-$C_6$-halocycloalkyl, $C_4$-$C_8$-alkylcycloalkyl, $C_4$-$C_8$-cycloalkylalkyl, $C_4$-$C_8$-halocycloalkylalkyl, $C_5$-$C_8$-alkylcycloalkylalkyl, $C_2$-$C_6$-alkoxyalkyl, $C_4$-$C_8$-cycloalkoxyalkyl, $C_3$-$C_6$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_6$-dialkylaminoalkyl, $C_2$-$C_6$-haloalkylaminoalkyl, $C_4$-$C_8$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxylcarbonyl, $C_2$-$C_6$-alkylaminocarbonyl, $C_3$-$C_8$-dialkylaminocarbonyl, tri ($C_1$-$C_4$-alkyl)silyl or $C_4$-$C_8$-cycloalkylaminocarbonyl, $R^9$ represents hydrogen, cyano, hydroxyl, amino, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_3$-$C_6$-cycloalkyl, $C_4$-$C_8$-cycloalkylalkyl, $C_2$-$C_6$-alkoxyalkyl, $C_1$-$C_6$-alkoxy, $C_1$-$C_6$-haloalkoxy, $C_1$-$C_6$-alkylsulphonyl, $C_1$-$C_6$-haloalkylsulphonyl, $C_2$-$C_6$-alkylcarbonyl, $C_2$-$C_6$-haloalkylcarbonyl, $C_1$-$C_6$-alkylamino, $C_2$-$C_8$-dialkylamino, $C_1$-$C_6$-haloalkylamino or $C_2$-$C_8$-halodialkylamino, $R^{10}$ represents hydrogen, $C_1$-$C_6$-alkyl, $C_2$-$C_6$-alkenyl, $C_2$-$C_6$-alkynyl, $C_1$-$C_6$-haloalkyl or $C_3$-$C_6$-cycloalkyl, or $R^9$, $R^{10}$ together form a —$(CH_2)_4$—, —$(CH_2)_5$—, —$(CH_2)_2$S$(CH_2)_2$—, —$(CH_2)_2$S(=O)$(CH_2)_2$—, —$(CH_2)_2$S(=O)$_2$$(CH_2)_2$—, —$(CH_2)_2$$NR^3$$(CH_2)_2$— or —$(CH_2)_2$O$(CH_2)_2$— radical, $R^{11}$ represents hydrogen, halogen, cyano, $C_1$-$C_4$ alkyl $C_1$-$C_4$-haloalkyl, $C_2$-$C_4$-alkoxylalkyl, $C_2$-$C_4$-alkylcarbonyl, $C_2$-$C_4$-alkoxycarbonyl, $C_2$-$C_3$-alkylaminocarbonyl or $C_3$-$C_6$-dialkylaminocarbonyl, $R^{12}$ represents hydrogen, halogen, cyano, hydroxyl, OC(=O)Me, OC(=O)H, C(=O)H, C(=O)OH, C(=O)

OMe, C(=O)Me, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy or $C_1$-$C_4$-haloalkoxy, $R^{13}$ represents hydrogen, $C_1$-$C_3$-alkyl, $C_1$-$C_3$-haloalkyl or halogen, $R^{14}$ represents hydrogen or $C_1$-$C_3$-alkyl, C(=O)H, C(=O)Me or C(=O)OMe, $R^{15}$ are identical or different and independently of one another represent hydrogen, halogen, $C_1$-$C_4$-alkyl, $C_2$-$C_4$-alkenyl, $C_2$-$C_4$-alkynyl, $C_1$-$C_4$-alkoxy, oxo, $C_3$-$C_6$-cycloalkyl, $C_1$-$C_4$-haloalkyl or phenyl $R^{16}$ represents hydrogen, $C_1$-$C_4$-alkyl or $C_1$-$C_4$-haloalkyl, $R^{17}$ represents hydrogen, $C_1$-$C_6$-alkyl, $C_1$-$C_6$-haloalkyl, $C_3$-$C_8$-cycloalkyl, $C_2$-$C_6$-alkylcarbonyl, $C_2$-$C_6$-haloalkylcarbonyl, $C_2$-$C_6$-alkoxycarbonyl or $C_2$-$C_6$-haloalkoxycarbonyl, and also agrochemically active salts thereof,
except for the following compounds:
a) compounds in which
$A^2$ represents pyrazol-1-yl,
X represents CH,
G represents $G^1$,
b) compounds in which
X represents nitrogen,
G represents $G^{13}$, $G^{14}$, $G^{17}$ or $G^{20}$,
c) compounds in which
$Y^4$ represents sulphur,
$L^4$ represents C(=O).

Depending on the nature of the substituents defined above, the compounds of the formula (I) have acidic or basic properties and can form salts, if appropriate also inner salts, or adducts with inorganic or organic acids or with inorganic or organic bases or with metal ions. Suitable metal ions are in particular the ions of the elements of the second main group, in particular calcium and magnesium, of the third and fourth main group, in particular aluminium, tin and lead, and also of the first to eighth transition group, in particular chromium, manganese, iron, cobalt, nickel, copper, zinc and others. Particular preference is given to the metal ions of the elements of the fourth period. Here, the metals can be present in the various valencies that they can assume.

If the compounds of the formula (I) carry hydroxyl, carboxyl or other groups which induce acidic properties, these compounds can be reacted with bases to give salts. Suitable bases are, for example, hydroxides, carbonates, bicarbonates of the alkali metals and alkaline earth metals, in particular those of sodium, potassium, magnesium and calcium, furthermore ammonia, primary, secondary and tertiary amines having $C_1$-$C_4$-alkyl radicals, mono-, di- and trialkanolamines of $C_1$-$C_4$-alkanols, choline and also chlorocholine.

If the compounds of the formula (I) carry amino, alkylamino or other groups which induce basic properties, these compounds can be reacted with acids to give salts. Examples of inorganic acids are hydrohalic acids, such as hydrogen fluoride, hydrogen chloride, hydrogen bromide and hydrogen iodide, sulphuric acid, phosphoric acid and nitric acid, and acidic salts, such as $NaHSO_4$ and $KHSO_4$. Suitable organic acids are, for example, formic acid, carbonic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulphonic acids (sulphonic acids having straight-chain or branched alkyl radicals of 1 to 20 carbon atoms), arylsulphonic acids or aryldisulphonic acids (aromatic radicals, such as phenyl and naphthyl, which carry one or two sulphonic acid groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), where the alkyl and aryl radicals may carry further substituents, for example p-toluenesulphonic acid, salicylic acid, p-aminosalicylic acid, 2-phenoxybenzoic acid, 2-acetoxybenzoic acid, etc.

The salts obtainable in this manner also have fungicidal properties.

The formula (I) provides a general definition of the heteroarylpiperidine and -piperazine derivatives which can be used according to the invention. Preferred radical definitions for the formulae shown above and below are given below. These definitions apply to the end products of the formula (I) and likewise to all intermediates (see also below under "Illustration of the processes and intermediates").

E preferably represents E', $E^2$ or $E^3$,

E particularly preferably represents $E^2$, $A^1$, $A^2$ preferably represent cyano, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_4$-$C_8$-halocycloalkylalkyl, $C_2$-$C_8$-alkoxyalkyl, $C_2$-$C_8$-haloalkoxyalkyl, $C_2$-$C_8$-alkylthioalkyl, $C_2$-$C_8$-haloalkylthioalkyl, $C_2$-$C_8$-alkylsulphinylalkyl, $C_2$-$C_8$-alkylsulphonylalkyl, $C_3$-$C_8$-alkoxycarbonylalkyl, $C_3$-$C_8$-haloalkoxycarbonylalkyl, $C_2$-$C_8$-alkylaminoalkyl, $C_3$-$C_{10}$-dialkylaminoalkyl, $C_1$-$C_8$-alkoxy, $C_1$-$C_8$-haloalkoxy, $C_2$-$C_8$-alkylcarbonyloxy, $C_2$-$C_8$-haloalkylcarbonyloxy, $C_1$-$C_8$-alkylthio, $C_1$-$C_8$-haloalkylthio, tri($C_1$-$C_4$-alkyl)-silyl, $C_1$-$C_8$-alkylamino or $C_2$-$C_8$-dialkylamino, $A^1$, $A^2$, $A^3$ furthermore preferably represent phenyl which may contain up to two substituents, where the substituents independently of one another are selected from the list below:

halogen, cyano, hydroxyl, amino, nitro, $C_1$-$C_6$-alkyl, $C_2$-$C_6$-alkenyl, $C_2$-$C_6$-alkynyl, $C_3$-$C_{10}$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_2$-$C_4$-alkoxyalkyl, $C_1$-$C_4$-hydroxyalkyl, $C_2$-$C_4$-alkylcarbonyl, $C_2$-$C_6$-alkoxycarbonyl, $C_2$-$C_6$-alkylcarbonyloxy, C(=O)H or $CR^3$=$NOR^4$ $A^1$, $A^2$, $A^3$ furthermore preferably represent a heteroaromatic radical selected from the group below: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl which may contain up to two substituents, where the substituents independently of one another are selected from the list below:

substituents at carbon:
halogen, cyano, hydroxyl, amino, nitro, $C_1$-$C_6$-alkyl, $C_2$-$C_6$-alkenyl, $C_2$-$C_6$-alkynyl, $C_3$-$C_{10}$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_2$-$C_4$-alkoxyalkyl, $C_1$-$C_4$-hydroxyalkyl, $C_2$-$C_4$-alkylcarbonyl, $C_2$-$C_6$-alkoxycarbonyl, $C_2$-$C_6$-alkylcarbonyloxy, C(=O)H, $CR^3$=$NOR^4$ or phenyl substituents at nitrogen:
  $C_1$-$C_6$-alkyl, $C_1$-$C_4$-haloalkyl, $C_2$-$C_6$-alkenyl, $C_2$-$C_6$-haloalkenyl, $C_2$-$C_6$-alkynyl or $C_2$-$C_5$-haloalkynyl.

$A^1$, $A^2$ particularly preferably represent $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_4$-$C_8$-halocycloalkylalkyl, $C_2$-$C_8$-alkoxyalkyl, $C_2$-$C_8$-haloalkoxyalkyl, $C_2$-$C_8$-alkylthioalkyl, $C_2$-$C_8$-haloalkylthioalkyl, $C_1$-$C_8$-alkoxy, $C_1$-$C_8$-haloalkoxy, $C_1$-$C_8$-alkylthio or $C_1$-$C_8$-haloalkylthio, $A^1$, $A^2$, $A^3$ furthermore particularly preferably represent phenyl which may contain up to two substituents, where the substituents independently of one another are selected from the list below:
  halogen, cyano, nitro, $C_1$-$C_3$-alkyl, $C_1$-$C_3$-haloalkyl, cyclopropyl, $C_1$-$C_3$-alkoxy, $C_1$-$C_3$-haloalkoxy, $C_1$-$C_3$-alkylthio or $C_1$-$C_3$-haloalkylthio, $A^1$, $A^2$, $A^3$ furthermore particularly preferably represent a heteroaromatic radical selected from the group below:
  furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl or pyrimidin-5-yl which may contain up to two substituents, where the substituents independently of one another are selected from the list below:
    substituents at carbon:
      halogen, cyano, nitro, $C_1$-$C_3$-alkyl, $C_1$-$C_3$-haloalkyl, cyclopropyl, $C_1$-$C_3$-alkoxy, $C_1$-$C_3$-haloalkoxy, $C_1$-$C_3$-alkylthio, $C_1$-$C_3$-haloalkylthio or phenyl,
    substituents at nitrogen:
      $C_1$-$C_3$-alkyl or $C_1$-$C_3$-haloalkyl, $A^1$, $A^2$ very particularly preferably represent propyl, pentyl, 3,3,4,4,4-pentafluorobutyl or 3-(trifluoromethyl)cyclohexyl, $A^1$, $A^2$, $A^3$ furthermore very particularly preferably represent phenyl which may contain up to two substituents, where the substituents independently of one another are selected from the list below:
  chlorine, bromine, fluorine, iodine, methyl or trifluoromethyl, $A^1$, $A^2$, $A^3$ furthermore very particularly preferably represent a heteroaromatic radical selected from the group below:
  furan-2-yl, thiophen-2-yl, thiophen-3-yl, oxazol-4-yl, thiazol-4-yl, pyrazol-1-yl, pyrazol-4-yl, 1,2,4-triazol-1-yl or pyridin-2-yl which may contain up to two substituents, where the substituents independently of one another are selected from the list below:
    substituents at carbon:
      chlorine, methyl, difluoromethyl, trifluoromethyl or phenyl,
    substituents at nitrogen:
      methyl $L^1$ preferably represents a direct bond, —$CH_2$— or —CH($CH_3$)—,
$L^1$ particularly preferably represents a direct bond or —$CH_2$—,
$L^1$ very particularly preferably represents a direct bond,
$L^2$ preferably represents a direct bond,
$L^3$ preferably represents a direct bond,
$L^4$ preferably represents oxygen, $CHR^5$, $NR^6$,
$L^4$ particularly preferably represents $CHR^5$,
$L^5$ preferably represents a direct bond,
$L^6$ preferably represents $CHR^5$, $NR^6$,
$L^6$ particularly preferably represents $CHR^5$
$L^8$ preferably represents a direct bond, —O—,
$Y^1$ preferably represents oxygen, sulphur,
$Y^1$ particularly preferably represents oxygen,
$Y^2$ preferably represents oxygen, sulphur,
$Y^2$ particularly preferably represents oxygen,
$Y^3$ preferably represents $OR^7$, $SR^8$,
$Y^4$ preferably represents oxygen, sulphur,
$Y^4$ particularly preferably represents oxygen,
X preferably represents CH, CF, N,
X particularly preferably represents CH,
G preferably represents $G^1$, $G^2$, $G^3$, $G^{13}$, $G^{14}$ or $G^{18}$
G particularly preferably represents $G^1$, $G^{18}$
$R^1$ preferably represents $C_3$-$C_6$-alkyl, $C_3$-$C_6$-haloalkyl, $C_2$-$C_6$-alkenyl or $C_2$-$C_6$-alkynyl,
$R^1$ furthermore preferably represents unsubstituted or substituted $C_3$-$C_{10}$-cycloalkyl, where the substituents independently of one another are selected from the list below:
  cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, hydroxyl, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio, $C_1$-$C_6$-haloalkylthio or -Q, $R^1$ furthermore preferably represents unsubstituted or substituted $C_5$-$C_{10}$-cycloalkenyl, where the substituents independently of one another are selected from the list below:
  cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, phenyl, hydroxyl, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, $R^1$ furthermore preferably represents unsubstituted or substituted phenyl, where the substituents independently of one another are selected from the list below:
  halogen, cyano, hydroxyl, SH, amino, nitro, C(=O)H, C(=O)OH, $CONR^3R^4$, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkylaminoalkyl, $C_2$-$C_6$-haloalkylaminoalkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxyalkyl, $C_1$-$C_6$-alkoxy, $C_1$-$C_6$-haloalkoxy, $C_3$-$C_8$-cycloalkoxy, $C_3$-$C_8$-halocycloalkoxy, $C_4$-$C_{10}$-cycloalkylalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_8$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, $C_1$-$C_6$-alkylsulphonylamino, $C_1$-$C_6$-haloalkylsulphonylamino or -$L^8Q$, $R^1$ furthermore preferably represents saturated or partially or fully unsaturated unsubstituted or substituted naphthyl or indenyl, where the substituents independently of one another are selected from the list below:
cyano, nitro, halogen, $C_1$-$C_6$-alkyl, $C_1$-$C_4$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, benzyl, phenyl, hydroxyl, SH, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio or $C_1$-$C_6$-haloalkylthio, $R^1$ furthermore preferably represents an unsubstituted or substituted 5- or 6-membered heteroaryl radical where $L^1$ is attached to a carbon of the heteroaryl radical and where the substituents independently of one another are selected from the list below:
substituents at carbon: halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$ alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or -$L^8Q$,
substituents at nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl or phenyl, $R^1$ furthermore preferably represents benzo-fused unsubstituted or substituted 5- or 6-membered heteroaryl where $L^1$ is attached to a carbon of the heteroaryl radical and where the substituents independently of one another are selected from the list below:
substituents at carbon: halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl,
substituents at nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl or phenyl, $R^1$ furthermore preferably represents unsubstituted or substituted $C_5$-$C_{15}$-heterocyclyl where $L^1$ is attached to a carbon of the heterocyclyl radical and where possible substituents independently of one another are selected from the list below:
substituents at carbon: halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl,
substituents at nitrogen: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl or phenyl, $R^1$ particularly preferably represents $C_5$-$C_{10}$-cycloalkyl which may contain up to two substituents, where the substituents independently of one another are selected from the list below:
cyano, halogen, $C_1$-$C_4$-alkyl, $C_1$-$C_3$-haloalkyl, $C_3$-$C_6$-cycloalkyl, $C_2$-$C_4$-alkenyl, $C_2$-$C_4$-haloalkenyl, $C_2$-$C_4$-alkynyl, $C_2$-$C_4$-haloalkynyl, tri($C_1$-$C_4$-alkyl)silyl, phenyl, hydroxyl, oxo, $C_1$-$C_4$-alkoxy, $C_1$-$C_3$-haloalkoxy, $C_2$-$C_4$-alkenyloxy, $C_2$-$C_4$-alkynyloxy, $C_1$-$C_4$alkylthio or $C_1$-$C_3$-haloalkylthio, $R^1$ furthermore particularly preferably represents $C_5$-$C_{10}$-cycloalkenyl which may contain up to two substituents, where the substituents independently of one another are selected from the list below:
cyano, halogen, $C_1$-$C_4$-alkyl, $C_1$-$C_3$-haloalkyl, $C_3$-$C_6$-cycloalkyl, $C_2$-$C_4$-alkenyl, $C_2$-$C_4$-haloalkenyl, $C_2$-$C_4$-alkynyl, $C_2$-$C_4$-haloalkynyl, tri($C_1$-$C_4$-alkyl)silyl, phenyl, hydroxyl, oxo, $C_1$-$C_4$alkoxy, $C_1$-$C_3$-haloalkoxy, $C_2$-$C_4$-alkenyloxy, $C_2$-$C_4$-alkynyloxy, $C_1$-$C_4$-alkylthio or $C_1$-$C_3$-haloalkylthio, $R^1$ furthermore particularly preferably represents phenyl which may contain up to three substituents, where the substituents independently of one another are selected from the list below:
halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_2$-$C_6$-alkoxyalkyl, $C_2$-$C_6$-alkylcarbonyl, $C_2$-$C_6$-haloalkylcarbonyl, $C_2$-$C_6$-alkoxycarbonyl, $C_1$-$C_6$-alkoxy, $C_1$-$C_6$-haloalkoxy, $C_3$-$C_8$-cycloalkoxy, $C_3$-$C_8$-halocycloalkoxy, $C_2$-$C_6$-alkenyloxy, $C_2$-$C_6$-alkynyloxy, $C_2$-$C_6$-alkoxyalkoxy, $C_1$-$C_6$-alkylthio, $C_1$-$C_6$-haloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, tri($C_1$-$C_4$-alkyl)silyl or -$L^8Q$, $R^1$ furthermore particularly preferably represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl which may contain up to three substituents, where the substituents independently of one another are selected from the list below:
cyano, nitro, halogen, $C_1$-$C_4$-alkyl, $C_3$-$C_6$-cycloalkyl, $C_2$-$C_4$-alkenyl, $C_2$-$C_4$-haloalkenyl, $C_2$-$C_4$-alkynyl, $C_2$-$C_4$-haloalkynyl, tri($C_1$-$C_3$-alkyl)silyl, benzyl, phenyl, hydroxyl, $C_1$-$C_4$-alkoxy, $C_1$-$C_3$-haloalkoxy, $C_2$-$C_4$-alkenyloxy, $C_2$-$C_4$-alkynyloxy, $C_1$-$C_4$-alkylthio or $C_1$-$C_4$-haloalkylthio, $R^1$ furthermore particularly preferably represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, tetrazol-5-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl which may contain up to two substituents, where the substituents independently of one another are selected from the list below:
substituents at carbon: halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or -$L^8$Q,
substituents at nitrogen: $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl or phenyl, $R^1$ furthermore particularly preferably represents indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl which may contain up to two substituents, where the substituents independently of one another are selected from the list below:
substituents at carbon: halogen, cyano, nitro, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl or phenyl,
substituents at nitrogen: $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl or phenyl, $R^1$ furthermore particularly preferably represents $C_5$-$C_{10}$-heterocyclyl where $L^1$ is attached to a carbon of the heterocyclyl radical and the heterocyclyl radical may contain up to two substituents, where the substituents independently of one another are selected from the list below:
substituents at carbon: halogen, cyano, hydroxyl, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_2$-$C_4$-alkoxyalkyl, $C_1$-$C_4$-alkoxy, $C_1$-$C_4$-haloalkoxy, $C_1$-$C_4$-alkylthio, $C_1$-$C_4$-haloalkylthio, tri($C_1$-$C_4$-alkyl)silyl or phenyl,
substituents at nitrogen: $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_3$-$C_6$-cycloalkyl or phenyl, $R^1$ very particularly preferably represents cyclopentyl, cyclohexyl, cycloheptyl or cyclooctyl $R^1$ furthermore very particularly preferably represents cyclopent-2-en-1-yl, cyclopent-3-en-1-yl, cyclohex-1-en-1-yl, cyclohex-2-en-1-yl, cyclohex-3-en-1-yl, cyclohept-1-en-1-yl, cyclohept-2-en-1-yl, cyclohept-3-en-1-yl or cyclohept-4-en-1-yl, $R^1$ furthermore very particularly preferably represents phenyl which may contain up to two substituents, where the substituents independently of one another are selected from the list below:
chlorine, fluorine, bromine, iodine, cyano, nitro, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)CH_3$, —$C(CH_3)_3$, —$CH=CH_2$, —$CH=CHCH_3$, —$CH_2CH=CH_2$, —$CH=CHCH_2CH_3$, —$CH_2CH=CHCH_3$, —$CH_2CH_2CH=CH_2$, —$C\equiv CH$, —$C\equiv CCH_3$, —$CH_2C\equiv CH$, —$C\equiv CCH_2CH_3$, —$CH_2C\equiv CCH_3$, —$CH_2CH_2C\equiv CH$, —$CF_3$, —$CF_2H$, —$CF_2CF_3$, —$CCl_3$, cyclopropyl, cyclobutyl, cyclopentyl, cyclohexyl, —$CH_2OCH_3$, —$CH_2OCH_2CH_3$, —$CH_2CH_2OCH_3$, —$CH_2OCH_2CH_2CH_3$, —$CH_2CH_2OCH_2CH_3$, —$CH_2CH_2OCH_2CH_3$, —$CH_2CH_2CH_2OCH_3$, —$C(=O)CH_3$, —$C(=O)CH_2CH_3$, —$C(=O)CH_2CH_2CH_3$, —$C(=O)CH(CH_3)_2$, —$C(=O)CF_3$, —$C(=O)OCH_3$, —$C(=O)OCH_2CH_3$, —$C(=O)OCH_2CH_2CH_3$, —$C(=O)OCH(CH_3)_2$, —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, —$OCF_3$, —$OCF_2H$, —$OCH_2CF_3$, —$OCF_2CF_3$, O-cyclohexyl, O-cyclopentyl, O-cyclopropyl, —$SCH_3$, —$SCH_2CH_3$, —$SCH_2CH_2CH_3$, —$SCH(CH_3)_2$, —$SCH_2CH_2CH_2CH_3$, —$SCH_2CH(CH_3)_2$, —$SCH(CH_3)CH_2CH_3$, —$SC(CH_3)_3$, —$SCF_3$, —$SCF_2H$, —$SCH_2CF_3$, —$SCF_2CF_3$, —$S(^oO)Me$, —$S(O)CF_3$, —$S(=O)_2Me$, —$S(O)_2CF_3$, —$OCH_2CH=CH_2$, —$OCH_2C\equiv CH$, —$OCH_2OCH_3$, —$OCH_2OCH_2CH_3$, —$OCH_2CH_2OCH_3$, —$OCH_2OCH(CH_3)_2$, trimethylsilyl, phenyl or phenoxy $R^1$ furthermore very particularly preferably represents naphthalen-1-yl, naphthalen-2-yl, 1,2,3,4-tetrahydronaphthalen-1-yl, 1,2,3,4-tetrahydronaphthalen-2-yl, 5,6,7,8-tetrahydronaphthalen-1-yl, 5,6,7,8-tetrahydronaphthalen-2-yl, decalin-1-yl, decalin-2-yl, 1H-inden-1-yl, 1H-inden-2-yl, 1H-inden-3-yl, 1H-inden-4-yl, 1H-inden-5-yl, 1H-inden-6-yl, 1H-inden-7-yl, indan-1-yl, indan-2-yl, indan-3-yl, indan-4-yl or indan-5-yl, $R^1$ furthermore very particularly preferably represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, tetrazol-5-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl which may contain up to two substituents, where the substituents independently of one another are selected from the list below:

substituents at carbon: chlorine, fluorine, bromine, iodine, cyano, nitro, —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)CH_3$, —$C(CH_3)_3$, —$CH=CH_2$, —$CH=CHCH_3$, —$CH_2CH=CH_2$, —$CH=CHCH_2CH_3$, —$CH_2CH=CHCH_3$, —$CH_2CH_2CH=CH_2$, —$C\equiv CH$, —$C\equiv CCH_3$, —$CH_2C\equiv CH$, —$C\equiv CCH_2CH_3$, —$CH_2C\equiv CCH_3$, —$CH_2CH_2C\equiv CH$, —$CF_3$, —$CFH_2$, —$CF_2H$, —$CF_2CF_3$, —$CCl_3$, cyclopropyl, cyclobutyl, cyclopentyl, cyclohexyl, —$CH_2OCH_3$, —$CH_2OCH_2CH_3$, —$CH_2CH_2OCH_3$, —$CH_2OCH_2CH_2CH_3$, —$CH_2CH_2OCH_2CH_3$, —$CH_2CH_2CH_2OCH_3$, —$OCH_3$, —$OCH_2CH_3$, —$OCH_2CH_2CH_3$, —$OCH(CH_3)_2$, —$OCH_2CH_2CH_2CH_3$, —$OCH_2CH(CH_3)_2$, —$OCH(CH_3)CH_2CH_3$, —$OC(CH_3)_3$, —$OCF_3$, —$OCF_2H$, —$OCH_2CF_3$, —$OCF_2CF_3$, —$SCH_3$, —$SCH_2CH_3$, —$SCH_2CH_2CH_3$, —$SCH(CH_3)_2$, —$SCH_2CH_2CH_2CH_3$, —$SCH_2CH(CH_3)_2$, —$SCH(CH_3)CH_2CH_3$, —$SC(CH_3)_3$, —$SCF_3$, —$SCF_2H$, —$SCH_2CF_3$, —$SCF_2CF_3$, —$S(=O)Me$, —$S(O)CF_3$, —$S(=O)_2Me$, —$S(O)_2CF_3$, trimethylsilyl, phenyl or phenoxy substituents at nitrogen: —$CH_3$, —$CH_2CH_3$, —$CH_2CH_2CH_3$, —$CH(CH_3)_2$, —$CH_2CH_2CH_2CH_3$, —$CH(CH_3)CH_2CH_3$, —$CH_2CH(CH_3)CH_3$, —$C(CH_3)_3$, —$CH=CH_2$, —$CH=CHCH_3$, —$CH_2CH=CH_2$, —$CH=CHCH_2CH_3$, —$CH_2CH=CHCH_3$, —$CH_2CH_2CH=CH_2$, $C\equiv CH$, —$C\equiv CCH_3$, —$CH_2C\equiv CH$, —$C\equiv CCH_2CH_3$, —$CH_2C\equiv CCH_3$, —$CH_2CH_2C\equiv CH$, —$CF_3$, —$CFH_2$, —$CF_2H$, —$CF_2CF_3$, —$CCl_3$, cyclopropyl, cyclobutyl, cyclopentyl, cyclohexyl or phenyl, $R^1$ furthermore preferably represents indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl, 1,3-benzoxazol-7-yl, quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl or isoquinolin-8-yl, $R^1$ furthermore very particularly preferably represents piperidin-1-yl, piperidin-2-yl, piperidin-3-yl, piperidin-4-yl, piperazin-1-yl, piperazin-2-yl, piperazin-3-yl, morpholin-1-yl, morpholin-2-yl, morpholin-3-yl, tetrahydropyran-2-yl, tetrahydropyran-3-yl, tetrahydropyran-4-yl, 1,2,3,4-tetrahydroquinolin-1-yl, 1,2,3,4-tetrahydroisoquinolin-2-yl, 1,2,3,4-tetrahydroquinoxalin-1-yl, indolin-1-yl, isoindolin-2-yl, decahydroquinolin-1-yl or decahydroisoquinolin-2-yl, $R^1$ especially preferably represents cyclohexyl, $R^1$ furthermore especially preferably represents phenyl which may contain up to two substituents, where the substituents independently of one another are selected from the list below:
fluorine, chlorine, trifluoromethyl, methoxy, $R^1$ furthermore especially preferably represents naphthalen-1-yl, naphthalen-2-yl, 2,3-dihydro-1H-inden-2-yl, 1,2,3,4-tetrahydronaphthalen-1-yl or 1,2,3,4-tetrahydronaphthalen-2-yl, $R^1$ furthermore especially preferably represents quinolin-8-yl, Q preferably represents phenyl which may contain up to two substituents, where the substituents independently of one another are selected from the list below:
halogen, cyano, hydroxyl, SH, nitro, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio or phenyl, Q furthermore preferably represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, tetrazol-5-yl, 1,2,4-thiadiazol-3-yl, 1,2,4-thiadiazol-5-yl, 1,3,4-thiadiazol-2-yl, 1,2,3-triazol-1-yl, 1,2,3-triazol-2-yl, 1,2,3-triazol-4-yl, 1,2,4-triazol-1-yl, 1,2,4-triazol-3-yl, 1,2,4-triazol-4-yl, tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl which may contain up to two substituents, where the substituents independently of one another are selected from the list below:

substituents at carbon:
halogen, cyano, hydroxyl, SH, nitro, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio or phenyl, substituents at nitrogen: $C_1$-$C_6$-alkyl, $C_2$-$C_6$-alkenyl, $C_2$-$C_6$-alkynyl, $C_3$-$C_6$-cycloalkyl or phenyl, Q particularly preferably represents phenyl, Q furthermore particularly preferably represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, tetrazol-5-yl, 1,2,4-thiadiazol-3-yl, 1,2,4-thiadiazol-5-yl, 1,3,4-thiadiazol-2-yl, 1,2,3-triazol-1-yl, 1,2,3-triazol- 2-yl, 1,2,3-triazol-4-yl, 1,2,4-triazol-1-yl, 1,2,4-triazol-3-yl, 1,2,4-triazol-4-yl, tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl or 1,2,4-triazin-3-yl, Q very particularly preferably represents phenyl, $R^3$, $R^4$ independently of one another preferably represent hydrogen, $R^3$, $R^4$ independently of one another furthermore preferably represent methyl, ethyl, propyl, isopropyl, butyl, isobutyl or tert-butyl, $R^5$ preferably represents hydrogen, $R^5$ furthermore preferably represents methyl, ethyl, propyl, isopropyl, butyl, isobutyl or tert-butyl, $R^5$ particularly preferably represents hydrogen, $R^5$ furthermore particularly preferably represents methyl;

$R^6$ preferably represents hydrogen, $R^6$ furthermore preferably represents methyl, ethyl, propyl, isopropyl, butyl, isobutyl or tert-butyl, $R^6$ particularly preferably represents hydrogen, $R^6$ furthermore particularly preferably represents methyl, $R^7$ preferably represents methyl, ethyl, propyl, isopropyl, butyl, isobutyl or tert-butyl, $R^7$ particularly preferably represents methyl, $R^8$ preferably represents methyl, ethyl, propyl, isopropyl, butyl, isobutyl or tert-butyl, $R^8$ particularly preferably represents methyl, $R^{13}$ preferably represents hydrogen.

The radical definitions and explanations stated above in general or stated in preferred ranges can, however, also be combined as desired with one another, that is to say between the respective ranges and preferred ranges. They apply both to the end products and, correspondingly, to precursors and intermediates. Moreover, individual definitions may not apply.

Preference is given to compounds of the formula (I) in which all radicals in each case have the preferred meanings mentioned above.

Particular preference is given to compounds of the formula (I) in which all radicals in each case have the particularly preferred meanings mentioned above.

Very particular preference is given to compounds of the formula (I) in which all radicals in each case have the very particularly preferred meanings mentioned above.

Special preference is given to compounds of the formula (I) in which all radicals in each case have the especially preferred meanings mentioned above.

Preference is furthermore given to compounds of the formula (I) in which E represents (2,5-dibromophenyl)acetyl.

Preference is furthermore given to compounds of the formula (I) in which E represents (2,5-dichlorophenyl)acetyl.

Preference is furthermore given to compounds of the formula (I) in which E represents (2,5-difluorobenzyl)sulphonyl.

Preference is furthermore given to compounds of the formula (I) in which E represents (2,5-dimethyl-1,3-thiazol-4-yl)acetyl.

Preference is furthermore given to compounds of the formula (I) in which E represents (2,5-dimethylthiophen-3-yl)acetyl.

Preference is furthermore given to compounds of the formula (I) in which E represents (3,5-dimethyl-1H-1,2,4-triazol-1-yl)acetyl.

Preference is furthermore given to compounds of the formula (I) in which E represents (3-chlorophenyl)acetyl.

Preference is furthermore given to compounds of the formula (I) in which E represents (5-bromo-2-methylphenyl)acetyl.

Preference is furthermore given to compounds of the formula (I) in which E represents (5-chloro-1-methyl-1H-pyrazol-4-yl)acetyl.

Preference is furthermore given to compounds of the formula (I) in which E represents (5-iodo-2-methylphenyl)acetyl.

Preference is furthermore given to compounds of the formula (I) in which E represents (5-methyl-2-phenyl-1,3-oxazol-4-yl)acetyl.

Preference is furthermore given to compounds of the formula (I) in which E represents (5-methyl-2-phenyl-1,3-thiazol-4-yl)acetyl.

Preference is furthermore given to compounds of the formula (I) in which E represents [2,5-bis(trifluoromethyl)phenyl]acetyl.

Preference is furthermore given to compounds of the formula (I) in which E represents [2-bromo-5-(trifluoromethyl)phenyl]acetyl.

Preference is furthermore given to compounds of the formula (I) in which E represents [2-chloro-5-(trifluoromethyl)phenyl]acetyl.

Preference is furthermore given to compounds of the formula (I) in which E represents [2-methyl-5-(trifluoromethyl)phenoxy]carbonyl.

Preference is furthermore given to compounds of the formula (I) in which E represents [3-(trifluoromethyl)phenyl]acetyl.

Preference is furthermore given to compounds of the formula (I) in which E represents [3-(trifluoromethyl)cyclohexyl]acetyl.

Preference is furthermore given to compounds of the formula (I) in which E represents [3-chloro-6-(trifluoromethyl)pyridin-2-yl]acetyl.

Preference is furthermore given to compounds of the formula (I) in which E represents [5-chloro-2-(trifluoromethyl)phenyl]acetyl.

Preference is furthermore given to compounds of the formula (I) in which E represents [5-methyl-3-(trifluoromethyl)-1H-pyrazol-1-yl]acetyl.

Preference is furthermore given to compounds of the formula (I) in which E represents 5,5,6,6,6-pentafluorohexanoyl.

Preference is furthermore given to compounds of the formula (I) in which E represents heptanoyl.

Preference is furthermore given to compounds of the formula (I) in which E represents (2,5-dimethylphenyl)carbamoyl.

Preference is furthermore given to compounds of the formula (I) in which E represents furan-2-yl(oxo)acetyl.

Preference is furthermore given to compounds of the formula (I) in which E represents oxo(thiophen-2-yl)acetyl.

Preference is furthermore given to compounds of the formula (I) in which E represents pentanoyl.

Preference is furthermore given to compounds of the formula (I) in which E represents thiophen-3-ylacetyl.

Preference is furthermore given to compounds of the formula (I) in which E represents [2-chloro-5-(trifluoromethyl)phenyl]carbamoyl.

Preference is furthermore given to compounds of the formula (I) in which E represents (2-chloro-5-methylphenyl)carbamoyl.

Preference is furthermore given to compounds of the formula (I) in which E represents (2,5-dimethylphenyl)carbamothioyl.

Preference is furthermore given to compounds of the formula (I) in which E represents (2-fluoro-5-methylphenyl)carbamoyl.

Preference is furthermore given to compounds of the formula (I) in which E represents (3,5-dimethylphenyl)acetyl.

Preference is furthermore given to compounds of the formula (I) in which E represents (2,4-dimethylphenyl)acetyl.

Preference is furthermore given to compounds of the formula (I) in which E represents (2,5-difluorophenyl)carbamothioyl.

Preference is furthermore given to compounds of the formula (I) in which E represents [3,5-bis(difluoromethyl)-1H-pyrazol-1-yl]acetyl.

Preference is furthermore given to compounds of the formula (I) in which E represents (Z)-{[2-chloro-5-(trifluoromethyl)phenyl]imino}(methoxy)methyl.

Preference is furthermore given to compounds of the formula (I) in which E represents (2-methoxy-5-methylphenyl)carbamoyl.

Preference is furthermore given to compounds of the formula (I) in which E represents (5-chloro-2-methylphenyl)carbamoyl.

Preference is furthermore given to compounds of the formula (I) in which E represents (3,5-dimethyl-1,2-oxazol-4-yl)carbamothioyl.

Preference is furthermore given to compounds of the formula (I) in which E represents (5-fluoro-2-methylphenyl)carbamoyl.

Preference is furthermore given to compounds of the formula (I) in which E represents (5-chloro-2-methoxyphenyl)carbamoyl.

Preference is furthermore given to compounds of the formula (I) in which E represents (2,5-dimethylphenyl)carbamothioyl.

Preference is furthermore given to compounds of the formula (I) in which E represents (2,5-dimethoxyphenyl)carbamoyl.

Preference is furthermore given to compounds of the formula (I) in which E represents cyclopentylacetyl.

Preference is furthermore given to compounds of the formula (I) in which E represents (2,5-difluorophenyl)carbamoyl.

Preference is furthermore given to compounds of the formula (I) in which E represents (1,3-dimethyl-1H-pyrazol-5-yl)acetyl.

Preference is furthermore given to compounds of the formula (I) in which E represents (1,5-dimethyl-1H-pyrazol-3-yl)acetyl.

Preference is furthermore given to compounds of the formula (I) in which E represents (2-methyl-5-nitrophenyl)carbamoyl.

Preference is furthermore given to compounds of the formula (I) in which E represents (2,5-dichlorophenyl)carbamoyl.

Preference is furthermore given to compounds of the formula (I) in which E represents (2,5-dimethylphenyl)acetyl.

Preference is furthermore given to compounds of the formula (I) in which E represents (3,5-dimethyl-1,2-oxazol-4-yl)carbamoyl.

Preference is furthermore given to compounds of the formula (I) in which E represents {[1-methyl-3-(trifluoromethyl)-1H-pyrazol-5-yl]oxy}carbonyl.

Preference is furthermore given to compounds of the formula (I) in which E represents [2-fluoro-5-(trifluoromethyl)phenyl]carbamoyl.

Preference is furthermore given to compounds of the formula (I) in which E represents (5-chloro-2-methylphenyl)carbamothioyl.

Preference is furthermore given to compounds of the formula (I) in which E represents (2,5-dichlorophenyl)carbamothioyl.

Preference is furthermore given to compounds of the formula (I) in which E represents (2-bromo-5-fluorophenyl)carbamothioyl.

Preference is furthermore given to compounds of the formula (I) in which E represents (5-chloro-2-fluorophenyl)carbamothioyl.

Preference is furthermore given to compounds of the formula (I) in which E represents (5-fluoro-2-methylphenyl)carbamothioyl.

Preference is furthermore given to compounds of the formula (I) in which E represents [2-fluoro-5-(trifluoromethyl)phenyl]carbamothioyl.

Preference is furthermore given to compounds of the formula (I) in which E represents (2-methoxyethoxy)acetyl.

Preference is furthermore given to compounds of the formula (I) in which $Y^1$ represents oxygen.

Preference is furthermore given to compounds of the formula (I) in which $Y^2$ represents oxygen.

Preference is furthermore given to compounds of the formula (I) in which $Y^2$ represents sulphur.

Preference is furthermore given to compounds of the formula (I) in which X represents CH.

Preference is furthermore given to compounds of the formula (I) in which X represents CF.

Preference is furthermore given to compounds of the formula (I) in which X represents nitrogen.

Preference is furthermore given to compounds of the formula (I) in which G represents $G^1$.

Preference is furthermore given to compounds of the formula (I) in which G represents $G^{18}$.

Preference is furthermore given to compounds of the formula (I) in which $L^1$ represents a direct bond.

Preference is furthermore given to compounds of the formula (I) in which $L^1$ represents —CH$_2$—.

Preference is furthermore given to compounds of the formula (I) in which $L^1$ represents —CHCH$_3$—.

Preference is furthermore given to compounds of the formula (I) in which $R^1$ represents cyclohexyl.

Preference is furthermore given to compounds of the formula (I) in which $R^1$ represents (3-trifluoromethyl)cyclohexyl.

Preference is furthermore given to compounds of the formula (I) in which $R^1$ represents 2-chlorophenyl.

Preference is furthermore given to compounds of the formula (I) in which $R^1$ represents 2,4-dichlorophenyl.

Preference is furthermore given to compounds of the formula (I) in which $R^1$ represents 2,5-dichlorophenyl.

Preference is furthermore given to compounds of the formula (I) in which $R^1$ represents 2,6-difluorophenyl.

Preference is furthermore given to compounds of the formula (I) in which $R^1$ represents 2,4-difluorophenyl.

Preference is furthermore given to compounds of the formula (I) in which $R^1$ represents 2-chloro-5-(trifluoromethyl)phenyl.

Preference is furthermore given to compounds of the formula (I) in which $R^1$ represents 4-methoxyphenyl.

Preference is furthermore given to compounds of the formula (I) in which $R^1$ represents naphthalen-1-yl.

Preference is furthermore given to compounds of the formula (I) in which $R^1$ represents naphthalen-2-yl.

Preference is furthermore given to compounds of the formula (I) in which $R^1$ represents 2,3-dihydro-1H-inden-2-yl.

Preference is furthermore given to compounds of the formula (I) in which $R^1$ represents 1,2,3,4-tetrahydronaphthalen-2-yl.

Preference is furthermore given to compounds of the formula (I) in which $R^1$ represents 1,2,3,4-tetrahydronaphthalen-1-yl.

Preference is furthermore given to compounds of the formula (I) in which $R^1$ represents quinolin-8-yl.

Preference is furthermore given to compounds of the formula (I) in which $R^1$ represents (1R)-1,2,3,4-tetrahydronaphthalen-1-yl.

Preference is furthermore given to compounds of the formula (I) in which $R^1$ represents (1R,2S)-2-phenylcyclohexyl.

Preference is furthermore given to compounds of the formula (I) in which $R^1$ represents (1S,2R)-2-phenylcyclohexyl.

Preference is furthermore given to compounds of the formula (I) in which $R^1$ represents (1R,2S)-2-(3,4-difluorophenyl)cyclohexyl.

Preference is furthermore given to compounds of the formula (I) in which $R^1$ represents 2,3-dimethylphenyl.

Preference is furthermore given to compounds of the formula (I) in which $R^1$ represents 2,6-dibromophenyl.

Preference is furthermore given to compounds of the formula (I) in which $R^1$ represents 2,6-dichlorophenyl.

Preference is furthermore given to compounds of the formula (I) in which $R^1$ represents 2-bromo-6-fluorophenyl.

Preference is furthermore given to compounds of the formula (I) in which $R^1$ represents 2-bromo-6-methoxyphenyl.

Preference is furthermore given to compounds of the formula (I) in which $R^1$ represents 2-bromo-6-methylphenyl.

Preference is furthermore given to compounds of the formula (I) in which $R^1$ represents 2-bromophenyl.

Preference is furthermore given to compounds of the formula (I) in which $R^1$ represents 2-chloro-6-fluorophenyl.

Preference is furthermore given to compounds of the formula (I) in which $R^1$ represents 2-chloro-6-methylphenyl.

Preference is furthermore given to compounds of the formula (I) in which $R^1$ represents 2-fluoro-6-methoxyphenyl.

Preference is furthermore given to compounds of the formula (I) in which $R^1$ represents 2-fluorophenyl.

Preference is furthermore given to compounds of the formula (I) in which $R^1$ represents 2-iodophenyl.

Preference is furthermore given to compounds of the formula (I) in which $R^1$ represents 3-chloropyridin-4-yl.

Preference is furthermore given to compounds of the formula (I) in which $R^{13}$ represents hydrogen.

In the definitions of the symbols given in the formulae above, collective terms were used which are generally representative of the following substituents:

halogen: fluorine, chlorine, bromine and iodine;

alkyl: saturated, straight-chain or branched hydrocarbon radicals having 1 to 8 carbon atoms, for example (but not limited thereto) $C_1$-$C_6$-alkyl, such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl;

alkenyl: unsaturated, straight-chain or branched hydrocarbon radicals having 2 to 8 carbon atoms and a double bond in any position, for example (but not limited thereto) $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl; "alkenyl" also includes polyenes, for example (but not limited thereto) $C_3$-$C_6$-polyenes, such as 1,2-propadienyl and 2,4-hexadienyl;

alkynyl: straight-chain or branched hydrocarbon groups having 2 to 8 carbon atoms and a triple bond in any position, for example (but not limited thereto) $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl; "alkynyl" also includes fragments having a plurality of triple bonds, for example (but not limited thereto) $C_4$-$C_6$-polyenes, such as 2,5-hexadiynyl;

alkoxy: saturated, straight-chain or branched alkoxy radicals having 1 to 8 carbon atoms, for example (but not limited thereto) $C_1$-$C_6$-alkoxy, such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy; "alkoxy" also includes "alkenyloxy", for example (but not limited thereto) $C_2$-$C_6$-alkenyloxy, such as $H_2C$=$CHCH_2O$, $(CH_3)_2C$=$CHCH_2O$, $CH_3CH$=$CHCH_2O$, $CH_3CH$=$C(CH_3)CH_2O$ and $CH_2$=$CHCH_2CH_2O$; "alkoxy" also includes "alkynyloxy", for example (but not limited thereto) $C_2$-$C_6$-alkynyloxy, such as HC≡CCH$_2$O, CH$_3$C≡CCH$_2$O and CH$_3$C≡CCH$_2$CH$_2$O;

alkylthio: saturated, straight-chain or branched alkylthio radicals having 1 to 8 carbon atoms, for example (but not limited thereto) $C_1$-$C_6$-alkylthio, such as methylthio, ethylthio, propylthio, 1-methylethylthio, butylthio, 1-methylpropylthio, 2-methylpropylthio, 1,1-dimethylethylthio, pentylthio, 1-methylbutylthio, 2-methylbutylthio, 3-methylbutylthio, 2,2-dimethylpropylthio, 1-ethylpropylthio, hexylthio, 1,1-dimethylpropylthio, 1,2-dimethylpropylthio, 1-methylpentylthio, 2-methylpentylthio, 3-methylpentylthio, 4-methylpentylthio, 1,1-dimethylbutylthio, 1,2-dimethylbutylthio, 1,3-dimethylbutylthio, 2,2-dimethylbutylthio, 2,3-dimethylbutylthio, 3,3-dimethylbutylthio, 1-ethylbutylthio, 2-ethylbutylthio, 1,1,2-trimethylpropylthio, 1,2,2-trimethylpropylthio, 1-ethyl-1-methylpropylthio and 1-ethyl-2-methylpropylthio;

alkoxycarbonyl: an alkoxy group having 1 to 6 carbon atoms (as mentioned above) which is attached to the skeleton via a carbonyl group (—CO—);

alkylsulphinyl: saturated, straight-chain or branched alkylsulphinyl radicals having 1 to 8 carbon atoms, for example (but not limited thereto) $C_1$-$C_6$-alkylsulphinyl, such as methylsulphinyl, ethylsulphinyl, propylsulphinyl, 1-methylethylsulphinyl, butylsulphinyl, 1-methylpropylsulphinyl, 2-methylpropylsulphinyl, 1,1-dimethylethylsulphinyl, pentylsulphinyl, 1-methylbutylsulphinyl, 2-methylbutylsulphinyl, 3-methylbutylsulphinyl, 2,2-dimethylpropylsulphinyl, 1-ethylpropylsulphinyl, hexylsulphinyl, 1,1-dimethylpropylsulphinyl, 1,2-dimethylpropylsulphinyl, 1-methylpentylsulphinyl, 2-methylpentylsulphinyl, 3-methylpentylsulphinyl, 4-methylpentylsulphinyl, 1,1-dimethylbutylsulphinyl, 1,2-dimethylbutylsulphinyl, 1,3-dimethylbutylsulphinyl, 2,2-dimethylbutylsulphinyl, 2,3-dimethylbutylsulphinyl, 3,3-dimethylbutylsulphinyl, 1-ethylbutylsulphinyl, 2-ethylbutylsulphinyl, 1,1,2-trimethylpropyl sulphinyl, 1,2,2-trimethylpropylsulphinyl, 1-ethyl-1-methylpropylsulphinyl and 1-ethyl-2-methylpropylsulphinyl; alkylsulphinyl includes both enantiomers of the alkylsulphinyl fragments.

alkylsulphonyl: saturated, straight-chain or branched alkylsulphonyl radicals having 1 to 8 carbon atoms, for example (but not limited thereto) $C_1$-$C_6$-alkylsulphonyl, such as methylsulphonyl, ethylsulphonyl, propylsulphonyl, 1-methylethylsulphonyl, butylsulphonyl, 1-methylpropylsulphonyl, 2-methylpropylsulphonyl, 1,1-dimethylethylsulphonyl, pentylsulphonyl, 1-methylbutylsulphonyl, 2-methylbutylsulphonyl, 3-methylbutylsulphonyl, 2,2-dimethylpropylsulphonyl, 1-ethylpropylsulphonyl, hexylsulphonyl, 1,1-dimethylpropylsulphonyl, 1,2-dimethylpropylsulphonyl, 1-methylpentylsulphonyl, 2-methylpentylsulphonyl, 3-methylpentylsulphonyl, 4-methylpentylsulphonyl, 1,1-dimethylbutylsulphonyl, 1,2-dimethylbutylsulphonyl, 1,3-dimethylbutylsulphonyl, 2,2-dimethylbutylsulphonyl, 2,3-dimethylbutylsulphonyl, 3,3-dimethylbutylsulphonyl, 1-ethylbutylsulphonyl, 2-ethylbutylsulphonyl, 1,1,2-trimethylpropylsulphonyl, 1,2,2-trimethylpropylsulphonyl, 1-ethyl-1-methylpropylsulphonyl and 1-ethyl-2-methylpropylsulphonyl;

cycloalkyl: monocyclic saturated hydrocarbon groups having 3 to 10 carbon ring members, for example (but not limited thereto) cyclopropyl, cyclopentyl and cyclohexyl;

haloalkyl: straight-chain or branched alkyl groups having 1 to 8 carbon atoms (as mentioned above), where in these groups some or all of the hydrogen atoms may be replaced by halogen atoms as mentioned above, for example (but not limited thereto) $C_1$-$C_3$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl;

haloalkoxy: straight-chain or branched alkoxy groups having 1 to 8 carbon atoms (as mentioned above), where in these groups some or all of the hydrogen atoms may be replaced by halogen atoms as mentioned above, for example (but not limited thereto) $C_1$-$C_3$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy and 1,1,1-trifluoroprop-2-oxy;

haloalkylthio: straight-chain or branched alkylthio groups having 1 to 8 carbon atoms (as mentioned above), where in these groups some or all of the hydrogen atoms may be replaced by halogen atoms as mentioned above, for example (but not limited thereto) $C_1$-$C_3$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio, pentafluoroethylthio and 1,1,1-trifluoroprop-2-ylthio;

heteroaryl: a 5 or 6-membered fully unsaturated monocyclic ring system comprising one to four heteroatoms from the group consisting of oxygen, nitrogen and sulphur; if the ring contains a plurality of oxygen atoms, these are not directly adjacent;

5-membered heteroaryl which contains one to four nitrogen atoms or one to three nitrogen atoms and one sulphur or oxygen atom: 5-membered heteroaryl groups which, in addition to carbon atoms, may contain one to four nitrogen atoms or one to three nitrogen atoms and one sulphur or oxygen atom as ring members, for example (but not limited thereto) 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl;

5-membered heteroaryl which contains one to four nitrogen atoms and is attached via nitrogen or benzo-fused 5-membered heteroaryl which contains one to three nitrogen atoms and is attached via nitrogen: 5-membered heteroaryl groups which, in addition to carbon atoms, may contain one to four nitrogen atoms or one to three nitrogen atoms as ring members and in which two adjacent carbon ring members or one nitrogen and one adjacent carbon ring member may be bridged by a buta-1,3-diene-1,4-diyl group in which one or two carbon atoms may be replaced by nitrogen atoms, where these rings are attached to the skeleton via one of the nitrogen ring members, for example (but not limited thereto) 1-pyrrolyl, 1-pyrazolyl, 1,2,4-triazol-1-yl, 1-imidazolyl, 1,2,3-triazol-1-yl, 1,3,4-triazol-1-yl;

6-membered heteroaryl which contains one to four nitrogen atoms: 6-membered heteroaryl groups which, in addition to carbon atoms, may contain, respectively, one to three and one to four nitrogen atoms as ring members, for example (but not limited thereto) 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl and 1,2,4,5-tetrazin-3-yl;

benzo-fused 5-membered heteroaryl which contains one to three nitrogen atoms or one nitrogen atom and one oxygen or sulphur atom: for example (but not limited thereto) indol-1-yl, indol-2-yl, indol-3-yl, indol-4-yl, indol-5-yl, indol-6-yl, indol-7-yl, benzimidazol-1-yl, benzimidazol-2-yl, benzimidazol-4-yl, benzimidazol-5-yl, indazol-1-yl, indazol-3-yl, indazol-4-yl, indazol-5-yl, indazol-6-yl, indazol-7-yl, indazol-2-yl, 1-benzofuran-2-yl, 1-benzofuran-3-yl, 1-benzofuran-4-yl, 1-benzofuran-5-yl, 1-benzofuran-6-yl, 1-benzofuran-7-yl, 1-benzothiophen-2-yl, 1-benzothiophen-3-yl, 1-benzothiophen-4-yl, 1-benzothiophen-5-yl, 1-benzothiophen-6-yl, 1-benzothiophen-7-yl, 1,3-benzothiazol-2-yl, 1,3-benzothiazol-4-yl, 1,3-benzothiazol-5-yl, 1,3-benzothiazol-6-yl, 1,3-benzothiazol-7-yl, 1,3-benzoxazol-2-yl, 1,3-benzoxazol-4-yl, 1,3-benzoxazol-5-yl, 1,3-benzoxazol-6-yl and 1,3-benzoxazol-7-yl, benzo-fused 6-membered heteroaryl which contains one to three nitrogen atoms: for example (but not limited thereto) quinolin-2-yl, quinolin-3-yl, quinolin-4-yl, quinolin-5-yl, quinolin-6-yl, quinolin-7-yl, quinolin-8-yl, isoquinolin-1-yl, isoquinolin-3-yl, isoquinolin-4-yl, isoquinolin-5-yl, isoquinolin-6-yl, isoquinolin-7-yl and isoquinolin-8-yl;

heterocyclyl: a three- to fifteen-membered saturated or partially unsaturated heterocycle which contains one to four heteroatoms from the group consisting of oxygen, nitrogen and sulphur: mono-, bi- or tricyclic heterocycles which contain, in addition to carbon ring members, one to three nitrogen atoms and/or one oxygen or sulphur atom or one or two oxygen and/or sulphur atoms; if the ring contains a plurality of oxygen atoms, these are not directly adjacent; such as, for example (but not limited thereto), oxiranyl, aziridinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-piperidinyl, 3-piperidinyl, 4-piperidinyl, 1,3-dioxan-5-yl, 2-tetrahydropyranyl, 4-tetrahydropyranyl, 2-tetrahydrothienyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl;

Illustration of the Processes and Intermediates

The heteroarylpiperidine and -piperazine derivatives of the formula (I) can be prepared by various routes. Initially, the feasable processes are shown schematically below. Unless indicated otherwise, the radicals given have the meanings given above.

Process A

Equation 1: Process A

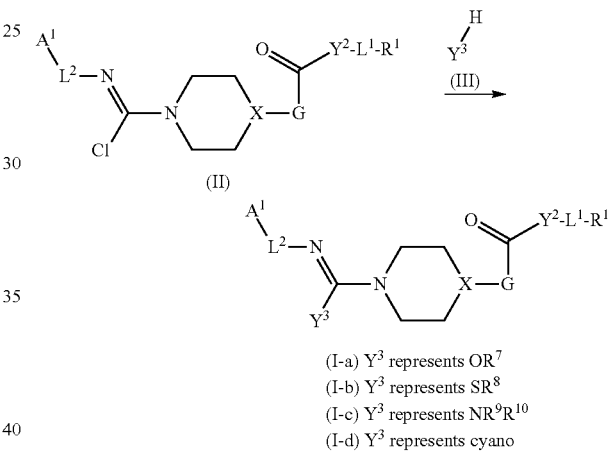

(I-a) $Y^3$ represents $OR^7$
(I-b) $Y^3$ represents $SR^8$
(I-c) $Y^3$ represents $NR^9R^{10}$
(I-d) $Y^3$ represents cyano The compounds of the structure (II) required as starting materials for carrying out process A according to the invention are described further below under process M.

If appropriate, process A is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Alternatively, some of the compounds of the structure (I) obtained when carrying out process A according to the invention can also be obtained without the use of an acid acceptor as corresponding acid chlorides [(I)-HCl]. If required, the compounds of the structure (I) are released by methods described in the literature.

Some of the products of the formulae I-a, I-c and I-d obtained when carrying out process A according to the invention can also be obtained by reacting a compound I-b with a compound III. Thus, for example, the synthesis of thiouronium salts and their conversion into guanidines have been described in the literature (Synthesis (1988), 6, 460-466).

Process A according to the invention is preferably carried out using one or more diluents. Suitable diluents are virtually all inert organic solvents. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process A according to the invention, the reaction temperatures can be varied within a relatively wide range. In general, the process is carried out at temperatures of from −78° C. to +150° C., preferably at temperatures of from −78° C. to +50° C., very particularly preferably at from 0° C. to 30° C.

For carrying out the reaction of process A according to the invention, in general from 0.5 to 20 mol, preferably from 1 to 5 mol, of the compound (III) and from 0 to 20 mol, preferably from 1 to 5 mol, of acid acceptor are employed per mole of the compound of the formula (II). The reaction time is from 1 to 48 hours. The reaction is preferably carried out under an atmosphere of protective gas such as nitrogen or argon. Work-up is carried out by customary methods.

The products I-a, I-b, I-c and I-d obtained when carrying out process A according to the invention can generally be referred to as isoureas, isothioureas, guanidines and cyanoamidines. Selected references for these compounds are Organic Preparations and Procedures International (1980), 12 (5), 309-326, Comprehensive Organic Chemistry, vol. 2, Pergamon Press, Oxford, Rodd's Chemistry of Carbon Compounds, vol. 1C, Elsevier, N.Y. and Journal of Organic Chemistry (2004), 69, 309-313.

Process B

Equation 2: Process B

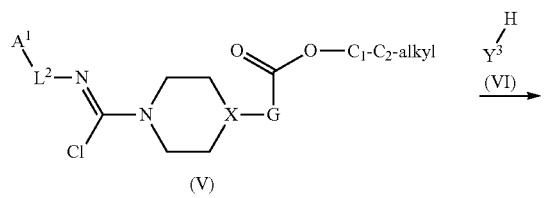

(V)

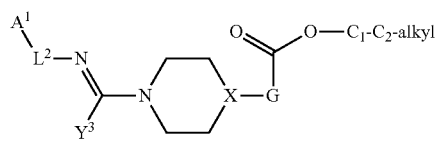

(IV-a) $Y^3$ represents $OR^7$
(IV-b) $Y^3$ represents $SR^8$
(IV-c) $Y^3$ represents $NR^9R^{10}$
(IV-d) $Y^3$ represents cyano The compounds of the structure (V) required as starting materials for carrying out process B according to the invention are described further below under process N.

Process B is carried out analogously to process A.

Process C

Equation 3: Process C

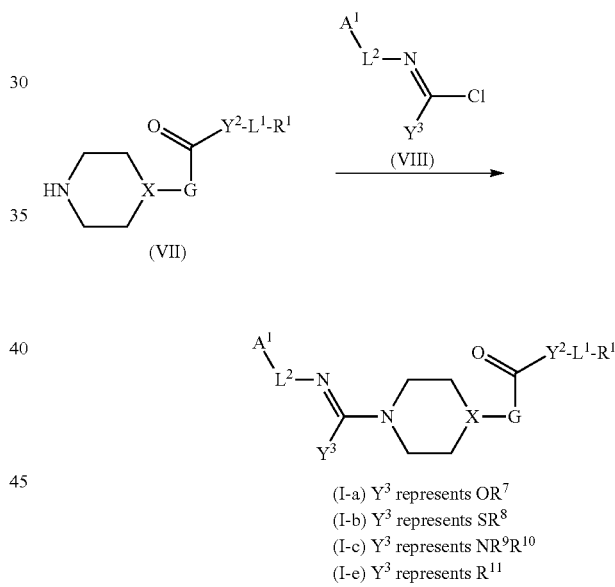

(I-a) $Y^3$ represents $OR^7$
(I-b) $Y^3$ represents $SR^8$
(I-c) $Y^3$ represents $NR^9R^{10}$
(I-e) $Y^3$ represents $R^{11}$ The compounds (VII) required as starting materials for carrying out process C according to the invention are described further below under process AI.

Some of the imidoyl chlorides of the formula (VIII) required as starting materials for carrying out the process C according to the invention are novel. Imidoyl chlorides of the formula (VIII) can be prepared by known methods (for example The Chemistry of the Carbon-Nitrogen Double Bond, S. Patei, Interscience Publishers and the references mentioned therein). Some imidoyl chlorides of the formula (VIII) are commercially available (for example where $A^1$=phenyl, substituted phenyl or alkyl, $L^2$=a direct bond and $Y^2$=OMe, SMe or N(Me)$_2$) and can be prepared with the aid of methods described in the literature.

The reaction conditions are to be chosen analogously to process A.

Process D

Equation 4: Process D

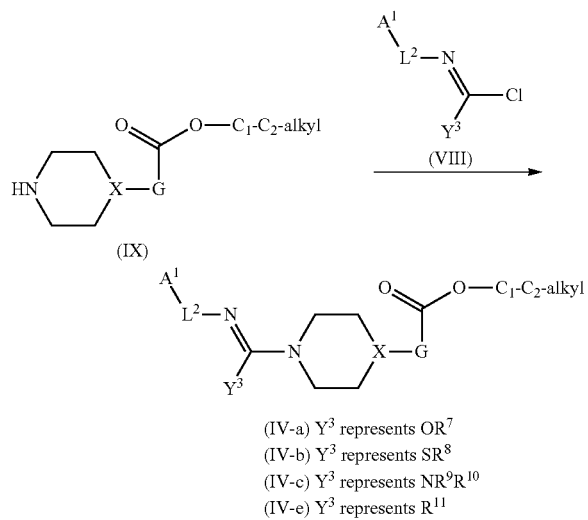

(IV-a) $Y^3$ represents $OR^7$
(IV-b) $Y^3$ represents $SR^8$
(IV-c) $Y^3$ represents $NR^9R^{10}$
(IV-e) $Y^3$ represents $R^{11}$ The compounds (IX) required as starting materials for carrying out process D according to the invention are described further below under process AJ.

Process D is carried out analogously to process C.

Process E

Equation 5: Process E

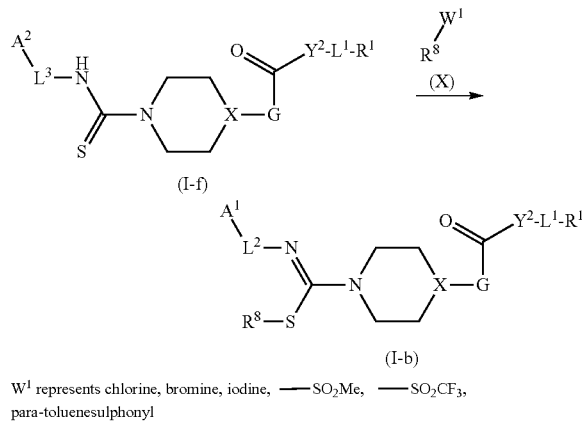

$W^1$ represents chlorine, bromine, iodine, —$SO_2Me$, —$SO_2CF_3$, para-toluenesulphonyl The compounds (I-f) required as starting materials for carrying out process E according to the invention are described further below under processes K and M.

Methods for preparing compounds of the structure (I-b) have already been described in processes A and C according to the invention.

The synthesis of thiouronium salts and their reactions have been described in the literature (for example Synthesis (1988), 6, 460-466).

Process E describes the preparation of compounds of the structures (I-b) by reaction of thioureas (I-f) with alkylating and acylating agents of the structure (X).

If appropriate, process E is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, N,N-diisopropylethylamine, tributylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU).

Alternatively, some of the compounds (I-b) obtained when carrying out process E according to the invention can also be obtained without the use of an acid acceptor as corresponding salts [(I-b)-$HW^1$]. If required, the compounds (I-b) are released by customary methods.

Process E according to the invention is preferably carried out using one or more diluents. The following solvents are preferred for carrying out process E according to the invention: alcohols, such as, for example, methanol, ethanol or isopropanol; aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide, or mixtures thereof with water or pure water.

When carrying out process E according to the invention, the reaction temperatures can be varied within a relatively wide range. In general, the process is carried out at temperatures of from −78° C. to +150° C., preferably at temperatures of from −20° C. to +150° C., very particularly preferably at from 0° C. to 100° C.

For carrying out the reaction of process E according to the invention, in general from 0.5 to 20 mol, preferably from 1 to 5 mol, of the compound (X) and from 0 to 20 mol, preferably from 1 to 5 mol, of acid acceptor are employed per mole of the compound of the formula (I-f). The reaction time is from 1 to 48 hours. The reaction is preferably carried out under an atmosphere of protective gas such as nitrogen or argon. Work-up is carried out by customary methods.

Process F

Equation 6: Process F

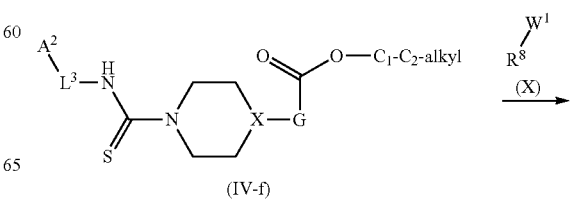

-continued

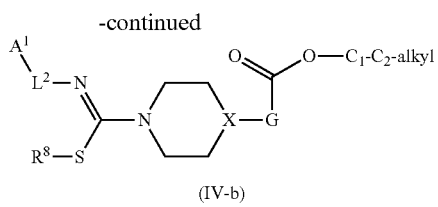

(IV-b)

$W^1$ represents chlorine, bromine, iodine, —SO$_2$Me, —SO$_2$CF$_3$, para-toluenesulphonyl The compounds (IV-f) required as starting materials for carrying out process F according to the invention are described further below under processes L and N.

Methods for preparing compounds of the structures (IV-b) have already been described in processes B and D according to the invention.

Process F is carried out analogously to process E.

Process G

Equation 7: Process G

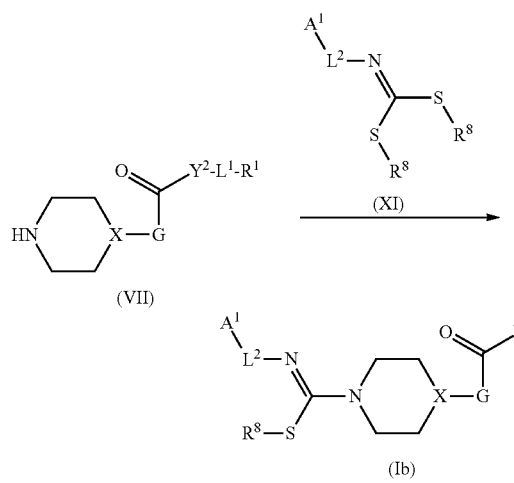

Methods for preparing compounds of the structures (I-b) have already been described in processes A, C and E according to the invention.

The dithiocarbamate derivatives of the formula (XI) required as starting materials for carrying out process G according to the invention can be prepared by known methods (for example Organic Preparations and Procedures (1991), 23(5), 611-616). Starting with the corresponding amines, carbon disulphide, two equivalents of a suitable base and subsequent alkylation, it is possible to prepare the compounds of the formula (XI).

Process G describes the preparation of compounds of the structures (I-b) by reaction of amines (VII) with dithiocarbamate derivatives of the structure (XI).

Process G according to the invention is preferably carried out using one or more diluents. The following solvents are preferred for carrying out process G according to the invention: alcohols, such as, for example, methanol, ethanol or isopropanol; aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide, or mixtures thereof with water or pure water.

When carrying out process G according to the invention, the reaction temperatures can be varied within a relatively wide range. In general, the process is carried out at temperatures of from −78° C. to +150° C., preferably at temperatures of from −20° C. to +150° C., very particularly preferably at from 0° C. to 100° C.

For carrying out the reaction of process G according to the invention, in general from 0.5 to 20 mol, preferably from 1 to 5 mol of compound (XI) are employed per mole of the compound of the formula (VII). The reaction time is from 1 to 48 hours. The reaction is preferably carried out under an atmosphere of protective gas such as nitrogen or argon. Work-up is carried out by customary methods.

Process H

Equation 8: Process H

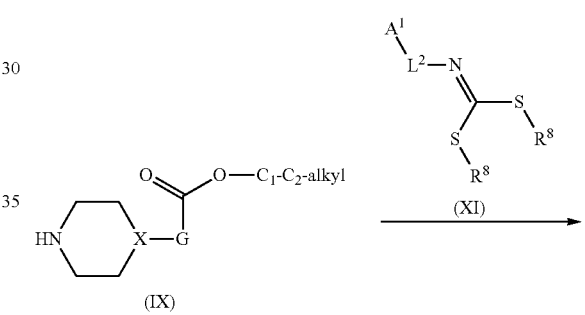

(IV-b)

Methods for preparing compounds of the structures (IV-b) have already been described in processes B, D and F according to the invention.

The dithiocarbamate derivatives of the formula (XI) required as starting materials for carrying out process H according to the invention can be prepared by known methods (for example Organic Preparations and Procedures (1991), 23(5), 611-616). Starting with the corresponding amines, carbon disulphide, two equivalents of a suitable base and subsequent alkylation, it is possible to prepare the compounds of the formula (XI).

Process H describes the preparation of compounds of the structures (IV-b) by reaction of amines (IX) with dithiocarbamate derivatives of the structure (XI).

Process H is carried out analogously to process G.

Process I

Equation 9: Process I

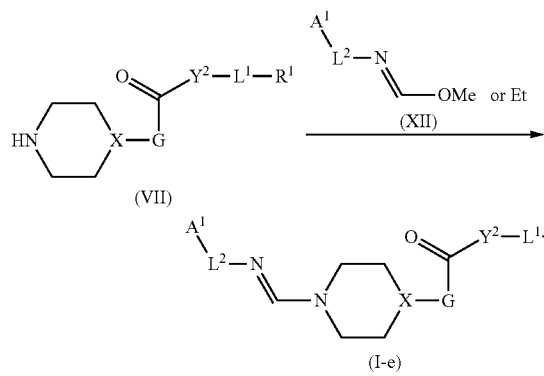

A method for preparing compounds of the structure (I-e) has already been described in process C according to the invention.

The methyl and ethyl imidoformate derivatives of the formula (XII) required as starting materials for carrying out process I according to the invention can be prepared by known methods (Journal of Organic Chemistry (1988), 53(22), 5309-5315; Journal of Medicinal Chemistry (2006), 49(3), 955-970). The compounds (XII) are obtained starting with the corresponding amines and trimethyl or triethyl orthoformate. All inert organic solvents are preferred for carrying out the synthesis of (XII). These preferably include aliphatic, alicyclic or aromatic hydrocarbons, such as, for example, petroleum ether, hexane, heptane, cyclohexane, methylcyclohexane, benzene, toluene, xylene or decalin. When carrying out the synthesis of (XII), the reaction temperatures can be varied within a relatively wide range. In general, the process is carried out at temperatures of from 0° C. to +150° C., preferably at temperatures of from 50° C. to +150° C., very particularly preferably at from 100° C. to 150° C.

Suitable catalysts for synthesizing the imidoformate derivatives (XII) are acids such as, for example, p-toluenesulphonic acid and trifluoroacetic acid.

Process I describes the preparation of compounds of the structures (I-e) by reaction of amines (VII) with methyl or ethyl imidoformate derivatives of the structure (XII).

Process I according to the invention is preferably carried out using one or more diluents. Suitable diluents are virtually all inert organic solvents. The following solvents are preferred for carrying out process I according to the invention: aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process I according to the invention, the reaction temperatures can be varied within a relatively wide range. In general, the process is carried out at temperatures of from 0° C. to +150° C., preferably at temperatures of from +50° C. to +150° C., very particularly preferably at from +60° C. to +120° C.

For carrying out the reaction of process I according to the invention, in general from 0.5 to 20 mol, preferably from 1 to 5 mol of compound (XII) are employed per mole of the compound of the formula (VII). The reaction time is from 1 to 48 hours. The reaction is preferably carried out under an atmosphere of protective gas such as nitrogen or argon. Work-up is carried out by customary methods.

Process J

Equation 10: Process J

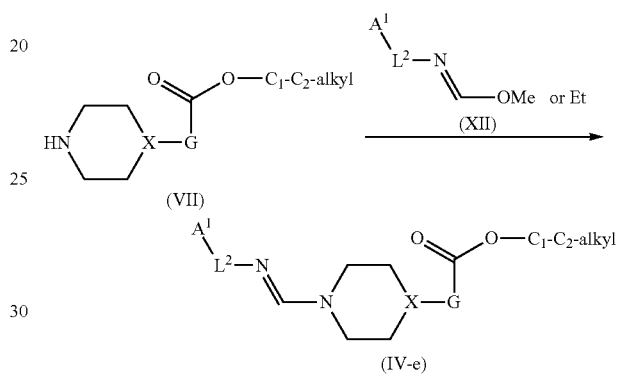

A method for preparing compounds of the structure (IV-e) has already been described in process D according to the invention.

The synthesis of the methyl and ethyl imidoformate derivatives of the formula (XII) required as starting materials has already been described in process I according to the invention.

Process J describes the preparation of compounds of the structures (IV-e) by reaction of amines (IX) with methyl or ethyl imidoformate derivatives of the structure (XII).

Process J is carried out analogously to process I.

Process K

Equation 11: Process K

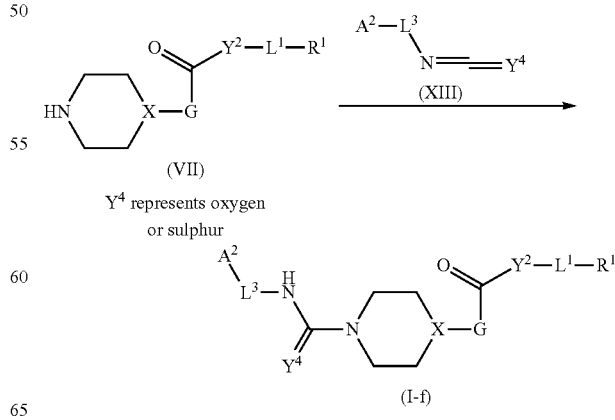

Process K describes the preparation of compounds of the structure (I-f) by reaction of amines (VII) with isocyanates or isothiocyanates of the structure (XIII).

Process K according to the invention is preferably carried out using one or more diluents. All inert organic solvents are preferred for carrying out process K according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process K according to the invention, the reaction temperatures can be varied within a relatively wide range. In general, the process is carried out at temperatures of from −78° C. to +150° C., preferably at temperatures of from −20° C. to +100° C., very particularly preferably at from 0° C. to 50° C.

For carrying out the reaction of process K according to the invention, in general from 0.5 to 20 mol, preferably from 1 to 5 mol of compound (XIII) are employed per mole of the compound of the formula (VII). The reaction time is from 0.1 to 48 hours. The reaction is preferably carried out under an atmosphere of protective gas such as nitrogen or argon. Work-up is carried out by customary methods.

Process L

Equation 12: Process L

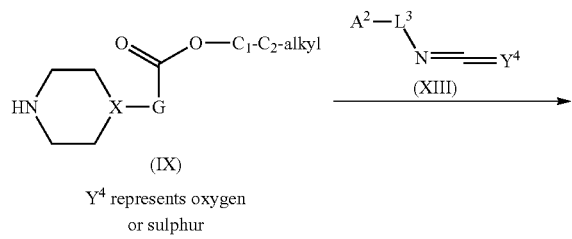

(IX)

$Y^4$ represents oxygen or sulphur

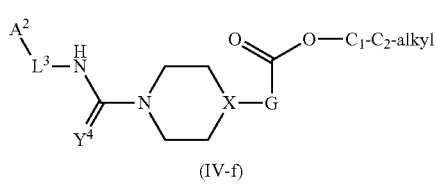

(IV-f)

Process L describes the preparation of compounds of the structure (IV-f) by reaction of amines (IX) with isocyanates or isothiocyanates of the structure (XIII).

Process L is carried out analogously to process K.

Process M

Equation 13: Process M

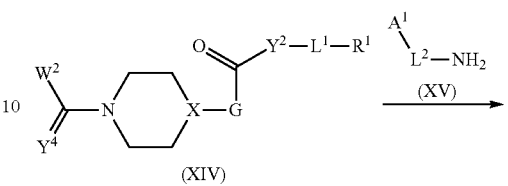

(XIV)

$W^2$ represents chlorine or imidazol-1-yl

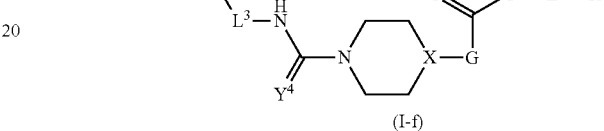

(I-f)

The carbamoyl and thiocarbamoyl chlorides of the formula (XIV, $W^2$=chlorine) required as starting materials for carrying out process M according to the invention can be prepared by methods described in the literature (for example Tetrahedron (2008), 64(32), 7605-7610; Journal of Organic Chemistry (2004), 69(11), 3787-3793; Journal of Organic Chemistry (1983), 48(24), 4750-4761; European Journal of Organic Chemistry (2006), 5, 1177-1184). Typically, the compounds of the formula (XIV, $W^2$=chlorine) are prepared from amines of the formula (VII) and phosgene, thiophosgene or equivalents thereof.

The carbamoyl- and thiocarbamoylimidazoles of the formula (XIV, $W^2$=imidazol-1-yl) required as starting materials for carrying out process M according to the invention can be prepared by methods described in the literature (for example Tetrahedron Letters (2008), 49(36), 5279-5282; Tetrahedron (2005), 61(30), 7153-7175). Typically, the compounds of the formula (XIV, $W^2$=imidazol-1-yl) are prepared from amines of the formula (VII) and 1,1'-carbonyldiimidazoles or 1,1'-thiocarbonyldiimidazoles.

Process M describes the preparation of compounds of the structure (I-f) by reaction of compounds of the structure (XIV, $W^2$=chlorine or imidazol-1-yl) and amines (XV).

If appropriate, process M is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicylononene (DBN) or diazabicycloundecene (DBU).

Alternatively, some of the compounds (I-f) obtained when carrying out process M according to the invention can also be obtained without the use of an acid acceptor as corresponding acid chlorides [(I-f)·HCl] (starting material: $W^2$=Cl). If required, the compounds (I-f) are released by customary methods.

Process M according to the invention is preferably carried out using one or more diluents. All inert organic solvents are preferred for carrying out process M according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process M according to the invention, the reaction temperatures can be varied within a relatively wide range. In general, the process is carried out at temperatures of from −78° C. to +150° C., preferably at temperatures of from −20° C. to +100° C., very particularly preferably at from 0° C. to 60° C.

For carrying out the reaction of process M according to the invention, in general from 0.5 to 20 mol, preferably from 1 to 5 mol, of the compound (XV) and from 0 to 20 mol, preferably from 1 to 5 mol, of acid acceptor are employed per mole of the compound of the formula (XIV). The reaction time is from 1 to 48 hours. The reaction is preferably carried out under an atmosphere of protective gas such as nitrogen or argon. Work-up is carried out by customary methods.

The imidoyl chlorides of the formula (II) required as starting materials for carrying out process A according to the invention can be prepared by methods known from the literature (for example Heterocycles (1998), 48, 319-327; references for processes A and C). Typically, the compounds of the formula (II) are prepared from ureas or thioureas of the formula (I-f) and thionyl chloride, phosphorus oxychloride or phosphorus pentachloride. All inert organic solvents are preferred for this purpose. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

Process N

Equation 14: Process N

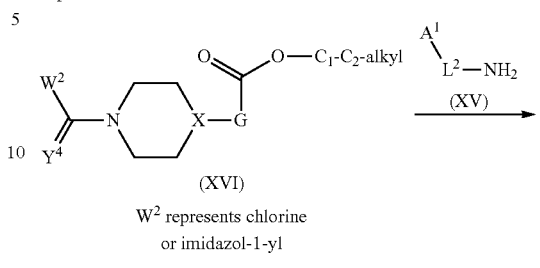

$W^2$ represents chlorine or imidazol-1-yl

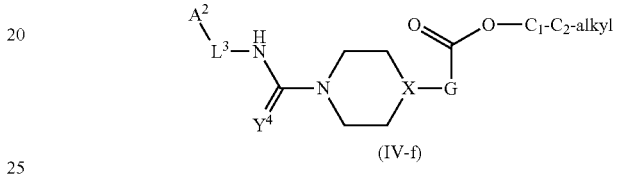

The carbamoyl and thiocarbamoyl chlorides of the formula (XVI, $W^2$=chlorine) required as starting materials for carrying out process N according to the invention can be prepared by methods described in the literature (e.g. Tetrahedron (2008), 64(32), 7605-7610; Journal of Organic Chemistry (2004), 69(11), 3787-3793; Journal of Organic Chemistry (1983), 48(24), 4750-4761; European Journal of Organic Chemistry (2006), 5, 1177-1184). Typically, the compounds of the formula (XVI, $W^2$=chlorine) are prepared from amines of the formula (IX) and phosgene, thiophosgene or equivalents thereof.

The carbamoyl- and thiocarbamoylimidazoles of the formula (XVI, $W^2$=imidazol-1-yl) required as starting materials for carrying out process N according to the invention can be prepared by methods described in the literature (e.g. Tetrahedron Letters (2008), 49(36), 5279-5282; Tetrahedron (2005), 61(30), 7153-7175). Typically, the compounds of the formula (XVI, $W^2$=imidazol-1-yl) are prepared from amines of the formula (IX) and 1,1'-carbonyldiimidazoles or 1,1'-thiocarbonyldiimidazoles.

Process N describes the preparation of compounds of the structure (IV-f) by reaction of compounds of the structure (XVI, $W^2$=chlorine or imidazol-1-yl) and amines (XV).

Process N is carried out analogously to process M.

Process O

Equation 15: Process O

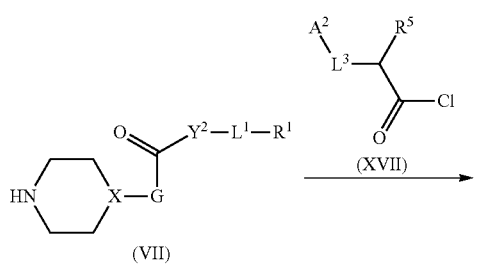

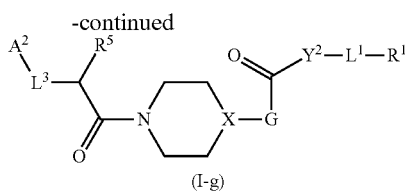

(I-g)

The amides (I-g) obtained when carrying out process O according to the invention can be converted by methods known from the literature into the corresponding thioamides (for example Bioorganic & Medicinal Chemistry Letters (2009), 19(2), 462-468). Here, the compounds of the formula (I-g) are typically reacted with phosphorus pentasulphide or 2,4-bis(4-methoxyphenyl)-1,3-dithia-2,4-diphosphetane 2,4-disulphide (Lawesson's reagent).

The preparation of the carbonyl chlorides (XVII) used for carrying out the process P according to the invention is carried out by customary methods from the corresponding carboxylic acids (XVIII). The reaction of the carboxylic acids of the formula (XVIII) is carried out using a chlorinating agent (for example thionyl chloride/oxalyl chloride) in the presence of a diluent (for example toluene or methylene chloride). When carrying out this step, the reaction temperatures can be varied within a relatively wide range. In general, the process is carried out at temperatures of from 0° C. to +150° C., preferably at temperatures of from 20° C. to the boiling point of the solvent in question. For carrying out the chlorination, in general from 0.5 to 20 mol, preferably from 1 to 1.5 mol, of chlorinating agent are employed per mole of the compound of the formula (XVIII). The reaction time is from 1 to 48 hours. The reaction is preferably carried out under an atmosphere of protective gas such as nitrogen or argon. Work-up is carried out by customary methods.

Process O describes the preparation of compounds of the structure (I-g) by reaction of acid chlorides (XVII) with amines of the structure (VII). It is also possible to use salts of the amines (VII) as starting materials, typically the corresponding hydrochlorides, oxalates or trifluoroacetates.

If appropriate, process O is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU), and also polymer-supported acid acceptors, such as polymer-supported N,N-diisopropylethylamine or polymer-supported N,N-dimethylaminopyridine.

Process O according to the invention is preferably carried out using one or more diluents. All inert organic solvents are preferred for carrying out process O according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process O according to the invention, the reaction temperatures can be varied within a relatively wide range. In general, the process is carried out at temperatures of from −78° C. to +150° C., preferably at temperatures of from −20° C. to +120° C., very particularly preferably at from 0° C. to 80° C.

For carrying out the reaction of process O according to the invention, in general from 0.5 to 20 mol, preferably from 1 to 5 mol, of the compound (VII) and from 0 to 20 mol, preferably from 1 to 5 mol, of acid acceptor are employed per mole of the compound of the formula (XVII). The reaction time is from 1 to 48 hours. The reaction is preferably carried out under an atmosphere of protective gas such as nitrogen or argon. Work-up is carried out by customary methods.

Process P

Equation 16: Process P

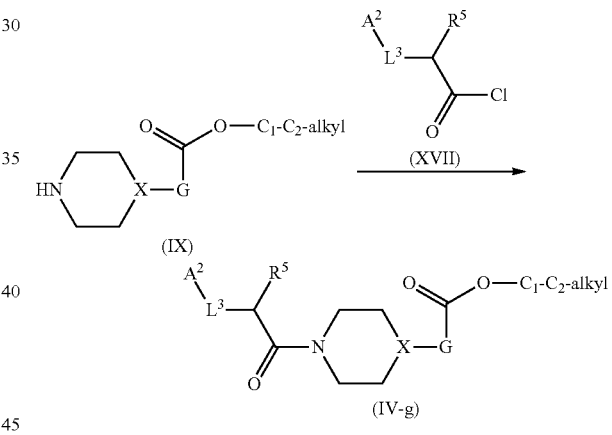

Process P describes the preparation of compounds of the structure (IV-g) by reaction of acid chlorides (XVII) with amines of the structure (IX). It is also possible to use salts of the amines (IX) as starting materials, typically the corresponding hydrochlorides, oxalates or trifluoroacetates.

Process P is carried out analogously to process O.

Process Q

Equation 17: Process Q

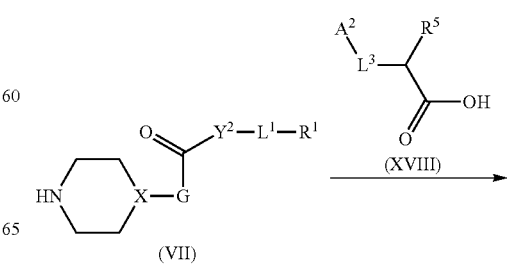

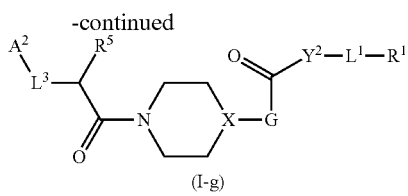

(I-g)

The amides (I-g) obtained when carrying out process Q according to the invention can be converted by methods known from the literature into the corresponding thioamides (for example Bioorganic & Medicinal Chemistry Letters (2009), 19(2), 462-468; European Journal of Organic Chemistry (200), 19, 3273-3278). Here, the compounds of the formula (I-g) are typically reacted with phosphorus pentasulphide or 2,4-bis(4-methoxyphenyl)-1,3-dithia-2,4-diphosphetane 2,4-disulphide (Lawesson's reagent).

The carboxylic acids (XVIII) used for carrying out process Q according to the invention can be prepared by methods described in the literature.

Process Q describes the preparation of compounds of the structure (I-g) by reaction of carboxylic acids (XVIII) with amines of the structure (VII). It is also possible to use salts of the amines (VII) as starting materials, typically the corresponding hydrochlorides, oxalates or trifluoroacetates.

Suitable coupling agents are all customary coupling agents, such as, for example, dicyclohexylcarbodiimide (DCC), 1-(3-dimethylaminopropyl)-3-ethylcarbodiimide hydrochloride (EDC), O-benzotriazol-1-yl-N,N,N',N'-tetramethyluronium hexafluorophosphate (HBTU) or polymer-supported agents, such as, for example, polymer-supported cyclohexylcarbodiimide.

If appropriate, process Q is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU), and also polymer-supported acid acceptors, such as polymer-supported N,N-diisopropylethylamine or polymer-supported N,N-dimethylaminopyridine.

Process Q according to the invention is preferably carried out using one or more diluents. All inert organic solvents are preferred for carrying out process Q according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process Q according to the invention, the reaction temperatures can be varied within a relatively wide range. In general, the process is carried out at temperatures of from −78° C. to +150° C., preferably at temperatures of from −20° C. to +100° C., very particularly preferably at from 0° C. to 40° C.

For carrying out the reaction of process Q according to the invention, in general from 0.5 to 20 mol, preferably from 1 to 2 mol, of the compound (VII) and from 0 to 20 mol, preferably from 1 to 5 mol, of acid acceptor, and also 1-10 mol, preferably from 1 to 2 mol, of coupling agent are employed per mole of the compound of the formula (XVIII). The reaction time is from 1 to 48 hours. The reaction is preferably carried out under an atmosphere of protective gas such as nitrogen or argon. Work-up is carried out by customary methods.

Process R

Equation 18: Process R

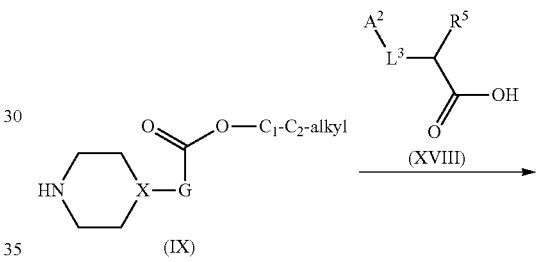

Process R describes the preparation of compounds of the structure (W-g) by reaction of carboxylic acids (XVIII) with amines of the structure (IX). It is also possible to use salts of the amines (IX) as starting materials, typically the corresponding hydrochlorides, oxalates or trifluoroacetates.

Process R is carried out analogously to process Q.

Process S

Equation 19: Process S

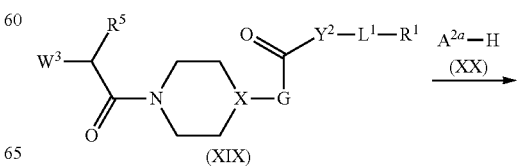

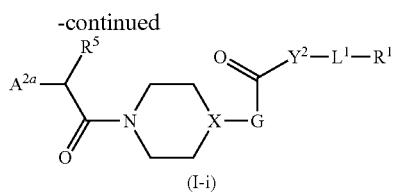

(I-i)

$A^{2a}$ represents cyano or any radical attached via a heteroatom.
$W^3$ represents chlorine, bromine or iodine The α-haloacetamides of the formula (XIX, $W^3$=chlorine, bromine or iodine) required as starting materials for carrying out process S according to the invention can be prepared by methods described in the literature (for example Journal of Organic Chemistry (2008), 73(12), 4452-4457, Journal of the American Chemical Society (2007), 129(29), 8928-8929, Heterocycles (2005), 65(8), 1857-1869, Bioorganic & Medicinal Chemistry Letters (2002), 12(18), 2519-2522). The compounds of the formula (XIX, $W^2$=chlorine, bromine or iodine) are typically prepared from amines of the formula (VII) and α-halocarbonyl halides, α-halocarboxylic acids or α-halocarboxylic anhydrides in analogy to processes O and Q.

Process S describes the preparation of compounds of the structure (I-i) by reaction of α-haloacetamides of the formula (XIX, $W^3$=chlorine, bromine or iodine) with compounds of the structure (XX).

If appropriate, process S is carried out in the presence of a suitable base. Suitable bases are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU), and also polymer-supported acid acceptors, such as polymer-supported N,N-diisopropylethylamine or polymer-supported N,N-dimethylaminopyridine.

Process S according to the invention is preferably carried out using one or more diluents. All inert organic solvents are preferred for carrying out process S according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process S according to the invention, the reaction temperatures can be varied within a relatively wide range. In general, the process is carried out at temperatures of from −78° C. to +150° C., preferably at temperatures of from −20° C. to +100° C., very particularly preferably at from 0° C. to 80° C.

For carrying out the reaction of process S according to the invention, in general from 0.5 to 20 mol, preferably from 1 to 2 mol, of the compound (XX) and also from 0 to 20 mol, preferably from 1 to 5 mol, of base are employed per mole of the compound of the formula (XIX). The reaction time is from 1 to 48 hours. The reaction is preferably carried out under an atmosphere of protective gas such as nitrogen or argon. Work-up is carried out by customary methods.

Process T

Equation 20: Process T

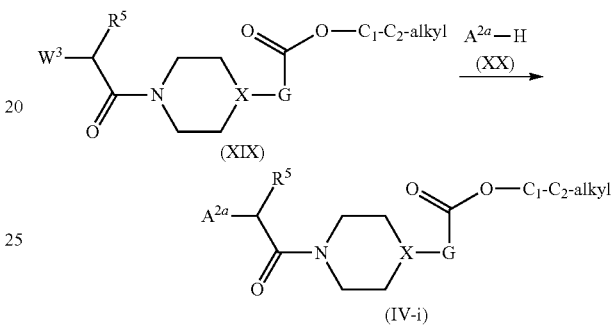

$A^{2a}$ represents cyano or any radical attached via a heteroatom.
$W^3$ represents chlorine, bromine or iodine Process T describes the preparation of compounds of the structure (IV-i) by reaction of α-haloacetamides of the formula (XXI, $W^3$=chlorine, bromine or iodine) with compounds of the structure (XX).

Process T is carried out analogously to process S.

Process U

Equation 21: Process U

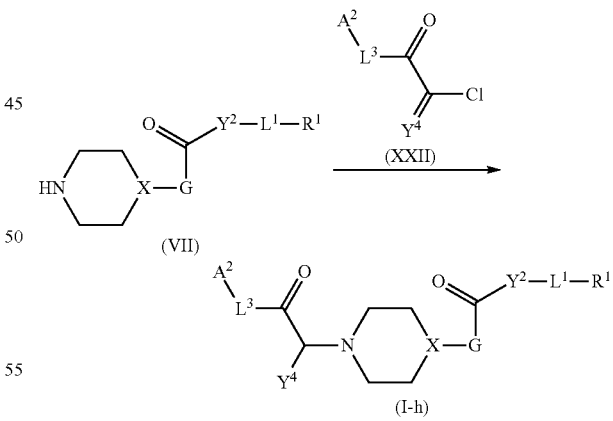

The α-ketocarbonyl chlorides of the formula (XXII) required as starting materials for carrying out process U according to the invention can be prepared by methods described in the literature from the corresponding carboxylic acids (for example Bioorganic & Medicinal Chemistry Letters (2008), 18(20), 5456-5459; Synlett (1999), 11, 1763-1765; Journal of Heterocyclic Chemistry (1981), 18(5), 953-956). The chlorination is carried out by customary methods. The reaction of the corresponding carboxylic acids of the formula (XXIII) is carried out using a chlorinating agent (for example thionyl chloride/oxalyl chloride) in the presence of a diluent (for example toluene or methylene chloride). When carrying out the chlorination of compounds of the formula (XXIII), the reaction temperatures can be varied within a relatively wide range. In general, the process is carried out at temperatures of from 0° C. to +150° C., preferably at temperatures of from 20° C. to the boiling point of the solvent in question. For carrying out the chlorination, in general from 0.5 to 20 mol, preferably from 1 to 1.5 mol, of chlorinating agent are employed per mole of the compound of the formula (XXIII). The reaction time is from 1 to 48 hours. The reaction is preferably carried out under an atmosphere of protective gas such as nitrogen or argon. Work-up is carried out by customary methods.

Process U describes the preparation of compounds of the structure (1-h) by reaction of α-ketocarbonyl chlorides of the formula (XXII) with amines of the structure (VII).

The coupling reaction (VII and XXII) of process U according to the invention is carried out analogously to process O already described.

Process V

Equation 22: Process V

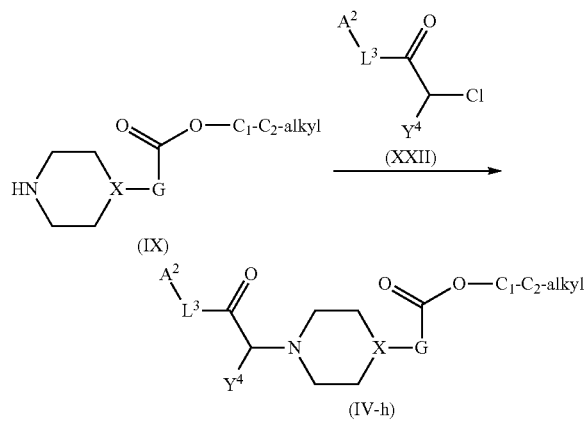

(IV-h)

Process V describes the preparation of compounds of the structure (IV-h) by reaction of α-ketocarbonyl chlorides of the formula (XXII) with amines of the structure (IX).

The coupling reaction (IX and XXII) of process V according to the invention is carried out analogously to process O already described.

Process W

Equation 23: Process W

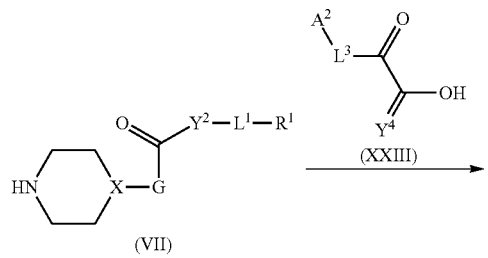

(VII)

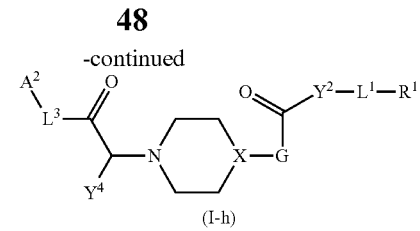

(I-h)

The α-ketocarboxylic acids of the formula (XXIII) required as starting materials for carrying out process W according to the invention can be prepared by methods described in the literature.

Process W describes the preparation of compounds of the structure (I-h) by reaction of α-ketocarboxylic acids of the formula (XXIII) with amines of the structure (VII).

Suitable coupling agents are all customary coupling agents, such as, for example, dicyclohexylcarbodiimide (DCC), 1-(3-dimethylaminopropyl)-3-ethylcarbodiimide hydrochloride (EDC), O-benzotriazol-1-yl-N,N,N',N'-tetramethyluronium hexafluorophosphate (HBTU) or polymer-supported agents, such as, for example, polymer-supported cyclohexylcarbodiimide.

If appropriate, process W is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU), and also polymer-supported acid acceptors, such as polymer-supported N,N-diisopropylethylamine or polymer-supported N,N-dimethylaminopyridine.

Process W according to the invention is preferably carried out using one or more diluents. All inert organic solvents are preferred for carrying out process W according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process W according to the invention, the reaction temperatures can be varied within a substantial range. In general, the process is carried out at temperatures of from −78° C. to +150° C., preferably at temperatures of from −20° C. to +100° C., very particularly preferably at from 0° C. to 40° C.

For carrying out the reaction of process W according to the invention, in general from 0.5 to 20 mol, preferably from 1 to 2 mol, of the compound (VII) and from 0 to 20 mol, preferably from 1 to 5 mol, of acid acceptor, and also 1-10 mol, preferably from 1 to 2 mol, of coupling agent are employed per mole of the compound of the formula (XXIII). The reaction time is from 1 to 48 hours. The reaction is preferably carried out under an atmosphere of protective gas such as nitrogen or argon. Work-up is carried out by customary methods.

Process X

Equation 24: Process X

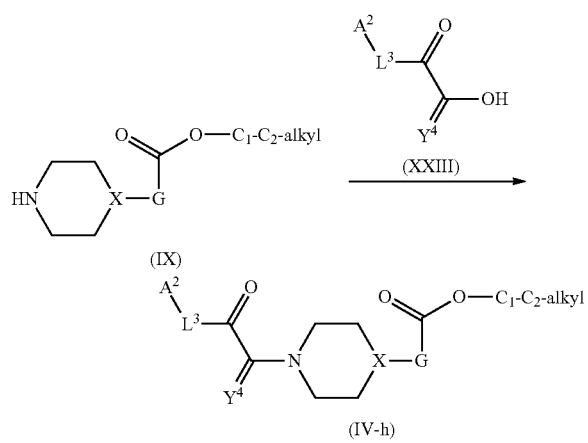

The α-ketocarboxylic acids of the formula (XXIII) required as starting materials for carrying out process X according to the invention can be prepared by methods described in the literature.

Process X describes the preparation of compounds of the structure (IV-h) by reaction of α-ketocarboxylic acids (XXIII) with amines of the structure (IX).

Process X is carried out analogously to process W.

Process Y

Equation 25: Process Y

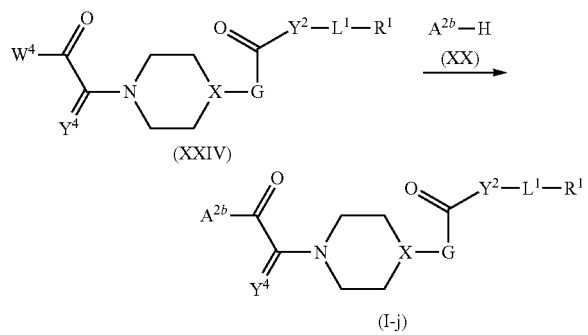

$A^{2b}$ represents any radical attached via a heteroatom.
$W^4$ represents chlorine or OH The compounds of the formula (XXIV, $W^4$=Cl) required as starting materials for carrying out process Y according to the invention can be prepared by methods described in the literature from the corresponding amines (VII) (for example European Journal of Medicinal Chemistry (2006), 41(6), 786-792; Journal of Medicinal Chemistry (2007), 50(5), 901-914). The reaction of the corresponding amines of the formula (VII) is carried out using a carbonylating agent (for example oxalyl chloride, ethyl chlorooxoacetate) in the presence of a diluent (for example toluene or methylene chloride). When carrying out the carbonylation of compounds of the formula (VII), the reaction temperatures can be varied within a relatively wide range. In general, the process is carried out at temperatures of from 0° C. to +150° C., preferably at temperatures of from 0° C. to the boiling point of the solvent in question. For carrying out the carbonylation, in general from 0.5 to 20 mol, preferably from 1 to 1.5 mol, of carbonylating agent are employed per mole of the compound of the formula (VII). The reaction time is from 1 to 48 hours. The reaction is preferably carried out under an atmosphere of protective gas such as nitrogen or argon. Work-up is carried out by customary methods. Some of the products obtained have to be reacted further to obtain compounds of the formula (XXIV, $W^4$=Cl). Thus, for example, when using ethyl chloroacetate, initially the corresponding esters are obtained, which are then hydrolyzed to the corresponding carboxylic acids by methods described in the literature and can then be converted by methods described in the literature into the required compounds of the formula (XXIV, $W^4$=Cl) (for example Journal of Medicinal Chemistry (2007), 50(5), 901-914). The reaction of the corresponding carboxylic acids is carried out using a chlorinating agent (for example thionyl chloride/oxalyl chloride) in the presence of a diluent (for example toluene or methylene chloride).

The compounds of the formula (XXIV, $W^4$=OH) required as starting materials for carrying out process Y according to the invention can be prepared by methods described in the literature from the corresponding amines (VII) (for example European Journal of Medicinal Chemistry (2006), 41(6), 786-792; Journal of Medicinal Chemistry (2007), 50(5), 901-914). The reaction of the corresponding amines of the formula (VII) is carried out using a carbonylating agent (for example oxalyl chloride, ethyl chlorooxoacetate) in the presence of a diluent (for example toluene or methylene chloride). Some of the products obtained have to be reacted further to obtain compounds of the formula (XXIV, $W^4$=OH). Thus, when using, for example, ethyl chloroacetate, initially the corresponding esters are obtained, which can then be hydrolyzed to the corresponding carboxylic acids by methods described in the literature. It is also possible to prepare the compounds of the formula (XXIV, $W^4$=OH) by hydrolysis of the compounds of the formula (XXIV, $W^4$=Cl) described above. The hydrolysis is carried out by customary methods.

Process Y describes the preparation of compounds of the structure (I-j) by reaction of compounds of the formula (XXIV) with compounds of the structure (XX).

The reaction (XX and XXIV; $W^4$=Cl) of process Y according to the invention is carried out analogously to process O already described.

The reaction (XX and XXIV; $W^4$=OH) of process Y according to the invention is carried out analogously to process Q already described.

Process Z

Equation 26: Process Z

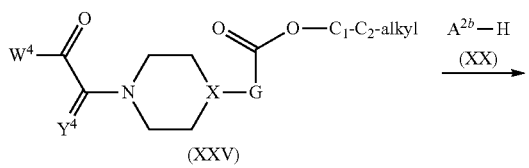

51

-continued

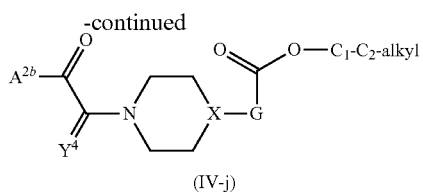

(IV-j)

$A^{2b}$ represents any radical attached via a heteroatom.
$W^4$ represents chlorine or OH Process Z describes the preparation of compounds of the structure (IV-j) by reaction of compounds of the formula (XXV) with compounds of the structure (XX).

The starting materials (XXV) can be prepared analogously to the starting materials (Xw) (see process Y).

The reaction (XX and XXV; $W^4$=Cl) of process Z according to the invention is carried out analogously to process P already described.

The reaction (XX and XXV; $W^4$=OH) of process Z according to the invention is carried out analogously to process R already described.

Process AA

Equation 27: Process AA

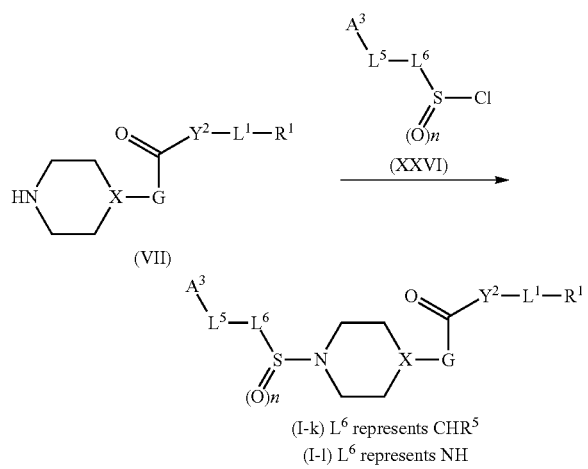

(I-k) $L^6$ represents $CHR^5$
(I-l) $L^6$ represents NH

The preparation of the sulphinyl, sulphonyl, sulphanyl and sulphamyl chlorides of the formula (XXVI) used for carrying out process AA according to the invention is carried out by customary methods. For the preparation of sulphinyl, sulphonyl, sulphanyl and sulphamyl chlorides and their conversion into the corresponding sulphinyl-, sulphonyl-, sulphanyl- and sulphamylamides and sulphuric diamides see, for example, The Chemistry of Sulfinic Acids, Esters and their Derivatives (1990), S. Patai, John Wiley & Sons; Tetrahedron Letters (1986), 27(13), 1493-1494 and references cited therein; Comprehensive Organic Chemistry (1979), vol. 3, N. Jones, Pergamon Press.

Process AA describes the preparation of compounds of the structure (I-k and I-l) by reaction of compounds of the formula (XXVI) with amines of the structure (VII). It is also possible to use salts of the amines (VII) as starting materials, for example the corresponding hydrochlorides, oxalates or trifluoroacetates.

If appropriate, process AA is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU), and also polymer-supported acid acceptors, such as polymer-supported N,N-diisopropylethylamine or polymer-supported N,N-dimethylaminopyridine.

Process AA according to the invention is preferably carried out using one or more diluents. All inert organic solvents are preferred for carrying out process AA according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process AA according to the invention, the reaction temperatures can be varied within a substantial range. In general, the process is carried out at temperatures of from −78° C. to +150° C., preferably at temperatures of from −20° C. to +150° C., very particularly preferably at from −20° C. to +100° C.

For carrying out the reaction of process AA according to the invention, in general from 0.5 to 20 mol, preferably from 1 to 2 mol, of the compound (VII) and from 0 to 20 mol, preferably from 1 to 5 mol, of acid acceptor are employed per mole of the compound of the formula (XXVI). The reaction time is from 1 to 48 hours. The reaction is preferably carried out under an atmosphere of protective gas such as nitrogen or argon. Work-up is carried out by customary methods.

Process AB

Equation 28: Process AB

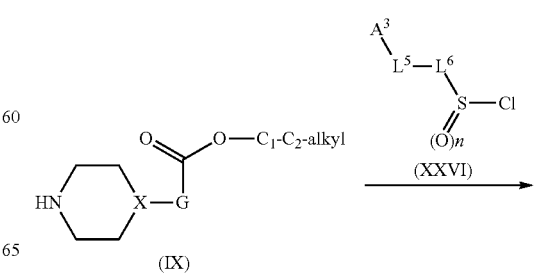

(IX)

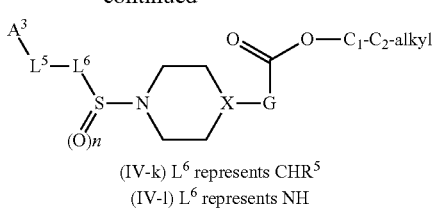

(IV-k) $L^6$ represents $CHR^5$
(IV-l) $L^6$ represents NH

Process AB is carried out analogously to process AA.

Process AC

Equation 29: Process AC

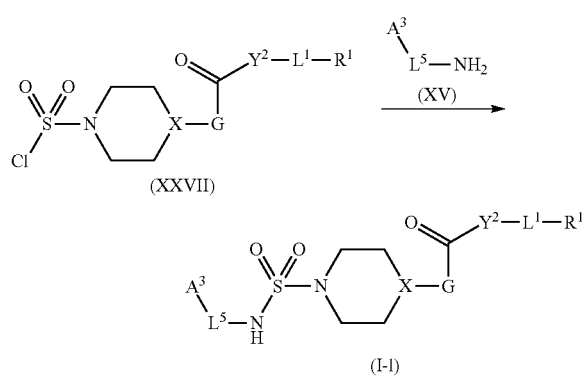

The preparation of the sulphamyl chlorides of the formula (XXVII) used for carrying out process AC according to the invention is carried out by customary methods (for example Biorganic & Medicinal Chemistry Letters (2005), 15(4), 983-987, references for process AB). Typically, the compounds of the formula (XXVII) are prepared from amines of the formula (VII) and sulphuryl chloride. Alternatively, it is possible to prepare initially, typically from amines of the formula (VII) and chlorosulphuric acid or sulphur trioxide, the corresponding sulphonic acids, which are then chlorinated by methods known from the literature (for example Biorganic & Medicinal Chemistry Letters (2006), 16(13), 3367-3370).

Process AC describes the preparation of compounds of the structure (1-1) by reaction of compounds of the formula (XXVII) with amines of the structure (XV). It is also possible to use salts of the amines as starting materials, for example the corresponding hydrochlorides, oxalates or trifluoroacetates.

The reaction (XXVII and XV) of process AC according to the invention is carried out analogously to process AA already described.

Process AD

Equation 30: Process AD

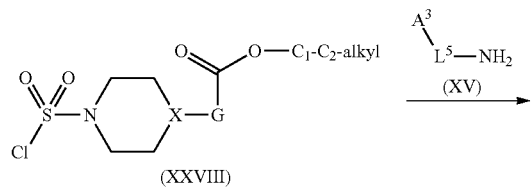

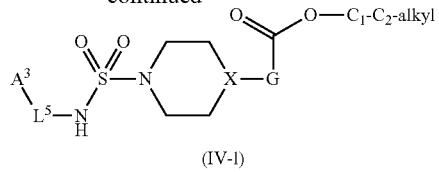

The preparation of the sulphamyl chlorides of the formula (XXVIII) used for carrying out process AD according to the invention is carried out by customary methods (for example Biorganic & Medicinal Chemistry Letters (2005), 15(4), 983-987, references for process AB). Typically, the compounds of the formula (XXVIII) are prepared from amines of the formula (IX) and sulphuryl chloride. Alternatively, it is possible to prepare initially, typically from amines of the formula (IX) and chlorosulphuric acid or sulphur trioxide, the corresponding sulphonic acids, which are then chlorinated by methods known from the literature (for example Biorganic & Medicinal Chemistry Letters (2006), 16(13), 3367-3370).

Process AD describes the preparation of compounds of the structure (IV-1) by reaction of compounds of the formula (XXVIII) with amines of the structure (XV). It is also possible to use salts of the amines as starting materials, for example the corresponding hydrochlorides, oxalates or trifluoroacetates.

Process AD is carried out analogously to process AA already described.

Process AE

Equation 31: Process AE

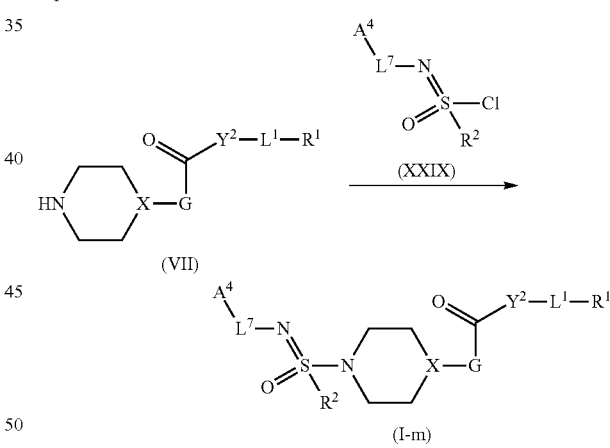

The preparation of the sulphonimidoyl chlorides of the formula (XXIX) used for carrying out the process AE according to the invention is carried out by customary methods. For the preparation of sulphonimidoyl chlorides of the formula (XXIX) and their conversion into the corresponding sulphonimidoamides see, for example, Journal of Organic Chemistry (1979), 44, 2055-2061, Journal of Organic Chemistry (1988), 53, 4190-4193, Comprehensive Organic Chemistry (1979), vol. 3, part 11, Pergamon Press).

Process AE describes the preparation of compounds of the structure (I-m) by reaction of compounds of the formula (XXIX) with amines of the structure (VII). It is also possible to use salts of the amines (VII) as starting materials, for example the corresponding hydrochlorides, oxalates or trifluoroacetates.

If appropriate, process AE is carried out in the presence of a suitable acid acceptor. Suitable acid acceptors are all customary inorganic or organic bases. These preferably include the hydrides, hydroxides, amides, alkoxides, acetates, carbonates or bicarbonates of alkaline earth metals or alkali metals, such as, for example, sodium hydride, sodium amide, lithium diisopropylamide, sodium methoxide, sodium ethoxide, potassium tert-butoxide, sodium hydroxide, potassium hydroxide, sodium acetate, sodium carbonate, potassium carbonate, potassium bicarbonate, sodium bicarbonate or ammonium carbonate, and also tertiary amines, such as trimethylamine, triethylamine, tributylamine, N,N-diisopropylethylamine, N,N-dimethylaniline, N,N-dimethylbenzylamine, pyridine, N-methylpiperidine, N-methylmorpholine, N,N-dimethylaminopyridine, diazabicyclooctane (DABCO), diazabicyclononene (DBN) or diazabicycloundecene (DBU), and also polymer-supported acid acceptors, such as polymer-supported N,N-diisopropylethylamine or polymer-supported N,N-dimethylaminopyridine.

Process AE according to the invention is preferably carried out using one or more diluents. All inert organic solvents are preferred for carrying out process AE according to the invention. These preferably include aliphatic, alicyclic or aromatic hydrocarbons, such as, for example, petroleum ether, hexane, heptane, cyclohexane, methylcyclohexane, benzene, toluene, xylene or decalin; halogenated hydrocarbons, such as, for example, chlorobenzene, dichlorobenzene, dichloromethane, chloroform, carbon tetrachloride, dichloroethane or trichloroethane; ethers, such as diethyl ether, diisopropyl ether, methyl tert-butyl ether, methyl tert-amyl ether, dioxane, tetrahydrofuran, 1,2-dimethoxyethane, 1,2-diethoxyethane or anisole; ketones, such as acetone, butanone, methyl isobutyl ketone or cyclohexanone; nitriles, such as acetonitrile, propionitrile, n- or isobutyronitrile or benzonitrile; amides, such as N,N-dimethylformamide, N,N-dimethylacetamide, N-methylformanilide, N-methylpyrrolidone or hexamethylphosphoric triamide.

When carrying out process AE according to the invention, the reaction temperatures can be varied within a relatively wide range. In general, the process is carried out at temperatures of from $-78°$ C. to $+150°$ C., preferably at temperatures of from $-20°$ C. to $+150°$ C., very particularly preferably at from $-20°$ C. to $+100°$ C.

For carrying out the reaction of process AE according to the invention, in general from 0.5 to 20 mol, preferably from 1 to 2 mol, of the compound (VII) and from 0 to 20 mol, preferably from 1 to 5 mol, of acid acceptor are employed per mole of the compound of the formula (XXIX). The reaction time is from 1 to 48 hours. The reaction is preferably carried out under an atmosphere of protective gas such as nitrogen or argon. Work-up is carried out by customary methods.

Process AF

Equation 32: Process AF

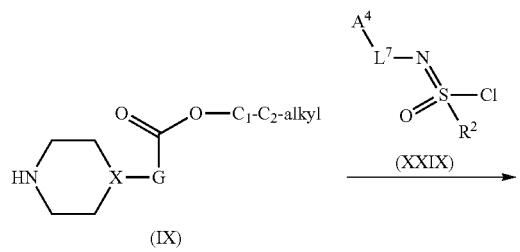

(IX)

(XXIX)

-continued

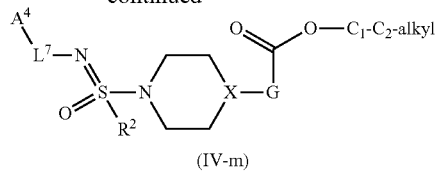

(IV-m)

The preparation of the sulphonimidoyl chlorides of the formula (XXIX) used for carrying out the process AF according to the invention is carried out by customary methods. For the preparation of sulphonimidoyl chlorides of the formula (XXIX) and their conversion into the corresponding sulphonimidoamides see, for example, Journal of Organic Chemistry (1979), 44, 2055-2061, Journal of Organic Chemistry (1988), 53, 4190-4193, Comprehensive Organic Chemistry (1979), vol. 3, part 11, Pergamon Press).

Process AF describes the preparation of compounds of the structure (IV-m) by reaction of compounds of the formula (XXIX) with amines of the structure (IX). It is also possible to use salts of the amines (IX) as starting materials, for example the corresponding hydrochlorides, oxalates or trifluoroacetates.

Process AF is carried out analogously to process AE.

Process AG

Equation 33: Process AG

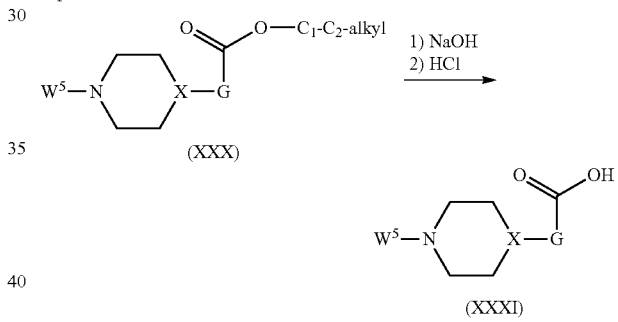

$W^5$ represents acetyl, $C_1$-$C_4$-alkoxycarbonyl, benzyl or benzyloxycarbonyl One way of preparing the intermediate (XXXI) from corresponding compounds (XXX) is shown in Equation 33.

The carboxylic acid of the formula (XXXI) can be prepared by hydrolysis of the corresponding $C_1$-$C_2$-alkyl ester of the formula (XXX). It is possible to use, for example, the method described in WO2007/014290.

Suitable solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride) and halogenated aromatic hydrocarbons (for example chlorobenzene, dichlorobenzene), or the reaction can be carried out in mixtures of two or more of these solvents.

Suitable alkali metal hydroxides are, for example, LiOH, NaOH or KOH, usually in the presence of water together with a cosolvent, preferably THF and/or methanol, to facilitate dissolution of the ester. The starting material and the alkali metal hydroxide are employed in equimolar amounts; however, the alkali metal hydroxide may, if required, also be used in excess. The carboxylate salt formed is converted into the free acid by treatment with a slight excess of mineral acids, such as, for example, hydrochloric acid or sulphuric acid.

The reaction is usually carried out at temperatures of 0° C.-60° C., but it can also be carried out at the reflux temperature of the reaction mixture. The reaction time varies depending on the scale of the reaction and the reaction temperature, but is generally between a few minutes and 48 hours.

After the reaction has ended, the compounds (XXXI) are removed from the reaction mixture using one of the customary separation techniques. If required, the compounds are purified by recrystallization, distillation or chromatography.

Process AH

Equation 34: Process AH

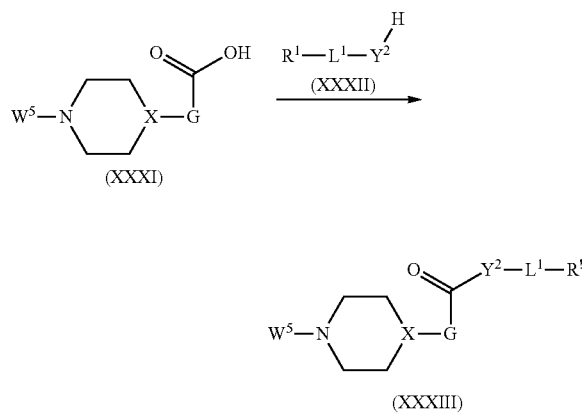

(XXXIII)

$W^5$ represents acetyl, $C_1$-$C_4$-alkoxycarbonyl, benzyl or benzyloxycarbonyl One way of preparing compounds of the formula (XXXIII) from corresponding compounds (XXXI) is shown in Equation 34.

A compound of the formula (XXXIII) can be synthesized from the corresponding compound of the formula (XXXI) using a substrate of the formula (XXXII) in the presence of a coupling agent analogously to procedures described in the literature (for example Tetrahedron 2005, 61, 10827-10852, and the references cited therein).

Suitable coupling agents are, for example, peptide coupling agents (for example N-(3-dimethylaminopropyl)-N'-ethylcarbodiimide mixed with 4-dimethylaminopyridine, N-(3-dimethylaminopropyl)-N'-ethylcarbodiimide mixed with 1-hydroxybenzotriazole, bromotripyrrolidinophosphonium hexafluorophosphate, O-(7-azabenzotriazol-1-yl)-N,N,N',N'-tetramethyluronium hexafluorophosphate, etc.).

If appropriate, a base, such as, for example, triethylamine or Hünig base can be employed in the reaction.

Suitable solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile) and amides (for example N,N-dimethylformamide, N,N-dimethylacetamide), or the reaction can be carried out in mixtures of two or more of these solvents. The preferred solvents are N,N-dimethylformamide and dichloromethane.

The reaction is usually carried out at temperatures of 0° C.-100° C. and preferably at 0° C.-30° C., but it can also be carried out at the reflux temperature of the reaction mixture. The reaction time varies depending on the scale of the reaction and the reaction temperature, but is generally between a few minutes and 48 hours.

After the reaction has ended, the compounds (XXXIII) are removed from the reaction mixture using one of the customary separation techniques. If required, the compounds are purified by recrystallization, distillation or chromatography, or they can, if appropriate, also be used for the next step without prior purification.

Alternatively, a compound of the formula (XXXIII) can also be synthesized from the compound of the formula (XXXI) by a two-step transformation using processes known from the literature (for example Tetrahedron 2005, 61, 10827-10852, and the literature cited therein), if appropriate in the presence of an acid scavenger/a base. Typically, a compound of the formula (XXXI) is initially converted into the corresponding acid halide or sulphonate, followed by a coupling reaction with a substrate of the formula (XXXII).

Substrates of the general formula (XXXII) are commercially available or can be prepared by processes described in the literature (see, for example, "The Chemistry of Functional groups"; "The Chemistry of the Thiol Group"; John Wiley & Sons, 1974, 163-269, and the references cited therein; "The Chemistry of Functional groups"; "Supplement F2: The Chemistry of amino, nitroso, nitro and related groups"; John Wiley & Sons, and the references cited therein; "Science of Synthesis"; "Alcohols", Volume 36, Thieme, 2008 and the references cited therein; "Science of Synthesis"; "Amines and Ammonium Salts", Volume 40a, Thieme, 2008, and the references cited therein).

Suitable for carrying out process AH according to the invention are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene) and nitriles (for example acetonitrile), or the reaction can be carried out in mixtures of two or more of these solvents. The preferred solvents are tetrahydrofuran and dichloromethane.

At least one equivalent of an acid scavenger/a base (for example Hünig base, triethylamine or commercially available polymeric acid scavengers), based on the starting material of the general formula (XXXII), is employed. If the starting material is a salt, at least two equivalents of the acid scavenger are required.

The reaction is usually carried out at temperatures of 0° C.-100° C. and preferably at 20° C.-30° C., but it can also be carried out at the reflux temperature of the reaction mixture. The reaction time varies depending on the scale of the reaction and the reaction temperature, but is generally between a few minutes and 48 hours.

After the reaction has ended, the compounds (XXXIII) are removed from the reaction mixture using one of the customary separation techniques. If required, the compounds are purified by recrystallization, distillation or chromatography, or they can, if appropriate, also be used for the next step without prior purification.

Process AI

Equation 35: Process AI

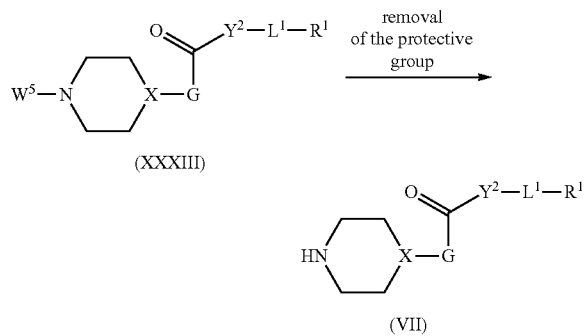

(XXXIII)

(VII)

$W^5$ represents acetyl, $C_1$-$C_4$-alkoxycarbonyl, benzyl or benzyloxycarbonyl One way of preparing compounds of the formula (VII) from corresponding compounds (XXXIII) is shown in Equation 35.

A compound of the formula (XXXIII) is converted into a compound of the formula (VII) using suitable methods for removing protective groups, which methods are described in the literature ("*Protective Groups in Organic Synthesis*"; Third Edition; 494-653, and the literature cited therein).

tert-Butoxycarbonyl and benzyloxycarbonyl protective groups can be removed in an acidic medium (for example using hydrochloric acid or trifluoroacetic acid). Acetyl protective groups can be removed under basic conditions (using, for example, potassium carbonate or caesium carbonate). Benzylic protective groups can be removed hydrogenolytically using hydrogen in the presence of a catalyst (for example palladium on activated carbon).

Suitable solvents are all customary solvents which are inert under the reaction conditions, such as, for example, alcohols (for example methanol, ethanol, propanol), cyclic and acyclic ethers (for example diethyl ether, tetrahydrofuran, dioxane), aromatic hydrocarbons (for example benzene, toluene, xylene), halogenated hydrocarbons (for example dichloromethane, chloroform, carbon tetrachloride), halogenated aromatic hydrocarbons (for example chlorobenzene, dichlorobenzene), nitriles (for example acetonitrile), carboxylic esters (for example ethyl acetate), amides (for example N,N-dimethylformamide, N,N-dimethylacetamide), dimethyl sulphoxide, 1,3-dimethyl-2-imidazolinone, water and acetic acid, or the reaction can be carried out in mixtures of two or more of these solvents. Acids which can be used for this reaction of deprotecting t-butoxycarbonyl and benzyloxycarbonyl groups are, for example, trifluoroacetic acid, hydrochloric acid or other acids, as described in the literature (for example "*Protective Groups in Organic Synthesis*"; Third Edition; pp. 494-653).

The reaction is usually carried out at temperatures of 0° C.-150° C. and preferably at room temperature, but it can also be carried out at the reflux temperature of the reaction mixture. The reaction time varies depending on the scale of the reaction and the reaction temperature, but is generally between half an hour and 72 hours.

After the reaction has ended, the compounds (VII) are removed from the reaction mixture using one of the customary separation techniques. If required, the compounds are purified by recrystallization, distillation or chromatography, or they can, if appropriate, also be used for the next step without prior purification. Moreover, it is possible to isolate the compound of the general formula (VII) as a salt, for example as a salt of hydrochloric acid or trifluoroacetic acid.

Process AJ

Equation 36: Process AJ

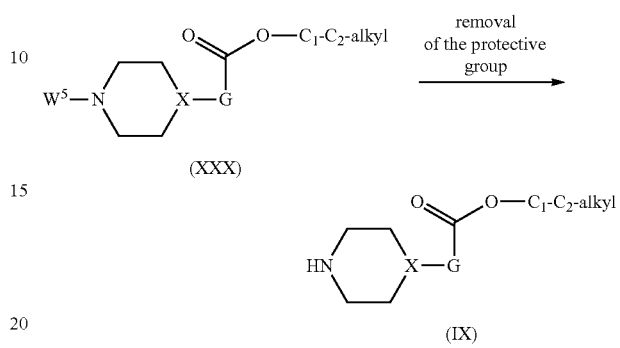

(XXX)

(IX)

$W^5$ represents acetyl, $C_1$-$C_4$-alkoxycarbonyl, benzyl or benzyloxycarbonyl One way of preparing compounds of the formula (IX) from corresponding compounds (XXX) is shown in Equation 36.

The same process as already described in Equation 35 (process AI) is used.

Process AK

Equation 37: Process AK

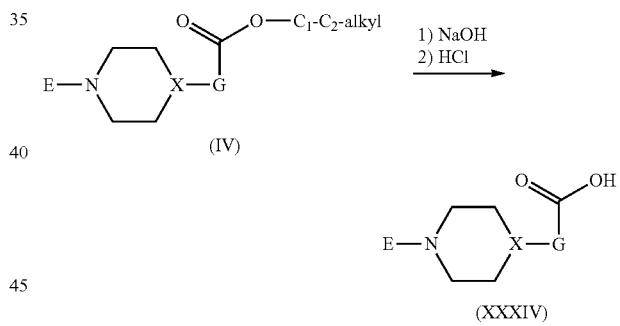

(IV)

(XXXIV)

One way of preparing compounds of the formula (XXXIV) from corresponding compounds (IV) is shown in Equation 37.

The same process as already described in Equation 33 (process AG) is used.

Process AL

Equation 38: Process AL

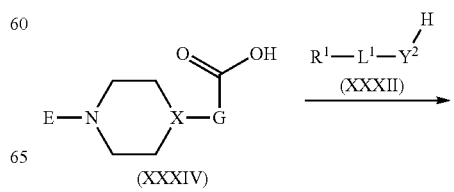

(XXXIV)

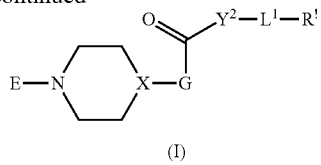

(I)

One way of preparing compounds of the formula (I) from corresponding compounds (XXXIV) is shown in Equation 38.

The same process as already described in Equation 34 (process AH) is used.

All processes according to the invention are generally (unless indicated otherwise) carried out under atmospheric pressure. However, it is also possible to operate under elevated or reduced pressure—in general between 0.1 and 10 bar.

Preferred radical definitions for the formulae and equations mentioned above and below have already been given above. These definitions apply not only to the end products of the formula (I) but likewise to all intermediates.

The present invention furthermore relates to a composition for controlling unwanted microorganisms which comprises the active compounds according to the invention. These are preferably fungicidal compositions which comprise agriculturally suitable auxiliaries, solvents, carriers, surfactants or extenders.

Moreover, the invention relates to a method for controlling unwanted microorganisms, characterized in that the active compounds according to the invention are applied to the phytopathogenic fungi and/or their habitat.

According to the invention, a carrier is a natural or synthetic organic or inorganic substance with which the active compounds are mixed or bonded for better applicability, in particular for application to plants or plant parts or seed. The carrier, which may be solid or liquid, is generally inert and should be suitable for use in agriculture.

Suitable solid or liquid carriers are: for example ammonium salts and ground natural minerals, such as kaolins, clays, talc, chalk, quartz, attapulgite, montmorillonite or diatomaceous earth, and ground synthetic minerals, such as finely divided silica, alumina and natural or synthetic silicates, resins, waxes, solid fertilizers, water, alcohols, especially butanol, organic solvents, mineral and vegetable oils and derivatives of these. Mixtures of such carriers may also be used. Suitable solid carriers for granules are: for example crushed and fractionated natural rocks such as calcite, marble, pumice, sepiolite, dolomite, and synthetic granules of inorganic and organic meals, and also granules of organic material such as sawdust, coconut shells, maize cobs and tobacco stalks.

Suitable liquefied gaseous extenders or carriers are liquids which are gaseous at ambient temperature and under atmospheric pressure, for example aerosol propellants, such as halogenated hydrocarbons, and also butane, propane, nitrogen and carbon dioxide.

Tackifiers such as carboxymethylcellulose and natural and synthetic polymers in the form of powders, granules or latices, such as gum arabic, polyvinyl alcohol and polyvinyl acetate, or else natural phospholipids such as cephalins and lecithins and synthetic phospholipids can be used in the formulations. Other possible additives are mineral and vegetable oils.

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, and also water.

The compositions according to the invention may comprise additional further components, such as, for example, surfactants. Suitable surfactants are emulsifiers and/or foam formers, dispersants or wetting agents having ionic or nonionic properties, or mixtures of these surfactants. Examples of these are salts of polyacrylic acid, salts of lignosulphonic acid, salts of phenolsulphonic acid or naphthalenesulphonic acid, polycondensates of ethylene oxide with fatty alcohols or with fatty acids or with fatty amines, substituted phenols (preferably alkylphenols or arylphenols), salts of sulphosuccinic esters, taurine derivatives (preferably alkyl taurates), phosphoric esters of polyethoxylated alcohols or phenols, fatty esters of polyols, and derivatives of the compounds containing sulphates, sulphonates and phosphates, for example alkylaryl polyglycol ethers, alkylsulphonates, alkyl sulphates, arylsulphonates, protein hydrolyzates, lignosulphite waste liquors and methylcellulose. The presence of a surfactant is required if one of the active compounds and/or one of the inert carriers is insoluble in water and when the application takes place in water. The proportion of surfactants is between 5 and 40 percent by weight of the composition according to the invention.

It is possible to use colorants such as inorganic pigments, for example iron oxide, titanium oxide and Prussian Blue, and organic colorants such as alizarin colorants, azo colorants and metal phthalocyanine colorants, and trace nutrients such as salts of iron, manganese, boron, copper, cobalt, molybdenum and zinc.

If appropriate, other additional components may also be present, for example protective colloids, binders, adhesives, thickeners, thixotropic substances, penetrants, stabilizers, sequestering agents, complex formers. In general, the active compounds can be combined with any solid or liquid additive customarily used for formulation purposes.

The compositions and formulations according to the invention generally comprise between 0.05 and 99% by weight, 0.01 and 98% by weight, preferably between 0.1 and 95% by weight, particularly preferably between 0.5 and 90% of active compound, very particularly preferably between 10 and 70% by weight.

The active compounds or compositions according to the invention can be used as such or, depending on their respective physical and/or chemical properties, in the form of their formulations or the use forms prepared therefrom, such as aerosols, capsule suspensions, cold-fogging concentrates, warm-fogging concentrates, encapsulated granules, fine granules, flowable concentrates for the treatment of seed, ready-to-use solutions, dustable powders, emulsifiable concentrates, oil-in-water emulsions, water-in-oil emulsions, macrogranules, microgranules, oil-dispersible powders, oil-miscible flowable concentrates, oil-miscible liquids, foams, pastes, pesticide coated seed, suspension concentrates, suspoemulsion concentrates, soluble concentrates, suspensions, wettable powders, soluble powders, dusts and granules, water-soluble granules or tablets, water-soluble powders for the treatment of seed, wettable powders, natural products and synthetic substances impregnated with active compound, and also microencapsulations in polymeric substances and in coating materials for seed, and also ULV coldfogging and warm-fogging formulations.

The formulations mentioned can be prepared in a manner known per se, for example by mixing the active compounds with at least one customary extender, solvent or diluent, emulsifier, dispersant, and/or binder or fixative, wetting agent, water repellent, if appropriate desiccants and UV stabilizers and, if appropriate, dyes and pigments, defoamers, preservatives, secondary thickeners, adhesives, gibberellins and also further processing auxiliaries.

The compositions according to the invention include not only formulations which are already ready for use and can be applied with a suitable apparatus to the plant or the seed, but also commercial concentrates which have to be diluted with water prior to use.

The active compounds according to the invention can be present as such or in their (commercial) formulations and in the use forms prepared from these formulations as a mixture with other (known) active compounds, such as insecticides, attractants, sterilants, bactericides, acaricides, nematicides, fungicides, growth regulators, herbicides, fertilizers, safeners and/or semiochemicals.

The treatment according to the invention of the plants and plant parts with the active compounds or compositions is carried out directly or by action on their surroundings, habitat or storage space using customary treatment methods, for example by dipping, spraying, atomizing, irrigating, evaporating, dusting, fogging, broadcasting, foaming, painting, spreading-on, watering (drenching), drip irrigating and, in the case of propagation material, in particular in the case of seeds, furthermore as a powder for dry seed treatment, a solution for seed treatment, a water-soluble powder for slurry treatment, by incrusting, by coating with one or more coats, etc. It is furthermore possible to apply the active compounds by the ultra-low volume method or to inject the active compound preparation or the active compound itself into the soil.

The invention furthermore includes a method for treating seed.

The invention furthermore relates to seed which has been treated in accordance with one of the methods described in the previous paragraph. The seeds according to the invention are used in methods for the protection of seed from undesirable microorganisms. In these methods, seed treated with at least one active compound according to the invention is employed.

The active compounds or compositions according to the invention are also suitable for treating seed. A large part of the damage to crop plants caused by harmful organisms is triggered by the infection of the seed during storage or after sowing both during and after germination of the plant. This phase is particularly critical since the roots and shoots of the growing plant are particularly sensitive, and even small damage may result in the death of the plant. Accordingly, there is great interest in protecting the seed and the germinating plant by using appropriate compositions.

The control of phytopathogenic fungi by treating the seed of plants has been known for a long time and is the subject of continuous improvements. However, the treatment of seed entails a series of problems which cannot always be solved in a satisfactory manner. Thus, it is desirable to develop methods for protecting the seed and the germinating plant which dispense with, or at least reduce considerably, the additional application of crop protection agents after sowing or after emergence of the plants. It is furthermore desirable to optimize the amount of active compound employed in such a way as to provide optimum protection for the seed and the germinating plant from attack by phytopathogenic fungi, but without damaging the plant itself by the active compound employed. In particular, methods for the treatment of seed should also take into consideration the intrinsic fungicidal properties of transgenic plants in order to achieve optimum protection of the seed and the germinating plant with a minimum of crop protection agents being employed.

The present invention therefore also relates to a method for the protection of seed and germinating plants, from attack by phytopathogenic fungi, by treating the seed with a composition according to the invention. The invention also relates to the use of the compositions according to the invention for treating seed for protecting the seed and the germinating plant against phytopathogenic fungi. Furthermore, the invention relates to seed treated with a composition according to the invention for protection against phytopathogenic fungi.

The control of phytopathogenic fungi which damage plants post-emergence is carried out primarily by treating the soil and the above-ground parts of plants with crop protection agents. Owing to the concerns regarding a possible impact of the crop protection agents on the environment and the health of humans and animals, there are efforts to reduce the amount of active compounds applied.

One of the advantages of the present invention is that the particular systemic properties of the active compounds and compositions according to the invention mean that treatment of the seed with these active compounds and compositions not only protects the seed itself, but also the resulting plants after emergence, from phytopathogenic fungi. In this manner, the immediate treatment of the crop at the time of sowing or shortly thereafter can be dispensed with.

It is also considered to be advantageous that the active compounds or compositions according to the invention can be used in particular also for transgenic seed where the plant growing from this seed is capable of expressing a protein which acts against pests. By treating such seed with the active compounds or compositions according to the invention, even by the expression of the, for example, insecticidal protein, certain pests may be controlled. Surprisingly, a further synergistic effect may be observed here, which additionally increases the effectiveness of the protection against attack by pests.

The compositions according to the invention are suitable for protecting seed of any plant variety which is employed in agriculture, in the greenhouse, in forests or in horticulture and viticulture. In particular, this takes the foam of seed of cereals (such as wheat, barley, rye, triticale, sorghum/millet and oats), maize, cotton, soya beans, rice, potatoes, sunflower, bean, coffee, beet (for example sugar beet and fodder beet), peanut, oilseed rape, poppy, olive, coconut, cacao, sugar cane, tobacco, vegetables (such as tomato, cucumbers, onions and lettuce), turf and ornamentals (see also hereinbelow). The treatment of the seed of cereals (such as wheat, barley, rye, triticale and oats), maize and rice is of particular importance.

As also described further below, the treatment of transgenic seed with the active compounds or compositions according to the invention is of particular importance. This refers to the seed of plants containing at least one heterologous gene which allows the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. Preferably, this heterologous gene is from *Bacillus* sp., the gene product having activity against the European corn borer and/or the Western corn rootworm. Particularly preferably, the heterologous gene originates from *Bacillus thuringiensis*.

Within the context of the present invention, the composition according to the invention is applied to the seed either alone or in a suitable formulation. Preferably, the seed is treated in a state in which it is stable enough to avoid damage during treatment. In general, the seed may be treated at any point in time between harvest and sowing. The seed usually used has been separated from the plant and freed from cobs, shells, stalks, coats, hairs or the flesh of the fruits. Thus, it is possible to use, for example, seed which has been harvested, cleaned and dried to a moisture content of less than 15% by weight. Alternatively, it is also possible to use seed which, after drying, has been treated, for example, with water and then dried again.

When treating the seed, care must generally be taken that the amount of the composition according to the invention applied to the seed and/or the amount of further additives is chosen in such a way that the germination of the seed is not adversely affected, or that the resulting plant is not damaged. This must be borne in mind in particular in the case of active compounds which can have phytotoxic effects at certain application rates.

The compositions according to the invention can be applied directly, i.e. without containing any other components and undiluted. In general, it is preferred to apply the compositions to the seed in the form of a suitable formulation. Suitable formulations and methods for treating seed are known to the person skilled in the art and are described, for example, in the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The active compounds which can be used in accordance with the invention can be converted into the customary seed-dressing formulations, such as solutions, emulsions, suspensions, powders, foams, slurries or other coating compositions for seed, and also ULV formulations.

These formulations are prepared in a known manner, by mixing the active compounds with customary additives such as, for example, customary extenders and also solvents or diluents, colorants, wetting agents, dispersants, emulsifiers, antifoams, preservatives, secondary thickeners, adhesives, gibberellins and also water.

Colorants which may be present in the seed-dressing formulations which can be used in accordance with the invention are all colorants which are customary for such purposes. In this context, not only pigments, which are sparingly soluble in water, but also dyes, which are soluble in water, may be used. Examples which may be mentioned are the colorants known by the names Rhodamin B, C.I. Pigment Red 112 and C.I. Solvent Red 1.

Suitable wetting agents which may be present in the seed-dressing formulations which can be used in accordance with the invention are all substances which promote wetting and which are conventionally used for the formulation of agrochemical active compounds. Preference is given to using alkylnaphthalenesulphonates, such as diisopropyl- or diisobutylnaphthalenesulphonates.

Suitable dispersants and/or emulsifiers which may be present in the seed-dressing formulations which can be used in accordance with the invention are all nonionic, anionic and cationic dispersants conventionally used for the formulation of agrochemical active compounds. Preference is given to using nonionic or anionic dispersants or mixtures of nonionic or anionic dispersants. Suitable nonionic dispersants which may be mentioned are, in particular, ethylene oxide/propylene oxide block polymers, alkylphenol polyglycol ethers and tristryrylphenol polyglycol ether, and their phosphated or sulphated derivatives. Suitable anionic dispersants are, in particular, lignosulphonates, polyacrylic acid salts and arylsulphonate/formaldehyde condensates.

Antifoams which may be present in the seed-dressing formulations which can be used in accordance with the invention are all foam-inhibiting substances conventionally used for the formulation of agrochemical active compounds. Silicone antifoams and magnesium stearate can preferably be used.

Preservatives which may be present in the seed-dressing formulations which can be used in accordance with the invention are all substances which can be employed for such purposes in agrochemical compositions. Dichlorophene and benzyl alcohol hemiformal may be mentioned by way of example.

Secondary thickeners which may be present in the seed-dressing formulations which can be used in accordance with the invention are all substances which can be employed for such purposes in agrochemical compositions. Cellulose derivatives, acrylic acid derivatives, xanthan, modified clays and finely divided silica are preferred.

Adhesives which may be present in the seed-dressing formulations which can be used in accordance with the invention are all customary binders which can be employed in seed-dressing products. Polyvinylpyrrolidone, polyvinyl acetate, polyvinyl alcohol and tylose may be mentioned as being preferred.

Gibberellins which can be present in the seed-dressing formulations which can be used in accordance with the invention are preferably the gibberellins A1, A3 (=gibberellic acid), A4 and A7; gibberellic acid is especially preferably used. The gibberellins are known (cf. R. Wegler "Chemie der Pflanzenschutz- and Schädlingsbekämpfungsmittel" [Chemistry of crop protection agents and pesticides], vol. 2, Springer Verlag, 1970, p. 401-412).

The seed-dressing formulations which can be used in accordance with the invention can be employed for the treatment of a wide range of seed, including the seed of transgenic plants, either directly or after previously having been diluted with water. In this context, additional synergistic effects may also occur in cooperation with the substances formed by expression.

All mixers which can conventionally be employed for the seed-dressing operation are suitable for treating seed with the seed-dressing formulations which can be used in accordance with the invention or with the preparations prepared therefrom by addition of water. Specifically, a procedure is followed during the seed-dressing operation in which the seed is placed into a mixer, the specific desired amount of seed-dressing formulations, either as such or after previously having been diluted with water, is added, and everything is mixed until the formulation is distributed uniformly on the seed. If appropriate, this is followed by a drying process.

The active compounds or compositions according to the invention have a potent microbicidal activity and can be employed for controlling undesirable microorganisms, such as fungi and bacteria, in crop protection and in the protection of materials.

Fungicides can be employed in crop protection for controlling Plasmodiophoromycetes, Oomycetes, Chytridiomycetes, Zygomycetes, Ascomycetes, Basidiomycetes and Deuteromycetes.

Bactericides can be employed in crop protection for controlling Pseudomonadaceae, Rhizobiaceae, Enterobacteriaceae, Corynebacteriaceae and Streptomycetaceae.

The fungicidal compositions according to the invention can be used for the curative or protective control of phytopathogenic fungi. Accordingly, the invention also relates to curative and protective methods for controlling phytopathogenic fungi using the active compounds or compositions according to the invention, which are applied to the seed, the plant or plant parts, the fruit or the soil in which the plants grow.

The compositions according to the invention for controlling phytopathogenic fungi in crop protection comprise an effective, but non-phytotoxic amount of the active compounds according to the invention. "Effective, but non-phytotoxic amount" means an amount of the composition according to the invention which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on a plurality of factors, for example on the fungus to be controlled, the plant, the climatic conditions and the ingredients of the compositions according to the invention.

The fact that the active compounds are well tolerated by plants at the concentrations required for controlling plant diseases permits the treatment of above-ground parts of plants, of propagation stock and seeds, and of the soil.

All plants and plant parts can be treated in accordance with the invention. By plants are understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant varieties which can or cannot be protected by varietal property rights. Plant parts are to be understood as meaning all parts and organs of plants above and below the ground, such as shoot, leaf, flower and root, examples which may be mentioned being leaves, needles, stalks, stems, flowers, fruit bodies, fruits, seeds, roots, tubers and rhizomes. Parts of plants also include harvested plants and vegetative and generative propagation material, for example seedlings, tubers, rhizomes, cuttings and seeds.

The active compounds according to the invention are suitable for the protection of plants and plant organs, for increasing the harvest yields, for improving the quality of the harvested crop, while being well tolerated by plants, having favourable toxicity to warm-blooded species and being environmentally friendly. They may be preferably employed as crop protection agents. They are active against normally sensitive and resistant species and also against all or some stages of development.

The following plants may be mentioned as plants which can be treated according to the invention: cotton, flax, grapevine, fruit, vegetables, such as *Rosaceae* sp. (for example pome fruits such as apples and pears, but also stone fruits such as apricots, cherries, almonds and peaches, and soft fruits such as strawberries), *Ribesioidae* sp., *Juglandaceae* sp., *Betulaceae* sp., *Anacardiaceae* sp., *Fagaceae* sp., *Moraceae* sp., *Oleaceae* sp., *Actimidaceae* sp., *Lauraceae* sp., *Musaceae* sp. (for example banana plants and banana plantations), *Rubiaceae* sp. (for example coffee), *Theaceae* sp., *Sterculiceae* sp., *Rutaceae* sp. (for example lemons, oranges and grapefruit); *Solanaceae* sp. (for example tomatoes), *Liliaceae* sp., *Asteraceae* sp. (for example lettuce), *Umbelliferae* sp., *Cruciferae* sp., *Chenopodiaceae* sp., *Cucurbitaceae* sp. (for example cucumber), *Alliaceae* sp. (for example leeks, onions), *Papilionaceae* sp. (for example peas); major crop plants such as *Gramineae* sp. (for example maize, turf, cereals such as wheat, rye, rice, barley, oats, millet and triticale), *Asteraceae* sp. (for example sunflower), *Brassicaceae* sp. (for example white cabbage, red cabbage, broccoli, cauliflower, Brussels sprouts, pak Choi, kohlrabi, small radishes, and also oilseed rape, mustard, horseradish and cress), *Fabacae* sp. (for example beans, peanuts), *Papilionaceae* sp. (for example soya beans), *Solanaceae* sp. (for example potatoes), *Chenopodiaceae* sp. (for example sugar beet, fodder beet, Swiss chard, beetroot); useful plants and ornamental plants in gardens and forests; and in each case genetically modified types of these plants.

As already mentioned above, it is possible to treat all plants and their parts according to the invention. In a preferred embodiment, wild plant species and plant cultivars, or those obtained by conventional biological breeding methods, such as crossing or protoplast fusion, and also parts thereof, are treated.

In a further preferred embodiment, transgenic plants and plant cultivars obtained by genetic engineering, if appropriate in combination with conventional methods (Genetically Modified Organisms), and parts thereof are treated. The term "parts" or "parts of plants" or "plant parts" has been explained above. Particularly preferably, plants of the plant cultivars which are in each case commercially available or in use are treated according to the invention. Plant cultivars are to be understood as meaning plants having new properties ("traits") and which have been obtained by conventional breeding, by mutagenesis or by recombinant DNA techniques. They can be cultivars, varieties, bio- or genotypes.

The method of treatment according to the invention can be used in the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which are present in the plant (using for example antisense technology, cosuppression technology or RNAi technology [RNA interference]). A heterologous gene that is located in the genome is also called a transgene. A transgene that is defined by its particular location in the plant genome is called a transformation or transgenic event.

Depending on the plant species or plant varieties, their location and growth conditions (soils, climate, vegetation period, diet), the treatment according to the invention may also result in superadditive ("synergistic") effects. Possible are thus, for example, the following effects which exceed the effects which were actually to be expected: reduced application rates and/or a widening of the activity spectrum and/or an increase in the activity of the active compounds and compositions which can be used according to the invention, better plant growth, increased tolerance to high or low temperatures, increased tolerance to drought or to water or soil salt content, increased flowering performance, easier harvesting, accelerated maturation, higher harvest yields, bigger fruits, larger plant height, greener leaf colour, earlier flowering, higher quality and/or a higher nutritional value of the harvested products, higher sugar concentration within the fruits, better storage stability and/or processability of the harvested products.

At certain application rates, the active compounds according to the invention may also have a strengthening effect on plants. Accordingly, they are suitable for mobilizing the defence system of the plant against attack by unwanted phytopathogenic fungi and/or microorganisms and/or viruses. This may, if appropriate, be one of the reasons for the enhanced activity of the combinations according to the invention, for example against fungi. Plant-strengthening (resistance-inducing) substances are to be understood as meaning, in the present context, also those substances or combinations of substances which are capable of stimulating the defence system of plants in such a way that, when subsequently inoculated with unwanted phytopathogenic fungi, the treated plants display a substantial degree of resistance to these unwanted phytopathogenic fungi. Thus, the substances according to the invention can be employed for protecting plants against attack by the abovementioned pathogens within a certain period of time after the treatment. The period within which protection is brought about generally extends from 1 to 10 days, preferably 1 to 7 days, after the treatment of the plants with the active compounds.

Plants and plant varieties which are preferably treated according to the invention include all plants which have genetic material which imparts particularly advantageous, useful traits to these plants (whether obtained by breeding and/or biotechnological means).

Plants and plant varieties which are also preferably treated according to the invention are resistant against one or more biotic stress factors, i.e. said plants have a better defence against animal and microbial pests, such as against nematodes, insects, mites, phytopathogenic fungi, bacteria, viruses and/or viroids.

Plants and plant varieties which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant varieties which may also be treated according to the invention are those plants characterized by enhanced yield characteristics. Enhanced yield in said plants can be the result of, for example, improved plant physiology, growth and development, such as water use efficiency, water retention efficiency, improved nitrogen use, enhanced carbon assimilation, improved photosynthesis, increased germination efficiency and accelerated maturation. Yield can furthermore be affected by improved plant architecture (under stress and non-stress conditions), including early flowering, flowering control for hybrid seed production, seedling vigour, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid effect, which results in generally higher yield, vigour, health and resistance towards biotic and abiotic stress factors. Such plants are typically made by crossing an inbred male-sterile parent line (the female parent) with another inbred male-fertile parent line (the male parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically useful to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility. Genetic determinants for male sterility may be located in the cytoplasm. Examples of cytoplasmic male sterility (CMS) were for instance described for *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as a barnase is selectively expressed in the tapetum cells in the stamens. Fertility can then be restored by expression in the tapetum cells of a ribonuclease inhibitor such as barstar.

Plants or plant varieties (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium*, the CP4 gene of the bacterium *Agrobacterium* sp., the genes encoding a petunia EPSPS, a tomato EPSPS, or an *Eleusine* EPSPS. It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyltransferase enzyme. Glyphosate-tolerant plants can also be obtained by selecting plants containing naturally occurring mutations of the abovementioned genes.

Other herbicide-resistant plants are for example plants which have been made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species for example). Plants expressing an exogenous phosphinothricin acetyltransferase have been described.

Further herbicide-tolerant plants are also plants that have been made tolerant to the herbicides inhibiting the enzyme hydroxyphenylpyruvatedioxygenase (HPPD). Hydroxyphenylpyruvatedioxygenases are enzymes that catalyse the reaction in which para-hydroxyphenylpyruvate (HPP) is transformed into homogentisate. Plants tolerant to HPPD inhibitors can be transformed with a gene encoding a naturally occurring resistant HPPD enzyme, or a gene encoding a mutated HPPD enzyme. Tolerance to HPPD inhibitors can also be obtained by transforming plants with genes encoding certain enzymes enabling the formation of homogentisate despite the inhibition of the native HPPD enzyme by the HPPD inhibitor. Tolerance of plants to HPPD inhibitors can also be improved by transforming plants with a gene encoding an enzyme prephenate dehydrogenase in addition to a gene encoding an HPPD-tolerant enzyme.

Further herbicide-resistant plants are plants that have been made tolerant to acetolactate synthase (ALS) inhibitors. Known ALS inhibitors include, for example, sulphonylurea, imidazolinone, triazolopyrimidines, pyrimidinyl oxy(thio) benzoates, and/or sulphonylaminocarbonyltriazolinone herbicides. Different mutations in the ALS enzyme (also known as acetohydroxy acid synthase, AHAS) are known to confer tolerance to different herbicides and groups of herbicides. The production of sulphonylurea-tolerant plants and imidazolinone-tolerant plants has been described in the international publication WO 1996/033270. Further sulphonylurea- and imidazolinone-tolerant plants have also been described, for example in WO 2007/024782.

Other plants tolerant to imidazolinone and/or sulphonylurea can be obtained by induced mutagenesis, by selection in cell cultures in the presence of the herbicide or by mutation breeding.

Plants or plant varieties (obtained by plant biotechnology methods such as genetic engineering) which may also be treated according to the invention are insect-resistant transgenic plants, i.e. plants made resistant to attack by certain target insects. Such plants can be obtained by genetic transformation, or by selection of plants containing a mutation imparting such insect resistance.

In the present context, the term "insect-resistant transgenic plant" includes any plant containing at least one transgene comprising a coding sequence encoding:
1) an insecticidal crystal protein from *Bacillus thuringiensis* or an insecticidal portion thereof, such as the insecticidal crystal proteins listed online at: http://www.lifesci.sussex-.ac.uk/Home/Neil_Crickmore/Bt/, or insecticidal portions thereof, for example proteins of the Cry protein classes Cry1Ab, Cry1Ac, Cry1F, Cry2Ab, Cry3Ae or Cry3Bb or insecticidal portions thereof; or
2) a crystal protein from *Bacillus thuringiensis* or a portion thereof which is insecticidal in the presence of a second other crystal protein from *Bacillus thuringiensis* or a portion thereof, such as the binary toxin made up of the Cy34 and Cy35 crystal proteins; or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by maize event MON98034 (WO 2007/027777); or
4) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation, such as the Cry3Bb1 protein in maize events MON863 or MON88017, or the Cry3A protein in maize event MIR 604;
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/Home/Neil_Crickmore/Bt/vip.html, e.g. proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins;
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of points 1) to 3) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102.

Of course, insect-resistant transgenic plants, as used herein, also include any plant comprising a combination of genes encoding the proteins of any one of the above classes 1 to 8. In one embodiment, an insect-resistant plant contains more than one transgene encoding a protein of any one of the above classes 1 to 8, to expand the range of target insect species affected or to delay insect resistance development to the plants, by using different proteins insecticidal to the same target insect species but having a different mode of action, such as binding to different receptor binding sites in the insect.

Plants or plant varieties (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:
a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant varieties (obtained by plant biotechnology methods such as genetic engineering) which may also be treated according to the invention show altered quantity, quality and/or storage stability of the harvested product and/or altered properties of specific ingredients of the harvested product such as, for example:
1) Transgenic plants which synthesize a modified starch which is altered with respect to its chemophysical traits, in particular the amylose content or the amylose/amylopectin ratio, the degree of branching, the average chain length, the distribution of the side chains, the viscosity behaviour, the gel resistance, the grain size and/or grain morphology of the starch in comparison to the synthesized starch in wild-type plant cells or plants, such that this modified starch is better suited for certain applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4- glucans, plants which produce alpha-1,6-branched alpha-1,4-glucans, and plants producing alternan.

3) Transgenic plants which produce hyaluronan.

Plants or plant varieties (obtained by plant biotechnology methods such as genetic engineering) which may also be treated according to the invention are plants, such as cotton plants, with altered fibre characteristics. Such plants can be obtained by genetic transformation, or by selection of plants containing a mutation imparting such altered fibre characteristics and include:

a) plants, such as cotton plants, which contain an altered form of cellulose synthase genes;
b) plants, such as cotton plants, which contain an altered form of rsw2 or rsw3 homologous nucleic acids;
c) plants, such as cotton plants, with an increased expression of sucrose phosphate synthase;
d) plants, such as cotton plants, with an increased expression of sucrose synthase;
e) plants, such as cotton plants, wherein the timing of the plasmodesmatal gating at the basis of the fibre cell is altered, for example through downregulation of fiber-selective β-1,3-glucanase;
f) plants, such as cotton plants, which have fibres with altered reactivity, for example through the expression of the N-acetylglucosaminetransferase gene including nodC and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;
b) plants, such as oilseed rape plants, which produce oil having a low linolenic acid content;
c) plants, such as oilseed rape plants, which produce oil having a low level of saturated fatty acids.

Particularly useful transgenic plants which may be treated according to the invention are plants which comprise one or more genes which encode one or more toxins and are the transgenic plants available under the following trade names: YIELD GARD® (for example maize, cotton, soya beans), KnockOut® (for example maize), BiteGard® (for example maize), BT-Xtra® (for example maize), StarLink® (for example maize), Bollgard® (cotton), Nucotn® (cotton), Nucotn 33B® (cotton), NatureGard® (for example maize), Protecta® and NewLeaf® (potato). Examples of herbicide-tolerant plants which may be mentioned are maize varieties, cotton varieties and soya bean varieties which are available under the following trade names: Roundup Ready® (tolerance to glyphosate, for example maize, cotton, soya beans), Liberty Link® (tolerance to phosphinothricin, for example oilseed rape), IMI® (tolerance to imidazolinone) and SCS® (tolerance to sulphonylurea, for example maize). Herbicide-resistant plants (plants bred in a conventional manner for herbicide tolerance) which may be mentioned include the varieties sold under the name Clearfield® (for example maize). Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://www.agbios.com/dbase.php).

Moreover, in the protection of materials, the active compounds or compositions according to the invention can be employed for protecting industrial materials against attack and destruction by unwanted microorganisms, such as, for example, fungi and insects.

Furthermore, the compounds according to the invention can be used alone or in combinations with other active compounds as antifouling compositions.

Industrial materials in the present context are understood as meaning non-living materials which have been prepared for use in industry. For example, industrial materials which are intended to be protected by active compounds according to the invention from microbial change or destruction can be adhesives, sizes, paper, wallpaper, and board, textiles, carpets, leather, wood, paints and plastic articles, cooling lubricants and other materials which can be infected with, or destroyed by, microorganisms. Parts of production plants and buildings, for example cooling-water circuits, cooling and heating systems and ventilation and air-conditioning units, which may be impaired by the proliferation of microorganisms may also be mentioned within the scope of the materials to be protected. Industrial materials which may be mentioned within the scope of the present invention are preferably adhesives, sizes, paper and board, leather, wood, paints, cooling lubricants and heat-transfer liquids, particularly preferably wood. The active compounds or compositions according to the invention may prevent disadvantageous effects, such as rotting, decay, discoloration, decoloration or formation of mould. Moreover, the compounds according to the invention can be employed for protecting objects which come into contact with saltwater or brackish water, in particular hulls, screens, nets, buildings, moorings and signalling systems, against fouling.

The method according to the invention for controlling unwanted fungi can also be employed for protecting storage goods. Here, storage goods are to be understood as meaning natural substances of vegetable or animal origin or processed products thereof of natural origin, for which long-term protection is desired. Storage goods of vegetable origin, such as, for example, plants or plant parts, such as stems, leaves, tubers, seeds, fruits, grains, can be protected freshly harvested or after processing by (pre)drying, moistening, comminuting, grinding, pressing or roasting. Storage goods also include timber, both unprocessed, such as construction timber, electricity poles and barriers, or in the form of finished products, such as furniture. Storage goods of animal origin are, for example, hides, leather, furs and hairs. The active compounds according to the invention may prevent disadvantageous effects, such as rotting, decay, discoloration, decoloration or formation of mould.

Some pathogens of fungal diseases which can be treated according to the invention may be mentioned by way of example, but not by way of limitation:

diseases caused by powdery mildew pathogens, such as, for example, *Blumeria* species, such as, for example, *Blumeria graminis*; *Podosphaera* species, such as, for example, *Podosphaera leucotricha*; *Sphaerotheca* species, such as, for example, *Sphaerotheca fuliginea*; *Uncinula* species, such as, for example, *Uncinula necator*;

diseases caused by rust disease pathogens, such as, for example, *Gymnosporangium* species, such as, for example, *Gymnosporangium sabinae*; *Hemileia* species, such as, for example, *Hemileia vastatrix*; *Phakopsora* species, such as, for example, *Phakopsora pachyrhizi* and *Phakopsora meibomiae*; *Puccinia* species, such as, for example, *Puccinia recondita* or *Puccinia triticina*; *Uromyces* species, such as, for example, *Uromyces appendiculatus*;

diseases caused by pathogens from the group of the Oomycetes, such as, for example, *Bremia* species, such as, for example, *Bremia lactucae; Peronospora* species, such as, for example, *Peronospora pisi* or *P. brassicae; Phytophthora* species, such as, for example, *Phytophthora infestans; Plasmopara* species, such as, for example, *Plasmopara viticola; Pseudoperonospora* species, such as, for example, *Pseudoperonospora humuli* or *Pseudoperonospora cubensis; Pythium* species, such as, for example, *Pythium ultimum;* leaf blotch diseases and leaf wilt diseases caused, for example, by *Alternaria* species, such as, for example, *Alternaria solani; Cercospora* species, such as, for example, *Cercospora beticola; Cladiosporium* species, such as, for example, *Cladiosporium cucumerinum; Cochliobolus* species, such as, for example, *Cochliobolus sativus (conidia* form: *Drechslera,* syn: *Helminthosporium); Colletotrichum* species, such as, for example, *Colletotrichum lindemuthanium; Cycloconium* species, such as, for example, *Cycloconium oleaginum; Diaporthe* species, such as, for example, *Diaporthe citri; Elsinoe* species, such as, for example, *Elsinoe fawcettii; Gloeosporium* species, such as, for example, *Gloeosporium laeticolor; Glomerella* species, such as, for example, *Glomerella cingulata; Guignardia* species, such as, for example, *Guignardia bidwelli; Leptosphaeria* species, such as, for example, *Leptosphaeria maculans; Magnaporthe* species, such as, for example, *Magnaporthe grisea; Microdochium* species, such as, for example, *Microdochium nivale; Mycosphaerella* species, such as, for example, *Mycosphaerella graminicola* and *M. fijiensis; Phaeosphaeria* species, such as, for example, *Phaeosphaeria nodorum; Pyrenophora* species, such as, for example, *Pyrenophora teres; Ramularia* species, such as, for example, *Ramularia collo-cygni; Rhynchosporium* species, such as, for example, *Rhynchosporium secalis; Septoria* species, such as, for example, *Septoria apii; Typhula* species, such as, for example, *Typhula incarnata; Venturia* species, such as, for example, *Venturia inaequalis;* root and stem diseases caused, for example, by *Corticium* species, such as, for example, *Corticium graminearum; Fusarium* species, such as, for example, *Fusarium oxysporum; Gaeumannomyces* species, such as, for example, *Gaeumannomyces graminis; Rhizoctonia* species, such as, for example *Rhizoctonia solani; Tapesia* species, such as, for example, *Tapesia acuformis; Thielaviopsis* species, such as, for example, *Thielaviopsis basicola;* ear and panicle diseases (including corn cobs) caused, for example, by *Alternaria* species, such as, for example, *Alternaria* spp.; *Aspergillus* species, such as, for example, *Aspergillus flavus; Cladosporium* species, such as, for example, *Cladosporium cladosporioides; Claviceps* species, such as, for example, *Claviceps purpurea; Fusarium* species, such as, for example, *Fusarium culmorum; Gibberella* species, such as, for example, *Gibberella zeae; Monographella* species, such as, for example, *Monographella nivalis; Septoria* species, such as, for example, *Septoria nodorum;* diseases caused by smut fungi, such as, for example, *Sphacelotheca* species, such as, for example, *Sphacelotheca reiliana; Tilletia* species, such as, for example, *Tilletia caries, T. controversa; Urocystis* species, such as, for example, *Urocystis occulta; Ustilago* species, such as, for example, *Ustilago nuda, U. nuda tritici;* fruit rot caused, for example, by *Aspergillus* species, such as, for example, *Aspergillus flavus; Botrytis* species, such as, for example, *Botrytis cinerea; Penicillium* species, such as, for example, *Penicillium expansum* and *P. purpurogenum; Sclerotinia* species, such as, for example, *Sclerotinia sclerotiorum;*

*Verticilium* species, such as, for example, *Verticilium alboatrum;* seed- and soil-borne rot and wilt diseases, and also diseases of seedlings, caused, for example, by *Fusarium* species, such as, for example, *Fusarium culmorum; Phytophthora* species, such as, for example, *Phytophthora cactorum; Pythium* species, such as, for example, *Pythium ultimum; Rhizoctonia* species, such as, for example, *Rhizoctonia solani; Sclerotium* species, such as, for example, *Sclerotium rolfsii;* cancerous diseases, galls and witches' broom caused, for example, by *Nectria* species, such as, for example, *Nectria galligena;* wilt diseases caused, for example, by *Monilinia* species, such as, for example, *Monilinia laxa;* deformations of leaves, flowers and fruits caused, for example, by *Taphrina* species, such as, for example, *Taphrina deformans;* degenerative diseases of woody plants caused, for example, by *Esca* species, such as, for example, *Phaeomoniella chlamydospora* and *Phaeoacremonium aleophilum* and *Fomitiporia mediterranea;* diseases of flowers and seeds caused, for example, by *Botrytis* species, such as, for example, *Botrytis cinerea;* diseases of plant tubers caused, for example, by *Rhizoctonia* species, such as, for example, *Rhizoctonia solani; Helminthosporium* species, such as, for example, *Helminthosporium solani;* diseases caused by bacterial pathogens, such as, for example, *Xanthomonas* species, such as, for example, *Xanthomonas campestris* pv. *oryzae; Pseudomonas* species, such as, for example, *Pseudomonas syringae* pv. *lachrymans; Erwinia* species, such as, for example, *Erwinia amylovora.*

Preference is given to controlling the following diseases of soya beans:

Fungal diseases on leaves, stems, pods and seeds caused, for example, by alternaria leaf spot (*Alternaria* spec. *atrans tenuissima*), anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Microorganisms capable of degrading or changing the industrial materials which may be mentioned are, for example, bacteria, fungi, yeasts, algae and slime organisms. The active compounds according to the invention preferably act against fungi, in particular molds, wood-discoloring and wood-destroying fungi (Basidiomycetes), and against slime organisms and algae. Microorganisms of the following genera may be mentioned as examples: *Alternaria*, such as *Alternaria tenuis; Aspergillus*, such as *Aspergillus niger; Chaetomium*, such as *Chaetomium globosum; Coniophora*, such as *Coniophora puetana; Lentinus*, such as *Lentinus tigrinus; Penicillium*, such as *Penicillium glaucum; Polyporus*, such as *Polyporus versicolor; Aureobasidium*, such as *Aureobasidium pullulans; Sclerophoma*, such as *Sclerophoma pityophila; Trichoderma*, such as *Trichoderma viride; Escherichia*, such as *Escherichia coli; Pseudomonas*, such as *Pseudomonas aeruginosa; Staphylococcus*, such as *Staphylococcus aureus*.

In addition, the active compounds according to the invention also have very good antimycotic activity. They have a very broad antimycotic activity spectrum, in particular against dermatophytes and yeasts, moulds and diphasic fungi, (for example against *Candida* species, such as *Candida albicans, Candida glabrata*), and *Epidermophyton floccosum, Aspergillus* species, such as *Aspergillus niger* and *Aspergillus fumigatus, Trichophyton* species, such as *Trichophyton mentagrophytes, Microsporon* species such as *Microsporon canis* and *audouinii*. The list of these fungi by no means limits the mycotic spectrum covered, but is only for illustration.

Accordingly, the active compounds according to the invention can be used both in medical and in non-medical applications.

When using the active compounds according to the invention as fungicides, the application rates can be varied within a relatively wide range, depending on the kind of application. The application rate of the active compounds according to the invention is when treating plant parts, for example leaves: from 0.1 to 10 000 g/ha, preferably from 10 to 1000 g/ha, particularly preferably from 50 to 300 g/ha (when the application is carried out by watering or dripping, it is even possible to reduce the application rate, especially when inert substrates such as rock wool or perlite are used);

when treating seed: from 2 to 200 g per 100 kg of seed, preferably from 3 to 150 g per 100 kg of seed, particularly preferably from 2.5 to 25 g per 100 kg of seed, very particularly preferably from 2.5 to 12.5 g per 100 kg of seed;

when treating the soil: from 0.1 to 10 000 g/ha, preferably from 1 to 5000 g/ha.

These application rates are mentioned only by way of example and are not limiting in the sense of the invention.

The active compounds or compositions according to the invention can thus be employed for protecting plants for a certain period of time after treatment against attack by the pathogens mentioned. The period for which protection is provided extends generally for 1 to 28 days, preferably for 1 to 14 days, particularly preferably for 1 to 10 days, very particularly preferably for 1 to 7 days after the treatment of the plants with the active compounds, or for up to 200 days after a seed treatment.

In addition, by the treatment according to the invention it is possible to reduce the mycotoxin content in the harvested material and the foodstuffs and feedstuffs prepared therefrom. Particular, but not exclusive, mention may be made here of the following mycotoxins: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaproliferin, fusarenol, ochratoxins, patulin, ergot alkaloids and aflatoxins produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

The active compounds according to the invention, in combination with good plant tolerance and favourable toxicity to warm-blooded animals and being tolerated well by the environment, are suitable for protecting plants and plant organs, for increasing the harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They may be preferably employed as crop protection agents. They are active against normally sensitive and resistant species and also against all or some stages of development. The abovementioned pests include:

From the order of the Anoplura (Phthiraptera), for example, *Damalinia* spp., *Haematopinus* spp., *Linognathus* spp., *Pediculus* spp., *Trichodectes* spp.

From the class of the Arachnida, for example, *Acarus siro, Aceria sheldoni, Aculops* spp., *Aculus* spp., *Amblyomma* spp., *Argas* spp., *Boophilus* spp., *Brevipalpus* spp., *Bryobia praetiosa, Chorioptes* spp., *Dermanyssus gallinae, Eotetranychus* spp., *Epitrimerus pyri, Eutetranychus* spp., *Eriophyes* spp., *Hemitarsonemus* spp., *Hyalomma* spp., *Ixodes* spp., *Latrodectus mactans, Metatetranychus* spp., *Oligonychus* spp., *Ornithodoros* spp., *Panonychus* spp., *Phyllocoptruta oleivora, Polyphagotarsonemus latus, Psoroptes* spp., *Rhipicephalus* spp., *Rhizoglyphus* spp., *Sarcoptes* spp., *Scorpio maurus, Stenotarsonemus* spp., *Tarsonemus* spp., *Tetranychus* spp., *Vasates lycopersici*.

From the class of the Bivalva, for example, *Dreissena* spp.

From the order of the Chilopoda, for example, *Geophilus* spp., *Scutigera* spp.

From the order of the Coleoptera, for example, *Acanthoscelides obtectus, Adoretus* spp., *Agelastica alni, Agriotes* spp., *Amphimallon solstitialis, Anobium punctatum, Anoplophora* spp., *Anthonomus* spp., *Anthrenus* spp., *Apogonia* spp., *Atomaria* spp., *Attagenus* spp., *Bruchidius obtectus, Bruchus* spp., *Ceuthorhynchus* spp., *Cleonus mendicus, Conoderus* spp., *Cosmopolites* spp., *Costelytra zealandica, Curculio* spp., *Cryptorhynchus lapathi, Dermestes* spp., *Diabrotica* spp., *Epilachna* spp., *Faustinus cubae, Gibbium psylloides, Heteronychus arator, Hylamorpha elegans, Hylotrupes bajulus, Hypera postica, Hypothenemus* spp., *Lachnostema consanguinea, Leptinotarsa decemlineata, Lissorhoptrus oryzophilus, Lixus* spp., *Lyctus* spp., *Meligethes aeneus, Melolontha melolontha, Migdolus* spp., *Monochamus* spp., *Naupactus xanthographus, Niptus hololeucus, Oryctes rhinoceros, Oryzaephilus surinamensis, Otiorrhynchus sulcatus, Oxycetonia jucunda, Phaedon cochleariae, Phyllophaga* spp., *Popillia japonica, Premnotrypes* spp., *Psylliodes chrysocephala, Ptinus* spp., *Rhizobius ventralis, Rhizopertha dominica, Sitophilus* spp., *Sphenophorus* spp., *Stemechus* spp., *Symphyletes* spp., *Tenebrio molitor, Tribolium* spp., *Trogoderma* spp., *Tychius* spp., *Xylotrechus* spp., *Zabrus* spp.

From the order of the Collembola, for example, *Onychiurus armatus*.

From the order of the Dermaptera, for example, *Forficula auricularia*.

From the order of the Diplopoda, for example, *Blaniulus guttulatus*.

From the order of the Diptera, for example, *Aedes* spp., *Anopheles* spp., *Bibio hortulanus*, *Calliphora erythrocephala*, *Ceratitis capitata*, *Chrysomyia* spp., *Cochliomyia* spp., *Cordylobia anthropophaga*, *Culex* spp., *Cuterebra* spp., *Dacus oleae*, *Dermatobia hominis*, *Drosophila* spp., *Fannia* spp., *Gastrophilus* spp., *Hylemyia* spp., *Hyppobosca* spp., *Hypoderma* spp., *Liriomyza* spp. *Lucilia* spp., *Musca* spp., *Nezara* spp., *Oestrus* spp., *Oscinella frit*, *Pegomyia hyoscyami*, *Phorbia* spp., *Stomoxys* spp., *Tabanus* spp., *Tannia* spp., *Tipula paludosa*, *Wohlfahrtia* spp.

From the class of the Gastropoda, for example, *Arion* spp., *Biomphalaria* spp., *Bulinus* spp., *Deroceras* spp., *Galba* spp., *Lymnaea* spp., *Oncomelania* spp., *Succinea* spp.

From the class of the helminths, for example, *Ancylostoma duodenale*, *Ancylostoma ceylanicum*, *Acylostoma braziliensis*, *Ancylostoma* spp., *Ascaris lubricoides*, *Ascaris* spp., *Brugia malayi*, *Brugia timori*, *Bunostomum* spp., *Chabertia* spp., *Clonorchis* spp., *Cooperia* spp., *Dicrocoelium* spp, *Dictyocaulus filaria*, *Diphyllobothrium latum*, *Dracunculus medinensis*, *Echinococcus granulosus*, *Echinococcus multilocularis*, *Enterobius vermicularis*, *Faciola* spp., *Haemonchus* spp., *Heterakis* spp., *Hymenolepis nana*, *Hyostrongulus* spp., *Loa Loa*, *Nematodirus* spp., *Oesophagostomum* spp., *Opisthorchis* spp., *Onchocerca volvulus*, *Ostertagia* spp., *Paragonimus* spp., *Schistosomen* spp., *Strongyloides fuelleborni*, *Strongyloides stercoralis*, *Stronyloides* spp., *Taenia saginata*, *Taenia solium*, *Trichinella spiralis*, *Trichinella nativa*, *Trichinella britovi*, *Trichinella nelsoni*, *Trichinella pseudopsiralis*, *Trichostrongulus* spp., *Trichuris trichuria*, *Wuchereria bancrofti*.

It is furthermore possible to control Protozoa, such as Eimeria.

From the order of the Heteroptera, for example, *Anasa tristis*, *Antestiopsis* spp., *Blissus* spp., *Calocoris* spp., *Campylomma livida*, *Cavelerius* spp., *Cimex* spp., *Creontiades dilutus*, *Dasynus piperis*, *Dichelops furcatus*, *Diconocoris hewetti*, *Dysdercus* spp., *Euschistus* spp., *Eurygaster* spp., *Heliopeltis* spp., *Horcias nobilellus*, *Leptocorisa* spp., *Leptoglossus phyllopus*, *Lygus* spp., *Macropes excavatus*, *Miridae*, *Nezara* spp., *Oebalus* spp., *Pentomidae*, *Piesma quadrata*, *Piezodorus* spp., *Psallus seriatus*, *Pseudacysta persea*, *Rhodnius* spp., *Sahlbergella singularis*, *Scotinophora* spp., *Stephanitis nashi*, *Tibraca* spp., *Triatoma* spp.

From the order of the Homoptera, for example, *Acyrthosipon* spp., *Aeneolamia* spp., *Agonoscena* spp., *Aleurodes* spp., *Aleurolobus barodensis*, *Aleurothrixus* spp., *Amrasca* spp., *Anuraphis cardui*, *Aonidiella* spp., *Aphanostigma piri*, *Aphis* spp., *Arboridia apicalis*, *Aspidiella* spp., *Aspidiotus* spp., *Atanus* spp., *Aulacorthum solani*, *Bemisia* spp., *Brachycaudus helichrysii*, *Brachycolus* spp., *Brevicoryne brassicae*, *Calligypona marginata*, *Cameocephala fulgida*, *Ceratovacuna lanigera*, *Cercopidae*, *Ceroplastes* spp., *Chaetosiphon fragaefolii*, *Chionaspis tegalensis*, *Chlorita onukii*, *Chromaphis juglandicola*, *Chrysomphalus ficus*, *Cicadulina mbila*, *Coccomytilus halli*, *Coccus* spp., *Cryptomyzus ribis*, *Dalbulus* spp., *Dialeurodes* spp., *Diaphorina* spp., *Diaspis* spp., *Doralis* spp., *Drosicha* spp., *Dysaphis* spp., *Dysmicoccus* spp., *Empoasca* spp., *Eriosoma* spp., *Erythroneura* spp., *Euscelis bilobatus*, *Geococcus coffeae*, *Homalodisca coagulata*, *Hyalopterus arundinis*, *Icerya* spp., *Idiocerus* spp., *Idioscopus* spp., *Laodelphax striatellus*, *Lecanium* spp., *Lepidosaphes* spp., *Lipaphis erysimi*, *Macrosiphum* spp., *Mahanarva fimbriolata*, *Melanaphis sacchari*, *Metcalfiella* spp., *Metopolophium dirhodum*, *Monellia costalis*, *Monelliopsis pecanis*, *Myzus* spp., *Nasonovia ribisnigri*, *Nephotettix* spp., *Nilaparvata lugens*, *Oncometopia* spp., *Orthezia praelonga*, *Parabemisia myricae*, *Paratrioza* spp., *Parlatoria* spp., *Pemphigus* spp., *Peregrinus maidis*, *Phenacoccus* spp., *Phloeomyzus passerinii*, *Phorodon humuli*, *Phylloxera* spp., *Pinnaspis aspidistrae*, *Planococcus* spp., *Protopulvinaria pyriformis*, *Pseudaulacaspis pentagona*, *Pseudococcus* spp., *Psylla* spp., *Pteromalus* spp., *Pyrilla* spp., *Quadraspidiotus* spp., *Quesada gigas*, *Rastrococcus* spp., *Rhopalosiphum* spp., *Saissetia* spp., *Scaphoides titanus*, *Schizaphis graminum*, *Selenaspidus articulatus*, *Sogata* spp., *Sogatella furcifera*, *Sogatodes* spp., *Stictocephala festina*, *Tenalaphara malayensis*, *Tinocallis caryaefoliae*, *Tomaspis* spp., *Toxoptera* spp., *Trialeurodes vaporariorum*, *Trioza* spp., *Typhlocyba* spp., *Unaspis* spp., *Viteus vitifolii*.

From the order of the Hymenoptera, for example, *Diprion* spp., *Hoplocampa* spp., *Lasius* spp., *Monomorium pharaonis* and *Vespa* spp.

From the order of the Isopoda, for example, *Armadillidium vulgare*, *Oniscus asellus* and *Porcellio scaber*.

From the order of the Isoptera, for example, *Reticulitermes* spp. and *Odontotermes* spp.

From the order of the Lepidoptera, for example, *Acronicta major*, *Aedia leucomelas*, *Agrotis* spp., *Alabama argillacea*, *Anticarsia* spp., *Barathra brassicae*, *Bucculatrix thurberiella*, *Bupalus piniarius*, *Cacoecia podana*, *Capua reticulana*, *Carpocapsa pomonella*, *Chematobia brumata*, *Chilo* spp., *Choristoneura fumiferana*, *Clysia ambiguella*, *Cnaphalocerus* spp., *Earias insulana*, *Ephestia kuehniella*, *Euproctis chrysorrhoea*, *Euxoa* spp., *Feltia* spp., *Galleria mellonella*, *Helicoverpa* spp., *Heliothis* spp., *Hofmannophila pseudospretella*, *Homona magnanima*, *Hyponomeuta padella*, *Laphygma* spp., *Lithocolletis blancardella*, *Lithophane antennata*, *Loxagrotis albicosta*, *Lymantria* spp., *Malacosoma neustria*, *Mamestra brassicae*, *Mocis repanda*, *Mythimna separata*, *Oria* spp., *Oulema oryzae*, *Panolis flammea*, *Pectinophora gossypiella*, *Phyllocnistis citrella*, *Pieris* spp., *Plutella xylostella*, *Prodenia* spp., *Pseudaletia* spp., *Pseudoplusia includens*, *Pyrausta nubilalis*, *Spodoptera* spp., *Thermesia gemmatalis*, *Tinea pellionella*, *Tineola bisselliella*, *Tortrix viridana*, *Trichoplusia* spp.

From the order of the Orthoptera, for example, *Acheta domesticus*, *Blatta orientalis*, *Blattella germanica*, *Gryllotalpa* spp., *Leucophaea maderae*, *Locusta* spp., *Melanoplus* spp., *Periplaneta americana*, *Schistocerca gregaria*.

From the order of the Siphonaptera, for example, *Ceratophyllus* spp. and *Xenopsylla cheopis*.

From the order of the Symphyla, for example, *Scutigerella immaculata*.

From the order of the Thysanoptera, for example, *Baliothrips biformis*, *Enneothrips flavens*, *Frankliniella* spp., *Heliothrips* spp., *Hercinothrips femoralis*, *Kakothrips* spp., *Rhipiphorothrips cruentatus*, *Scirtothrips* spp., *Taeniothrips cardamoni* and *Thrips* spp.

From the order of the Thysanura, for example, *Lepisma saccharina*.

The phytoparasitic nematodes include, for example, *Anguina* spp., *Aphelenchoides* spp., *Belonoaimus* spp., *Bursaphelenchus* spp., *Ditylenchus dipsaci*, *Globodera* spp., *Heliocotylenchus* spp., *Heterodera* spp., *Longidorus* spp., *Meloidogyne* spp., *Pratylenchus* spp., *Radopholus similis*, *Rotylenchus* spp., *Trichodorus* spp., *Tylenchorhynchus* spp., *Tylenchulus* spp., *Tylenchulus semipenetrans* and *Xiphinema* spp.

If appropriate, the compounds according to the invention can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (Mycoplasma-like organisms) and RLO (Rickettsia-like organisms). If appropriate, they can also be used as intermediates or precursors for the synthesis of other active compounds.

When used as insecticides, the active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

When used as insecticides, the active compounds according to the invention can furthermore be present in their commercially available formulations and in the use forms, prepared from these formulations, as a mixture with inhibitors which reduce degradation of the active compound after use in the environment of the plant, on the surface of parts of plants or in plant tissues.

The active compound content of the use forms prepared from the commercially available formulations can vary within wide limits. The active compound concentration of the use forms can be from 0.00000001 to 95% by weight of active compound, preferably between 0.00001 and 1% by weight.

The compounds are employed in a customary manner appropriate for the use forms.

The active compounds according to the invention act not only against plant, hygiene and stored product pests, but also in the veterinary medicine sector against animal parasites (ecto- and endoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Ischnocerina, for example, *Trimenopon* spp., *Menopon* spp., *Trinoton* spp., *Bovicola* spp., *Wemeckiella* spp., *Lepikentron* spp., *Damalina* spp., *Trichodectes* spp. and *Felicola* spp.

From the order of the Diptera and the suborders Nematocerina and Brachycerina, for example, *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattella germanica* and *Supella* spp.

From the subclass of the Acari (Acarina) and the orders of the Meta- and Mesostigmata, for example, *Argas* spp., *Ornithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Sternostoma* spp. and *Varroa* spp.

From the order of the Actinedida (Prostigmata) and Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compounds of the formula (I) according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compounds according to the invention are used in the veterinary sector and in animal husbandry in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants, by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for livestock, poultry, domestic animals and the like, the active compounds of the formula (I) can be used as formulations (for example powders, emulsions, flowables) comprising the active compounds in an amount of from 1 to 80% by weight, either directly or after 100 to 10 000-fold dilution, or they may be used as a chemical bath.

It has furthermore been found that the compounds according to the invention also have a strong insecticidal action against insects which destroy industrial materials.

The following insects may be mentioned as examples and as preferred—but without a limitation:

beetles, such as *Hylotrupes bajulus, Chlorophorus pilosis, Anobium punctatum, Xestobium rufovillosum, Ptilinus pecticomis, Dendrobium pertinex, Emobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus;* dermapterans, such as *Sirex juvencus, Urocerus gigas, Urocerus gigas taignus, Urocerus augur;* termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptoteimes formosanus;* bristletails, such as *Lepisma saccarina.*

The active compounds are also suitable for controlling animal pests in the domestic field, in hygiene and in the protection of stored products, in particular insects, arachnids and mites, which are found in enclosed spaces such as, for example, dwellings, factory halls, offices, vehicle cabins and the like. They can be employed alone or in combination with other active compounds and auxiliaries in domestic insecticide products for controlling these pests. They are active against sensitive and resistant species and against all developmental stages. These pests include:

From the order of the Scorpionidea, for example, *Buthus occitanus*.

From the order of the Acarina, for example, *Argas persicus, Argas reflexus, Bryobia* spp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleoptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga carnaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Ctenocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Pemphigus* spp., *Phylloera vastatrix, Phthirus pubis*.

From the order of the Heteroptera, for example, *Cimex hemipterus, Cimex lectularius, Rhodinus prolixus, Triatoma infestans*.

In the field of household insecticides, they are used alone or in combination with other suitable active compounds, such as phosphoric acid esters, carbamates, pyrethroids, neonicotinoids, growth regulators or active compounds from other known classes of insecticides.

They are used in aerosols, pressure-free spray products, for example pump and atomizer sprays, automatic fogging systems, foggers, foams, gels, evaporator products with evaporator tablets made of cellulose or plastic, liquid evaporators, gel and membrane evaporators, propeller-driven evaporators, energy-free, or passive, evaporation systems, moth papers, moth bags and moth gels, as granules or dusts, in baits for spreading or in bait stations.

The plants listed can be treated according to the invention in a particularly advantageous manner with the compounds of the general formula (I) and/or the compositions according to the invention. The preferred ranges stated above for the active compounds or compositions also apply to the treatment of these plants. Particular emphasis is given to the treatment of plants with the compounds or compositions specifically mentioned in the present text.

The invention is illustrated by the examples below. However, the invention is not limited to the examples.

Preparation of Starting Materials of the Formula (XXXI)

2-[1-(tert-Butoxycarbonyl)piperidin-4-yl]-1,3-thiazole-4-carboxylic acid (XXXI-1)

At room temperature, lithium hydroxide monohydrate (8.88 g) is added in one portion to a solution of tert-butyl 4-[4-(ethoxycarbonyl)-1,3-thiazol-2-yl]piperidine-1-carboxylate (24.0 g) in tetrahydrofuran (240 ml) and water (60 ml). The mixture is stirred for 4 hours and then stirred with dilute hydrochloric acid (1M) (100 ml) and ethyl acetate (100 ml). The aqueous phase is separated off and extracted with ethyl acetate, and the combined organic phases are then dried with sodium sulphate. The solid is filtered off and the solvent is removed by distillation. This gives 2-[1-(tert-butoxycarbonyl)piperidin-4-yl]-1,3-thiazole-4-carboxylic acid (21 g, 94%).

log P (pH 2.7): 2.04

$^1$H NMR (DMSO-d$_6$, 400 MHz): $\delta_{ppm}$: 1.41 (s, 9H), 1.59 (qd, 2H), 2.02 (dd, 2H), 2.91 (m, 2H), 3.23 (m, 1H), 3.97-4.02 (m, 2H), 8.27 (s, 1H)

MS (ESI): 256 ([M+H—C(CH$_3$)$_3$]$^+$)

Preparation of Starting Materials of the Formula (XXXIII)

tert-Butyl 4-{4-[(cyclohexyloxy)carbonyl]-1,3-thiazol-2-yl}piperidine-1-carboxylate (XXXIII-1)

At room temperature, cyclohexanol (1.21 g), dimethylaminopyridine (113 mg) and 1-ethyl-3-(3'-dimethylaminopropyl)carbodiimide (1.87 g) are added to a solution of 2-[1-(tert-butoxycarbonyl)piperidin-4-yl]-1,3-thiazole-4-carboxylic acid (XXXI-1, 2.90 g) in dichloromethane (30 ml). The mixture is stirred at room temperature overnight, and water is then added. The aqueous phase is separated off and extracted with ethyl acetate, and the combined organic phases are then dried with sodium sulphate. The solid is filtered off and the solvent is removed by distillation. The residue is purified chromatographically. This gives tert-butyl 4-{4-[(cyclohexyloxy)carbonyl]-1,3-thiazol-2-yl}piperidine-1-carboxylate (2.63 g, 72%).

log P (pH 2.7): 4.62

$^1$H NMR (DMSO-d$_6$, 400 MHz): δ$_{ppm}$: 1.13-1.81 (m+s, 21H), 2.02 (m, 2H), 2.90 (m, 2H), 3.40 (m, 1H), 3.98-4.01 (m, 2H), 4.90 (m, 1H), 8.32 (s, 1H)

MS (ESI): 339 ([M+2H—C(CH$_3$)$_3$]$^+$)

Preparation of Starting Materials of the Formula (VII)

4-{4-[(Cyclohexyloxy)carbonyl]-1,3-thiazol-2-yl}piperidinium chloride (VII-1)

Under argon and at 0° C., a 2-molar solution of hydrogen chloride in diethyl ether (50 ml) is added dropwise to a solution of tert-butyl 4-{4-[(cyclohexyloxy)carbonyl]-1,3-thiazol-2-yl}piperidine-1-carboxylate (XXXIII-1, 2.63 g) in dioxane (20 ml). The reaction mixture is stirred at 0° C. and then slowly warmed to room temperature. After stirring overnight, the solvent and excess hydrogen chloride are removed. This gives 4-{4-[(cyclohexyloxy)carbonyl]-1,3-thiazol-2-yl}piperidinium chloride (2.19 g, 99%).

log P (pH 2.7): 1.25

$^1$H NMR (DMSO-d$_6$, 400 MHz): δ$_{ppm}$: 1.15-1.55 (m, 6H), 1.71-1.75 (m, 2H), 1.85-1.90 (m, 2H), 1.98-2.04 (m, 2H), 2.20 (dd, 2H), 3.01-3.03 (m, 2H), 3.14-3.34 (m, 2H), 3.40 (m, 1H), 4.90 (m, 1H), 8.36 (s, 1H), 9.05 (bs, 1H), 9.25 (bs, 1H)

MS (ESI): 295 ([M−Cl]$^+$)

Preparation of Compounds of the Formula (I)

Cyclohexyl 2-{1-[(2,5-dibromophenyl)acetyl]piperidin-4-yl}-1,3-thiazole-4-carboxylate (I-15)

(2,5-Dibromophenyl)acetic acid (323 mg) and Hünig base (323 mg) are dissolved in dichloromethane (10 ml) and stirred at room temperature for 30 min. 4-{4-[(Cyclohexyloxy)carbonyl]-1,3-thiazol-2-yl}piperidinium chloride (VII-1, 330 mg) is added, and the mixture is stirred for a further 5 min before bromotrispyrrolidinophosphonium hexafluorophosphate (559 mg) is added. The reaction mixture is stirred at room temperature overnight. After removal of the solvent under reduced pressure, the residue is purified chromatographically. This gives cyclohexyl 2-{1-[(2,5-dibromophenyl)acetyl]piperidin-4-yl}-1,3-thiazole-4-carboxylate (250 mg, 43%).

log P (pH 2.7): 4.72

$^1$H NMR (DMSO-d$_6$, 400 MHz): δ$_{ppm}$: 1.25-1.57 (m, 6H), 1.68-1.80 (m, 4H), 1.88 (m, 2H), 2.09 (m, 2H), 2.83 (bs, 1H), 3.29 (bs, 1H), 3.37 (m, 1H), 3.86 (s, 2H), 4.06 (bs, 1H), 4.38 (bs, 1H), 4.90 (m, 1H), 7.36 (dd, 1H), 7.50-7.53 (m, 2H), 8.33 (s, 1H)

Cyclohexyl 2-{1-[(2,5-difluorobenzyl)sulphonyl]piperidin-4-yl}-1,3-thiazole-4-carboxylate (I-30)

At room temperature, (2,5-difluorophenyl)methanesulphonyl chloride (226 mg) is added to a solution of 4-{4-[(cyclohexyloxy)carbonyl]-1,3-thiazol-2-yl}piperidinium chloride (VII-1, 330 mg) and triethylamine (303 mg) in dichloromethane (5 ml). The mixture is stirred at room temperature overnight, and water is then added. The aqueous phase is separated off and extracted with ethyl acetate, and the combined organic phases are then dried with sodium sulphate. The solid is filtered off and the solvent is removed by distillation. The residue is purified chromatographically. This gives cyclohexyl 2-{1-[(2,5-difluorobenzyl)sulphonyl]piperidin-4-yl}-1,3-thiazole-4-carboxylate (156 mg, 32%).

log P (pH 2.7): 4.05

$^1$H NMR (DMSO-d$_6$, 400 MHz): δ$_{ppm}$: 1.25-1.60 (m, 6H), 1.63-1.78 (m, 4H), 1.85-1.89 (m, 2H), 2.09-2.13 (m, 2H), 2.95-3.01 (m, 2H), 3.22 (m, 1H), 3.63-3.66 (m, 2H), 4.44 (s, 2H), 4.90 (m, 1H), 7.21-7.34 (m, 3H), 8.34 (s, 1H)

MS (ESI): 485 ([M+H]$^+$)

2-Methyl-5-(trifluoromethyl)phenyl 4-{4-[(cyclohexyloxy)carbonyl]-1,3-thiazol-2-yl}piperidine-1-carboxylate (I-38)

At room temperature, 2-methyl-5-(trifluoromethyl)phenyl chlorocarbonate (239 mg) is added to a solution of 4-{4-[(cyclohexyloxy)carbonyl]-1,3-thiazol-2-yl}piperidinium chloride (VII-1, 324 mg) and diisopropylethylamine (323 mg) in dichloromethane (8 ml). The mixture is stirred at room temperature overnight, and water is then added. The aqueous phase is separated off and extracted with ethyl acetate, and the combined organic phases are then dried with sodium sulphate. The solid is filtered off and the solvent is removed by distillation. The residue is purified chromatographically. This gives 2-methyl-5-(trifluoromethyl)phenyl 4-{4-[(cyclohexyloxy)carbonyl]-1,3-thiazol-2-yl}piperidine-1-carboxylate (193 mg, 39%).

log P (pH 2.7): 5.28

$^1$H NMR (DMSO-d$_6$, 400 MHz): δ$_{ppm}$: 1.28-1.58 (m, 6H), 1.72-1.89 (m, 6H), 2.15 (m, 2H), 2.24 (s, 3H), 3.20 (m, 2H), 3.34-3.41 (m, 1H), 4.18 (m, 2H), 4.91 (m, 1H), 7.46-7.50 (m, 3H), 8.35 (s, 1H)

MS (ESI): 497 ([M+H]$^+$)

Cyclohexyl 2-{1-[(2,5-dimethylphenyl)carbamoyl]piperidin-4-yl}-1,3-thiazole-4-carboxylate (I-59)

4-{4-[(Cyclohexyloxy)carbonyl]-1,3-thiazol-2-yl}piperidinium chloride (VII-1, 330 mg) is stirred with dichloromethane and a saturated bicarbonate solution for 10 minutes. The organic phase is separated off, dried and concentrated by evaporation. The residue is dissolved in dichloromethane (5 ml). At room temperature, 2-isocyanato-1,4-dimethylbenzene (162 mg) and a drop of 2,3,4,6,7,8,9,10-octahydropyrimido[1,2-a]azepine (DBU) are added successively to this solution. The mixture is stirred at room temperature overnight, and water is then added. The aqueous phase is separated off and extracted with ethyl acetate, and the combined organic phases are then dried with sodium sulphate. The solid is filtered off and the solvent is removed by distillation. The residue is purified chromatographically. This gives cyclohexyl 2-{1-[2,5-dimethylphenyl)carbamoyl]piperidin-4-yl}-1,3-thiazole-4-carboxylate (95 mg, 19%).

log P (pH 2.7): 3.82

$^1$H NMR (DMSO-d$_6$, 400 MHz): δ$_{ppm}$: 1.22-1.58 (m, 6H), 1.59-1.75 (m, 4H), 1.88 (m, 2H), 2.08 (m, 2H), 2.11 (s, 3H), 2.23 (s, 3H), 2.94-2.99 (m, 2H), 3.04-3.34 (m, 1H), 4.14-4.17 (m, 2H), 4.89 (m, 1H), 6.84 (d, 1H), 7.00 (s, 1H), 7.03 (d, 1H), 7.99 (s, 1H), 8.40 (s, 1H)

MS (ESI): 442 ([M+H]$^+$)

Cyclohexyl 2-(4-{[5-methyl-3-(trifluoromethyl)-1H-pyrazol-1-yl]acetyl}piperazin-1-yl)-1,3-thiazole-4-carboxylate (I-46)

At room temperature, cyclohexanol (82 mg), dimethylaminopyridine (10 mg) and 1-ethyl-3-(3'-dimethylaminopropyl)

carbodiimide (150 mg) are added to a solution of 2-(4-{[5-methyl-3-(trifluoromethyl)-1H-pyrazol-1-yl]acetyl}piperazin-1-yl)-1,3-thiazole-4-carboxylic acid (XXXIV-1, 300 mg) in dichloromethane (5 ml). The mixture is stirred overnight, and water is then added. The aqueous phase is separated off and extracted with ethyl acetate. The combined organic phases are dried with sodium sulphate. The solid is filtered off and the solvent is removed by distillation. The residue is purified chromatographically. This gives cyclohexyl 2-(4-{[5-methyl-3-(trifluoromethyl)-1H-pyrazol-1-yl]acetyl}piperazin-1-yl)-1,3-thiazole-4-carboxylate (45 mg, 12%).

log P (pH 2.7): 3.69

$^1$H NMR (DMSO-$d_6$, 400 MHz): $\delta_{ppm}$: 1.23-1.58 (m, 6H), 1.65-1.78 (m, 2H), 1.80-1.90 (m, 2H), 2.22 (s, 3H), 3.40-3.70 (m, 8H), 4.80-4.89 (m, 1H), 5.25 (s, 2H), 6.46 (s, 1H), 7.67 (s, 1H)

MS (ESI): 486 ([M+H]$^+$)

Analogously to the above examples and in accordance with the general descriptions of the processes according to the invention, it is possible to obtain the compounds of the formula (I) listed in Table 1 below.

TABLE I (I)

| Example | E | X | G | Y$^2$ | L$^1$ | R$^1$ | logP |
|---|---|---|---|---|---|---|---|
| 1 | [3-(trifluoromethyl)phenyl]acetyl | CH | G1 | O | bond | naphthalen-1-yl | 4.16[b] |
| 2 | [3-(trifluoromethyl)phenyl]acetyl | CH | G1 | O | bond | cyclohexyl | 4.21[b] |
| 3 | pentanoyl | CH | G1 | O | bond | naphthalen-1-yl | 3.66[b] |
| 4 | pentanoyl | CH | G1 | O | bond | cyclohexyl | 3.64[b] |
| 5 | (5-chloro-1-methyl-1H-pyrazol-4-yl)acetyl | CH | G1 | O | bond | naphthalen-1-yl | 3.00[b] |
| 6 | (5-chloro-1-methyl-1H-pyrazol-4-yl)acetyl | CH | G1 | O | bond | cyclohexyl | 2.93[b] |
| 7 | thiophen-3-ylacetyl | CH | G1 | O | bond | naphthalen-1-yl | 3.46[b] |
| 8 | thiophen-3-ylacetyl | CH | G1 | O | bond | cyclohexyl | 3.42[b] |
| 9 | (3-chlorophenyl)acetyl | CH | G1 | O | bond | cyclohexyl | 4.04[b] |
| 10 | (3-chlorophenyl)acetyl | CH | G1 | O | bond | naphthalen-1-yl | 4.01[b] |
| 11 | [2-chloro-5-(trifluoromethyl)phenyl]acetyl | CH | G1 | O | bond | naphthalen-1-yl | 4.56[b] |
| 12 | [2-chloro-5-(trifluoromethyl)phenyl]acetyl | CH | G1 | O | bond | cyclohexyl | 4.64[b] |
| 13 | [2-bromo-5-(trifluoromethyl)phenyl]acetyl | CH | G1 | O | bond | cyclohexyl | 4.75[b] |
| 14 | (2,5-dichlorophenyl)acetyl | CH | G1 | O | bond | cyclohexyl | 4.49[b] |
| 15 | (2,5-dibromophenyl)acetyl | CH | G1 | O | bond | cyclohexyl | 4.72[b] |
| 16 | [2,5-bis(trifluoromethyl)phenyl]acetyl | CH | G1 | O | bond | cyclohexyl | 4.81[b] |
| 17 | (5-bromo-2-methylphenyl)acetyl | CH | G1 | O | bond | cyclohexyl | 4.47[b] |
| 18 | [5-chloro-2-(trifluoromethyl)phenyl]acetyl | CH | G1 | O | bond | cyclohexyl | 4.68[b] |
| 19 | (5-iodo-2-methylphenyl)acetyl | CH | G1 | O | bond | cyclohexyl | 4.66[b] |
| 20 | (2,5-dimethylthiophen-3-yl)acetyl | CH | G1 | O | bond | cyclohexyl | 4.24[b] |
| 21 | (5-methyl-2-phenyl-1,3-thiazol-4-yl)acetyl | CH | G1 | O | bond | cyclohexyl | 4.57[b] |
| 22 | (5-methyl-2-phenyl-1,3-oxazol-4-yl)acetyl | CH | G1 | O | bond | cyclohexyl | 4.15[b] |
| 23 | (5-methyl-2-phenyl-1,3-thiazol-4-yl)acetyl | CH | G1 | O | bond | naphthalen-1-yl | 4.43[b] |
| 24 | (5-methyl-2-phenyl-1,3-oxazol-4-yl)acetyl | CH | G1 | O | bond | naphthalen-1-yl | 4.04[b] |
| 25 | (2,5-dimethylthiophen-3-yl)acetyl | CH | G1 | O | bond | naphthalen-1-yl | 4.12[b] |
| 26 | (2,5-dimethyl-1,3-thiazol-4-yl)acetyl | CH | G1 | O | bond | naphthalen-1-yl | 3.10[b] |
| 27 | (2,5-dimethyl-1,3-thiazol-4-yl)acetyl | CH | G1 | O | bond | cyclohexyl | 3.02[b] |
| 28 | (3,5-dimethyl-1H-1,2,4-triazol-1-yl)acetyl | CH | G1 | O | bond | naphthalen-1-yl | 2.17[b] |
| 29 | (3,5-dimethyl-1H-1,2,4-triazol-1-yl)acetyl | CH | G1 | O | bond | cyclohexyl | 2.08[b] |
| 30 | (2,5-difluorobenzyl)sulphonyl | CH | G1 | O | bond | cyclohexyl | 4.05[b] |
| 31 | [5-methyl-3-(trifluoromethyl)-1H-pyrazol-1-yl]acetyl | N | G1 | O | CHCH$_3$ | 2,5-dichlorophenyl | 4.28[b] |
| 32 | [5-methyl-3-(trifluoromethyl)-1H-pyrazol-1-yl]acetyl | N | G1 | O | bond | 3-(trifluoromethyl)cyclohexyl | 3.81[c] |
| 33 | [5-methyl-3-(trifluoromethyl)-1H-pyrazol-1-yl]acetyl | N | G1 | S | bond | 2-chloro-5-(trifluoromethyl)phenyl | 4.51[c] |
| 34 | [5-methyl-3-(trifluoromethyl)-1H-pyrazol-1-yl]acetyl | N | G1 | S | bond | cyclohexyl | 4.43[c] |
| 35 | [5-methyl-3-(trifluoromethyl)-1H-pyrazol-1-yl]acetyl | N | G1 | O | CH$_2$ | 4-methoxyphenyl | 3.19[c] |
| 36 | [5-methyl-3-(trifluoromethyl)-1H-pyrazol-1-yl]acetyl | N | G1 | O | bond | quinolin-8-yl | 2.83[c]; 2.85[b] |
| 37 | [5-methyl-3-(trifluoromethyl)-1H-pyrazol-1-yl]acetyl | N | G1 | O | bond | 2,4-dichlorophenyl | 3.87[c]; 3.96[b] |
| 38 | [2-methyl-5-(trifluoromethyl)phenoxy]carbonyl | CH | G1 | O | bond | cyclohexyl | 5.28[b] |
| 39 | [5-methyl-3-(trifluoromethyl)-1H-pyrazol-1-yl]acetyl | N | G1 | O | bond | 2-chlorophenyl | 3.41[c]; 3.46[b] |
| 40 | [5-methyl-3-(trifluoromethyl)-1H-pyrazol-1-yl]acetyl | N | G1 | O | bond | naphthalen-2-yl | 3.76[c]; 3.81[b] |
| 41 | [5-methyl-3-(trifluoromethyl)-1H-pyrazol-1-yl]acetyl | N | G1 | O | bond | 2,3-dihydro-1H-inden-2-yl | 3.56[c]; 3.64[b] |
| 42 | [5-methyl-3-(trifluoromethyl)-1H-pyrazol-1-yl]acetyl | N | G1 | O | bond | 1,2,3,4-tetrahydronaphthalen-2-yl | 3.82[c]; 3.87[b] |
| 43 | [5-methyl-3-(trifluoromethyl)-1H-pyrazol-1-yl]acetyl | N | G1 | O | bond | 1,2,3,4-tetrahydronaphthalen-1-yl | 3.91[c]; 3.98[b] |
| 44 | [5-methyl-3-(trifluoromethyl)-1H-pyrazol-1-yl]acetyl | N | G1 | O | CH$_2$ | 2,4-dichlorophenyl | 4.12[c]; 4.12[b] |
| 45 | [5-methyl-3-(trifluoromethyl)-1H-pyrazol-1-yl]acetyl | N | G1 | S | bond | naphthalen-2-yl | 4.33[c]; 4.33[b] |
| 46 | [5-methyl-3-(trifluoromethyl)-1H-pyrazol-1-yl]acetyl | N | G1 | O | bond | cyclohexyl | 3.68[c]; 3.69[b] |
| 47 | [5-methyl-3-(trifluoromethyl)-1H-pyrazol-1-yl]acetyl | N | G1 | S | bond | 2,4-dichlorophenyl | 4.5[c]; 4.49[b] |
| 48 | [5-methyl-3-(trifluoromethyl)-1H-pyrazol-1-yl]acetyl | N | G1 | O | CH$_2$ | 2-chlorophenyl | 3.64[c]; 3.64[b] |
| 49 | [5-methyl-3-(trifluoromethyl)-1H-pyrazol-1-yl]acetyl | N | G1 | S | CH$_2$ | 2-chlorophenyl | 4.32[c]; 4.29[b] |
| 50 | [5-methyl-3-(trifluoromethyl)-1H-pyrazol-1-yl]acetyl | N | G1 | S | CH$_2$ | 2,4-dichlorophenyl | 4.87[c]; 4.79[b] |
| 51 | [5-methyl-3-(trifluoromethyl)-1H-pyrazol-1-yl]acetyl | N | G1 | O | CH$_2$ | 2,6-difluorophenyl | 3.33[c]; 3.28[b] |
| 52 | [3-chloro-6-(trifluoromethyl)pyridin-2-yl]acetyl | CH | G1 | O | bond | cyclohexyl | 4.08[b] |
| 53 | [5-methyl-3-(trifluoromethyl)-1H-pyrazol-1-yl]acetyl | N | G1 | O | CH$_2$ | 2,4-difluorophenyl | 3.45[c]; 3.42[b] |
| 54 | [5-methyl-3-(trifluoromethyl)-1H-pyrazol-1-yl]acetyl | N | G1 | O | CHCH$_3$ | cyclohexyl | 4.46[c]; 4.4[b] |
| 55 | oxo(thiophen-2-yl)acetyl | CH | G1 | O | bond | cyclohexyl | 3.46[b] |

TABLE I-continued (I)

$$E-\underset{u}{N}\underset{}{\overset{Y^1}{=}}\underset{v}{\overset{Y^2-L^1-R^1}{\underset{w}{\bigvee}}}$$

| Example | E | X | G | Y² | L¹ | R¹ | logP |
|---|---|---|---|---|---|---|---|
| 56 | [3-(trifluoromethyl)cyclohexyl]acetyl | CH | G1 | O | bond | cyclohexyl | 4.58[b] |
| 57 | 5,5,6,6,6-pentafluorohexanoyl | CH | G1 | O | bond | cyclohexyl | 4.22[b] |
| 58 | heptanoyl | CH | G1 | O | bond | cyclohexyl | 4.51[b] |
| 59 | (2,5-dimethylphenyl)carbamoyl | CH | G1 | O | bond | cyclohexyl | 3.82 [b] |
| 60 | furan-2-yl(oxo)acetyl | CH | G1 | O | bond | cyclohexyl | 3.07[b] |
| 61 | [2-chloro-5-(trifluoromethyl)phenyl]carbamoyl | CH | G1 | O | bond | cyclohexyl | 4.76[b] |
| 62 | (2-chloro-5-methylphenyl)carbamoyl | CH | G1 | O | bond | cyclohexyl | 4.30[b] |
| 63 | (2,5-dimethylphenyl)carbamothioyl | CH | G1 | O | bond | cyclohexyl | 4.17[b] |
| 64 | (2-fluoro-5-methylphenyl)carbamoyl | CH | G1 | O | bond | cyclohexyl | 3.81[b] |
| 65 | (3,5-dimethylphenyl)acetyl | CH | G1 | O | bond | cyclohexyl | 4.34[c]; 4.32[b] |
| 66 | (2,4-dimethylphenyl)acetyl | CH | G1 | O | bond | cyclohexyl | 4.33[c]; 4.3[b] |
| 67 | (2,5-difluorophenyl)carbamothioyl | CH | G1 | O | bond | cyclohexyl | 3.86[b] |
| 68 | [3,5-bis(difluoromethyl)-1H-pyrazol-1-yl]acetyl | CF | G1 | O | bond | (1R)-1,2,3,4-tetrahydronaphthalen-1-yl | 4.12[b] |
| 69 | [3,5-bis(difluoromethyl)-1H-pyrazol-1-yl]acetyl | CF | G1 | O | bond | cyclohexyl | 3.91[b] |
| 70 | (Z)-{[2-chloro-5-(trifluoromethyl)phenyl]imino}(methoxy)methyl | CH | G1 | O | bond | cyclohexyl | |
| 71 | (2-methoxy-5-methylphenyl)carbamoyl | CH | G1 | O | bond | cyclohexyl | 4.18[b] |
| 72 | (5-chloro-2-methylphenyl)carbamoyl | CH | G1 | O | bond | cyclohexyl | 4.10[b] |
| 73 | (3,5-dimethyl-1,2-oxazol-4-yl)carbamothioyl | CH | G1 | O | bond | cyclohexyl | 3.18[b] |
| 74 | (5-fluoro-2-methylphenyl)carbamoyl | CH | G1 | O | bond | cyclohexyl | 3.74[b] |
| 75 | (5-chloro-2-methoxyphenyl)carbamoyl | CH | G1 | O | bond | cyclohexyl | 4.35[b] |
| 76 | (3,5-dimethyl-1,2-oxazol-4-yl)carbamoyl | CH | G1 | O | bond | cyclohexyl | 2.66[b] |
| 77 | (2,5-dimethoxyphenyl)carbamoyl | CH | G1 | O | bond | 1,2,3,4-tetrahydronaphthalen-1-yl | 4.05[b] |
| 78 | (2,5-dimethylphenyl)carbamoyl | CH | G1 | O | bond | 1,2,3,4-tetrahydronaphthalen-1-yl | 4.09[b] |
| 79 | (5-fluoro-2-methylphenyl)carbamoyl | CH | G1 | O | bond | 1,2,3,4-tetrahydronaphthalen-1-yl | 4.00[b] |
| 80 | (2-fluoro-5-methylphenyl)carbamoyl | CH | G1 | O | bond | 1,2,3,4-tetrahydronaphthalen-1-yl | 4.08[b] |
| 81 | (2,5-dimethylphenyl)carbamothioyl | CH | G1 | O | bond | 1,2,3,4-tetrahydronaphthalen-1-yl | 4.39[b] |
| 82 | (2-methoxy-5-methylphenyl)carbamoyl | CH | G1 | O | bond | 1,2,3,4-tetrahydronaphthalen-1-yl | 4.33[b] |
| 83 | cyclopentylacetyl | CH | G1 | O | bond | cyclohexyl | 4.12[c]; 4.15[b] |
| 84 | (2,5-difluorophenyl)carbamoyl | CH | G1 | O | CH₂ | 2-bromophenyl | 3.79[c]; 3.79[b] |
| 85 | (5-chloro-2-methylphenyl)carbamoyl | CH | G1 | O | CH₂ | 2-bromophenyl | 4.06[c]; 4.04[b] |
| 86 | (1,3-dimethyl-1H-pyrazol-5-yl)acetyl | CH | G1 | O | bond | cyclohexyl | 2.67[c]; 2.6[b] |
| 87 | (2,5-dichlorophenyl)acetyl | CH | G1 | O | CH₂ | 2-bromophenyl | 4.44[c]; 4.41[b] |
| 88 | (2,5-dimethylphenyl)carbamothioyl | CH | G1 | O | CH₂ | 2-bromophenyl | 3.71[c]; 3.68[b] |
| 89 | (1,5-dimethyl-1H-pyrazol-3-yl)acetyl | CH | G1 | O | bond | cyclohexyl | 2.68[c]; 2.66[b] |
| 90 | (5-fluoro-2-methylphenyl)carbamoyl | CH | G1 | O | CH₂ | 2-bromophenyl | 3.75[c]; 3.77[b] |
| 91 | (2,5-dimethylphenyl)carbamoyl | CH | G1 | O | CH₂ | 2-bromophenyl | 3.84[c]; 3.86[b] |
| 92 | (2-fluoro-5-methylphenyl)carbamoyl | CH | G1 | O | CH₂ | 2-bromophenyl | 3.83[c]; 3.85[b] |
| 93 | (2,5-dimethoxyphenyl)carbamoyl | CH | G1 | O | bond | cyclohexyl | 3.76[b] |
| 94 | (2-methyl-5-nitrophenyl)carbamoyl | CH | G1 | O | bond | cyclohexyl | 3.62[b] |
| 95 | (2,5-dichlorophenyl)carbamoyl | CH | G1 | O | bond | 1,2,3,4-tetrahydronaphthalen-1-yl | 4.92[b] |
| 96 | (2,5-dimethylphenyl)acetyl | CH | G1 | O | bond | 1,2,3,4-tetrahydronaphthalen-1-yl | 4.54[b] |
| 97 | (5-chloro-2-methoxyphenyl)carbamoyl | CH | G1 | O | bond | 1,2,3,4-tetrahydronaphthalen-1-yl | 4.64[b] |
| 98 | (3,5-dimethyl-1,2-oxazol-4-yl)carbamoyl | CH | G1 | O | bond | 1,2,3,4-tetrahydronaphthalen-1-yl | 2.97[b] |
| 99 | (2,5-dichlorophenyl)acetyl | CH | G1 | O | bond | 1,2,3,4-tetrahydronaphthalen-1-yl | 4.73[b] |
| 100 | (2-chloro-5-methylphenyl)carbamoyl | CH | G1 | O | bond | 1,2,3,4-tetrahydronaphthalen-1-yl | 4.61[b] |
| 101 | (2,5-dibromophenyl)acetyl | CH | G1 | O | CH₂ | 2-bromophenyl | 4.64[c]; 4.68[b] |
| 102 | (2,5-dimethylphenyl)acetyl | CH | G1 | O | CH₂ | 2-bromophenyl | 4.27[c]; 4.23[b] |
| 103 | (2,5-dimethoxyphenyl)carbamoyl | CH | G1 | O | CH₂ | 2-bromophenyl | 3.81[c]; 3.83[b] |
| 104 | (2-methoxy-5-methylphenyl)carbamoyl | CH | G1 | O | CH₂ | 2-bromophenyl | 4.12[c]; 4.08[b] |
| 105 | (5-chloro-2-methoxyphenyl)carbamoyl | CH | G1 | O | CH₂ | 2-bromophenyl | 4.36[c]; 4.35[b] |
| 106 | [2-chloro-5-(trifluoromethyl)phenyl]carbamoyl | CH | G1 | O | CH₂ | 2-bromophenyl | 4.75[c]; 4.7[b] |
| 107 | (2-chloro-5-methylphenyl)carbamoyl | CH | G1 | O | CH₂ | 2-bromophenyl | 4.33[c]; 4.28[b] |
| 108 | (2,5-dichlorophenyl)carbamoyl | CH | G1 | O | CH₂ | 2-bromophenyl | 4.61[c]; 4.56[b] |
| 109 | {[1-methyl-3-(trifluoromethyl)-1H-pyrazol-5-yl]oxy}carbonyl | CH | G1 | O | bond | cyclohexyl | 4.37[c]; 4.36[b] |
| 110 | (2-methyl-5-nitrophenyl)carbamoyl | CH | G1 | O | CH₂ | 2-bromophenyl | 3.70[c]; 3.69[b] |
| 111 | [2-fluoro-5-(trifluoromethyl)phenyl]carbamoyl | CH | G1 | O | CH₂ | 2-bromophenyl | 4.29[c]; 4.29[b] |
| 112 | (5-chloro-2-methylphenyl)carbamothioyl | CH | G1 | O | CH₂ | 2-bromophenyl | 4.27[c]; 4.3[b] |
| 113 | (2,5-dichlorophenyl)carbamothioyl | CH | G1 | O | CH₂ | 2-bromophenyl | 4.39[c]; 4.4[b] |
| 114 | (2-bromo-5-fluorophenyl)carbamothioyl | CH | G1 | O | CH₂ | 2-bromophenyl | 4.02[c]; 4.04[b] |
| 115 | (5-chloro-2-fluorophenyl)carbamothioyl | CH | G1 | O | CH₂ | 2-bromophenyl | 4.14[c]; 4.15[b] |
| 116 | (2,5-difluorophenyl)carbamothioyl | CH | G1 | O | CH₂ | 2-bromophenyl | 3.87[c]; 3.83[b] |
| 117 | (5-fluoro-2-methylphenyl)carbamothioyl | CH | G1 | O | CH₂ | 2-bromophenyl | 3.98[c]; 3.98[b] |
| 118 | [2-fluoro-5-(trifluoromethyl)phenyl]carbamothioyl | CH | G1 | O | CH₂ | 2-bromophenyl | 4.37[c]; 4.34[b] |
| 119 | (3,5-dimethyl-1,2-oxazol-4-yl)carbamothioyl | CH | G1 | O | CH₂ | 2-bromophenyl | 3.21[c]; 3.2[b] |
| 120 | (2,5-dimethylphenyl)carbamoyl | CH | G1 | O | CH₂ | 2-chloro-6-fluorophenyl | 3.66[b] |
| 121 | (2,5-dimethylphenyl)carbamoyl | CH | G1 | O | CH₂ | 2,6-difluorophenyl | 3.38[b] |
| 122 | (2,5-dimethylphenyl)carbamoyl | CH | G1 | O | bond | (1R,2S)-2-phenylcyclohexyl | 4.43[b] |
| 123 | (2,5-dimethylphenyl)carbamoyl | CH | G1 | O | bond | (1S,2R)-2-phenylcyclohexyl | 4.42[b] |

TABLE I-continued

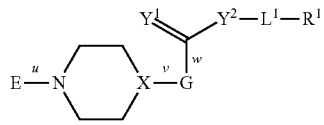

(I)

| Example | E | X | G | Y² | L¹ | R¹ | logP |
|---|---|---|---|---|---|---|---|
| 124 | (2,5-difluorophenyl)carbamothioyl | CH | G1 | O | bond | 1,2,3,4-tetrahydronaphthalen-1-yl | 3.94[c]; 4.06[b] |
| 125 | (5-chloro-2-methylphenyl)carbamoyl | CH | G1 | O | bond | 1,2,3,4-tetrahydronaphthalen-1-yl | 4.14[c]; 4.27[b] |
| 126 | (2,5-dimethylphenyl)carbamoyl | CF | G1 | O | bond | (1R)-1,2,3,4-tetrahydronaphthalen-1-yl | 4.30[b] |
| 127 | [5-methyl-3-(trifluoromethyl)-1H-pyrazol-1-yl]acetyl | CF | G1 | O | bond | (1R)-1,2,3,4-tetrahydronaphthalen-1-yl | 4.25[b] |
| 128 | (2,5-dichlorophenyl)acetyl | CF | G1 | O | bond | (1R)-1,2,3,4-tetrahydronaphthalen-1-yl | |
| 129 | (3,5-dimethyl-1,2-oxazol-4-yl)carbamoyl | CH | G1 | O | CH₂ | 2-bromophenyl | |
| 130 | (2-fluoro-5-methylphenyl)carbamoyl | CH | G1 | O | bond | (1R,2S)-2-phenylcyclohexyl | 4.45[b] |
| 131 | [2-chloro-5-(trifluoromethyl)phenyl]carbamoyl | CH | G1 | O | bond | (1R,2S)-2-phenylcyclohexyl | 5.32[b] |
| 132 | (2-methoxy-5-methylphenyl)carbamoyl | CH | G1 | O | bond | (1R,2S)-2-phenylcyclohexyl | 4.74[b] |
| 133 | (5-chloro-2-methylphenyl)carbamoyl | CH | G1 | O | bond | (1R,2S)-2-phenylcyclohexyl | 4.65[b] |
| 134 | (2-chloro-5-methylphenyl)carbamoyl | CH | G1 | O | bond | (1R,2S)-2-phenylcyclohexyl | 4.96[b] |
| 135 | (2,5-dimethylphenyl)carbamoyl | CH | G1 | O | CH₂ | 2-chlorophenyl | 3.73[b] |
| 136 | (2,5-dimethylphenyl)carbamoyl | CH | G1 | O | CH₂ | 2-iodophenyl | 3.96[b] |
| 137 | (2,5-dimethylphenyl)carbamoyl | CH | G1 | O | CH₂ | 2,6-dichlorophenyl | 3.97[b] |
| 138 | (2,5-dimethylphenyl)carbamoyl | CH | G1 | O | CHCH₃ | 2-fluoro-6-methoxyphenyl | 3.79[b] |
| 139 | (2,5-dimethylphenyl)carbamoyl | CH | G1 | O | CH₂ | 3-chloropyridin-4-yl | 2.77[b] |
| 140 | (2,5-dimethylphenyl)carbamoyl | CH | G1 | O | CH₂ | 2-fluorophenyl | 3.39[b] |
| 141 | (2,5-dimethylphenyl)carbamoyl | CH | G1 | O | bond | 2-bromo-6-methylphenyl | 3.82[b] |
| 142 | (2,5-dimethylphenyl)carbamoyl | CH | G1 | O | bond | 2-bromo-6-methoxyphenyl | 3.56[b] |
| 143 | (2,5-dimethylphenyl)carbamoyl | CH | G1 | O | bond | 2-chloro-6-methylphenyl | 3.76[b] |
| 144 | (2,5-dimethylphenyl)carbamoyl | CH | G1 | O | bond | 2,6-dibromophenyl | 3.93[b] |
| 145 | (2,5-dimethylphenyl)carbamoyl | CH | G1 | O | bond | 2-fluoro-6-methoxyphenyl | 3.28[b] |
| 146 | (2,5-dimethylphenyl)carbamoyl | CH | G1 | O | bond | 2-bromophenyl | 3.58[b] |
| 147 | (2,5-dimethylphenyl)carbamoyl | CH | G1 | O | bond | 2-fluorophenyl | 3.27[b] |
| 148 | (2,5-dimethylphenyl)carbamoyl | CH | G1 | O | bond | 2-chlorophenyl | 3.51[b] |
| 149 | (2,5-dimethylphenyl)carbamoyl | CH | G1 | O | bond | 2-chloro-6-fluorophenyl | 3.62[b] |
| 150 | (2,5-dimethylphenyl)carbamoyl | CH | G1 | O | bond | 2,6-difluorophenyl | 3.39[b] |
| 151 | (2,5-dimethylphenyl)carbamoyl | CH | G1 | O | bond | 2,6-dichlorophenyl | 3.82[b] |
| 152 | (2,5-dimethylphenyl)carbamoyl | CH | G1 | O | bond | 2-bromo-6-fluorophenyl | 3.86[b] |
| 153 | (2,5-dimethylphenyl)carbamoyl | CH | G1 | O | CHCH₃ | 2-fluorophenyl | 3.71[b] |
| 154 | (2,5-dimethylphenyl)carbamoyl | CH | G1 | O | bond | 2-iodophenyl | 3.69[b] |
| 155 | (2,5-dimethylphenyl)carbamoyl | CH | G1 | O | CH₂ | 2-bromo-6-fluorophenyl | 3.79[b] |
| 156 | (2,5-dimethylphenyl)carbamoyl | CH | G1 | O | CHCH₃ | 2,6-dichlorophenyl | 4.35[b] |
| 157 | (2,5-dimethylphenyl)carbamoyl | CH | G1 | O | CH₂CH₂ | 2,6-dichlorophenyl | 4.29[b] |
| 158 | (2,5-dimethylphenyl)carbamothioyl | CH | G1 | O | bond | (1R,2S)-2-phenylcyclohexyl | 4.73[b] |
| 159 | (5-chloro-2-methylphenyl)carbamothioyl | CH | G1 | O | bond | (1R,2S)-2-phenylcyclohexyl | 4.83[b] |
| 160 | (2,5-dimethylphenyl)carbamoyl | CH | G1 | O | bond | (1R,2S)-2-(3,4-difluorophenyl)cyclohexyl | 4.52[b] |
| 161 | (5-chloro-2-methylphenyl)carbamoyl | CH | G1 | O | CH₂ | 2-chloro-6-fluorophenyl | 3.89[b] |
| 162 | (2-methoxy-5-methylphenyl)carbamoyl | CH | G1 | O | CH₂ | 2-chloro-6-fluorophenyl | 3.92[b] |
| 163 | (5-chloro-2-methylphenyl)carbamoyl | CH | G1 | O | CH₂ | 2,6-difluorophenyl | 3.62[b] |
| 164 | (2-methoxy-5-methylphenyl)carbamoyl | CH | G1 | O | CH₂ | 2,6-difluorophenyl | 3.66[b] |
| 165 | [5-methyl-3-(trifluoromethyl)-1H-pyrazol-1-yl]acetyl | CF | G1 | O | CH₂ | 2,6-difluorophenyl | 3.67[c]; 3.65[b] |
| 166 | (5-chloro-2-methylphenyl)carbamoyl | CF | G1 | O | CH₂ | 2,6-difluorophenyl | 3.86[c]; 3.87[b] |
| 167 | (5-chloro-2-methylphenyl)carbamoyl | CF | G1 | O | bond | cyclohexyl | 4.32[c]; 4.33[b] |
| 168 | [3,5-bis(difluoromethyl)-1H-pyrazol-1-yl]acetyl | CF | G1 | O | CH₂ | 2,6-difluorophenyl | 3.56[c]; 3.53[b] |
| 169 | (2-methoxy-5-methylphenyl)carbamoyl | CF | G1 | O | bond | cyclohexyl | 4.42[c]; 4.4[b] |
| 170 | [5-methyl-3-(trifluoromethyl)-1H-pyrazol-1-yl]acetyl | CF | G1 | O | bond | cyclohexyl | 4.09[c]; 4.07[b] |
| 171 | (2,5-dimethylphenyl)carbamoyl | CF | G1 | O | CH₂ | 2,6-difluorophenyl | 3.71[c]; 3.69[b] |
| 172 | (2,5-dimethylphenyl)carbamoyl | CF | G1 | O | bond | cyclohexyl | 4.15[c]; 4.15[b] |
| 173 | (2-methoxy-5-methylphenyl)carbamoyl | CF | G1 | O | CH₂ | 2,6-difluorophenyl | 3.92[c]; 3.80[b] |
| 174 | (2-methoxyethoxy)acetyl | CH | G1 | O | bond | cyclohexyl | 2.37[a] |
| 175 | [3,5-bis(difluoromethyl)-1H-pyrazol-1-yl]acetyl | CH | G18 | O | CH₂ | 2,6-difluorophenyl | 3.45[b] |
| 176 | [3,5-bis(difluoromethyl)-1H-pyrazol-1-yl]acetyl | CH | G18 | O | bond | 2-chloro-6-fluorophenyl | 3.67[b] |

TABLE I-continued

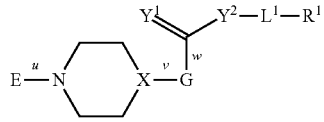

(I)

| Example | E | X | G | $Y^2$ | $L^1$ | $R^1$ | logP |
|---|---|---|---|---|---|---|---|
| 177 | [3,5-bis(difluoromethyl)-1H-pyrazol-1-yl]acetyl | CH | G18 | O | $CH_2$ | 2,3-dimethylphenyl | 4.00[b] |
| 178 | [3,5-bis(difluoromethyl)-1H-pyrazol-1-yl]acetyl | CH | G18 | O | bond | cyclohexyl | 3.97[b] |

In Examples 68, 122, 123, 126, 127, 128, 130, 131, 132, 133, 134, 158, 159 and 160, $R^1$ has the specification of chirality which results after the incorporation of $R^1$ into the product.
The logP values were measured in accordance with EEC Directive 79/831 Annex V.A8 by HPLC (High Performance Liquid Chromatography)

[a] The determination in the acidic range is carried out at pH 2.3 using the mobile phases 0.1% aqueous phosphoric acid and acetonitrile; linear gradient from 10% acetonitrile to 95% acetonitrile.
[b] The LC-MS determination in the acidic range is carried out at pH 2.7 using the mobile phases 0.1% aqueous formic acid and acetonitrile (contains 0.1% formic acid); linear gradient from 10% acetonitrile to 95% acetonitrile
[c] The LC-MS determination in the neutral range is carried out at pH 7.8 using the mobile phases 0.001 molar aqueous ammonium bicarbonate solution and acetonitrile; linear gradient from 10% acetonitrile to 95% acetonitrile
The calibration is carried out using unbranched alkan-2-ones (having 3 to 16 carbon atoms) with known logP values (determination of the logP values by the retention times using linear interpolation between two successive alkanones). The lambda-maX values were determined in the maxima of the chromatographic signals using the UV spectra from 200 nm to 400 nm.

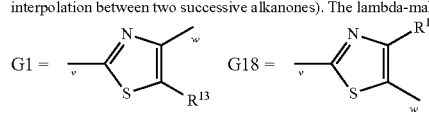

$Y^1$ = O for all examples from Table I.
$R^{13}$ = H for all examples from Table I.

NMR Data of Selected Examples

| Ex. | NMR Data |
|---|---|
| I-15 | $^1$HNMR δ = 1.25-1.57 (m, 6H), 1.68-1.80 (m, 4H), 1.88 (m, 2H), 2.09 (m, 2H), 2.83 (bs, 1H), 3.29 (bs, 1H), 3.37 (m, 1H), 3.86 (s, 2H), 4.06 (bs, 1H), 4.38 (bs, 1H), 4.90 (m, 1H), 7.36 (dd, 1H), 7.50-7.53 (m, 2H), 8.33 (s, 1H) ppm |
| I-30 | $^1$HNMR δ = 1.25-1.60 (m, 6H), 1.63-1.78 (m, 4H), 1.85-1.89 (m, 2H), 2.09-2.13 (m, 2H), 2.95-3.01 (m, 2H), 3.22 (m, 1H), 3.63-3.66 (m, 2H), 4.44 (s, 2H), 4.90 (m, 1H), 7.21-7.34 (m, 3H), 8.34 (s, 1H) ppm |
| I-31 | $^1$HNMR δ = 1.59 (d, 3H), 1.94 (s, 1H), 2.21 (s, 3H), 3.46-3.61 (m, 4H), 3.61-3.70 (m, 4H), 5.22 (s, 2H), 6.48 (s, 1H), 7.41 (dd, 1H), 7.49 (d, 1H), 7.60 (s, 1H), 7.89 (s, 1H) ppm |
| I-32 | $^1$HNMR δ = 1.21-1.30 (m, 1H), 1.32-1.49 (m, 2H), 1.58-1.72 (m, 2H), 1.80-1.97 (m, 2H), 1.98-2.03 (m, 1H), 2.22 (s, 3H), 2.32 (s, 1H), 3.41-3.60 (m, 4H), 3.60-3.69 (m, 4H), 5.24 (s, 2H), 6.43 (s, 1H), 7.69 (s, 1H) ppm |
| I-33 | $^1$HNMR δ = 2.21 (s, 3H), 3.52-3.65 (m, 4H), 3.65-3.72 (m, 4H), 5.25 (s, 2H), 6.49 (s, 1H), 7.81-7.92 (m, 3H), 7.99 (s, 1H) ppm |
| I-34 | $^1$HNMR δ = 1.21-1.32 (m, 1H), 1.45-1.51 (m, 4H), 1.51-1.59 (m, 1H), 1.63-1.72 (m, 2H), 1.88-1.97 (m, 2H), 2.22 (s, 3H), 2.50 (s, 1H), 3.45-3.58 (m, 4H), 3.61-3.70 (m, 4H), 5.24 (s, 2H), 6.47 (s, 1H), 7.62 (s, 1H) ppm |
| I-35 | $^1$HNMR δ = 1.18 (t, 2H), 1.99 (s, 2H), 2.21 (s, 3H), 3.52 (s, 2H), 3.65 (s, 2H), 3.76 (s, 3H), 4.12 (q, 1H), 5.22 (d, 3H), 6.46 (s, 1H), 6.93 (d, 2H), 7.38 (d, 2H), 7.72 (s, 1H) ppm |
| I-38 | $^1$HNMR δ = 1.28-1.58 (m, 6H), 1.72-1.89 (m, 6H), 2.15 (m, 2H), 2.24 (s, 3H), 3.20 (m, 2H), 3.34-3.41 (m, 1H), 4.18 (m, 2H), 4.91 (m, 1H), 7.46-7.50 (m, 3H), 8.35 (s, 1H) ppm |
| I-41 | $^1$HNMR δ = 2.22 (s, 3H), 3.03 (dd, 2H), 3.38 (dd, 2H), 3.49 (bs, 4H), 3.63 (bs, 4H), 2.23 (s, 2H), 5.61 (tt, 1H), 6.45 (s, 1H), 7.14-7.20 (m, 2H), 7.22-7.29 (m, 2H), 7.63 (s, 1H) ppm |
| I-42 | $^1$HNMR δ = 1.90-2.12 (m, 2H), 2.23 (s, 3H), 2.75-3.00 (m, 4H), 3.51 (bs, 4H), 3.65 (bs, 4H), 5.24 (s, 2H), 5.21-5.23 (m, 1H), 6.45 (s, 1H), 7.07-7.13 (m, 4H), 7.62 (s, 1H) ppm |
| I-43 | $^1$HNMR δ = 1.75-1.89 (m, 1H), 1.90-2.10 (m, 3H), 2.22 (s, 3H), 2.68-2.91 (m, 2H), 3.51 (bs, 4H), 3.64 (bs, 4H), 5.26 (s, 2H), 6.07 (t, 1H), 6.45 (s, 1H), 7.16 (t, 2H), 7.19-7.28 (m, 2H), 7.67 (s, 1H) ppm |
| I-44 | $^1$HNMR δ = 2.23 (s, 3H), 3.58 (bs, 4H), 3.68 (bs, 4H), 5.26 (s, 2H), 6.46 (s, 1H), 7.41-7.53 (m, 2H), 7.75 (d, 1H), 8.08 (s, 1H) ppm |
| I-45 | $^1$HNMR δ = 2.23 (s, 3H), 3.59 (bs, 4H), 3.69 (bs, 4H), 5.27 (s, 2H), 6.46 (s, 1H), 7.39 (dd, 1H), 7.49-7.58 (m, 2H), 7.76 (d, 1H), 7.89-7.99 (m, 2H), 7.99 (d, 1H), 8.06 (s, 1H) ppm |
| I-46 | $^1$HNMR δ = 1.23-1.58 (m, 6H), 1.65-1.78 (m, 2H), 1.80-1.90 (m, 2H), 2.22 (s, 3H), 3.40-3.70 (m, 8H), 4.80-4.89 (m, 1H), 5.25 (s, 2H), 6.46 (s, 1H), 7.67 (s, 1H) ppm |
| I-48 | $^1$HNMR δ = 2.23 (s, 3H), 3.58 (bs, 4H), 3.68 (bs, 4H), 5.26 (s, 2H), 6.46 (s, 1H), 7.30-7.48 (m, 3H), 7.59 (dd, 1H), 8.06 (s, 1H) ppm |
| I-49 | $^1$HNMR δ = 2.22 (s, 3H), 3.53 (bs, 4H), 3.65 (bs, 4H), 4.29 (s, 2H), 5.24 (s, 2H), 6.54 (s, 1H), 7.28-7.33 (m, 2H), 7.41-7.48 (m, 1H), 7.49-7.55 (m, 1H), 7.72 (s, 1H) ppm |
| I-51 | $^1$HNMR δ = 2.21 (s, 3H), 3.40-3.70 (m, 8H), 5.29 (s, 2H), 5.34 (s, 2H), 6.50 (s, 1H), 7.17 (t, 2H), 7.47-7.58 (m, 1H), 7.75 (s, 1H) ppm |
| I-52 | $^1$HNMR δ = 1.23-1.59 (m, 6H), 1.68-1.79 (m, 4H), 1.88 (m, 2H), 2.09 (m, 2H), 2.80 (m, 1H), 3.20-3.40 (m, 2H), 4.05 (m, 1H), 4.12 (d, 1H), 4.21 (d, 1H), 4.42 (m, 1H), 4.89 (m, 1H), 7.85 (d, 1H), 8.20 (d, 1H), 8.40 (s, 1H) ppm |
| I-53 | $^1$HNMR δ = 2.21 (s, 3H), 3.40-3.70 (m, 8H), 5.30 (s, 4H), 6.50 (s, 1H), 7.13 (td, 1H), 7.30 (td, 1H), 7.60 (q, 1H), 7.80 (s, 1H) ppm |
| I-59 | $^1$HNMR δ = 1.22-1.58 (m, 6H), 1.59-1.75 (m, 4H), 1.88 (m, 2H), 2.08 (m, 2H), 2.11 (s, 3H), 2.23 (s, 3H), 2.94-2.99 (m, 2H), 3.04-3.34 (m, 1H), 4.14-4.17 (m, 2H), 4.89 (m, 1H), 6.84 (d, 1H), 7.00 (s, 1H), 7.03 (d, 1H), 7.99 (s, 1H), 8.40 (s, 1H) ppm |

The chemical NMR shifts in ppm were measured at 400 MHz, unless indicated otherwise in the solvent DMSO-$d_6$ with tetramethylsilane as internal reference.

The following abbreviations describe the signal splitting: b=broad, s=singlet, d=doublet, t=triplet, q=quadruplet, m=multiplet NMR-Peak list method 1H-NMR data of the examples I-3 to I-178 are written in form of 1H-NMR-peak lists. To each signal peak are listed the d-value in ppm and the signal intensity:

| Ex. | NMR Data |
|---|---|
| I-3 | 8.826 (2.01); 8.025 (0.41); 8.019 (0.43); 8.001 (0.46); 7.902 (0.93); 7.880 (0.91); 7.595 (0.63); 7.594 (0.64); 7.589 (0.52); 7.584 (0.60); 7.577 (1.80); 7.569 (0.58); 7.564 (0.50); 7.560 (0.54); 7.556 (0.62); 7.459 (0.71); 7.457 (0.70); 7.441 (0.53); 7.439 (0.53); 5.686 (16.00); 3.418 (0.37); 3.112 (49.27); 2.498 (3.35); 2.493 (6.63); 2.488 (9.18); 2.484 (6.63); 2.479 (3.39); 2.351 (0.75); 2.332 (1.16); 2.314 (0.86); 2.134 (0.35); 1.532 (0.55); 1.513 (0.79); 1.495 (0.65); 1.476 (0.34); 1.351 (0.46); 1.332 (0.71); 1.313 (0.73); 1.295 (0.43); 0.904 (1.58); 0.886 (3.15); 0.872 (0.54); 0.868 (1.36); −0.000 (0.33); |
| I-4 | 8.323 (10.22); 4.922 (0.99); 4.910 (1.15); 4.900 (1.91); 4.890 (1.23); 4.878 (0.97); 4.868 (0.51); 3.356 (0.51); 3.346 (1.00); 3.337 (0.68); 3.328 (1.15); 3.318 (2.09); 3.308 (1.31); 3.305 (1.14); 3.300 (0.88); 3.290 (1.27); 3.280 (0.72); 3.125 (113.32); 3.086 (0.67); 3.075 (0.54); 2.697 (2.08); 2.501 (4.55); 2.496 (8.73); 2.491 (11.92); 2.487 (8.48); 2.482 (4.24); 2.335 (3.89); 2.317 (5.98); 2.298 (4.37); 2.282 (0.78); 2.263 (0.54); 2.082 (1.56); 2.053 (1.74); 1.906 (0.98); 1.903 (1.27); 1.891 (1.75); 1.888 (1.69); 1.881 (1.78); 1.870 (1.80); 1.860 (1.87); 1.851 (1.91); 1.768 (0.57); 1.760 (1.00); 1.753 (1.23); 1.746 (1.52); 1.738 (1.63); 1.729 (1.73); 1.722 (1.84); 1.714 (1.84); 1.572 (1.70); 1.563 (1.74); 1.547 (2.89); 1.540 (4.31); 1.522 (5.01); 1.517 (4.78); 1.504 (5.30); 1.486 (4.34); 1.466 (1.53); 1.445 (0.87); 1.437 (1.11); 1.421 (1.35); 1.413 (2.28); 1.405 (1.51); 1.397 (1.08); 1.389 (2.02); 1.380 (2.00); 1.373 (0.99); 1.363 (1.45); 1.356 (1.33); 1.344 (3.36); 1.325 (4.24); 1.306 (4.22); 1.289 (3.03); 1.271 (0.87); 0.901 (8.16); 0.891 (1.67); 0.883 (16.00); 0.873 (2.20); 0.864 (6.70); 0.855 (0.81); |
| I-5 | 8.830 (4.68); 8.026 (1.00); 8.020 (0.99); 8.011 (0.63); 8.002 (1.11); 7.949 (0.54); 7.903 (2.25); 7.881 (2.20); 7.607 (0.59); 7.595 (1.70); 7.590 (1.35); 7.586 (1.53); 7.578 (4.14); 7.570 (1.45); 7.567 (1.23); 7.562 (1.24); 7.557 (1.44); 7.549 (0.43); 7.461 (1.72); 7.459 (1.70); 7.443 (1.29); 7.441 (1.26); 7.409 (3.24); 5.688 (1.03); 4.065 (0.70); 4.047 (1.79); 4.029 (1.79); 4.011 (0.65); 3.758 (16.00); 3.510 (5.62); 3.460 (1.14); 3.450 (0.35); 3.441 (0.51); 3.431 (0.89); 3.422 (0.56); 3.413 (0.34); 3.403 (0.48); 3.188 (0.36); 3.170 (0.44); 3.153 (0.58); 3.109 (98.29); 2.887 (4.97); 2.751 (0.53); 2.733 (4.15); 2.526 (0.73); 2.497 (11.23); 2.492 (21.48); 2.488 (29.17); 2.483 (20.61); 2.478 (10.14); 2.170 (0.94); 2.161 (0.87); 2.134 (1.00); 2.040 (0.77); 1.974 (7.34); 1.901 (0.40); 1.693 (0.54); 1.675 (0.54); 1.657 (0.52); 1.389 (1.62); 1.195 (1.98); 1.177 (3.88); 1.159 (1.93); −0.000 (1.12); |
| I-6 | 8.326 (4.86); 7.398 (3.25); 5.688 (2.51); 4.922 (0.46); 4.910 (0.55); 4.900 (0.90); 4.890 (0.57); 4.878 (0.45); 4.065 (0.33); 4.047 (0.77); 4.029 (0.79); 4.012 (0.36); 3.759 (16.00); 3.493 (5.90); 3.368 (0.34); 3.359 (0.55); 3.348 (0.46); 3.340 (0.65); 3.330 (1.08); 3.320 (0.69); 3.312 (0.52); 3.302 (0.70); 3.292 (0.50); 3.146 (1.78); 2.526 (0.43); 2.497 (7.21); 2.493 (13.97); 2.488 (19.11); 2.483 (13.64); 2.479 (6.83); 2.086 (0.86); 2.079 (0.87); 2.053 (0.98); 2.047 (0.96); 1.974 (2.85); 1.901 (9.04); 1.881 (0.83); 1.860 (0.84); 1.852 (0.85); 1.746 (0.70); 1.738 (0.79); 1.730 (0.79); 1.723 (0.86); 1.715 (0.85); 1.572 (0.84); 1.563 (0.83); 1.548 (1.29); 1.540 (1.56); 1.532 (1.07); 1.525 (1.13); 1.517 (1.60); 1.509 (1.12); 1.495 (0.72); 1.486 (0.64); 1.446 (0.37); 1.439 (0.48); 1.423 (0.61); 1.414 (1.04); 1.406 (0.73); 1.398 (0.52); 1.390 (0.95); 1.382 (0.92); 1.375 (0.45); 1.366 (0.38); 1.357 (0.54); 1.351 (0.53); 1.322 (0.46); 1.315 (0.46); 1.291 (0.39); 1.195 (0.78); 1.178 (1.51); 1.160 (0.75); −0.000 (0.86); |
| I-7 | 8.818 (12.52); 8.025 (2.64); 8.020 (2.77); 8.010 (1.66); 8.002 (2.86); 7.900 (4.94); 7.881 (6.58); 7.607 (1.40); 7.595 (5.51); 7.590 (3.49); 7.585 (3.84); 7.577 (10.45); 7.570 (3.77); 7.565 (3.08); 7.561 (3.38); 7.556 (3.90); 7.548 (1.16); 7.458 (4.64); 7.456 (4.69); 7.444 (3.56); 7.437 (6.68); 7.432 (3.85); 7.425 (3.50); 7.253 (3.14); 7.250 (3.35); 7.246 (3.16); 7.243 (2.82); 7.019 (3.78); 7.016 (3.73); 7.007 (3.64); 7.004 (3.64); 4.065 (1.66); 4.047 (4.11); 4.030 (4.03); 4.012 (1.53); 3.746 (12.85); 3.698 (1.94); 3.599 (2.34); 3.570 (1.50); 3.441 (1.47); 3.434 (1.61); 3.424 (1.49); 3.416 (1.63); 3.406 (2.62); 3.396 (1.70); 3.388 (1.00); 3.378 (1.55); 3.368 (0.99); 3.317 (1.12); 3.299 (1.59); 3.283 (1.41); 3.131 (210.09); 3.043 (1.41); 3.033 (1.16); 2.888 (4.59); 2.734 (3.76); 2.528 (1.56); 2.499 (26.76); 2.494 (51.16); 2.489 (69.18); 2.485 (48.91); 2.480 (24.21); 2.276 (2.69); 2.126 (1.96); 2.098 (2.16); 1.974 (16.00); 1.677 (1.40); 1.659 (1.50); 1.615 (2.02); 1.606 (2.16); 1.584 (2.05); 1.577 (1.99); 1.400 (1.39); 1.281 (3.09); 1.263 (3.01); 1.244 (1.01); 1.195 (5.78); 1.178 (9.12); 1.160 (4.17); −0.000 (1.63); |
| I-8 | 8.316 (15.93); 7.439 (3.58); 7.432 (4.36); 7.427 (4.09); 7.419 (4.10); 7.239 (3.48); 7.235 (3.96); 7.233 (3.79); 7.231 (3.79); 7.008 (4.55); 7.005 (4.80); 6.996 (4.42); 6.993 (4.48); 4.906 (1.82); 4.896 (2.96); 4.886 (1.90); 4.048 (2.65); 4.030 (2.71); 3.730 (16.00); 3.699 (2.74); 3.600 (1.97); 3.333 (1.75); 3.314 (2.17); 3.304 (3.67); 3.295 (2.31); 3.286 (1.73); 3.276 (2.12); 3.135 (108.67); 2.889 (6.65); 2.735 (5.69); 2.499 (13.57); 2.495 (26.31); 2.490 (36.01); 2.485 (25.70); 2.481 (12.85); 2.040 (2.71); 2.015 (2.70); 1.974 (9.89); 1.903 (2.79); 1.893 (2.21); 1.878 (2.80); 1.865 (3.08); 1.857 (2.90); 1.848 (3.23); 1.759 (1.78); 1.751 (2.35); 1.744 (2.77); 1.735 (3.17); 1.727 (2.95); 1.719 (3.04); 1.712 (2.88); 1.569 (1.99); 1.561 (2.71); 1.546 (4.47); 1.537 (6.03); 1.530 (5.41); 1.523 (5.89); 1.515 (6.44); 1.506 (5.10); 1.492 (4.42); 1.484 (2.93); 1.436 (1.65); 1.420 (2.05); 1.412 (3.50); 1.403 (2.39); 1.395 (1.66); 1.387 (3.12); 1.379 (3.09); 1.354 (1.92); 1.349 (1.87); 1.314 (1.66); 1.295 (4.27); 1.285 (2.37); 1.280 (6.44); 1.267 (3.28); 1.264 (4.00); 1.196 (2.69); 1.178 (5.23); 1.160 (2.59); |
| I-9 | 8.322 (5.69); 7.340 (0.74); 7.321 (1.97); 7.302 (3.75); 7.275 (1.34); 7.272 (1.56); 7.267 (0.90); 7.255 (0.66); 7.252 (0.63); 7.247 (0.45); 7.209 (1.30); 7.190 (0.96); 5.687 (0.41); 4.920 (0.44); 4.908 (0.55); 4.898 (0.89); 4.888 (0.57); 4.876 (0.46); 4.047 (0.85); 4.029 (0.89); 4.011 (0.39); 3.761 (6.14); 3.727 (1.11); 3.352 (0.49); 3.333 (0.52); 3.323 (0.94); 3.313 (0.58); 3.295 (0.56); 3.181 (0.38); 3.114 (184.58); 3.064 (0.57); 3.053 (0.41); 2.526 (1.32); 2.510 (0.98); 2.497 (16.42); 2.493 (32.78); 2.488 (45.47); 2.484 (32.30); 2.479 (16.00); 2.068 (0.84); 2.063 (0.85); 2.040 (1.72); 1.974 (3.34); 1.878 (0.75); 1.867 (0.81); 1.857 (0.87); 1.849 (0.91); 1.760 (0.44); 1.751 (0.54); 1.745 (0.66); 1.737 (0.70); 1.729 (0.76); 1.721 (0.82); 1.714 (0.82); 1.600 (0.47); 1.590 (0.52); 1.570 (1.08); 1.561 (1.20); 1.545 (1.49); 1.539 (1.99); 1.530 (1.50); 1.515 (1.67); 1.493 (0.74); 1.484 (0.63); 1.438 (0.47); 1.422 (0.59); 1.413 (1.03); 1.404 (0.83); 1.398 (0.48); 1.389 (0.92); 1.381 (0.91); 1.356 (0.53); 1.351 (0.54); 1.322 (0.46); 1.315 (0.46); 1.290 (0.38); 1.195 (0.92); 1.177 (1.81); 1.160 (0.91); −0.000 (3.86); |
| I-10 | 8.825 (3.09); 8.026 (0.58); 8.021 (0.64); 8.010 (0.35); 8.003 (0.61); 7.901 (1.15); 7.882 (1.50); 7.608 (0.32); 7.595 (1.11); 7.590 (0.74); 7.585 (0.82); 7.578 (2.53); 7.571 (0.78); 7.565 (0.64); 7.561 (0.77); 7.557 (0.90); 7.459 (1.05); 7.457 (1.09); 7.440 (0.77); 7.438 (0.73); 7.345 (0.50); 7.325 (1.25); 7.317 (0.77); 7.312 (1.13); 7.306 (1.66); 7.277 (0.85); 7.274 (1.01); 7.270 (0.66); 7.253 (0.44); 7.220 (0.76); 7.201 (0.55); 4.065 (0.35); 4.047 (0.90); 4.029 (0.85); 4.011 (0.33); 3.778 (3.47); 3.727 (0.81); 3.425 (0.54); 3.398 (0.34); 3.116 (198.58); 2.526 (1.61); 2.510 (1.25); 2.497 (17.37); 2.493 (34.14); 2.488 (46.95); 2.483 (32.98); 2.479 (16.00); 2.151 (0.48); 2.117 (0.56); 1.974 (3.51); 1.658 (0.44); 1.650 (0.44); 1.633 (0.34); 1.624 (0.48); 1.195 (1.17); 1.177 (2.04); 1.160 (0.95); −0.000 (3.66); |
| I-13 | 8.340 (16.00); 7.828 (3.30); 7.807 (3.60); 7.691 (4.25); 7.686 (4.54); 7.532 (2.35); 7.527 (2.54); 7.511 (2.01); 7.506 (2.14); 5.688 (15.00); 4.929 (1.17); 4.917 (1.29); 4.907 (2.31); 4.897 (1.41); 4.885 (1.14); 3.983 (3.97); 3.860 (2.85); 3.847 (1.33); 3.549 (0.93); 3.410 (1.06); 3.391 (1.19); 3.381 (2.22); 3.371 (1.27); 3.363 (0.84); 3.353 (1.27); 3.343 (1.04); 3.324 (1.09); 3.112 (169.11); 2.527 (1.49); 2.506 (1.10); 2.498 (18.57); 2.493 (38.66); 2.489 (54.80); 2.484 (38.20); 2.479 (18.19); 2.126 (1.32); 2.102 (1.47); 1.974 (1.67); 1.901 (2.27); 1.896 (1.58); 1.893 (1.57); 1.886 (1.76); 1.880 (1.63); 1.874 (1.73); 1.870 (1.71); 1.865 (1.81); 1.857 (1.96); 1.848 (1.13); 1.766 (1.24); 1.760 (1.51); 1.751 (1.84); 1.743 (1.97); 1.734 (2.06); 1.727 (2.23); 1.719 (2.26); 1.578 (1.18); 1.569 (1.16); 1.554 (2.35); 1.546 (3.07); 1.531 (2.19); 1.522 (3.38); 1.513 (2.46); 1.500 (1.60); 1.492 (1.42); 1.442 (1.12); 1.427 (1.36); 1.418 (2.53); 1.413 (2.25); 1.402 (1.03); 1.394 (2.20); 1.386 (2.18); 1.378 (0.92); 1.361 (1.20); 1.355 (1.15); 1.349 (1.06); 1.327 (1.00); 1.320 (1.04); 1.296 (0.91); 1.178 (0.95); −0.000 (3.63); |
| I-14 | 8.408 (0.05); 8.406 (0.04); 7.470 (0.02); 7.449 (0.03); 7.437 (0.02); 7.431 (0.02); 7.371 (0.02); 7.364 (0.01); 7.349 (0.01); 7.343 (0.01); 5.732 (0.03); 5.729 (0.03); 3.885 (0.02); 3.864 (0.02); 3.641 (0.04); 3.636 (0.03); 3.540 (16.00); 3.537 (13.32); 3.484 (0.05); 3.475 (0.05); 3.436 (0.02); 3.420 (0.01); 3.410 (0.01); 3.401 (0.01); 3.391 (0.01); 3.381 (0.01); 3.372 (0.01); 2.538 (0.01); 2.525 (0.20); 2.521 (0.43); 2.516 (0.59); 2.512 (0.44); 2.508 (0.21); 1.885 (0.01); 1.738 (0.01); 1.730 (0.01); 1.712 (0.01); 1.548 (0.01); 1.531 (0.01); 1.523 (0.01); 1.508 (0.01); 1.500 (0.01); −0.000 (0.09); |

| Ex. | NMR Data |
|---|---|
| I-16 | 8.345 (14.29); 7.925 (2.07); 7.904 (2.84); 7.825 (2.33); 7.807 (5.74); 5.688 (16.00); 4.933 (0.98); 4.920 (1.08); 4.911 (1.91); 4.901 (1.15); 4.889 (0.94); 4.066 (0.94); 4.048 (4.34); 4.030 (1.10); 3.924 (0.94); 3.509 (0.60); 3.412 (0.28); 3.402 (0.56); 3.393 (0.94); 3.383 (1.75); 3.374 (0.99); 3.365 (0.64); 3.355 (0.99); 3.345 (0.57); 3.314 (0.71); 3.117 (77.91); 2.500 (8.77); 2.495 (18.33); 2.490 (26.00); 2.485 (18.09); 2.481 (8.59); 2.124 (1.01); 2.101 (1.11); 1.975 (2.22); 1.913 (0.63); 1.903 (1.37); 1.898 (1.25); 1.888 (1.41); 1.883 (1.31); 1.873 (1.38); 1.868 (1.48); 1.859 (1.57); 1.850 (0.89); 1.768 (0.96); 1.761 (1.15); 1.753 (1.43); 1.745 (1.56); 1.737 (1.64); 1.729 (1.78); 1.721 (1.81); 1.581 (1.06); 1.572 (1.03); 1.557 (2.11); 1.549 (2.59); 1.535 (1.96); 1.526 (2.75); 1.517 (1.91); 1.504 (1.50); 1.495 (1.21); 1.452 (0.68); 1.444 (0.90); 1.429 (1.12); 1.420 (2.08); 1.413 (1.46); 1.403 (2.99); 1.396 (1.83); 1.387 (1.82); 1.380 (0.75); 1.372 (0.65); 1.363 (0.99); 1.357 (0.94); 1.351 (0.87); 1.343 (0.55); 1.328 (0.83); 1.321 (0.85); 1.297 (0.73); 1.196 (0.68); 1.179 (1.27); 1.161 (0.67); −0.000 (1.77); |
| I-17 | 8.335 (8.17); 7.303 (0.78); 7.298 (1.97); 7.290 (2.46); 7.284 (3.23); 7.276 (1.01); 7.115 (1.81); 7.104 (0.71); 7.093 (1.47); 5.687 (2.09); 4.925 (0.58); 4.913 (0.64); 4.903 (1.14); 4.894 (0.67); 4.881 (0.55); 4.047 (0.81); 4.029 (0.80); 3.728 (4.35); 3.606 (1.96); 3.486 (0.66); 3.382 (0.53); 3.363 (0.60); 3.353 (1.11); 3.343 (0.64); 3.334 (0.68); 3.325 (0.70); 3.316 (0.86); 3.118 (107.81); 2.527 (0.72); 2.506 (0.69); 2.498 (10.83); 2.493 (22.54); 2.489 (31.96); 2.484 (22.20); 2.479 (10.51); 2.162 (16.00); 2.143 (0.56); 2.104 (0.95); 2.098 (0.97); 2.072 (1.12); 2.066 (1.06); 1.974 (3.12); 1.901 (1.10); 1.889 (1.08); 1.872 (0.93); 1.862 (0.90); 1.854 (0.94); 1.762 (0.53); 1.757 (0.64); 1.749 (0.75); 1.741 (0.82); 1.732 (0.85); 1.724 (0.93); 1.717 (0.94); 1.575 (0.72); 1.566 (0.68); 1.551 (1.21); 1.543 (1.58); 1.533 (0.96); 1.528 (1.10); 1.519 (1.73); 1.511 (1.22); 1.497 (0.76); 1.489 (0.70); 1.440 (0.53); 1.424 (0.65); 1.416 (1.22); 1.408 (0.76); 1.404 (0.77); 1.392 (1.08); 1.383 (1.06); 1.359 (0.57); 1.352 (0.54); 1.292 (0.91); 1.277 (0.91); 1.263 (0.90); 1.195 (0.91); 1.178 (1.84); 1.160 (0.90); −0.000 (2.28); |
| I-18 | 8.342 (12.37); 7.698 (2.53); 7.678 (3.08); 7.526 (2.04); 7.524 (1.91); 7.505 (6.07); 4.930 (0.92); 4.918 (1.02); 4.908 (1.79); 4.898 (1.08); 4.886 (0.89); 4.065 (0.83); 4.047 (2.13); 4.029 (2.14); 4.011 (0.84); 3.928 (4.41); 3.806 (0.52); 3.403 (0.80); 3.393 (0.52); 3.385 (0.90); 3.375 (1.68); 3.365 (0.95); 3.356 (0.61); 3.346 (0.94); 3.111 (247.02); 2.657 (0.52); 2.511 (1.11); 2.506 (1.52); 2.498 (26.57); 2.493 (55.40); 2.488 (78.58); 2.484 (54.88); 2.479 (26.25); 2.117 (1.07); 2.089 (1.18); 1.974 (8.77); 1.901 (1.30); 1.887 (1.33); 1.880 (1.25); 1.874 (1.30); 1.871 (1.29); 1.866 (1.40); 1.857 (1.49); 1.849 (0.81); 1.766 (0.84); 1.760 (1.03); 1.751 (1.29); 1.744 (1.39); 1.735 (1.50); 1.727 (1.65); 1.719 (1.68); 1.579 (1.03); 1.570 (1.00); 1.556 (1.99); 1.547 (2.44); 1.533 (1.82); 1.524 (2.55); 1.515 (1.82); 1.502 (1.37); 1.493 (1.11); 1.451 (0.67); 1.443 (0.86); 1.427 (1.08); 1.419 (1.99); 1.410 (1.45); 1.404 (16.00); 1.395 (1.97); 1.386 (1.72); 1.379 (0.73); 1.370 (0.61); 1.362 (0.94); 1.356 (0.90); 1.350 (0.84); 1.327 (0.79); 1.320 (0.81); 1.296 (0.68); 1.195 (2.57); 1.178 (5.18); 1.160 (2.53); −0.000 (1.65); |
| I-19 | 8.335 (8.65); 7.472 (1.02); 7.467 (2.03); 7.462 (1.84); 7.458 (2.52); 7.452 (3.81); 7.446 (1.01); 6.969 (1.81); 6.968 (1.81); 6.960 (0.74); 6.947 (1.72); 5.688 (5.81); 4.925 (0.64); 4.913 (0.71); 4.903 (1.23); 4.893 (0.75); 4.881 (0.62); 4.047 (0.96); 4.029 (0.99); 3.698 (3.47); 3.576 (2.31); 3.480 (0.81); 3.361 (0.62); 3.351 (1.15); 3.341 (0.90); 3.332 (0.64); 3.323 (0.76); 3.312 (1.03); 3.112 (177.24); 2.526 (1.04); 2.510 (0.74); 2.506 (1.02); 2.497 (15.73); 2.493 (32.74); 2.488 (46.45); 2.483 (32.35); 2.479 (15.39); 2.183 (0.60); 2.161 (1.29); 2.151 (16.00); 2.101 (1.05); 2.095 (1.07); 2.069 (1.24); 2.062 (1.19); 1.974 (3.86); 1.901 (1.53); 1.886 (1.29); 1.869 (1.05); 1.863 (1.00); 1.854 (1.05); 1.846 (0.58); 1.788 (0.57); 1.756 (0.69); 1.749 (0.82); 1.740 (0.88); 1.732 (0.93); 1.725 (0.99); 1.717 (1.01); 1.575 (0.84); 1.566 (0.80); 1.551 (1.37); 1.543 (1.76); 1.528 (1.22); 1.520 (1.90); 1.511 (1.34); 1.497 (0.85); 1.488 (0.77); 1.440 (0.60); 1.424 (0.73); 1.416 (1.35); 1.408 (0.86); 1.404 (0.64); 1.391 (1.16); 1.383 (1.17); 1.359 (0.64); 1.353 (0.62); 1.195 (1.17); 1.177 (2.26); 1.160 (1.13); −0.000 (3.04); |
| I-20 | 8.320 (11.08); 6.493 (4.42); 6.491 (4.51); 5.687 (4.37); 4.919 (0.84); 4.907 (0.94); 4.898 (1.64); 4.888 (0.99); 4.876 (0.80); 3.517 (6.35); 3.486 (0.49); 3.436 (0.67); 3.419 (1.28); 3.401 (0.87); 3.394 (3.91); 3.338 (0.81); 3.327 (0.53); 3.319 (0.89); 3.309 (1.78); 3.299 (1.16); 3.286 (1.38); 3.281 (1.24); 3.270 (1.00); 3.117 (179.61); 2.511 (0.44); 2.506 (0.63); 2.498 (10.25); 2.493 (21.22); 2.489 (30.04); 2.484 (21.00); 2.479 (10.08); 2.316 (14.91); 2.253 (16.00); 2.240 (5.26); 2.040 (1.38); 2.011 (1.40); 1.974 (0.52); 1.894 (1.04); 1.885 (1.51); 1.867 (1.97); 1.857 (1.47); 1.850 (1.99); 1.840 (0.85); 1.776 (0.74); 1.759 (1.44); 1.743 (1.37); 1.739 (1.40); 1.729 (1.24); 1.721 (1.36); 1.713 (1.31); 1.569 (0.76); 1.559 (1.43); 1.547 (2.19); 1.538 (2.40); 1.530 (2.89); 1.515 (3.40); 1.506 (1.83); 1.497 (2.13); 1.490 (2.03); 1.487 (1.92); 1.468 (0.70); 1.457 (0.60); 1.445 (0.60); 1.437 (0.79); 1.421 (0.98); 1.413 (1.80); 1.405 (1.10); 1.396 (0.71); 1.388 (1.55); 1.380 (1.54); 1.372 (0.64); 1.364 (0.56); 1.355 (0.84); 1.349 (0.79); 1.335 (0.45); 1.321 (0.69); 1.314 (0.74); 1.298 (0.44); 1.289 (0.61); −0.000 (1.24); |
| I-22 | 8.320 (7.94); 7.900 (3.02); 7.895 (2.20); 7.893 (2.12); 7.890 (1.30); 7.886 (1.23); 7.884 (1.47); 7.880 (3.55); 7.876 (3.45); 7.495 (1.05); 7.491 (0.82); 7.483 (2.86); 7.482 (2.96); 7.478 (1.80); 7.471 (2.61); 7.469 (3.16); 7.466 (4.68); 7.463 (4.70); 7.461 (2.57); 7.457 (0.72); 7.453 (0.92); 7.449 (0.74); 5.687 (6.02); 4.918 (0.62); 4.906 (0.68); 4.896 (1.18); 4.886 (0.69); 3.637 (1.87); 3.512 (0.98); 3.352 (0.62); 3.347 (1.17); 3.338 (0.68); 3.329 (0.62); 3.319 (0.73); 3.310 (0.67); 3.145 (0.82); 3.116 (280.09); 2.511 (0.74); 2.506 (1.07); 2.498 (18.61); 2.493 (38.58); 2.489 (54.93); 2.484 (38.45); 2.479 (18.40); 2.340 (16.00); 2.324 (2.22); 2.099 (0.84); 2.069 (0.96); 1.974 (2.20); 1.888 (0.90); 1.876 (0.90); 1.871 (0.90); 1.855 (0.95); 1.846 (0.98); 1.752 (0.76); 1.744 (0.92); 1.735 (0.99); 1.727 (1.04); 1.719 (1.13); 1.712 (1.15); 1.565 (0.70); 1.556 (0.78); 1.541 (1.37); 1.533 (1.60); 1.510 (1.84); 1.501 (1.15); 1.487 (0.73); 1.479 (0.67); 1.419 (0.67); 1.411 (1.27); 1.404 (0.84); 1.387 (1.11); 1.379 (1.13); 1.292 (1.04); 1.277 (1.33); 1.262 (1.16); 1.195 (0.67); 1.178 (1.30); 1.160 (0.64); −0.000 (0.94); |
| I-23 | 8.818 (7.72); 8.026 (1.17); 8.022 (1.56); 8.009 (0.84); 8.003 (1.33); 7.903 (1.71); 7.894 (1.17); 7.892 (1.21); 7.882 (1.99); 7.876 (1.42); 7.874 (1.22); 7.872 (1.08); 7.870 (1.22); 7.832 (2.60); 7.828 (3.27); 7.823 (1.12); 7.816 (1.80); 7.812 (3.47); 7.808 (2.93); 7.802 (0.53); 7.610 (0.51); 7.606 (0.70); 7.597 (1.79); 7.593 (1.74); 7.589 (1.46); 7.578 (3.99); 7.575 (3.25); 7.573 (2.49); 7.569 (1.66); 7.561 (0.85); 7.557 (2.96); 7.555 (1.61); 7.541 (0.59); 7.456 (2.98); 7.453 (3.37); 7.447 (0.86); 7.441 (1.14); 7.437 (4.51); 7.435 (5.43); 7.431 (1.82); 7.430 (1.55); 7.420 (1.60); 7.417 (3.11); 7.415 (2.35); 7.409 (1.29); 7.405 (2.33); 7.401 (1.30); 7.394 (0.63); 7.387 (1.51); 7.369 (0.47); 5.690 (10.05); 4.047 (0.72); 4.029 (0.73); 3.868 (0.65); 3.849 (0.67); 3.731 (0.51); 3.701 (0.52); 3.453 (0.52); 3.444 (0.98); 3.434 (0.55); 3.415 (0.53); 3.115 (65.03); 2.506 (0.58); 2.497 (9.26); 2.493 (19.16); 2.488 (27.00); 2.483 (18.86); 2.479 (9.02); 2.424 (16.00); 2.407 (1.09); 2.399 (1.08); 2.175 (0.93); 2.169 (0.96); 2.143 (1.11); 2.137 (1.06); 1.974 (3.35); 1.195 (0.93); 1.177 (1.90); 1.159 (0.93); −0.000 (1.94); |
| I-24 | 8.826 (8.23); 8.026 (1.25); 8.022 (1.68); 8.010 (0.86); 8.003 (1.43); 7.904 (4.89); 7.899 (4.27); 7.894 (2.02); 7.891 (1.19); 7.883 (5.70); 7.880 (5.34); 7.875 (1.63); 7.610 (0.52); 7.606 (0.73); 7.597 (1.89); 7.593 (1.82); 7.589 (1.56); 7.578 (3.61); 7.576 (3.49); 7.569 (1.78); 7.562 (0.90); 7.558 (2.91); 7.542 (0.62); 7.538 (0.46); 7.494 (0.95); 7.490 (0.77); 7.487 (1.20); 7.483 (0.70); 7.479 (0.73); 7.472 (3.52); 7.469 (1.73); 7.464 (1.14); 7.458 (4.52); 7.456 (5.21); 7.454 (4.86); 7.453 (4.45); 7.447 (2.21); 7.443 (0.99); 7.439 (2.14); 7.437 (2.88); 7.435 (1.40); 7.417 (0.37); 5.690 (10.09); 4.047 (0.87); 4.029 (0.88); 3.652 (0.83); 3.487 (0.70); 3.476 (0.32); 3.467 (0.35); 3.458 (0.57); 3.448 (1.06); 3.438 (0.59); 3.430 (0.37); 3.420 (0.57); 3.118 (63.22); 2.887 (0.61); 2.733 (0.39); 2.511 (0.42); 2.506 (0.64); 2.498 (9.29); 2.493 (19.23); 2.489 (27.08); 2.484 (18.89); 2.479 (9.02); 2.347 (16.00); 2.341 (1.58); 2.327 (0.56); 2.183 (0.88); 2.146 (0.97); 1.974 (4.03); 1.195 (1.15); 1.177 (2.30); 1.159 (1.11); −0.000 (2.84); |
| I-25 | 8.824 (10.79); 8.026 (1.80); 8.020 (2.02); 8.010 (1.06); 8.002 (1.94); 7.901 (3.88); 7.894 (0.98); 7.882 (4.36); 7.879 (3.03); 7.611 (0.55); 7.606 (0.84); 7.595 (2.90); 7.594 (2.83); 7.589 (2.03); 7.584 (2.36); 7.577 (8.26); 7.570 (2.24); 7.567 (1.28); 7.564 (1.89); 7.560 (2.42); 7.556 (2.88); 7.547 (0.79); 7.543 (0.54); 7.459 (3.17); 7.457 (3.21); 7.440 (2.38); 7.438 (2.25); 6.507 (3.60); 6.505 (3.60); 6.493 (0.42); 5.689 (12.66); 4.047 (0.48); 4.029 (0.51); 3.534 (6.52); 3.448 (0.38); 3.438 (0.83); 3.428 (0.53); 3.419 (1.12); 3.410 (1.63); 3.400 (1.17); 3.393 (1.63); 3.382 (0.84); 3.372 (0.45); 3.286 (0.47); 3.269 (0.32); 3.118 (55.30); 2.886 (0.42); 2.510 (0.32); 2.505 (0.48); 2.497 (7.69); 2.493 (15.95); 2.488 (22.55); 2.483 (15.84); 2.478 (7.65); 2.316 (14.53); 2.240 (1.97); 2.120 (1.25); 2.093 (1.39); 1.974 (1.73); 1.645 (0.73); 1.634 (0.87); 1.615 (1.59); 1.605 (1.71); 1.583 (1.60); 1.572 (1.43); 1.554 (0.73); 1.543 (0.62); 1.195 (0.51); 1.177 (0.98); 1.159 (0.49); −0.000 (1.62); |
| I-26 | 8.826 (6.65); 8.106 (0.60); 8.027 (1.15); 8.021 (1.13); 8.011 (0.69); 8.003 (1.28); 7.903 (2.45); 7.897 (0.63); 7.882 (2.46); 7.881 (2.47); 7.607 (0.52); 7.597 (1.69); 7.595 (1.66); 7.590 (1.36); 7.586 (1.56); 7.578 (5.15); 7.571 (1.50); 7.566 (1.32); 7.562 (1.36); 7.558 (1.65); 7.549 (0.46); 7.545 (0.33); 7.462 (1.98); 7.460 (1.98); 7.444 (1.54); 7.441 (1.49); 5.689 (11.82); 3.726 (1.06); 3.668 (0.36); 3.659 (0.36); 3.652 (0.84); 3.642 (0.83); 3.635 (1.13); 3.625 (1.09); 3.619 (0.87); 3.609 (0.81); 3.602 (0.35); 3.452 (0.44); 3.433 (0.51); 3.423 (0.94); 3.413 (0.51); 3.405 (0.33); 3.395 (0.51); 3.171 (6.93); 3.153 (2.88); 3.142 (2.14); 3.135 (1.95); 3.124 (1.76); 3.116 (0.74); 3.105 (0.65); 3.034 (0.33); 3.024 (0.33); 2.526 (12.18); 2.526 (12.18); 2.506 (0.36); 2.498 (5.19); 2.493 (10.72); 2.488 (15.10); 2.484 (10.56); 2.479 (5.04); |

| Ex. | NMR Data |
|---|---|
| | 2.307 (10.78); 2.287 (0.48); 2.223 (1.06); 2.221 (1.03); 2.133 (0.89); 2.126 (0.91); 2.101 (1.04); 2.095 (0.98); 1.974 (0.95); 1.734 (0.44); 1.650 (0.41); 1.643 (0.42); 1.291 (10.06); 1.282 (4.29); 1.276 (16.00); 1.263 (7.89); 1.260 (10.66); 1.245 (2.99); 1.177 (0.54); −0.000 (1.76); |
| I-27 | 8.328 (3.99); 5.689 (5.11); 4.900 (0.56); 3.758 (0.66); 3.665 (0.89); 3.656 (1.31); 3.649 (2.82); 3.633 (11.06); 3.623 (7.35); 3.606 (1.64); 3.599 (0.76); 3.590 (0.54); 3.334 (0.58); 3.325 (0.36); 3.168 (0.65); 3.157 (0.66); 3.149 (1.95); 3.138 (1.91); 3.131 (1.99); 3.120 (1.91); 3.112 (0.66); 3.102 (0.62); 3.065 (1.47); 3.062 (0.62); 3.059 (0.92); 3.055 (2.27); 3.049 (3.93); 3.045 (1.72); 3.043 (1.73); 3.039 (3.91); 3.032 (2.26); 3.029 (0.84); 3.022 (1.46); 2.579 (7.00); 2.507 (0.44); 2.499 (6.28); 2.494 (12.91); 2.489 (18.14); 2.484 (12.62); 2.480 (6.00); 2.318 (6.29); 2.065 (0.50); 2.058 (0.51); 2.041 (0.42); 2.033 (0.59); 2.026 (0.56); 1.891 (0.38); 1.882 (0.42); 1.860 (0.45); 1.854 (0.46); 1.764 (2.17); 1.756 (2.26); 1.747 (5.50); 1.740 (2.36); 1.731 (2.34); 1.715 (0.64); 1.707 (0.39); 1.572 (0.42); 1.563 (0.45); 1.548 (0.76); 1.540 (0.90); 1.532 (0.62); 1.525 (0.65); 1.516 (0.96); 1.495 (0.40); 1.485 (0.37); 1.423 (0.39); 1.414 (0.63); 1.407 (0.39); 1.390 (0.54); 1.382 (0.54); 1.314 (0.39); 1.302 (12.41); 1.292 (4.58); 1.284 (15.46); 1.283 (16.00); 1.274 (7.88); 1.266 (12.80); 1.255 (3.60); −0.000 (1.24); |
| I-28 | 8.846 (2.60); 8.029 (0.49); 8.023 (0.42); 8.005 (0.56); 7.906 (1.06); 7.884 (1.18); 7.600 (0.71); 7.597 (0.72); 7.592 (0.67); 7.590 (0.79); 7.581 (2.15); 7.573 (0.73); 7.570 (0.61); 7.565 (0.59); 7.561 (0.71); 7.466 (0.84); 7.464 (1.18); 7.447 (0.65); 7.445 (0.64); 5.690 (6.95); 5.115 (0.41); 3.651 (0.66); 3.641 (0.65); 3.635 (0.91); 3.625 (0.86); 3.618 (0.70); 3.608 (0.65); 3.473 (0.42); 3.315 (0.40); 3.311 (0.47); 3.307 (0.42); 3.294 (0.43); 3.254 (3.37); 3.171 (0.44); 3.160 (0.45); 3.152 (1.21); 3.141 (1.21); 3.134 (1.23); 3.123 (1.21); 3.115 (0.45); 3.105 (0.41); 3.051 (3.08); 3.048 (1.37); 3.044 (2.00); 3.041 (4.90); 3.034 (8.46); 3.031 (3.92); 3.028 (3.95); 3.024 (8.48); 3.018 (5.08); 3.014 (2.02); 3.008 (3.23); 2.999 (0.35); 2.497 (3.17); 2.493 (6.52); 2.488 (9.19); 2.483 (6.50); 2.479 (3.16); 2.275 (7.72); 2.200 (0.33); 2.174 (7.65); 2.166 (1.03); 2.160 (0.53); 1.958 (0.35); 1.766 (0.47); 1.751 (4.53); 1.742 (4.47); 1.734 (11.49); 1.726 (4.49); 1.717 (4.37); 1.702 (0.49); 1.295 (8.19); 1.285 (3.35); 1.278 (16.00); 1.267 (5.86); 1.262 (8.57); 1.248 (2.43); −0.000 (1.52); |
| I-36 | 8.916 (2.04); 8.912 (2.13); 8.906 (2.25); 8.902 (2.16); 8.875 (1.69); 8.871 (1.91); 8.865 (1.99); 8.861 (1.92); 8.570 (2.38); 8.566 (3.28); 8.555 (3.15); 8.552 (2.39); 8.444 (2.05); 8.441 (2.77); 8.438 (1.79); 8.424 (2.24); 8.420 (2.91); 8.417 (1.72); 8.065 (5.68); 7.941 (2.38); 7.936 (2.91); 7.922 (2.16); 7.917 (2.79); 7.778 (1.54); 7.763 (1.38); 7.759 (3.14); 7.754 (1.27); 7.740 (1.87); 7.656 (1.73); 7.652 (2.71); 7.637 (4.13); 7.633 (2.69); 7.627 (2.84); 7.622 (2.98); 7.618 (7.13); 7.613 (6.21); 7.608 (1.38); 7.603 (3.03); 7.599 (1.40); 7.593 (3.89); 7.582 (3.50); 7.572 (1.73); 7.562 (1.63); 7.414 (1.28); 7.387 (1.15); 7.373 (4.13); 7.369 (2.70); 7.362 (2.47); 7.359 (4.16); 7.354 (3.63); 7.350 (2.21); 7.343 (2.21); 7.340 (3.64); 6.541 (3.06); 6.462 (2.55); 5.688 (6.36); 5.596 (11.79); 5.267 (6.01); 3.692 (2.00); 3.117 (361.56); 2.888 (1.84); 2.733 (1.60); 2.657 (1.33); 2.527 (2.12); 2.511 (3.69); 2.506 (5.05); 2.498 (72.66); 2.493 (149.60); 2.488 (210.69); 2.484 (146.89); 2.479 (70.03); 2.467 (16.00); 2.466 (15.65); 2.315 (1.30); 2.258 (1.68); 2.256 (1.72); 2.236 (10.12); 2.234 (10.07); 2.040 (5.37); −0.000 (17.78); |
| I-37 | 8.076 (9.48); 7.753 (3.46); 7.747 (3.62); 7.518 (1.96); 7.512 (1.79); 7.497 (4.00); 7.491 (3.96); 7.459 (5.85); 7.438 (2.67); 6.459 (3.62); 5.688 (12.82); 5.258 (9.74); 5.222 (0.36); 4.064 (0.45); 4.047 (1.36); 4.029 (1.40); 4.011 (0.46); 3.675 (2.84); 3.578 (1.57); 3.112 (162.99); 2.657 (0.34); 2.526 (0.64); 2.510 (0.82); 2.505 (1.22); 2.497 (19.87); 2.493 (41.04); 2.488 (57.99); 2.483 (40.44); 2.478 (19.28); 2.315 (0.33); 2.230 (16.00); 2.229 (15.89); 2.198 (0.93); 2.040 (1.07); 1.974 (6.34); 1.195 (1.86); 1.177 (3.74); 1.160 (1.79); 0.008 (0.33); −0.000 (10.58); −0.008 (0.33); |
| I-39 | 8.059 (8.89); 7.604 (1.88); 7.600 (1.96); 7.584 (2.19); 7.580 (2.26); 7.455 (0.78); 7.451 (0.81); 7.437 (1.19); 7.434 (1.78); 7.431 (1.76); 7.417 (2.53); 7.413 (2.36); 7.396 (2.49); 7.392 (3.48); 7.376 (1.47); 7.372 (1.16); 7.359 (2.03); 7.354 (1.61); 7.341 (1.57); 7.339 (1.86); 7.336 (1.42); 7.334 (1.53); 7.321 (1.17); 7.316 (1.01); 6.460 (3.56); 5.686 (4.33); 5.259 (9.73); 4.065 (0.85); 4.047 (2.58); 4.029 (2.60); 4.011 (0.89); 3.679 (2.83); 3.578 (1.51); 3.127 (357.80); 3.104 (3.10); 2.511 (0.58); 2.507 (0.84); 2.499 (13.08); 2.494 (27.02); 2.489 (38.10); 2.484 (26.59); 2.480 (12.69); 2.232 (15.92); 2.230 (16.00); 2.200 (0.68); 1.974 (11.80); 1.404 (1.33); 1.195 (3.42); 1.178 (6.93); 1.160 (3.39); −0.000 (1.11); |
| I-40 | 8.055 (9.05); 8.005 (2.47); 7.983 (2.71); 7.971 (1.46); 7.953 (1.49); 7.949 (1.42); 7.937 (1.34); 7.933 (1.40); 7.914 (1.57); 7.766 (2.56); 7.761 (2.63); 7.575 (0.58); 7.571 (0.78); 7.558 (1.87); 7.554 (2.13); 7.544 (2.13); 7.542 (2.59); 7.538 (2.70); 7.534 (1.76); 7.524 (1.61); 7.520 (1.85); 7.507 (0.75); 7.503 (0.54); 7.407 (2.23); 7.401 (2.12); 7.385 (2.10); 7.379 (2.05); 6.463 (3.58); 5.688 (10.03); 5.265 (9.68); 4.047 (0.92); 4.029 (0.91); 3.689 (2.89); 3.594 (1.56); 3.119 (403.30); 2.662 (0.38); 2.658 (0.48); 2.653 (0.34); 2.511 (1.18); 2.506 (1.73); 2.498 (26.27); 2.493 (54.16); 2.488 (76.31); 2.484 (53.30); 2.479 (25.44); 2.320 (0.33); 2.315 (0.48); 2.236 (15.84); 2.234 (16.00); 2.201 (0.52); 2.040 (1.31); 1.974 (4.10); 1.195 (1.24); 1.177 (2.40); 1.160 (1.21); −0.000 (0.92); |
| I-47 | 7.797 (2.97); 7.793 (7.88); 7.792 (7.88); 7.660 (2.88); 7.639 (3.85); 7.529 (2.11); 7.528 (2.15); 7.524 (2.03); 7.523 (2.01); 7.509 (1.57); 7.507 (1.60); 7.503 (1.51); 7.502 (1.47); 6.464 (3.59); 5.690 (5.99); 5.689 (5.80); 5.269 (8.95); 5.233 (0.37); 4.047 (0.64); 4.029 (0.64); 3.697 (3.18); 3.594 (1.65); 3.112 (130.20); 2.526 (0.66); 2.497 (16.88); 2.493 (31.87); 2.489 (42.91); 2.484 (31.22); 2.480 (15.81); 2.316 (0.37); 2.236 (16.00); 2.203 (0.76); 1.974 (2.71); 1.195 (0.74); 1.178 (1.41); 1.177 (1.47); 1.160 (0.73); 0.001 (1.51); −0.000 (1.56); |
| I-50 | 7.728 (8.04); 7.581 (3.01); 7.576 (3.16); 7.547 (3.05); 7.527 (3.86); 7.391 (2.45); 7.385 (2.32); 7.370 (1.91); 7.364 (1.80); 6.453 (3.71); 5.689 (8.61); 5.244 (9.88); 5.208 (0.32); 4.269 (11.32); 4.065 (0.53); 4.047 (1.58); 4.029 (1.62); 4.011 (0.55); 3.654 (3.17); 3.530 (1.72); 3.109 (93.11); 2.526 (0.66); 2.510 (0.90); 2.497 (14.93); 2.493 (29.66); 2.488 (41.08); 2.483 (28.89); 2.479 (14.03); 2.220 (16.00); 2.219 (15.92); 2.193 (0.77); 1.974 (7.26); 1.403 (0.52); 1.195 (2.01); 1.178 (4.05); 1.160 (1.99); −0.000 (6.20); |
| I-54 | 7.715 (8.71); 6.504 (3.89); 5.744 (5.54); 5.305 (7.80); 5.263 (0.37); 4.828 (0.31); 4.812 (1.30); 4.796 (2.01); 4.780 (1.33); 4.765 (0.34); 4.040 (0.87); 4.022 (0.88); 4.004 (0.31); 3.668 (2.12); 3.656 (2.05); 3.623 (2.26); 3.609 (1.77); 3.573 (1.83); 3.561 (2.10); 3.473 (1.85); 3.460 (2.25); 3.329 (596.33); 3.306 (6.50); 2.891 (0.45); 2.733 (0.39); 2.676 (0.33); 2.671 (0.41); 2.667 (0.31); 2.524 (2.00); 2.511 (22.75); 2.506 (40.65); 2.502 (51.31); 2.498 (34.94); 2.493 (16.59); 2.333 (0.31); 2.329 (0.38); 2.215 (15.00); 2.197 (0.96); 2.069 (0.34); 1.987 (3.83); 1.778 (0.81); 1.729 (1.47); 1.721 (1.34); 1.696 (2.41); 1.670 (0.92); 1.641 (0.89); 1.613 (0.79); 1.552 (0.36); 1.544 (0.38); 1.524 (0.70); 1.516 (0.69); 1.508 (0.68); 1.495 (0.48); 1.487 (0.41); 1.480 (0.37); 1.398 (0.43); 1.270 (0.31); 1.242 (0.97); 1.214 (10.18); 1.198 (9.45); 1.194 (2.79); 1.181 (1.46); 1.176 (3.05); 1.158 (2.24); 1.134 (0.82); 1.102 (0.54); 1.088 (0.38); 1.075 (0.55); 1.047 (1.07); 1.016 (1.28); 0.987 (0.80); 0.008 (0.65); −0.000 (11.51); −0.008 (0.39); |
| I-55 | 8.410 (7.80); 8.248 (2.73); 8.245 (2.48); 8.235 (2.82); 8.233 (2.42); 7.904 (2.95); 7.901 (2.66); 7.894 (2.85); 7.891 (2.54); 7.345 (2.71); 7.335 (3.23); 7.333 (3.20); 7.323 (2.79); 4.899 (0.87); 4.889 (1.32); 4.879 (0.87); 4.468 (0.92); 4.435 (0.95); 4.058 (1.17); 4.040 (3.47); 4.023 (3.49); 4.005 (1.20); 3.615 (0.85); 3.580 (1.09); 3.432 (0.87); 3.423 (1.40); 3.414 (0.91); 3.395 (0.99); 3.347 (1.11); 3.340 (1.40); 3.307 (73.61); 3.284 (1.60); 3.276 (1.13); 3.062 (1.11); 3.056 (1.18); 2.994 (3.40); 2.916 (3.44); 2.541 (0.95); 2.524 (0.88); 2.511 (9.70); 2.507 (17.17); 2.502 (21.55); 2.498 (14.94); 2.493 (7.38); 2.181 (1.15); 2.069 (0.86); 1.988 (15.00); 1.910 (1.23); 1.882 (1.41); 1.861 (1.56); 1.854 (1.55); 1.756 (1.32); 1.748 (1.80); 1.740 (1.55); 1.727 (2.10); 1.717 (2.19); 1.709 (1.70); 1.698 (1.48); 1.621 (0.96); 1.611 (1.00); 1.589 (0.87); 1.550 (1.26); 1.542 (1.25); 1.526 (1.96); 1.519 (2.16); 1.495 (2.24); 1.472 (0.90); 1.464 (0.87); 1.411 (1.18); 1.403 (1.73); 1.397 (1.44); 1.385 (0.94); 1.378 (1.47); 1.371 (1.49); 1.298 (0.84); 1.293 (0.88); 1.194 (4.18); 1.176 (8.23); 1.158 (4.21); −0.000 (2.21); |
| I-57 | 8.395 (15.00); 5.747 (1.47); 4.919 (0.81); 4.909 (1.47); 4.896 (1.81); 4.886 (2.78); 4.877 (1.83); 4.864 (1.41); 4.473 (1.57); 4.439 (1.65); 3.940 (1.58); 3.905 (1.74); 3.362 (2.85); 3.333 (7.27); 3.303 (830.63); 3.184 (1.61); 3.154 (2.35); 3.125 (1.31); 2.936 (0.87); 2.815 (0.85); 2.754 (1.18); 2.723 (2.12); 2.696 (1.43); 2.674 (1.24); 2.669 (1.63); 2.665 (1.22); 2.565 (1.67); 2.539 (8.69); 2.509 (91.69); 2.505 (160.54); 2.500 (200.93); 2.496 (141.68); 2.470 (4.95); 2.451 (2.22); 2.434 (1.30); 2.424 (0.95); 2.331 (1.22); 2.327 (1.52); 2.322 (1.21); 2.311 (1.08); 2.289 (1.33); 2.262 (2.17); 2.242 (2.53); 2.221 (2.44); 2.194 (1.45); 2.172 (1.29); 2.089 (1.74); 2.058 (3.35); 2.032 (1.89); 1.987 (1.21); 1.856 (3.20); 1.783 (1.67); 1.765 (4.30); 1.745 (6.53); 1.725 (6.39); 1.707 (4.57); 1.672 (1.70); 1.664 (1.63); 1.641 (1.53); 1.633 (1.42); 1.540 (3.06); 1.523 (5.28); 1.516 (5.95); 1.492 (5.49); 1.468 (2.06); 1.461 (2.23); 1.436 (1.36); 1.428 (1.80); 1.403 (3.63); 1.399 (3.44); 1.378 (2.99); 1.370 (3.07); 1.355 (1.28); 1.346 (1.58); 1.322 (1.41); 1.293 (2.49); 1.273 (1.20); 1.267 (1.38); 1.243 (1.05); −0.000 (20.79); |
| I-58 | 8.392 (13.08); 5.747 (0.63); 4.918 (0.58); 4.908 (1.13); 4.896 (1.35); 4.886 (2.11); 4.876 (1.39); 4.864 (1.06); 4.468 (1.19); 4.435 (1.20); 3.964 (1.15); 3.929 (1.22); 3.359 (1.16); 3.350 (1.84); 3.330 (3.25); 3.302 (296.70); 3.180 (0.95); 3.149 (1.52); 3.118 (0.84); 2.941 (0.75); |

| Ex. | NMR Data |
|---|---|
| | 2.793 (0.63); 2.723 (0.86); 2.695 (1.67); 2.674 (0.80); 2.670 (1.04); 2.665 (1.17); 2.540 (3.28); 2.509 (32.20); 2.505 (56.80); 2.501 (71.51); 2.496 (49.20); 2.336 (2.82); 2.320 (4.97); 2.316 (4.60); 2.300 (3.24); 2.203 (1.00); 2.185 (1.95); 2.167 (1.11); 2.086 (1.19); 2.050 (2.42); 2.021 (1.30); 1.881 (2.14); 1.864 (2.28); 1.861 (2.28); 1.855 (2.30); 1.741 (1.90); 1.732 (1.99); 1.717 (2.20); 1.710 (2.24); 1.664 (0.61); 1.642 (1.11); 1.635 (1.13); 1.613 (1.05); 1.605 (1.02); 1.583 (0.60); 1.574 (0.59); 1.547 (1.96); 1.540 (2.35); 1.523 (4.26); 1.515 (4.98); 1.508 (5.20); 1.500 (5.65); 1.492 (7.55); 1.471 (4.80); 1.435 (1.45); 1.428 (1.68); 1.411 (1.71); 1.403 (2.96); 1.398 (3.72); 1.378 (2.31); 1.370 (2.38); 1.353 (1.07); 1.346 (1.33); 1.321 (1.70); 1.266 (15.00); 0.879 (4.30); 0.875 (4.38); 0.863 (13.35); 0.845 (4.83); −0.000 (9.42); |
| I-61 | 8.454 (2.70); 8.407 (5.50); 7.944 (2.11); 7.939 (2.08); 7.709 (1.51); 7.688 (1.78); 7.484 (1.23); 7.480 (1.22); 7.464 (1.02); 7.459 (0.98); 4.917 (0.51); 4.904 (0.65); 4.894 (0.98); 4.885 (0.65); 4.872 (0.49); 4.190 (1.39); 4.156 (1.44); 3.374 (1.01); 3.345 (2.43); 3.308 (324.98); 3.075 (0.98); 3.046 (1.74); 3.017 (0.94); 2.674 (0.35); 2.670 (0.45); 2.665 (0.35); 2.540 (1.89); 2.505 (46.20); 2.501 (58.54); 2.497 (41.93); 2.332 (0.34); 2.327 (0.42); 2.323 (0.33); 2.105 (1.19); 2.079 (1.38); 2.070 (1.62); 1.888 (0.99); 1.867 (1.07); 1.860 (1.07); 1.739 (1.30); 1.730 (1.44); 1.710 (1.96); 1.701 (1.80); 1.679 (1.13); 1.670 (1.05); 1.648 (0.45); 1.638 (0.38); 1.556 (0.75); 1.548 (0.86); 1.525 (1.61); 1.501 (1.68); 1.477 (0.63); 1.470 (0.61); 1.440 (0.49); 1.432 (0.66); 1.398 (15.00); 1.383 (1.32); 1.375 (1.21); 1.357 (0.50); 1.350 (0.59); 1.327 (0.50); 1.303 (0.60); 1.298 (0.61); 1.272 (0.47); −0.000 (0.44); |
| I-62 | 8.403 (7.83); 8.141 (3.34); 7.323 (2.86); 7.315 (4.00); 7.294 (3.56); 6.963 (1.57); 6.959 (1.58); 6.943 (1.43); 6.939 (1.41); 4.925 (0.33); 4.916 (0.66); 4.904 (0.82); 4.894 (1.27); 4.884 (0.84); 4.872 (0.65); 4.862 (0.33); 4.174 (1.79); 4.141 (1.87); 3.311 (564.80); 3.030 (1.31); 3.001 (2.28); 2.972 (1.28); 2.674 (0.46); 2.670 (0.59); 2.665 (0.46); 2.540 (2.56); 2.509 (32.65); 2.505 (57.69); 2.501 (72.56); 2.496 (50.29); 2.332 (0.47); 2.328 (0.58); 2.323 (0.46); 2.271 (15.00); 2.081 (1.52); 2.069 (1.08); 2.056 (1.77); 2.050 (1.75); 1.867 (1.35); 1.860 (1.35); 1.737 (1.25); 1.712 (1.80); 1.680 (1.45); 1.672 (1.54); 1.650 (1.41); 1.641 (1.31); 1.620 (0.57); 1.611 (0.48); 1.557 (0.95); 1.549 (1.08); 1.533 (1.86); 1.526 (2.07); 1.510 (1.64); 1.502 (2.15); 1.479 (0.79); 1.471 (0.75); 1.432 (0.77); 1.408 (1.77); 1.398 (5.26); 1.383 (1.39); 1.375 (1.37); 1.358 (0.57); 1.350 (0.70); 1.329 (0.58); 1.304 (0.72); 1.273 (0.55); −0.000 (0.60); |
| I-63 | 9.044 (3.29); 8.412 (7.37); 7.092 (2.22); 7.073 (2.85); 6.961 (1.98); 6.941 (1.58); 6.871 (3.33); 4.930 (0.44); 4.921 (0.80); 4.909 (0.98); 4.898 (1.44); 4.889 (0.97); 4.875 (0.80); 4.866 (0.44); 4.807 (1.88); 4.775 (1.93); 3.603 (0.32); 3.562 (0.31); 3.470 (1.07); 3.452 (1.33); 3.442 (1.79); 3.433 (4.27); 3.413 (1.76); 3.404 (1.49); 3.308 (1013.46); 3.260 (1.40); 3.184 (0.40); 3.157 (0.70); 2.669 (1.25); 2.665 (1.05); 2.539 (6.90); 2.504 (136.77); 2.500 (166.47); 2.496 (116.50); 2.327 (1.24); 2.323 (0.93); 2.290 (0.38); 2.256 (13.27); 2.118 (15.00); 2.092 (2.09); 2.069 (1.07); 2.049 (0.35); 1.890 (1.49); 1.870 (1.58); 1.754 (1.78); 1.725 (3.15); 1.703 (2.40); 1.672 (0.66); 1.552 (1.16); 1.536 (2.13); 1.531 (2.36); 1.512 (2.01); 1.507 (2.46); 1.484 (0.88); 1.475 (0.87); 1.465 (0.31); 1.435 (0.84); 1.411 (1.91); 1.398 (6.71); 1.386 (1.65); 1.378 (1.55); 1.354 (0.81); 1.332 (0.65); 1.305 (0.89); 1.292 (0.89); 1.277 (0.69); 1.244 (0.35); −0.000 (2.37); |
| I-64 | 8.404 (7.30); 8.228 (3.64); 7.255 (1.66); 7.251 (1.69); 7.236 (1.71); 7.232 (1.65); 7.062 (1.54); 7.041 (2.19); 7.035 (1.75); 7.014 (1.96); 6.910 (1.07); 6.905 (1.13); 6.898 (1.21); 6.892 (1.32); 6.884 (0.97); 6.878 (0.88); 5.747 (3.73); 4.926 (0.42); 4.916 (0.80); 4.905 (0.98); 4.894 (1.48); 4.885 (1.03); 4.872 (0.80); 4.177 (2.18); 4.144 (2.28); 4.039 (0.94); 4.022 (0.94); 3.340 (1.86); 3.301 (234.82); 3.004 (1.54); 2.975 (2.77); 2.946 (1.53); 2.669 (0.57); 2.665 (0.45); 2.539 (2.71); 2.504 (58.42); 2.500 (70.13); 2.496 (49.25); 2.327 (0.55); 2.249 (15.00); 2.076 (1.92); 2.049 (2.29); 1.987 (3.89); 1.908 (2.92); 1.869 (1.73); 1.745 (1.50); 1.737 (1.57); 1.722 (1.72); 1.715 (1.73); 1.691 (1.15); 1.682 (0.95); 1.660 (1.80); 1.651 (1.89); 1.629 (1.76); 1.621 (1.61); 1.599 (0.75); 1.590 (0.62); 1.557 (1.21); 1.549 (1.36); 1.526 (2.59); 1.502 (2.65); 1.479 (1.00); 1.472 (0.94); 1.432 (0.92); 1.408 (1.87); 1.401 (1.47); 1.383 (1.67); 1.375 (1.66); 1.357 (0.71); 1.350 (0.88); 1.328 (0.81); 1.303 (0.98); 1.280 (0.69); 1.273 (0.78); 1.247 (0.43); 1.237 (0.67); 1.193 (1.12); 1.175 (2.04); 1.158 (1.05); −0.000 (3.75); |
| I-65 | 8.384 (3.19); 6.838 (3.53); 4.882 (0.63); 4.873 (0.46); 4.475 (0.47); 4.442 (0.45); 4.002 (0.52); 3.994 (0.45); 3.973 (0.54); 3.958 (0.42); 3.651 (2.73); 3.611 (0.40); 3.574 (0.44); 3.552 (0.41); 3.526 (0.47); 3.500 (0.52); 3.484 (0.61); 3.475 (0.62); 3.460 (0.79); 3.452 (1.21); 3.395 (1.50); 3.304 (1232.16); 3.217 (0.78); 3.205 (0.60); 3.196 (0.57); 3.180 (0.51); 3.164 (0.54); 3.155 (0.63); 3.124 (0.68); 3.098 (0.50); 2.890 (0.49); 2.763 (0.50); 2.732 (1.07); 2.694 (0.70); 2.673 (1.69); 2.669 (2.12); 2.665 (1.71); 2.633 (0.51); 2.630 (0.51); 2.612 (0.66); 2.608 (0.79); 2.539 (13.94); 2.504 (229.40); 2.500 (283.39); 2.496 (198.65); 2.402 (0.57); 2.375 (0.43); 2.331 (1.59); 2.327 (2.10); 2.322 (1.56); 2.236 (15.00); 2.069 (0.41); 2.049 (1.19); 2.019 (0.50); 2.012 (0.49); 1.987 (0.69); 1.976 (0.43); 1.956 (0.53); 1.939 (0.49); 1.908 (0.51); 1.894 (0.66); 1.874 (0.73); 1.860 (0.77); 1.739 (0.68); 1.724 (0.69); 1.720 (0.76); 1.695 (0.54); 1.511 (1.18); 1.487 (1.22); 1.466 (0.84); 1.437 (0.59); 1.418 (0.65); 1.402 (0.99); 1.386 (0.65); 1.377 (0.75); 1.368 (0.75); 1.350 (0.40); 1.292 (0.99); 1.237 (0.75); −0.000 (21.13); |
| I-66 | 8.396 (6.51); 7.028 (0.44); 6.967 (4.51); 6.948 (3.70); 6.927 (2.44); 6.907 (1.27); 4.920 (0.43); 4.911 (0.72); 4.900 (0.79); 4.888 (1.25); 4.878 (0.82); 4.866 (0.60); 4.488 (0.69); 4.459 (0.74); 4.022 (0.43); 3.990 (0.70); 3.958 (0.74); 3.678 (0.45); 3.654 (6.07); 3.588 (0.90); 3.506 (1.31); 3.304 (754.62); 3.201 (0.74); 3.173 (0.98); 3.139 (0.58); 2.995 (1.21); 2.842 (1.19); 2.793 (0.51); 2.766 (0.89); 2.731 (0.71); 2.673 (1.02); 2.669 (1.31); 2.664 (1.07); 2.573 (0.74); 2.539 (8.82); 2.504 (143.74); 2.500 (178.45); 2.496 (124.83); 2.430 (0.60); 2.331 (1.05); 2.326 (1.35); 2.322 (1.03); 2.272 (0.53); 2.234 (15.00); 2.199 (0.59); 2.186 (1.94); 2.161 (14.02); 2.137 (1.42); 2.069 (0.97); 2.049 (1.93); 2.025 (0.99); 2.016 (0.97); 1.987 (1.77); 1.907 (2.25); 1.862 (1.38); 1.857 (1.37); 1.718 (1.33); 1.711 (1.33); 1.595 (0.69); 1.589 (0.70); 1.541 (1.77); 1.527 (2.45); 1.518 (2.42); 1.496 (2.36); 1.473 (0.97); 1.429 (0.82); 1.413 (0.98); 1.405 (1.51); 1.399 (1.53); 1.381 (1.34); 1.373 (1.35); 1.349 (0.80); 1.325 (0.65); 1.292 (0.93); 1.269 (0.32); 1.237 (0.65); 1.193 (0.51); 1.175 (0.85); 1.157 (0.48); −0.000 (17.27); |
| I-68 | 8.276 (1.46); 7.348 (0.30); 7.335 (0.34); 7.260 (0.38); 7.250 (0.28); 7.198 (0.74); 7.186 (0.67); 6.995 (0.30); 6.906 (0.62); 6.882 (0.32); 6.839 (0.59); 6.816 (0.32); 6.791 (0.68); 6.700 (0.34); 6.202 (0.42); 5.264 (0.50); 5.235 (0.50); 4.064 (0.76); 4.052 (0.77); 2.151 (13.50); 2.109 (0.27); 2.100 (0.29); 1.972 (3.43); 1.949 (3.20); 1.945 (6.14); 1.941 (8.69); 1.937 (6.02); 1.933 (3.05); 1.215 (0.91); 1.204 (1.91); 1.192 (0.90); −0.000 (4.63); |
| I-69 | 8.307 (2.02); 7.004 (0.38); 6.914 (0.77); 6.886 (0.41); 6.842 (0.67); 6.825 (0.39); 6.795 (0.88); 6.704 (0.43); 5.277 (0.64); 5.242 (0.64); 2.550 (0.39); 2.543 (0.38); 2.501 (1.12); 2.148 (8.67); 1.973 (1.17); 1.957 (0.31); 1.953 (0.41); 1.949 (5.03); 1.945 (9.53); 1.941 (13.50); 1.937 (9.27); 1.933 (4.79); 1.928 (0.32); 1.793 (0.32); 1.785 (0.31); 1.782 (0.32); 1.776 (0.35); 1.770 (0.30); 1.571 (0.31); 1.566 (0.38); 1.549 (0.31); 1.451 (0.34); 1.434 (0.28); 1.429 (0.31); 1.216 (0.32); 1.204 (0.72); 1.192 (0.33); −0.000 (7.24); |
| I-70 | 8.454 (5.80); 7.944 (1.93); 7.939 (1.89); 7.709 (1.42); 7.688 (1.72); 7.485 (1.15); 7.480 (1.14); 7.464 (0.95); 7.459 (0.91); 4.184 (1.33); 4.151 (1.39); 4.039 (0.46); 4.022 (0.47); 3.826 (15.00); 3.717 (0.55); 3.688 (0.56); 3.372 (0.87); 3.362 (0.89); 3.352 (1.31); 3.343 (2.00); 3.305 (239.93); 3.282 (4.16); 3.079 (0.93); 3.051 (1.66); 3.022 (0.92); 2.674 (0.31); 2.669 (0.40); 2.665 (0.31); 2.539 (0.85); 2.505 (41.57); 2.501 (51.47); 2.497 (36.19); 2.332 (0.30); 2.327 (0.38); 2.114 (1.10); 2.109 (1.12); 2.082 (1.31); 1.987 (1.87); 1.745 (0.45); 1.735 (0.49); 1.715 (1.03); 1.706 (1.11); 1.684 (1.02); 1.676 (0.95); 1.654 (0.42); 1.644 (0.35); 1.398 (1.22); 1.193 (0.54); 1.175 (1.00); 1.157 (0.51); 0.008 (0.39); −0.000 (5.66); |
| I-71 | 8.784 (0.36); 8.401 (5.13); 7.947 (0.30); 7.621 (2.33); 7.483 (2.00); 7.478 (2.00); 6.878 (1.85); 6.858 (3.13); 6.811 (1.37); 6.807 (1.33); 6.791 (0.77); 6.786 (0.75); 5.747 (5.23); 4.914 (0.49); 4.902 (0.60); 4.892 (0.91); 4.882 (0.61); 4.869 (0.46); 4.134 (1.29); 4.101 (1.35); 3.818 (2.29); 3.772 (15.00); 3.334 (1.21); 3.301 (156.89); 3.011 (0.93); 2.982 (1.64); 2.953 (0.91); 2.669 (0.31); 2.539 (1.29); 2.508 (19.68); 2.504 (33.50); 2.500 (41.15); 2.496 (28.48); 2.326 (0.32); 2.221 (2.28); 2.211 (10.77); 2.077 (1.13); 2.069 (0.91); 2.051 (1.34); 1.987 (0.41); 1.908 (1.17); 1.870 (1.02); 1.859 (1.00); 1.721 (1.02); 1.712 (1.06); 1.703 (1.10); 1.671 (1.07); 1.663 (1.11); 1.640 (1.04); 1.632 (0.97); 1.610 (0.42); 1.601 (0.37); 1.554 (0.72); 1.546 (0.82); 1.522 (1.49); 1.499 (1.55); 1.476 (0.57); 1.468 (0.55); 1.431 (0.55); 1.406 (1.12); 1.399 (0.85); 1.381 (0.99); 1.373 (0.99); 1.357 (0.42); 1.348 (0.53); 1.325 (0.45); 1.295 (0.54); 1.270 (0.42); −0.000 (3.35); |
| I-72 | 8.405 (6.84); 8.124 (3.14); 7.337 (3.01); 7.332 (3.02); 7.200 (2.12); 7.180 (2.78); 7.083 (2.06); 7.078 (1.97); 7.063 (1.49); 7.057 (1.37); 5.746 (2.89); 4.926 (0.35); 4.917 (0.66); 4.905 (0.82); 4.895 (1.25); 4.885 (0.82); 4.872 (0.63); 4.863 (0.32); 4.177 (1.79); 4.144 (1.87); 3.668 (0.55); 3.355 (1.12); 3.308 (165.80); 3.028 (1.26); 2.999 (2.25); 2.970 (1.24); 2.540 (0.96); 2.505 (24.88); 2.501 (30.53); 2.497 (21.33); 2.328 (0.30); 2.253 (0.81); 2.180 (0.77); 2.158 (15.00); 2.089 (1.56); 2.069 (1.58); 2.063 (1.79); 2.004 (0.53); 1.888 (1.28); 1.868 (1.39); 1.861 (1.36); 1.745 (1.18); 1.737 (1.26); 1.722 (1.44); 1.711 (1.68); 1.700 (1.44); 1.677 (1.46); 1.669 (1.56); 1.646 (1.46); 1.638 (1.34); |

| Ex. | NMR Data |
|---|---|
|  | 1.617 (0.59); 1.607 (0.49); 1.557 (0.95); 1.549 (1.11); 1.533 (1.90); 1.526 (2.11); 1.510 (1.69); 1.502 (2.21); 1.479 (0.83); 1.471 (0.78); 1.440 (0.59); 1.433 (0.76); 1.408 (1.60); 1.398 (1.44); 1.383 (1.43); 1.375 (1.44); 1.357 (0.76); 1.351 (0.83); 1.328 (0.69); 1.321 (0.55); 1.303 (0.90); 1.299 (0.90); 1.280 (0.70); 1.273 (0.73); 1.248 (0.37); 1.238 (0.39); 0.890 (0.34); 0.872 (0.58); 0.854 (0.32); −0.000 (1.78); |
| I-74 | 8.405 (8.57); 8.078 (3.67); 7.194 (1.43); 7.174 (2.11); 7.164 (2.09); 7.157 (3.23); 7.136 (1.82); 7.130 (1.75); 6.865 (1.10); 6.859 (1.04); 6.844 (2.00); 6.837 (1.76); 6.824 (0.97); 6.817 (0.88); 5.746 (4.60); 4.916 (0.78); 4.904 (0.99); 4.894 (1.52); 4.884 (1.00); 4.871 (0.74); 4.179 (2.16); 4.147 (2.23); 4.039 (0.66); 4.021 (0.65); 3.305 (930.93); 3.028 (1.70); 2.997 (2.80); 2.969 (1.56); 2.674 (0.94); 2.669 (1.18); 2.664 (0.90); 2.539 (3.41); 2.509 (72.46); 2.504 (122.62); 2.500 (149.80); 2.496 (103.35); 2.331 (0.92); 2.327 (1.14); 2.322 (0.86); 2.245 (0.79); 2.151 (15.00); 2.089 (1.90); 2.063 (2.18); 1.987 (2.71); 1.888 (1.56); 1.866 (1.68); 1.860 (1.67); 1.744 (1.41); 1.735 (1.50); 1.711 (2.02); 1.678 (1.78); 1.669 (1.86); 1.646 (1.73); 1.638 (1.61); 1.616 (0.70); 1.556 (1.20); 1.548 (1.36); 1.532 (2.28); 1.525 (2.52); 1.501 (2.61); 1.477 (0.97); 1.470 (0.92); 1.433 (0.90); 1.415 (1.17); 1.408 (1.86); 1.401 (1.44); 1.383 (1.63); 1.375 (1.65); 1.358 (0.76); 1.350 (0.88); 1.344 (0.72); 1.328 (0.81); 1.303 (0.93); 1.298 (0.94); 1.273 (0.76); 1.237 (0.83); 1.193 (0.81); 1.175 (1.52); 1.157 (0.75); −0.000 (2.35); |
| I-76 | 8.402 (5.02); 7.926 (2.23); 7.812 (1.27); 5.746 (1.03); 4.916 (0.49); 4.903 (0.59); 4.893 (0.91); 4.883 (0.60); 4.871 (0.46); 4.141 (1.29); 4.108 (1.37); 4.039 (0.36); 4.022 (0.35); 3.305 (207.08); 3.005 (0.93); 2.975 (1.64); 2.947 (0.89); 2.669 (0.32); 2.539 (0.80); 2.509 (18.33); 2.505 (31.25); 2.500 (38.41); 2.496 (26.55); 2.327 (0.33); 2.261 (9.69); 2.226 (12.69); 2.102 (11.59); 2.078 (1.43); 2.057 (15.00); 1.987 (1.43); 1.893 (0.95); 1.887 (0.93); 1.866 (0.99); 1.859 (0.97); 1.744 (0.86); 1.736 (0.90); 1.720 (1.00); 1.713 (1.00); 1.680 (0.48); 1.670 (0.53); 1.649 (1.03); 1.640 (1.09); 1.618 (1.02); 1.610 (0.94); 1.588 (0.42); 1.579 (0.38); 1.555 (0.72); 1.547 (0.82); 1.531 (1.34); 1.524 (1.48); 1.500 (1.52); 1.477 (0.57); 1.469 (0.53); 1.440 (0.40); 1.433 (0.54); 1.408 (1.13); 1.400 (0.84); 1.383 (0.96); 1.376 (0.97); 1.359 (0.40); 1.351 (0.51); 1.329 (0.43); 1.320 (0.32); 1.305 (0.52); 1.298 (0.51); 1.273 (0.40); 1.193 (0.39); 1.175 (0.75); 1.157 (0.37); −0.000 (1.02); |
| I-77 | 8.416 (4.67); 7.681 (2.21); 7.401 (2.11); 7.396 (2.14); 7.294 (0.93); 7.281 (1.32); 7.273 (0.46); 7.271 (0.45); 7.260 (1.22); 7.248 (0.96); 7.246 (0.75); 7.196 (0.86); 7.186 (2.09); 7.173 (1.37); 6.903 (1.94); 6.889 (2.09); 6.552 (1.19); 6.547 (1.18); 6.537 (1.11); 6.532 (1.09); 6.130 (0.67); 6.123 (1.36); 6.115 (0.66); 5.762 (5.27); 4.117 (1.01); 4.095 (1.02); 3.768 (0.52); 3.756 (12.28); 3.672 (13.50); 3.344 (79.72); 3.312 (0.37); 3.298 (0.40); 3.292 (0.69); 3.286 (0.39); 3.273 (0.35); 2.992 (0.67); 2.973 (1.26); 2.953 (0.65); 2.877 (0.44); 2.857 (0.37); 2.849 (0.71); 2.840 (0.34); 2.777 (0.31); 2.768 (0.43); 2.762 (0.40); 2.752 (0.42); 2.542 (0.59); 2.524 (0.61); 2.521 (0.79); 2.518 (0.93); 2.506 (27.38); 2.503 (36.28); 2.500 (26.62); 2.067 (0.94); 2.050 (1.15); 2.044 (1.41); 2.035 (0.88); 2.028 (1.13); 2.022 (0.95); 2.015 (0.45); 1.990 (0.83); 1.949 (0.33); 1.940 (0.37); 1.933 (0.41); 1.925 (0.37); 1.918 (0.29); 1.839 (0.35); 1.830 (0.44); 1.823 (0.39); 1.817 (0.30); 1.674 (0.30); 1.667 (0.35); 1.653 (0.77); 1.647 (0.84); 1.633 (0.80); 1.627 (0.74); 1.612 (0.31); 1.396 (0.30); 1.174 (0.43); −0.000 (5.26); |
| I-78 | 8.400 (7.71); 7.982 (3.59); 7.299 (1.69); 7.291 (0.71); 7.281 (2.93); 7.260 (2.19); 7.242 (1.99); 7.238 (1.61); 7.200 (2.11); 7.187 (3.45); 7.168 (1.93); 7.044 (2.62); 7.025 (3.12); 6.999 (3.47); 6.856 (2.07); 6.837 (1.72); 6.137 (1.58); 6.126 (2.57); 6.115 (1.27); 5.746 (6.04); 4.167 (2.11); 4.134 (2.12); 3.305 (258.83); 2.985 (1.46); 2.955 (2.59); 2.926 (1.43); 2.903 (0.49); 2.890 (0.83); 2.876 (0.51); 2.860 (0.86); 2.847 (1.56); 2.834 (0.79); 2.793 (0.76); 2.778 (1.04); 2.771 (1.02); 2.756 (0.95); 2.735 (0.49); 2.728 (0.53); 2.714 (0.46); 2.673 (0.38); 2.669 (0.44); 2.664 (0.35); 2.539 (1.04); 2.504 (41.27); 2.500 (50.77); 2.496 (35.41); 2.327 (0.41); 2.231 (14.92); 2.105 (15.00); 2.068 (2.47); 2.065 (2.56); 2.055 (2.47); 2.031 (4.31); 2.004 (0.64); 1.990 (0.61); 1.975 (0.60); 1.965 (0.75); 1.953 (0.84); 1.942 (0.94); 1.931 (0.83); 1.919 (0.62); 1.908 (0.51); 1.895 (0.34); 1.865 (0.41); 1.852 (0.86); 1.839 (1.10); 1.827 (0.91); 1.811 (0.61); 1.795 (0.41); 1.712 (0.41); 1.706 (0.34); 1.681 (0.80); 1.671 (0.91); 1.649 (1.68); 1.641 (1.74); 1.619 (1.60); 1.611 (1.46); 1.589 (0.61); 1.579 (0.50); −0.000 (1.35); |
| I-79 | 8.403 (7.10); 8.069 (3.66); 7.298 (1.74); 7.279 (3.30); 7.260 (2.26); 7.241 (2.08); 7.199 (2.37); 7.189 (4.42); 7.169 (4.10); 7.158 (2.62); 7.152 (3.39); 7.130 (1.89); 7.124 (1.79); 6.863 (1.08); 6.856 (1.04); 6.842 (1.98); 6.835 (1.78); 6.820 (1.00); 6.814 (0.95); 6.136 (1.35); 6.125 (2.68); 6.114 (1.35); 5.746 (4.52); 4.170 (2.23); 4.137 (2.26); 3.340 (2.29); 3.303 (278.67); 3.014 (1.55); 2.984 (2.78); 2.954 (1.53); 2.902 (0.47); 2.889 (0.88); 2.876 (0.53); 2.859 (0.93); 2.846 (1.64); 2.833 (0.85); 2.792 (0.83); 2.777 (1.11); 2.770 (1.07); 2.755 (1.01); 2.734 (0.53); 2.727 (0.56); 2.713 (0.46); 2.669 (0.56); 2.665 (0.46); 2.539 (1.69); 2.504 (57.20); 2.500 (68.16); 2.496 (47.83); 2.327 (0.51); 2.143 (15.00); 2.077 (2.15); 2.064 (1.78); 2.052 (3.39); 2.041 (3.79); 2.030 (2.87); 2.001 (0.60); 1.987 (0.69); 1.973 (0.63); 1.963 (0.77); 1.951 (0.87); 1.940 (0.92); 1.928 (0.88); 1.917 (0.67); 1.907 (0.53); 1.851 (0.90); 1.839 (1.13); 1.826 (0.94); 1.811 (0.63); 1.805 (0.59); 1.712 (0.44); 1.697 (0.84); 1.688 (0.90); 1.666 (1.72); 1.658 (1.81); 1.636 (1.69); 1.628 (1.52); 1.606 (0.64); 1.596 (0.52); −0.000 (1.34); |
| I-80 | 8.401 (8.55); 8.219 (3.56); 7.299 (1.85); 7.280 (3.10); 7.259 (2.65); 7.254 (2.24); 7.251 (2.24); 7.241 (2.92); 7.237 (2.29); 7.231 (1.98); 7.227 (1.80); 7.200 (2.24); 7.186 (3.87); 7.167 (2.11); 7.133 (1.20); 7.123 (1.44); 7.115 (1.21); 7.110 (1.07); 7.058 (1.72); 7.048 (1.11); 7.037 (2.68); 7.031 (2.20); 7.010 (2.06); 6.906 (1.10); 6.901 (1.17); 6.896 (1.24); 6.889 (1.34); 6.881 (0.95); 6.875 (0.87); 6.137 (1.37); 6.126 (2.66); 6.114 (1.31); 5.746 (2.24); 5.047 (0.99); 5.032 (1.04); 4.167 (2.20); 4.133 (2.23); 3.302 (231.17); 3.270 (1.67); 2.990 (1.53); 2.961 (2.71); 2.932 (1.50); 2.889 (0.85); 2.860 (0.90); 2.847 (1.62); 2.834 (0.83); 2.792 (0.82); 2.777 (1.10); 2.770 (1.09); 2.754 (1.06); 2.539 (1.40); 2.504 (47.68); 2.500 (58.54); 2.496 (40.93); 2.246 (15.00); 2.065 (2.61); 2.054 (2.30); 2.040 (4.15); 2.031 (4.32); 1.987 (0.99); 1.952 (0.87); 1.941 (0.93); 1.930 (0.90); 1.908 (1.04); 1.899 (0.87); 1.894 (0.90); 1.880 (0.97); 1.874 (1.00); 1.870 (1.00); 1.857 (0.79); 1.852 (1.03); 1.839 (1.22); 1.826 (0.96); 1.678 (1.36); 1.671 (1.58); 1.649 (2.15); 1.641 (2.00); 1.619 (1.71); 1.610 (1.60); −0.000 (2.27); |
| I-81 | 9.034 (3.32); 8.407 (6.28); 7.390 (0.94); 7.381 (1.00); 7.367 (1.11); 7.301 (1.58); 7.283 (2.79); 7.261 (2.08); 7.243 (1.90); 7.201 (2.03); 7.188 (3.52); 7.169 (2.06); 7.132 (1.95); 7.122 (2.22); 7.114 (2.09); 7.088 (2.40); 7.068 (2.43); 7.048 (1.58); 7.033 (1.10); 6.956 (2.17); 6.937 (1.69); 6.864 (3.39); 6.139 (1.21); 6.128 (2.46); 6.117 (1.25); 5.746 (0.90); 5.046 (2.02); 5.031 (2.14); 4.798 (1.93); 4.766 (1.93); 4.548 (0.96); 3.440 (0.97); 3.431 (1.40); 3.420 (1.02); 3.402 (1.04); 3.392 (0.91); 3.301 (556.78); 3.246 (3.94); 3.216 (2.08); 2.862 (0.91); 2.849 (1.58); 2.779 (1.21); 2.772 (1.25); 2.757 (1.19); 2.717 (1.01); 2.705 (1.12); 2.673 (1.56); 2.668 (1.63); 2.663 (1.44); 2.538 (2.89); 2.503 (125.14); 2.499 (149.04); 2.326 (1.18); 2.322 (0.96); 2.252 (13.90); 2.110 (15.00); 2.080 (2.41); 2.069 (2.54); 2.057 (1.69); 2.043 (2.19); 2.033 (2.56); 1.955 (0.95); 1.944 (1.01); 1.933 (0.98); 1.920 (0.90); 1.906 (1.14); 1.898 (1.39); 1.880 (1.63); 1.870 (1.70); 1.857 (1.31); 1.842 (1.25); 1.830 (1.07); 1.744 (0.97); 1.715 (2.45); 1.693 (2.49); 1.685 (2.42); 1.670 (1.60); 1.662 (1.41); 1.653 (1.61); −0.000 (5.09); |
| I-82 | 8.399 (5.09); 7.613 (2.35); 7.474 (2.09); 7.469 (2.04); 7.296 (1.11); 7.278 (2.13); 7.259 (1.42); 7.240 (1.29); 7.237 (1.03); 7.198 (1.39); 7.185 (2.11); 7.168 (1.18); 6.871 (1.59); 6.851 (2.91); 6.808 (1.47); 6.805 (1.40); 6.788 (0.78); 6.784 (0.75); 6.135 (0.85); 6.124 (1.65); 6.112 (0.82); 5.746 (0.52); 4.124 (1.36); 4.090 (1.37); 3.773 (1.13); 3.761 (15.00); 3.305 (180.80); 3.264 (1.07); 2.996 (0.95); 2.967 (1.68); 2.938 (0.92); 2.888 (0.53); 2.874 (0.33); 2.858 (0.56); 2.845 (1.00); 2.832 (0.52); 2.790 (0.51); 2.776 (0.66); 2.769 (0.65); 2.753 (0.60); 2.726 (0.36); 2.712 (0.30); 2.674 (0.34); 2.669 (0.41); 2.664 (0.32); 2.539 (0.98); 2.504 (38.99); 2.500 (48.02); 2.496 (33.62); 2.327 (0.36); 2.208 (11.00); 2.069 (1.68); 2.063 (1.56); 2.050 (1.49); 2.039 (2.63); 2.029 (2.54); 2.001 (0.39); 1.987 (0.48); 1.971 (0.37); 1.962 (0.46); 1.948 (0.53); 1.938 (0.57); 1.926 (0.54); 1.915 (0.41); 1.908 (0.35); 1.849 (0.56); 1.836 (0.71); 1.824 (0.58); 1.691 (0.51); 1.681 (0.58); 1.659 (1.08); 1.651 (1.15); 1.629 (1.05); 1.621 (0.97); 1.599 (0.40); 1.589 (0.32); −0.000 (2.57); |
| I-83 | 8.391 (15.00); 5.747 (0.93); 4.909 (1.40); 4.896 (1.74); 4.886 (2.67); 4.876 (1.79); 4.864 (1.37); 4.473 (1.49); 4.442 (1.53); 3.984 (1.45); 3.949 (1.54); 3.358 (1.57); 3.348 (2.51); 3.303 (368.64); 3.279 (7.02); 3.182 (1.24); 3.151 (1.99); 3.121 (1.10); 2.722 (1.11); 2.693 (1.95); 2.669 (1.31); 2.665 (1.48); 2.540 (1.54); 2.509 (35.82); 2.505 (61.89); 2.501 (76.77); 2.496 (53.39); 2.359 (7.31); 2.340 (10.12); 2.328 (1.17); 2.174 (0.97); 2.154 (2.09); 2.135 (2.71); 2.116 (2.15); 2.096 (2.06); 2.070 (2.66); 2.055 (3.11); 2.025 (1.73); 1.882 (2.74); 1.860 (2.94); 1.854 (2.93); 1.754 (4.31); 1.739 (5.34); 1.710 (4.06); 1.625 (1.87); 1.617 (1.56); 1.598 (3.30); 1.591 (3.64); 1.577 (4.31); 1.571 (3.37); 1.566 (3.46); 1.561 (3.98); 1.550 (3.97); 1.539 (4.28); 1.525 (6.51); 1.516 (6.12); 1.501 (7.33); 1.492 (8.27); 1.485 (6.43); 1.471 (5.42); 1.464 (4.57); 1.435 (1.97); 1.428 (2.11); 1.419 (1.34); 1.411 (2.12); 1.403 (3.44); 1.396 (2.58); 1.386 (1.83); 1.378 (2.91); 1.371 (2.98); 1.354 (1.30); 1.346 (1.56); 1.338 (1.16); 1.323 (1.34); 1.315 (1.01); 1.298 (1.64); 1.293 (1.60); 1.268 (1.28); 1.122 (2.65); −0.000 (2.88); |
| I-84 | 8.521 (9.42); 8.442 (4.29); 7.704 (2.98); 7.685 (3.34); 7.682 (3.17); 7.601 (2.37); 7.597 (2.39); 7.581 (3.07); 7.468 (1.82); 7.446 (3.88); 7.436 (1.86); 7.428 (2.95); 7.420 (2.16); 7.410 (1.47); 7.403 (1.41); 7.395 (1.19); 7.356 (1.86); 7.352 (1.88); 7.337 (2.70); 7.333 (2.59); 7.318 (1.27); 7.314 (1.18); 7.252 (1.09); 7.239 (1.29); 7.229 (1.73); 7.216 (1.72); 7.203 (1.43); 7.190 (1.27); 6.923 (0.83); 6.914 (1.33); 6.904 (1.28); 6.893 (1.85); 6.886 (1.16); 6.872 (1.05); 6.865 (0.61); 5.373 (15.00); 4.177 (2.81); 4.142 (3.01); 4.039 (0.40); 4.022 (0.39); |

| Ex. | NMR Data |
|---|---|
| | 3.506 (0.42); 3.502 (0.41); 3.456 (0.55); 3.427 (0.79); 3.415 (0.93); 3.305 (965.91); 3.177 (0.54); 3.141 (0.38); 3.136 (0.37); 3.098 (0.37); 3.025 (2.05); 2.995 (3.60); 2.967 (1.98); 2.674 (1.25); 2.669 (1.49); 2.664 (1.21); 2.539 (3.92); 2.504 (157.47); 2.500 (192.11); 2.496 (136.39); 2.417 (0.58); 2.327 (1.37); 2.322 (1.10); 2.093 (2.46); 2.069 (4.05); 1.987 (1.63); 1.711 (0.89); 1.702 (1.09); 1.680 (2.20); 1.671 (2.33); 1.649 (2.20); 1.641 (2.03); 1.619 (0.90); 1.610 (0.67); 1.398 (7.53); 1.236 (0.51); 1.193 (0.43); 1.175 (0.75); 1.157 (0.42); −0.000 (4.76); |
| I-85 | 8.539 (8.81); 8.160 (2.87); 7.708 (1.82); 7.706 (1.88); 7.695 (2.01); 7.693 (2.00); 7.602 (1.29); 7.599 (1.36); 7.589 (1.58); 7.587 (1.59); 7.466 (0.96); 7.464 (0.97); 7.454 (1.95); 7.452 (1.93); 7.441 (1.05); 7.439 (1.01); 7.356 (0.98); 7.353 (1.01); 7.343 (1.49); 7.340 (1.49); 7.330 (0.92); 7.326 (3.02); 7.322 (2.93); 7.198 (1.92); 7.184 (2.36); 7.086 (1.86); 7.082 (1.80); 7.072 (1.48); 7.069 (1.45); 5.372 (8.71); 4.170 (1.28); 4.147 (1.33); 4.034 (0.42); 4.022 (0.43); 3.347 (294.05); 3.336 (1.74); 3.329 (0.85); 3.323 (2.59); 3.316 (0.56); 3.310 (0.28); 3.012 (0.74); 3.009 (0.88); 2.989 (1.64); 2.970 (0.89); 2.966 (0.75); 2.926 (0.39); 2.618 (0.38); 2.615 (0.51); 2.612 (0.37); 2.524 (0.95); 2.521 (1.16); 2.518 (1.13); 2.509 (28.91); 2.506 (63.09); 2.503 (88.13); 2.500 (63.50); 2.497 (28.51); 2.390 (0.35); 2.387 (0.49); 2.384 (0.35); 2.150 (13.50); 2.139 (0.29); 2.091 (1.01); 2.087 (1.07); 2.077 (1.48); 2.070 (1.16); 1.990 (1.86); 1.689 (0.39); 1.682 (0.44); 1.668 (0.95); 1.662 (1.06); 1.648 (1.03); 1.642 (0.95); 1.628 (0.40); 1.621 (0.33); 1.397 (4.18); 1.186 (0.50); 1.174 (0.99); 1.163 (0.47); −0.000 (2.83); |
| I-86 | 8.399 (5.19); 5.833 (3.83); 5.747 (0.50); 4.911 (0.51); 4.898 (0.60); 4.889 (0.94); 4.878 (0.65); 4.866 (0.49); 4.448 (0.58); 4.416 (0.61); 4.057 (0.40); 4.039 (1.24); 4.021 (1.52); 4.003 (0.70); 3.992 (0.62); 3.788 (6.82); 3.651 (0.63); 3.619 (1.54); 3.607 (15.00); 3.369 (0.66); 3.350 (0.97); 3.341 (1.49); 3.299 (165.06); 3.230 (0.71); 3.200 (0.89); 3.170 (0.52); 2.804 (0.42); 2.798 (0.44); 2.769 (0.78); 2.741 (0.46); 2.669 (0.41); 2.539 (0.96); 2.504 (41.97); 2.500 (51.83); 2.496 (36.46); 2.326 (0.40); 2.322 (0.32); 2.074 (14.51); 2.050 (1.43); 1.987 (4.42); 1.908 (2.72); 1.899 (0.94); 1.864 (1.09); 1.741 (0.92); 1.734 (0.97); 1.712 (1.23); 1.688 (0.62); 1.680 (0.61); 1.643 (0.63); 1.542 (1.38); 1.525 (1.66); 1.517 (2.02); 1.502 (1.61); 1.494 (1.65); 1.471 (0.74); 1.463 (0.65); 1.437 (0.48); 1.429 (0.61); 1.405 (1.20); 1.397 (0.92); 1.380 (1.03); 1.372 (1.05); 1.355 (0.46); 1.348 (0.57); 1.324 (0.50); 1.298 (0.71); 1.283 (0.50); 1.268 (0.49); 1.237 (0.34); 1.193 (1.25); 1.175 (2.36); 1.157 (1.18); −0.000 (3.67); |
| I-87 | 8.523 (9.84); 7.707 (2.98); 7.687 (3.32); 7.684 (3.21); 7.601 (2.40); 7.597 (2.39); 7.582 (3.04); 7.578 (3.00); 7.567 (0.56); 7.467 (2.18); 7.460 (4.93); 7.451 (4.19); 7.449 (4.02); 7.438 (10.79); 7.432 (7.40); 7.393 (0.65); 7.360 (5.34); 7.354 (4.72); 7.339 (5.02); 7.321 (1.41); 5.374 (15.00); 4.511 (0.66); 4.434 (1.15); 4.403 (1.19); 4.064 (1.25); 3.915 (0.74); 3.876 (4.98); 3.860 (4.93); 3.835 (0.67); 3.825 (0.79); 3.804 (1.28); 3.603 (0.66); 3.591 (0.71); 3.575 (0.74); 3.546 (0.88); 3.493 (1.43); 3.414 (4.36); 3.386 (8.22); 3.313 (3660.05); 3.171 (1.55); 3.154 (1.30); 3.136 (1.07); 3.125 (1.03); 3.118 (1.04); 3.084 (0.81); 3.070 (2.28); 3.049 (0.67); 3.037 (0.59); 3.012 (0.64); 2.847 (1.83); 2.825 (1.08); 2.788 (1.73); 2.761 (1.21); 2.704 (0.59); 2.674 (2.87); 2.670 (3.61); 2.665 (2.80); 2.539 (8.98); 2.505 (367.09); 2.501 (452.69); 2.497 (316.87); 2.369 (0.69); 2.332 (2.74); 2.328 (3.34); 2.323 (2.63); 2.293 (0.55); 2.138 (1.31); 2.085 (10.31); 2.069 (9.49); 1.753 (1.07); 1.744 (1.05); 1.722 (0.96); 1.714 (0.95); 1.557 (0.97); 1.547 (1.05); 1.526 (1.00); 1.398 (5.04); 1.237 (1.12); −0.000 (18.59); |
| I-88 | 9.041 (3.08); 8.528 (7.31); 7.707 (2.19); 7.705 (2.15); 7.688 (2.46); 7.685 (2.31); 7.603 (1.69); 7.601 (1.74); 7.585 (2.21); 7.582 (2.09); 7.470 (1.26); 7.451 (2.44); 7.449 (2.32); 7.433 (1.35); 7.359 (1.39); 7.354 (1.40); 7.339 (1.97); 7.335 (1.89); 7.320 (0.92); 7.316 (0.82); 7.088 (2.46); 7.069 (3.17); 6.958 (2.26); 6.939 (1.68); 6.866 (3.55); 5.378 (10.89); 4.805 (1.88); 4.772 (1.97); 4.057 (0.35); 4.039 (1.07); 4.021 (1.07); 4.003 (0.38); 3.830 (0.47); 3.481 (0.75); 3.461 (0.92); 3.452 (1.39); 3.442 (0.95); 3.433 (0.74); 3.423 (0.89); 3.414 (0.64); 3.300 (304.43); 3.277 (15.00); 3.260 (3.50); 3.230 (1.71); 2.674 (0.59); 2.669 (0.73); 2.538 (1.63); 2.504 (76.49); 2.500 (94.36); 2.496 (66.21); 2.409 (0.32); 2.331 (0.60); 2.326 (0.75); 2.289 (0.38); 2.252 (14.68); 2.113 (15.00); 2.069 (0.72); 1.987 (4.54); 1.761 (0.88); 1.731 (1.73); 1.707 (1.54); 1.702 (1.49); 1.678 (0.62); 1.669 (0.53); 1.398 (8.81); 1.237 (0.34); 1.193 (1.25); 1.175 (2.46); 1.157 (1.24); 0.890 (0.32); −0.000 (1.99); |
| I-89 | 8.387 (4.79); 5.891 (0.31); 5.849 (3.05); 4.907 (0.54); 4.894 (0.65); 4.885 (0.94); 4.875 (0.60); 4.862 (0.47); 4.443 (0.61); 4.409 (0.60); 4.065 (0.61); 4.028 (0.72); 3.636 (15.00); 3.558 (3.44); 3.551 (3.39); 3.512 (0.60); 3.450 (0.74); 3.385 (2.46); 3.305 (938.53); 3.165 (0.70); 3.133 (0.90); 3.096 (0.56); 2.737 (0.50); 2.710 (0.82); 2.674 (1.48); 2.669 (1.60); 2.583 (0.68); 2.539 (3.04); 2.504 (165.53); 2.500 (203.24); 2.496 (142.33); 2.409 (0.76); 2.327 (1.66); 2.276 (1.37); 2.262 (0.31); 2.192 (12.48); 2.069 (1.49); 2.035 (0.68); 2.004 (1.28); 1.986 (1.06); 1.972 (0.83); 1.908 (2.22); 1.865 (1.13); 1.718 (1.09); 1.520 (1.97); 1.492 (2.07); 1.467 (1.14); 1.427 (0.81); 1.402 (1.26); 1.378 (1.07); 1.371 (1.09); 1.347 (0.57); 1.321 (0.54); 1.294 (0.71); 1.269 (0.59); 1.236 (0.55); 1.175 (0.39); 0.890 (0.37); −0.000 (3.24); |
| I-90 | 8.522 (8.15); 8.075 (3.66); 7.706 (2.43); 7.703 (2.33); 7.686 (2.68); 7.602 (1.92); 7.598 (1.86); 7.582 (2.35); 7.579 (2.14); 7.469 (1.41); 7.465 (1.39); 7.450 (2.69); 7.447 (2.44); 7.431 (1.41); 7.357 (1.58); 7.353 (1.51); 7.338 (2.12); 7.334 (2.02); 7.319 (0.96); 7.314 (0.83); 7.191 (1.51); 7.172 (2.16); 7.160 (2.17); 7.153 (3.11); 7.132 (1.77); 7.125 (1.65); 6.864 (1.19); 6.857 (1.04); 6.843 (2.02); 6.836 (1.79); 6.822 (0.96); 6.815 (0.79); 5.374 (11.68); 4.177 (2.17); 4.142 (2.29); 4.039 (0.52); 4.021 (0.54); 3.562 (0.32); 3.480 (0.50); 3.305 (826.38); 3.283 (9.10); 3.025 (1.50); 2.995 (2.74); 2.966 (1.48); 2.669 (1.13); 2.665 (0.86); 2.504 (119.25); 2.500 (147.12); 2.496 (103.21); 2.327 (1.06); 2.245 (0.71); 2.145 (15.00); 2.095 (1.91); 2.069 (3.08); 1.987 (2.06); 1.907 (0.30); 1.703 (0.82); 1.681 (1.62); 1.674 (1.79); 1.651 (1.68); 1.644 (1.63); 1.621 (0.72); 1.611 (0.58); 1.398 (7.85); 1.234 (0.31); 1.192 (0.57); 1.175 (1.11); 1.157 (0.59); −0.000 (1.29); |
| I-91 | 8.521 (8.12); 7.986 (3.24); 7.706 (2.18); 7.703 (2.18); 7.686 (2.61); 7.684 (2.51); 7.659 (0.41); 7.603 (1.75); 7.599 (1.75); 7.584 (2.29); 7.580 (2.14); 7.469 (1.30); 7.466 (1.35); 7.450 (2.60); 7.448 (2.44); 7.432 (1.43); 7.429 (1.35); 7.357 (1.45); 7.353 (1.39); 7.338 (2.03); 7.334 (1.97); 7.319 (1.01); 7.315 (0.97); 7.166 (0.40); 7.071 (0.78); 7.045 (2.54); 7.026 (3.02); 7.002 (3.15); 6.888 (0.36); 6.856 (2.02); 6.838 (1.70); 5.747 (0.41); 5.375 (11.05); 5.172 (1.52); 4.173 (2.02); 4.140 (2.09); 4.057 (0.38); 4.039 (1.04); 4.021 (1.04); 4.003 (0.39); 3.354 (1.54); 3.300 (400.47); 3.276 (17.79); 2.995 (1.45); 2.967 (2.65); 2.938 (1.47); 2.909 (0.62); 2.673 (0.75); 2.669 (0.89); 2.664 (0.68); 2.539 (1.87); 2.504 (96.48); 2.500 (117.29); 2.496 (81.20); 2.387 (0.42); 2.331 (0.81); 2.327 (0.93); 2.232 (15.00); 2.154 (2.31); 2.107 (14.89); 2.087 (2.14); 2.069 (1.65); 2.053 (2.17); 1.987 (4.59); 1.908 (0.40); 1.696 (0.68); 1.687 (0.70); 1.671 (1.66); 1.666 (1.67); 1.658 (1.74); 1.635 (1.64); 1.627 (1.53); 1.605 (0.66); 1.595 (0.57); 1.398 (3.72); 1.236 (0.45); 1.193 (1.31); 1.175 (2.43); 1.157 (1.27); 0.891 (0.34); −0.000 (5.11); |
| I-92 | 8.521 (7.30); 8.224 (3.16); 7.705 (2.27); 7.703 (2.26); 7.685 (2.52); 7.602 (1.80); 7.598 (1.83); 7.583 (2.32); 7.579 (2.20); 7.469 (1.29); 7.450 (2.63); 7.431 (1.43); 7.356 (1.38); 7.352 (1.43); 7.337 (2.03); 7.333 (1.97); 7.318 (0.97); 7.314 (0.93); 7.251 (1.54); 7.232 (1.59); 7.059 (1.52); 7.039 (2.18); 7.033 (1.77); 7.012 (1.96); 6.903 (1.13); 6.897 (1.24); 6.890 (1.34); 5.374 (11.63); 4.173 (2.15); 4.139 (2.28); 4.039 (0.63); 4.021 (0.56); 3.443 (0.32); 3.397 (0.51); 3.349 (2.17); 3.300 (432.74); 3.277 (20.18); 3.002 (1.56); 2.973 (2.76); 2.943 (1.58); 2.669 (1.08); 2.607 (0.42); 2.594 (0.53); 2.539 (2.40); 2.504 (112.41); 2.500 (137.57); 2.496 (97.19); 2.330 (0.87); 2.327 (1.10); 2.247 (15.00); 2.217 (0.33); 2.083 (2.11); 2.069 (1.66); 2.057 (2.16); 1.987 (2.34); 1.696 (0.70); 1.686 (0.83); 1.664 (1.70); 1.656 (1.83); 1.634 (1.69); 1.626 (1.60); 1.604 (0.70); 1.596 (0.58); 1.398 (4.72); 1.236 (0.40); 1.193 (0.70); 1.175 (1.28); 1.157 (0.62); 0.890 (0.36); −0.000 (3.42); |
| I-93 | 8.401 (4.58); 7.656 (2.34); 7.426 (2.35); 7.419 (2.37); 6.911 (2.14); 6.889 (2.39); 6.555 (1.37); 6.547 (1.34); 6.533 (1.21); 6.525 (1.19); 5.747 (1.15); 4.913 (0.46); 4.901 (0.58); 4.891 (0.87); 4.881 (0.59); 4.868 (0.45); 4.128 (1.26); 4.095 (1.33); 4.040 (0.60); 4.022 (0.60); 3.769 (13.81); 3.676 (15.00); 3.306 (12.00); 3.027 (0.90); 2.997 (1.61); 2.969 (0.91); 2.539 (0.32); 2.505 (15.53); 2.500 (19.17); 2.496 (13.59); 2.088 (1.09); 2.062 (1.26); 1.987 (2.46); 1.886 (0.92); 1.868 (1.00); 1.859 (0.99); 1.743 (0.83); 1.732 (0.90); 1.711 (1.34); 1.701 (1.14); 1.679 (1.07); 1.670 (1.11); 1.648 (1.03); 1.640 (0.95); 1.618 (0.42); 1.609 (0.35); 1.553 (0.70); 1.544 (0.81); 1.521 (1.47); 1.497 (1.50); 1.475 (0.58); 1.467 (0.55); 1.437 (0.41); 1.430 (0.54); 1.405 (1.11); 1.397 (0.83); 1.380 (0.96); 1.372 (0.97); 1.355 (0.42); 1.347 (0.51); 1.324 (0.43); 1.316 (0.33); 1.299 (0.53); 1.275 (0.40); 1.269 (0.43); 1.193 (0.70); 1.175 (1.36); 1.158 (0.69); −0.000 (1.62); |
| I-94 | 8.410 (6.62); 8.361 (3.32); 8.203 (2.94); 8.197 (3.03); 7.900 (1.65); 7.894 (1.68); 7.879 (1.83); 7.873 (1.80); 7.470 (2.62); 7.449 (2.70); 4.918 (0.68); 4.905 (0.84); 4.896 (1.27); 4.886 (0.86); 4.873 (0.65); 4.206 (1.81); 4.173 (1.94); 3.438 (0.42); 3.373 (2.02); 3.304 (638.85); 3.186 (1.11); 3.169 (0.69); 3.066 (1.50); 3.037 (2.45); 3.008 (1.39); 2.673 (1.17); 2.669 (1.42); 2.664 (1.15); 2.597 (0.56); 2.539 (2.98); 2.504 (150.80); 2.500 (187.87); 2.496 (134.00); 2.420 (0.97); 2.363 (0.47); 2.336 (1.18); 2.326 (1.99); 2.321 (2.03); 2.310 (15.00); 2.294 (1.07); 2.212 (0.49); 2.140 (1.69); 2.110 (1.73); 2.084 (1.98); 2.069 (4.85); 1.987 (0.52); 1.890 (1.48); 1.870 (1.61); 1.736 (2.16); 1.727 (2.33); 1.707 (2.76); 1.698 (2.47); 1.674 (1.65); 1.667 (1.57); 1.645 (0.89); 1.635 (0.79); 1.620 (0.50); 1.558 (1.13); 1.549 (1.27); 1.527 (2.28); |

| Ex. | NMR Data |
|---|---|
|  | 1.502 (2.32); 1.478 (1.03); 1.471 (1.00); 1.434 (0.94); 1.417 (1.11); 1.409 (1.68); 1.401 (1.34); 1.383 (1.50); 1.376 (1.54); 1.360 (0.73); 1.352 (0.88); 1.328 (0.74); 1.299 (0.93); 1.273 (0.83); 1.236 (0.99); 1.210 (0.39); 1.175 (0.55); 1.158 (0.62); 1.139 (0.48); −0.000 (15.44); |
| I-95 | 8.402 (15.00); 8.293 (6.73); 7.663 (6.76); 7.657 (6.74); 7.485 (7.37); 7.464 (8.40); 7.297 (3.17); 7.278 (6.01); 7.259 (4.14); 7.240 (3.69); 7.237 (2.99); 7.199 (8.61); 7.192 (7.65); 7.186 (6.73); 7.178 (6.86); 7.171 (7.12); 7.133 (1.52); 7.123 (1.72); 7.114 (1.44); 7.110 (1.29); 6.135 (2.37); 6.124 (4.72); 6.113 (2.34); 5.747 (10.38); 5.047 (1.84); 5.032 (1.92); 4.162 (3.88); 4.129 (3.95); 3.352 (3.16); 3.302 (618.90); 3.279 (25.37); 3.043 (2.75); 3.013 (4.87); 2.984 (2.88); 2.888 (1.50); 2.859 (1.65); 2.846 (2.89); 2.832 (1.53); 2.791 (1.47); 2.776 (1.94); 2.770 (1.94); 2.753 (1.88); 2.728 (1.18); 2.714 (1.16); 2.673 (1.45); 2.669 (1.62); 2.664 (1.36); 2.660 (1.23); 2.539 (2.97); 2.504 (130.48); 2.500 (161.64); 2.496 (113.53); 2.088 (3.58); 2.083 (3.57); 2.069 (2.87); 2.053 (5.94); 2.040 (5.09); 2.029 (4.70); 1.987 (2.08); 1.962 (1.38); 1.951 (1.54); 1.940 (1.70); 1.928 (1.66); 1.916 (1.33); 1.907 (1.33); 1.892 (1.29); 1.879 (1.21); 1.868 (1.24); 1.850 (1.77); 1.837 (2.15); 1.825 (1.76); 1.819 (1.32); 1.714 (1.86); 1.705 (1.94); 1.684 (3.59); 1.675 (3.91); 1.653 (3.68); 1.644 (3.17); 1.623 (1.31); −0.000 (3.03); |
| I-96 | 8.394 (7.76); 7.291 (1.67); 7.274 (3.32); 7.259 (2.20); 7.246 (2.29); 7.241 (2.00); 7.197 (2.26); 7.187 (2.93); 7.181 (2.86); 7.171 (1.92); 7.031 (2.49); 7.012 (3.43); 6.931 (2.16); 6.911 (1.57); 6.884 (3.52); 6.132 (1.31); 6.121 (2.59); 6.110 (1.29); 5.747 (9.05); 4.493 (0.91); 4.459 (0.89); 3.971 (0.84); 3.942 (0.87); 3.703 (0.53); 3.664 (3.66); 3.646 (3.50); 3.628 (1.65); 3.606 (0.55); 3.356 (2.13); 3.301 (417.50); 3.280 (12.22); 3.223 (0.67); 3.200 (0.94); 3.172 (1.22); 3.142 (0.72); 2.900 (0.51); 2.887 (0.91); 2.874 (0.58); 2.856 (0.93); 2.844 (1.67); 2.831 (0.94); 2.790 (1.32); 2.776 (1.51); 2.767 (1.47); 2.754 (1.96); 2.726 (1.15); 2.673 (0.85); 2.669 (1.01); 2.538 (2.30); 2.504 (99.12); 2.500 (122.16); 2.496 (85.39); 2.331 (0.76); 2.326 (0.92); 2.322 (0.74); 2.220 (14.66); 2.140 (15.00); 2.128 (2.99); 2.069 (2.01); 2.060 (1.73); 2.026 (3.78); 1.987 (2.95); 1.968 (0.78); 1.958 (0.83); 1.946 (0.87); 1.935 (0.88); 1.924 (0.86); 1.911 (0.69); 1.849 (0.98); 1.835 (1.20); 1.824 (1.08); 1.599 (0.53); 1.568 (0.93); 1.548 (1.02); 1.535 (1.10); 1.506 (0.75); 1.500 (0.83); 1.398 (1.03); 1.235 (0.55); 1.175 (0.96); −0.000 (4.41); |
| I-97 | 8.401 (5.44); 7.802 (2.26); 7.797 (2.34); 7.786 (2.44); 7.776 (1.10); 7.277 (2.19); 7.258 (1.44); 7.240 (1.32); 7.236 (1.07); 7.197 (1.04); 7.185 (2.11); 7.166 (1.23); 7.038 (0.52); 7.032 (0.41); 7.016 (3.16); 7.010 (4.11); 7.008 (4.43); 6.986 (0.60); 6.135 (0.85); 6.123 (1.69); 6.111 (0.84); 5.747 (4.61); 4.123 (1.32); 4.090 (1.37); 3.877 (0.60); 3.817 (15.00); 3.301 (141.53); 3.278 (6.58); 3.019 (0.96); 2.990 (1.71); 2.961 (0.95); 2.887 (0.54); 2.873 (0.33); 2.858 (0.56); 2.845 (1.02); 2.832 (0.53); 2.789 (0.51); 2.775 (0.65); 2.768 (0.65); 2.752 (0.61); 2.732 (0.32); 2.725 (0.34); 2.669 (0.33); 2.539 (0.65); 2.509 (18.74); 2.504 (2.32); 2.500 (40.84); 2.496 (28.76); 2.327 (0.33); 2.076 (1.32); 2.061 (1.10); 2.050 (2.13); 2.039 (2.28); 2.028 (1.81); 2.011 (0.85); 1.999 (0.39); 1.987 (0.79); 1.970 (0.39); 1.960 (0.49); 1.947 (0.56); 1.938 (0.59); 1.925 (0.57); 1.913 (0.43); 1.848 (0.58); 1.836 (0.75); 1.823 (0.61); 1.807 (0.42); 1.801 (0.40); 1.702 (0.56); 1.692 (0.59); 1.670 (1.08); 1.662 (1.16); 1.639 (1.07); 1.631 (1.00); 1.610 (0.45); 1.600 (0.35); 1.398 (0.55); 1.046 (0.33); 1.031 (0.34); −0.000 (1.79); |
| I-98 | 8.400 (5.10); 8.120 (0.47); 8.109 (0.48); 7.919 (2.17); 7.296 (1.30); 7.278 (2.13); 7.260 (1.39); 7.241 (1.30); 7.238 (1.03); 7.199 (1.43); 7.187 (1.98); 7.170 (1.19); 6.666 (0.66); 6.650 (0.65); 6.135 (0.84); 6.124 (1.65); 6.112 (0.82); 5.747 (3.82); 4.132 (1.37); 4.099 (1.39); 3.306 (124.63); 2.990 (10.16); 2.961 (1.73); 2.932 (0.95); 2.900 (0.32); 2.888 (0.55); 2.875 (0.35); 2.858 (0.59); 2.845 (1.03); 2.832 (0.54); 2.793 (0.53); 2.777 (0.70); 2.771 (0.68); 2.755 (0.62); 2.738 (0.40); 2.726 (0.37); 2.712 (0.31); 2.674 (0.38); 2.669 (0.44); 2.539 (1.03); 2.504 (44.14); 2.500 (54.13); 2.496 (37.93); 2.327 (0.43); 2.261 (0.30); 2.219 (12.57); 2.102 (0.43); 2.069 (1.81); 2.061 (2.40); 2.049 (15.00); 2.040 (3.16); 2.030 (2.76); 1.994 (0.39); 1.987 (0.62); 1.971 (0.41); 1.963 (0.49); 1.949 (0.55); 1.939 (0.58); 1.927 (0.53); 1.915 (0.44); 1.908 (0.46); 1.850 (0.56); 1.838 (0.69); 1.826 (0.57); 1.809 (0.39); 1.668 (0.46); 1.658 (0.56); 1.636 (1.06); 1.629 (1.13); 1.607 (1.03); 1.598 (0.95); 1.577 (0.40); 1.569 (0.33); −0.000 (0.94); |
| I-99 | 8.405 (14.59); 7.458 (6.08); 7.436 (15.00); 7.430 (8.22); 7.358 (5.26); 7.352 (4.44); 7.337 (3.51); 7.330 (3.16); 7.296 (3.33); 7.279 (6.54); 7.260 (4.34); 7.242 (3.94); 7.239 (3.19); 7.200 (4.21); 7.187 (6.28); 7.169 (3.71); 6.137 (2.52); 6.125 (5.02); 6.114 (2.58); 5.747 (12.59); 4.431 (1.68); 4.399 (1.73); 4.089 (1.60); 4.056 (1.72); 3.871 (7.14); 3.856 (6.97); 3.403 (0.96); 3.393 (1.63); 3.383 (1.39); 3.374 (2.12); 3.365 (3.28); 3.355 (2.62); 3.301 (515.55); 3.278 (25.09); 3.253 (3.91); 3.224 (2.02); 2.889 (1.60); 2.876 (1.02); 2.859 (1.77); 2.846 (3.11); 2.834 (1.67); 2.805 (1.49); 2.792 (2.14); 2.777 (3.93); 2.755 (2.43); 2.714 (0.92); 2.669 (1.17); 2.538 (2.38); 2.504 (121.13); 2.500 (149.59); 2.496 (106.17); 2.326 (1.24); 2.116 (1.75); 2.085 (2.90); 2.079 (2.96); 2.070 (3.06); 2.063 (3.16); 2.053 (3.72); 2.039 (5.63); 2.029 (5.79); 2.001 (1.23); 1.987 (1.76); 1.972 (1.22); 1.962 (1.53); 1.950 (1.68); 1.939 (1.82); 1.929 (1.69); 1.916 (1.32); 1.850 (1.69); 1.838 (2.19); 1.826 (1.88); 1.809 (1.33); 1.794 (1.01); 1.727 (1.66); 1.706 (1.66); 1.540 (1.46); 1.531 (1.49); 1.510 (1.36); 1.501 (1.29); −0.000 (6.73); |
| I-100 | 8.400 (7.05); 8.131 (3.14); 7.311 (5.05); 7.298 (1.97); 7.290 (4.05); 7.280 (2.93); 7.259 (1.98); 7.241 (1.77); 7.238 (1.40); 7.199 (1.86); 7.186 (3.00); 7.167 (1.68); 6.960 (1.70); 6.956 (1.63); 6.940 (1.53); 6.936 (1.44); 6.135 (1.12); 6.125 (2.24); 6.113 (1.12); 5.746 (7.80); 4.165 (1.83); 4.132 (1.89); 3.306 (392.68); 3.282 (12.84); 3.016 (1.35); 2.987 (2.34); 2.958 (1.28); 2.941 (1.95); 2.902 (0.39); 2.889 (0.74); 2.876 (0.46); 2.860 (0.82); 2.847 (1.37); 2.835 (0.73); 2.792 (0.71); 2.776 (0.91); 2.769 (0.91); 2.755 (0.85); 2.727 (0.52); 2.713 (0.45); 2.674 (0.56); 2.669 (0.65); 2.539 (1.41); 2.504 (62.43); 2.500 (76.46); 2.496 (53.76); 2.430 (0.35); 2.331 (0.55); 2.327 (0.64); 2.282 (2.06); 2.268 (15.00); 2.069 (2.07); 2.040 (3.49); 2.001 (0.57); 1.987 (0.74); 1.974 (0.50); 1.965 (0.66); 1.953 (0.73); 1.941 (0.80); 1.930 (0.75); 1.918 (0.60); 1.908 (0.43); 1.895 (0.34); 1.851 (0.73); 1.838 (0.97); 1.826 (0.82); 1.811 (0.55); 1.795 (0.37); 1.700 (0.76); 1.691 (0.84); 1.670 (1.55); 1.661 (1.60); 1.639 (1.44); 1.630 (1.35); 1.610 (0.57); 1.398 (0.38); 1.236 (0.30); −0.000 (3.93); |
| I-101 | 8.523 (8.20); 7.706 (2.61); 7.684 (2.97); 7.597 (2.26); 7.581 (3.12); 7.558 (4.54); 7.552 (4.86); 7.544 (4.52); 7.523 (5.16); 7.467 (1.80); 7.451 (3.07); 7.432 (2.00); 7.398 (2.96); 7.392 (2.91); 7.377 (2.82); 7.371 (2.07); 7.359 (1.82); 7.355 (1.93); 7.335 (2.59); 7.320 (1.30); 7.316 (1.35); 5.373 (12.70); 5.352 (0.81); 4.437 (0.96); 4.407 (0.94); 4.094 (0.88); 4.057 (1.06); 3.881 (3.40); 3.858 (3.23); 3.417 (1.33); 3.389 (2.87); 3.307 (1756.43); 3.180 (1.87); 3.171 (1.77); 3.155 (1.55); 3.110 (1.14); 3.092 (0.97); 3.075 (0.96); 3.061 (0.93); 3.038 (0.92); 3.005 (0.77); 2.989 (0.73); 2.959 (0.74); 2.818 (1.08); 2.791 (1.50); 2.759 (1.01); 2.674 (1.89); 2.669 (2.34); 2.617 (0.64); 2.590 (0.95); 2.539 (6.45); 2.504 (242.43); 2.500 (301.45); 2.496 (215.38); 2.393 (1.29); 2.341 (1.11); 2.327 (2.71); 2.323 (2.15); 2.292 (0.75); 2.274 (0.69); 2.257 (0.72); 2.217 (0.67); 2.171 (0.63); 2.141 (1.36); 2.104 (1.83); 2.069 (2.04); 2.049 (1.14); 1.987 (1.80); 1.908 (0.61); 1.781 (0.80); 1.758 (1.14); 1.730 (1.15); 1.583 (0.70); 1.552 (1.12); 1.527 (1.06); 1.398 (15.00); 1.235 (0.88); 1.175 (1.08); 1.158 (0.70); −0.000 (8.21); |
| I-102 | 8.512 (7.99); 7.705 (2.26); 7.702 (2.20); 7.685 (2.48); 7.596 (1.74); 7.592 (1.80); 7.577 (2.30); 7.573 (2.25); 7.467 (1.29); 7.464 (1.24); 7.449 (2.56); 7.446 (2.41); 7.430 (1.48); 7.427 (1.29); 7.357 (1.40); 7.353 (1.42); 7.338 (2.03); 7.334 (1.93); 7.319 (1.06); 7.314 (0.87); 7.033 (2.23); 7.014 (3.14); 6.932 (2.20); 6.912 (1.65); 6.887 (3.58); 5.369 (11.27); 4.496 (0.85); 4.463 (0.91); 4.022 (0.40); 3.980 (0.85); 3.950 (0.90); 3.707 (0.50); 3.668 (3.53); 3.651 (3.41); 3.610 (0.52); 3.451 (0.44); 3.446 (0.43); 3.436 (0.50); 3.421 (0.60); 3.410 (0.77); 3.401 (0.86); 3.388 (1.30); 3.379 (1.80); 3.349 (3.97); 3.303 (759.68); 3.217 (1.36); 3.183 (1.49); 3.162 (0.73); 3.155 (0.88); 2.796 (0.77); 2.767 (1.14); 2.735 (0.73); 2.669 (1.24); 2.621 (0.45); 2.539 (2.79); 2.504 (127.08); 2.500 (154.05); 2.496 (106.97); 2.331 (1.02); 2.327 (1.21); 2.298 (0.37); 2.222 (14.76); 2.186 (0.43); 2.143 (15.00); 2.085 (1.13); 2.069 (1.67); 2.048 (1.72); 2.015 (1.07); 1.987 (1.62); 1.618 (0.45); 1.587 (0.93); 1.565 (1.10); 1.556 (1.07); 1.550 (1.03); 1.518 (0.82); 1.398 (3.65); 1.193 (0.46); 1.175 (0.79); 1.157 (0.45); −0.000 (2.46); |
| I-103 | 8.519 (4.28); 7.703 (1.46); 7.684 (1.60); 7.653 (2.37); 7.595 (1.16); 7.575 (1.41); 7.466 (0.82); 7.448 (1.66); 7.428 (1.02); 7.416 (2.37); 7.409 (2.23); 7.355 (0.95); 7.335 (1.21); 7.317 (0.59); 6.906 (2.10); 6.884 (2.35); 6.554 (1.35); 6.546 (1.29); 6.531 (1.27); 6.523 (1.20); 5.371 (6.62); 4.123 (1.40); 4.089 (1.57); 4.067 (0.48); 4.039 (0.69); 4.022 (0.72); 3.922 (0.38); 3.852 (0.44); 3.808 (0.64); 3.805 (0.86); 3.760 (13.78); 3.730 (0.58); 3.673 (15.00); 3.641 (0.59); 3.627 (0.53); 3.614 (0.56); 3.604 (0.56); 3.578 (0.62); 3.567 (0.87); 3.488 (0.96); 3.460 (1.23); 3.442 (1.31); 3.303 (1289.43); 3.226 (0.76); 3.216 (0.70); 3.184 (0.43); 3.173 (0.39); 3.026 (0.98); 2.993 (1.61); 2.966 (0.98); 2.755 (0.41); 2.737 (0.41); 2.729 (0.45); 2.695 (0.66); 2.673 (1.90); 2.669 (2.29); 2.653 (0.87); 2.646 (0.82); 2.539 (12.25); 2.504 (224.27); 2.500 (268.36); 2.496 (186.30); 2.326 (1.73); 2.099 (1.08); 2.069 (4.18); 1.987 (1.23); 1.714 (0.47); 1.704 (0.52); 1.682 (1.06); 1.674 (1.07); 1.654 (1.01); 1.642 (0.99); 1.612 (0.37); 1.398 (1.88); 1.292 (0.75); 1.237 (0.54); 1.192 (0.58); 1.175 (1.00); 1.158 (0.91); −0.000 (29.58); |
| I-104 | 8.535 (6.09); 7.707 (1.18); 7.705 (1.22); 7.693 (1.32); 7.691 (1.31); 7.656 (1.95); 7.599 (0.83); 7.597 (0.86); 7.587 (1.05); 7.584 (1.02); 7.465 (0.66); 7.463 (0.70); 7.456 (1.57); 7.453 (2.75); 7.440 (0.72); 7.438 (0.69); 7.354 (0.65); 7.351 (0.67); 7.341 (0.94); 7.338 (0.94); |

| Ex. | NMR Data |
|---|---|
| | 7.328 (0.52); 7.326 (0.51); 6.871 (1.61); 6.857 (2.52); 6.813 (0.92); 6.812 (0.94); 6.810 (0.96); 6.799 (0.58); 6.799 (0.62); 6.796 (0.60); 5.370 (5.58); 4.130 (0.82); 4.108 (0.87); 3.766 (0.89); 3.760 (13.50); 3.388 (0.55); 3.376 (0.56); 3.367 (0.49); 3.364 (0.60); 3.348 (408.25); 3.325 (0.59); 3.321 (0.76); 3.314 (0.78); 2.992 (0.50); 2.989 (0.61); 2.969 (1.05); 2.950 (0.59); 2.946 (0.50); 2.618 (0.45); 2.615 (0.64); 2.612 (0.46); 2.542 (3.59); 2.524 (1.21); 2.521 (1.52); 2.518 (1.40); 2.509 (34.73); 2.506 (76.23); 2.503 (106.87); 2.500 (77.30); 2.497 (35.42); 2.390 (0.46); 2.387 (0.64); 2.384 (0.45); 2.208 (9.05); 2.077 (1.23); 2.074 (0.73); 2.057 (0.74); 2.053 (0.78); 1.990 (1.62); 1.661 (0.63); 1.655 (0.73); 1.640 (0.69); 1.635 (0.63); 1.186 (0.46); 1.174 (0.94); 1.163 (0.45); 1.102 (0.45); 1.091 (0.88); 1.079 (0.42); −0.000 (4.14); |
| I-105 | 9.154 (0.40); 8.520 (4.83); 8.204 (0.43); 7.803 (2.58); 7.798 (3.00); 7.791 (2.83); 7.704 (1.48); 7.683 (1.79); 7.598 (1.22); 7.580 (1.55); 7.467 (0.96); 7.448 (1.73); 7.430 (0.90); 7.426 (0.88); 7.354 (0.87); 7.351 (0.90); 7.336 (1.40); 7.316 (0.67); 7.039 (0.70); 7.034 (0.55); 7.017 (3.57); 7.010 (4.82); 6.990 (0.69); 6.569 (0.38); 5.371 (7.43); 4.131 (1.47); 4.095 (1.50); 4.038 (0.50); 4.021 (0.44); 3.877 (2.22); 3.819 (15.00); 3.500 (0.43); 3.483 (0.39); 3.454 (0.48); 3.437 (0.64); 3.412 (0.83); 3.379 (1.46); 3.299 (711.73); 3.249 (1.91); 3.227 (1.04); 3.205 (0.79); 3.187 (0.64); 3.168 (0.52); 3.136 (0.41); 3.098 (0.37); 3.031 (1.19); 3.001 (1.97); 2.972 (1.14); 2.931 (0.53); 2.713 (0.41); 2.696 (0.50); 2.673 (1.56); 2.669 (1.83); 2.664 (1.55); 2.653 (0.62); 2.630 (0.60); 2.539 (10.28); 2.504 (197.41); 2.500 (236.72); 2.496 (165.86); 2.331 (1.44); 2.327 (1.81); 2.096 (1.28); 2.069 (2.97); 1.987 (1.76); 1.715 (0.51); 1.710 (0.60); 1.686 (1.17); 1.677 (1.20); 1.655 (1.15); 1.647 (1.13); 1.626 (0.50); 1.617 (0.43); 1.398 (0.90); 1.292 (0.66); 1.236 (0.53); 1.193 (0.62); 1.175 (1.05); 1.159 (0.65); −0.000 (26.78); |
| I-106 | 9.465 (0.54); 8.524 (10.45); 8.448 (5.33); 8.426 (0.46); 7.939 (4.48); 7.934 (4.38); 7.758 (0.38); 7.737 (0.51); 7.705 (6.12); 7.685 (7.15); 7.601 (2.29); 7.598 (2.47); 7.582 (3.03); 7.579 (3.02); 7.482 (2.72); 7.478 (2.85); 7.465 (3.00); 7.457 (2.70); 7.449 (3.94); 7.447 (3.67); 7.431 (2.10); 7.428 (1.98); 7.357 (1.88); 7.353 (1.90); 7.338 (2.75); 7.333 (2.61); 7.318 (1.32); 7.314 (1.21); 5.374 (15.00); 4.185 (2.75); 4.151 (2.94); 3.489 (0.44); 3.482 (0.47); 3.451 (0.59); 3.383 (2.70); 3.353 (6.21); 3.305 (1392.67); 3.112 (0.82); 3.077 (2.40); 3.072 (2.40); 3.041 (3.83); 3.013 (2.22); 2.971 (0.39); 2.936 (0.54); 2.696 (0.54); 2.674 (1.80); 2.669 (2.17); 2.665 (1.70); 2.634 (0.56); 2.539 (10.84); 2.504 (222.38); 2.500 (275.02); 2.496 (194.12); 2.362 (0.62); 2.331 (1.81); 2.327 (2.19); 2.322 (1.71); 2.303 (0.47); 2.296 (0.42); 2.200 (0.35); 2.175 (0.34); 2.111 (2.63); 2.085 (3.05); 2.069 (2.74); 1.987 (0.61); 1.766 (0.34); 1.745 (1.04); 1.735 (1.24); 1.713 (2.31); 1.704 (2.49); 1.683 (2.35); 1.674 (2.13); 1.653 (1.01); 1.643 (0.87); 1.398 (12.78); 1.292 (0.77); 1.236 (0.70); 1.175 (0.40); 1.159 (0.39); −0.000 (52.96); |
| I-107 | 8.520 (5.77); 8.137 (3.46); 7.704 (2.01); 7.685 (2.25); 7.598 (1.63); 7.582 (2.00); 7.468 (1.11); 7.449 (2.25); 7.429 (1.20); 7.357 (1.23); 7.353 (1.27); 7.337 (2.05); 7.313 (5.45); 7.291 (3.32); 6.961 (1.70); 6.941 (1.57); 6.937 (1.45); 5.373 (9.91); 4.171 (1.93); 4.137 (2.05); 3.519 (0.35); 3.496 (0.42); 3.475 (0.48); 3.457 (0.58); 3.305 (863.19); 3.174 (0.58); 3.163 (0.49); 3.110 (0.33); 3.089 (0.32); 3.028 (1.52); 2.998 (2.52); 2.968 (1.44); 2.695 (0.38); 2.669 (1.50); 2.539 (7.14); 2.504 (155.89); 2.500 (184.35); 2.327 (1.44); 2.295 (0.48); 2.269 (15.00); 2.088 (1.73); 2.069 (2.38); 2.061 (2.00); 1.987 (0.34); 1.715 (0.65); 1.705 (0.76); 1.685 (1.53); 1.676 (1.62); 1.654 (1.54); 1.645 (1.45); 1.625 (0.63); 1.398 (8.39); 1.292 (0.45); 1.236 (0.38); −0.000 (34.88); |
| I-108 | 9.287 (0.98); 8.522 (10.14); 8.299 (5.23); 8.223 (1.12); 8.216 (1.12); 7.703 (3.22); 7.685 (3.40); 7.665 (5.34); 7.658 (5.03); 7.599 (2.47); 7.582 (2.98); 7.529 (1.42); 7.507 (1.40); 7.487 (5.63); 7.465 (7.80); 7.449 (3.73); 7.431 (2.08); 7.357 (1.98); 7.352 (1.89); 7.336 (2.83); 7.333 (2.73); 7.318 (1.48); 7.200 (3.53); 7.194 (3.75); 7.179 (3.05); 7.173 (3.00); 5.372 (15.00); 4.168 (2.80); 4.135 (3.10); 3.302 (4496.06); 3.147 (2.26); 3.053 (2.98); 3.025 (4.51); 3.011 (1.81); 2.996 (2.80); 2.939 (1.05); 2.910 (0.94); 2.838 (1.06); 2.820 (0.94); 2.801 (0.97); 2.780 (0.94); 2.775 (0.94); 2.765 (1.02); 2.706 (1.38); 2.695 (1.98); 2.673 (6.65); 2.669 (8.48); 2.664 (6.55); 2.641 (2.17); 2.539 (42.84); 2.504 (856.94); 2.500 (1055.52); 2.496 (741.08); 2.331 (6.33); 2.326 (8.20); 2.322 (6.29); 2.281 (1.24); 2.261 (1.14); 2.250 (1.01); 2.237 (1.05); 2.212 (0.93); 2.202 (0.96); 2.102 (2.87); 2.069 (8.51); 1.720 (1.21); 1.698 (2.53); 1.688 (2.50); 1.668 (2.68); 1.660 (2.42); 1.642 (1.19); 1.638 (1.19); 1.398 (6.16); 1.326 (0.99); 1.292 (2.77); 1.237 (1.89); 1.158 (0.94); 0.146 (1.44); −0.000 (295.19); −0.008 (17.22); −0.150 (1.17); |
| I-109 | 11.642 (0.57); 8.418 (7.18); 6.547 (4.82); 5.713 (0.65); 4.926 (0.37); 4.917 (0.67); 4.904 (0.86); 4.894 (1.29); 4.884 (0.86); 4.872 (0.65); 4.862 (0.35); 4.265 (0.67); 4.231 (0.75); 4.096 (0.72); 4.058 (0.80); 4.040 (0.81); 4.022 (0.74); 3.743 (15.00); 3.584 (1.94); 3.409 (0.78); 3.400 (0.66); 3.390 (0.99); 3.381 (1.54); 3.372 (1.14); 3.362 (1.06); 3.352 (1.44); 3.342 (1.44); 3.304 (209.83); 3.251 (0.94); 3.163 (0.62); 3.133 (0.93); 3.103 (0.53); 2.670 (0.36); 2.540 (1.82); 2.505 (37.38); 2.501 (45.14); 2.497 (31.39); 2.327 (0.36); 2.158 (1.59); 2.132 (1.85); 2.070 (1.12); 1.987 (3.02); 1.908 (1.19); 1.867 (1.70); 1.861 (1.72); 1.807 (0.69); 1.745 (1.85); 1.723 (1.99); 1.715 (1.97); 1.553 (1.09); 1.544 (1.26); 1.528 (1.99); 1.521 (2.26); 1.497 (2.11); 1.474 (0.87); 1.466 (0.84); 1.432 (0.81); 1.407 (1.69); 1.398 (2.25); 1.382 (1.43); 1.375 (1.43); 1.358 (0.62); 1.350 (0.76); 1.326 (0.65); 1.301 (0.82); 1.296 (0.81); 1.272 (0.65); 1.237 (1.09); 1.193 (0.86); 1.175 (1.67); 1.158 (0.86); −0.000 (9.84); −0.008 (0.57); |
| I-110 | 8.527 (6.56); 8.359 (3.34); 8.198 (2.94); 8.192 (2.99); 7.899 (1.72); 7.893 (1.61); 7.877 (1.81); 7.872 (1.75); 7.707 (2.04); 7.687 (2.20); 7.684 (2.17); 7.603 (1.65); 7.584 (2.01); 7.581 (2.07); 7.469 (3.67); 7.448 (4.12); 7.432 (1.76); 7.429 (1.74); 7.354 (1.24); 7.338 (1.82); 7.335 (1.76); 7.327 (0.49); 7.320 (0.89); 5.746 (0.42); 5.375 (9.77); 5.251 (0.59); 4.202 (1.86); 4.168 (1.97); 4.057 (0.40); 4.039 (1.16); 4.021 (1.19); 4.003 (0.48); 3.556 (0.46); 3.542 (0.55); 3.510 (0.58); 3.420 (1.60); 3.309 (1624.50); 3.207 (1.48); 3.138 (0.72); 3.129 (0.67); 3.065 (1.64); 3.034 (2.59); 3.006 (1.52); 2.960 (0.42); 2.934 (0.40); 2.669 (2.09); 2.665 (1.62); 2.634 (0.65); 2.609 (0.87); 2.539 (6.78); 2.505 (209.34); 2.500 (255.92); 2.496 (180.31); 2.419 (1.58); 2.356 (1.34); 2.331 (1.81); 2.327 (2.22); 2.322 (2.01); 2.305 (15.00); 2.280 (0.62); 2.262 (0.44); 2.157 (0.38); 2.116 (1.69); 2.088 (1.95); 2.084 (1.96); 2.069 (1.20); 1.987 (4.36); 1.907 (0.41); 1.730 (0.74); 1.708 (1.50); 1.701 (1.54); 1.679 (1.48); 1.674 (1.55); 1.650 (0.67); 1.398 (1.18); 1.235 (0.82); 1.193 (1.24); 1.175 (2.43); 1.157 (1.18); −0.000 (8.19); |
| I-111 | 8.641 (3.61); 8.540 (13.50); 7.916 (1.42); 7.912 (1.55); 7.904 (1.51); 7.900 (1.48); 7.708 (2.69); 7.706 (2.77); 7.694 (2.99); 7.692 (2.96); 7.601 (1.94); 7.599 (2.04); 7.589 (2.35); 7.586 (2.34); 7.484 (0.54); 7.481 (0.64); 7.474 (1.21); 7.470 (1.43); 7.466 (2.62); 7.464 (2.48); 7.454 (4.60); 7.452 (3.52); 7.441 (2.54); 7.439 (3.24); 7.423 (0.86); 7.355 (1.53); 7.352 (1.57); 7.342 (2.21); 7.339 (2.16); 7.329 (1.23); 7.327 (1.19); 5.761 (1.34); 5.372 (12.92); 4.183 (1.87); 4.160 (1.94); 4.034 (0.68); 4.022 (0.70); 3.351 (1150.97); 3.333 (2.35); 3.328 (1.92); 3.319 (1.34); 3.313 (0.75); 3.029 (1.21); 3.009 (2.30); 2.990 (1.24); 2.618 (0.90); 2.615 (1.27); 2.612 (0.91); 2.543 (7.71); 2.524 (2.35); 2.521 (2.99); 2.518 (2.84); 2.510 (66.55); 2.507 (145.74); 2.503 (201.18); 2.500 (144.14); 2.497 (66.42); 2.391 (0.94); 2.388 (1.29); 2.385 (0.93); 2.096 (1.62); 2.087 (0.76); 2.077 (3.12); 2.053 (0.52); 1.990 (3.12); 1.702 (0.57); 1.695 (0.67); 1.681 (1.40); 1.675 (1.59); 1.661 (1.53); 1.655 (1.41); 1.641 (0.62); 1.634 (0.52); 1.397 (4.93); 1.234 (0.56); 1.186 (0.89); 1.174 (1.82); 1.163 (0.88); 1.158 (0.59); −0.000 (3.30); |
| I-112 | 9.131 (2.19); 8.526 (6.62); 7.706 (1.44); 7.704 (1.46); 7.687 (1.64); 7.684 (1.65); 7.604 (1.03); 7.600 (1.11); 7.584 (1.38); 7.580 (1.38); 7.470 (0.83); 7.466 (0.84); 7.451 (1.70); 7.448 (1.64); 7.432 (0.92); 7.429 (0.88); 7.358 (0.97); 7.354 (0.97); 7.339 (1.26); 7.335 (1.26); 7.319 (0.65); 7.315 (0.62); 7.247 (1.00); 7.227 (2.73); 7.208 (1.96); 7.203 (2.09); 7.188 (0.64); 7.182 (0.82); 7.134 (2.28); 7.128 (1.96); 5.378 (7.61); 4.804 (1.03); 4.769 (1.09); 4.057 (1.08); 4.040 (3.34); 4.022 (3.38); 4.004 (1.12); 3.618 (1.17); 3.616 (0.82); 3.612 (0.76); 3.608 (1.05); 3.601 (2.77); 3.595 (1.07); 3.591 (0.72); 3.585 (1.17); 3.464 (0.70); 3.291 (1046.47); 3.268 (2.67); 3.257 (1.35); 2.673 (0.84); 2.668 (1.18); 2.664 (0.86); 2.538 (5.57); 2.521 (3.34); 2.517 (5.27); 2.508 (63.56); 2.504 (130.33); 2.499 (177.81); 2.494 (126.20); 2.490 (58.70); 2.330 (0.84); 2.326 (1.16); 2.322 (1.00); 2.143 (11.77); 2.118 (1.11); 2.067 (1.28); 1.986 (15.00); 1.781 (0.59); 1.777 (1.39); 1.769 (1.53); 1.760 (4.19); 1.752 (1.92); 1.744 (1.37); 1.731 (0.89); 1.725 (0.86); 1.399 (4.04); 1.193 (4.18); 1.175 (8.27); 1.157 (4.18); −0.000 (8.44); |
| I-113 | 9.290 (1.24); 8.526 (7.27); 7.706 (1.61); 7.703 (1.59); 7.686 (1.80); 7.683 (1.71); 7.603 (1.12); 7.599 (1.23); 7.584 (1.45); 7.580 (1.57); 7.546 (0.76); 7.543 (0.63); 7.516 (3.00); 7.495 (3.80); 7.469 (0.94); 7.467 (0.97); 7.451 (1.76); 7.448 (1.84); 7.432 (1.12); 7.429 (1.08); 7.420 (3.07); 7.413 (3.70); 7.358 (1.00); 7.353 (1.17); 7.347 (2.13); 7.340 (2.28); 7.334 (1.54); 7.326 (1.64); 7.319 (2.07); 5.393 (0.60); 5.378 (8.34); 4.806 (1.06); 4.773 (1.14); 4.518 (0.90); 4.504 (0.86); 4.040 (1.31); 4.022 (1.20); 3.608 (0.59); 3.601 (1.37); 3.475 (0.91); 3.465 (0.59); 3.447 (0.58); 3.352 (1.19); 3.346 (1.48); 3.331 (1.22); 3.291 (1334.77); 3.273 (4.30); 3.269 (3.11); 3.254 (1.00); 2.677 (0.65); |

| Ex. | NMR Data |
|---|---|
| | 2.673 (1.24); 2.668 (1.62); 2.664 (1.13); 2.538 (7.70); 2.521 (5.01); 2.517 (8.04); 2.508 (89.15); 2.504 (180.11); 2.499 (243.26); 2.494 (169.78); 2.490 (77.33); 2.330 (1.08); 2.326 (1.54); 2.321 (1.09); 2.153 (0.98); 2.126 (1.16); 2.067 (1.16); 1.986 (5.35); 1.777 (1.47); 1.770 (1.00); 1.760 (1.83); 1.752 (1.40); 1.744 (1.38); 1.399 (15.00); 1.193 (1.49); 1.175 (3.04); 1.157 (1.63); 0.955 (0.67); 0.937 (1.36); −0.000 (12.67); |
| I-114 | 9.228 (1.45); 8.524 (4.38); 7.706 (1.00); 7.703 (0.97); 7.686 (1.14); 7.683 (1.11); 7.600 (1.46); 7.593 (1.03); 7.579 (1.85); 7.572 (0.95); 7.469 (0.52); 7.467 (0.56); 7.451 (1.13); 7.448 (1.11); 7.432 (0.64); 7.429 (0.58); 7.358 (0.67); 7.353 (1.13); 7.338 (1.48); 7.334 (1.11); 7.331 (1.12); 7.316 (1.25); 7.260 (0.62); 7.253 (0.56); 7.239 (0.82); 7.232 (0.77); 7.218 (0.40); 7.211 (0.36); 5.377 (5.16); 4.821 (0.70); 4.788 (0.76); 4.040 (0.55); 4.022 (0.53); 3.485 (0.35); 3.475 (0.54); 3.446 (0.34); 3.356 (0.39); 3.337 (1.05); 3.292 (692.36); 3.259 (0.74); 2.677 (0.36); 2.673 (0.66); 2.668 (0.91); 2.664 (0.67); 2.659 (0.33); 2.538 (4.21); 2.521 (2.53); 2.516 (4.04); 2.508 (51.00); 2.504 (104.47); 2.499 (142.57); 2.494 (101.12); 2.490 (47.07); 2.330 (0.72); 2.326 (0.88); 2.321 (0.66); 2.317 (0.33); 2.149 (0.65); 2.123 (0.74); 2.067 (0.47); 1.986 (2.46); 1.806 (0.30); 1.783 (0.61); 1.776 (0.66); 1.753 (0.59); 1.745 (0.55); 1.399 (15.00); 1.193 (0.71); 1.175 (1.32); 1.157 (0.72); −0.000 (4.93); |
| I-115 | 9.211 (1.71); 8.532 (9.82); 7.707 (3.09); 7.705 (3.11); 7.687 (4.17); 7.685 (4.25); 7.665 (1.26); 7.604 (2.55); 7.601 (2.61); 7.585 (3.30); 7.581 (3.37); 7.568 (1.01); 7.547 (1.16); 7.530 (0.82); 7.489 (0.92); 7.485 (0.70); 7.469 (2.39); 7.452 (3.70); 7.449 (3.67); 7.433 (2.62); 7.415 (1.09); 7.397 (1.09); 7.378 (2.93); 7.371 (3.39); 7.354 (5.54); 7.337 (4.21); 7.335 (4.46); 7.320 (3.90); 7.315 (3.25); 7.309 (3.11); 7.302 (3.11); 7.298 (3.02); 7.292 (2.43); 7.281 (3.55); 7.258 (3.81); 7.235 (1.62); 5.529 (4.12); 5.393 (1.47); 5.379 (15.00); 5.115 (0.70); 4.799 (2.20); 4.765 (2.27); 4.519 (1.00); 4.504 (0.99); 4.039 (0.78); 4.022 (0.84); 3.494 (1.24); 3.485 (1.10); 3.476 (1.52); 3.467 (2.10); 3.457 (1.57); 3.449 (1.37); 3.438 (1.60); 3.429 (1.24); 3.307 (888.84); 2.674 (1.06); 2.669 (1.26); 2.539 (6.54); 2.505 (128.72); 2.500 (157.21); 2.496 (111.14); 2.331 (0.96); 2.327 (1.18); 2.152 (2.32); 2.125 (2.66); 2.095 (1.61); 1.987 (3.29); 1.800 (0.87); 1.792 (1.06); 1.762 (2.24); 1.739 (2.09); 1.733 (2.00); 1.709 (0.90); 1.398 (1.69); 1.237 (0.88); 1.193 (1.09); 1.175 (1.84); 1.157 (1.12); −0.000 (6.05); |
| I-116 | 9.196 (4.59); 8.527 (12.63); 7.706 (2.75); 7.703 (2.95); 7.686 (3.21); 7.683 (3.25); 7.603 (2.05); 7.599 (2.25); 7.584 (2.72); 7.580 (2.81); 7.470 (1.63); 7.467 (1.72); 7.451 (3.20); 7.448 (3.10); 7.432 (1.90); 7.429 (1.75); 7.357 (1.70); 7.353 (1.81); 7.338 (2.52); 7.333 (2.50); 7.319 (1.25); 7.314 (1.18); 7.274 (0.94); 7.261 (1.09); 7.250 (1.93); 7.238 (1.97); 7.227 (1.31); 7.214 (1.27); 7.194 (0.95); 7.187 (1.20); 7.179 (1.12); 7.171 (2.06); 7.163 (1.19); 7.155 (1.11); 7.148 (1.12); 7.119 (0.84); 7.110 (1.30); 7.098 (1.11); 7.089 (1.66); 7.082 (0.89); 7.067 (0.89); 5.742 (9.77); 5.379 (15.00); 4.802 (1.83); 4.768 (1.96); 3.475 (0.85); 3.465 (1.52); 3.456 (0.84); 3.437 (0.83); 3.334 (2.42); 3.295 (1174.36); 3.257 (1.73); 3.236 (0.86); 2.673 (1.09); 2.669 (1.43); 2.664 (1.04); 2.538 (2.28); 2.522 (4.29); 2.517 (7.02); 2.509 (82.92); 2.504 (168.98); 2.499 (230.04); 2.495 (163.28); 2.490 (76.10); 2.331 (1.23); 2.326 (1.54); 2.321 (1.15); 2.151 (1.79); 2.125 (2.16); 2.067 (3.02); 1.986 (1.32); 1.790 (0.80); 1.760 (1.83); 1.737 (1.78); 1.728 (1.60); 1.425 (1.22); 1.399 (5.61); 1.237 (1.51); 1.175 (0.81); −0.000 (9.51); |
| I-117 | 9.116 (3.53); 8.525 (10.01); 7.706 (2.31); 7.703 (2.45); 7.686 (2.75); 7.683 (2.79); 7.603 (1.77); 7.599 (1.88); 7.584 (2.36); 7.580 (2.38); 7.469 (1.35); 7.466 (1.47); 7.450 (2.73); 7.448 (2.70); 7.431 (1.55); 7.429 (1.53); 7.358 (1.69); 7.354 (1.58); 7.338 (2.21); 7.334 (2.23); 7.319 (1.14); 7.315 (1.13); 7.243 (1.29); 7.223 (1.80); 7.205 (1.52); 7.007 (0.94); 7.000 (1.12); 6.986 (1.74); 6.979 (1.93); 6.965 (0.82); 6.957 (1.01); 6.943 (1.88); 6.936 (1.51); 6.918 (1.88); 6.911 (1.51); 5.532 (0.65); 5.378 (12.81); 4.804 (1.80); 4.771 (1.89); 4.519 (0.80); 4.504 (0.74); 3.490 (0.72); 3.471 (0.82); 3.461 (1.33); 3.451 (0.83); 3.434 (0.77); 3.345 (0.78); 3.337 (0.78); 3.317 (3.52); 3.291 (1058.53); 3.267 (3.93); 3.258 (2.36); 2.673 (1.01); 2.668 (1.35); 2.664 (1.08); 2.538 (11.28); 2.521 (4.58); 2.508 (76.57); 2.503 (154.74); 2.499 (210.42); 2.494 (150.84); 2.490 (71.23); 2.330 (0.90); 2.326 (1.30); 2.321 (0.99); 2.316 (1.02); 2.159 (2.08); 2.130 (15.00); 2.067 (0.69); 1.986 (2.91); 1.781 (0.73); 1.751 (1.58); 1.728 (1.54); 1.722 (1.35); 1.399 (3.33); 1.236 (0.70); 1.193 (0.90); 1.175 (1.75); 1.157 (0.96); −0.000 (9.18); |
| I-118 | 9.297 (2.06); 8.531 (5.62); 7.706 (1.24); 7.704 (1.24); 7.686 (1.83); 7.684 (2.01); 7.678 (0.99); 7.661 (1.31); 7.650 (0.61); 7.640 (0.55); 7.629 (0.61); 7.605 (0.92); 7.600 (0.96); 7.585 (1.18); 7.582 (1.19); 7.470 (1.13); 7.467 (0.83); 7.451 (2.37); 7.449 (2.33); 7.432 (0.94); 7.429 (1.16); 7.358 (0.78); 7.353 (0.76); 7.338 (1.07); 7.334 (1.05); 7.319 (0.54); 7.315 (0.50); 5.380 (6.40); 4.816 (0.78); 4.783 (0.77); 3.505 (0.31); 3.486 (0.41); 3.476 (0.65); 3.466 (0.44); 3.448 (0.38); 3.358 (0.81); 3.328 (1.67); 3.291 (459.03); 3.271 (1.16); 3.261 (0.57); 2.673 (0.45); 2.668 (0.59); 2.664 (0.44); 2.538 (5.25); 2.522 (1.96); 2.517 (3.21); 2.508 (34.42); 2.504 (69.51); 2.499 (93.73); 2.495 (66.13); 2.490 (30.52); 2.331 (0.44); 2.326 (0.59); 2.321 (0.40); 2.172 (0.76); 2.167 (0.76); 2.139 (0.89); 1.986 (0.75); 1.824 (0.31); 1.814 (0.34); 1.790 (0.72); 1.785 (0.79); 1.761 (0.73); 1.755 (0.68); 1.399 (15.00); 1.175 (0.41); −0.000 (3.74); |
| I-119 | 8.770 (2.11); 8.523 (6.32); 7.705 (1.52); 7.702 (1.49); 7.685 (1.69); 7.682 (1.60); 7.600 (1.06); 7.596 (1.14); 7.580 (1.41); 7.577 (1.41); 7.566 (0.53); 7.563 (0.51); 7.546 (0.95); 7.529 (0.45); 7.466 (0.83); 7.464 (0.87); 7.448 (1.71); 7.445 (1.62); 7.429 (0.92); 7.426 (0.85); 7.395 (0.56); 7.357 (0.96); 7.352 (0.91); 7.338 (1.33); 7.333 (1.27); 7.318 (0.72); 7.314 (0.62); 5.545 (0.47); 5.392 (0.67); 5.375 (7.58); 5.365 (0.79); 4.787 (0.99); 4.753 (1.01); 4.518 (1.29); 4.504 (1.25); 3.470 (0.42); 3.460 (0.77); 3.450 (0.46); 3.432 (0.46); 3.333 (1.07); 3.289 (620.66); 3.269 (4.45); 3.239 (0.41); 2.673 (0.67); 2.668 (0.87); 2.664 (0.66); 2.538 (7.70); 2.521 (2.81); 2.516 (4.66); 2.508 (51.62); 2.504 (104.09); 2.499 (140.56); 2.494 (99.54); 2.490 (46.28); 2.434 (2.53); 2.330 (0.68); 2.326 (0.92); 2.321 (0.66); 2.265 (2.57); 2.259 (0.89); 2.203 (12.91); 2.155 (0.95); 2.151 (1.00); 2.118 (1.14); 2.107 (1.40); 2.094 (0.71); 2.063 (15.00); 2.049 (0.65); 1.986 (0.65); 1.770 (0.43); 1.747 (0.89); 1.741 (0.96); 1.717 (0.90); 1.709 (0.83); 1.688 (0.37); 1.399 (0.47); 1.237 (0.41); 1.175 (0.38); 1.159 (0.42); −0.000 (5.64); |
| I-120 | 8.428 (9.21); 7.968 (3.40); 7.549 (0.81); 7.534 (0.93); 7.529 (2.01); 7.513 (2.08); 7.508 (1.50); 7.493 (1.40); 7.439 (2.87); 7.419 (1.79); 7.351 (1.30); 7.349 (1.25); 7.328 (2.24); 7.307 (1.06); 7.304 (0.98); 7.042 (2.42); 7.023 (2.92); 6.998 (3.16); 6.854 (1.88); 6.835 (1.57); 5.742 (9.65); 5.448 (7.40); 5.444 (7.34); 4.163 (1.83); 4.129 (1.92); 4.040 (0.81); 4.022 (0.81); 3.341 (0.42); 3.332 (0.78); 3.292 (223.01); 2.985 (1.12); 2.980 (1.29); 2.951 (2.35); 2.922 (1.31); 2.669 (0.34); 2.539 (0.94); 2.522 (1.21); 2.509 (19.78); 2.504 (38.85); 2.500 (51.83); 2.495 (36.52); 2.490 (17.07); 2.326 (0.35); 2.230 (15.00); 2.102 (14.84); 2.067 (1.80); 2.058 (1.56); 2.032 (1.79); 1.986 (3.57); 1.908 (1.00); 1.676 (0.58); 1.666 (0.69); 1.645 (1.42); 1.636 (1.54); 1.614 (1.42); 1.606 (1.30); 1.584 (0.54); 1.575 (0.45); 1.193 (0.99); 1.175 (1.93); 1.158 (0.97); −0.000 (3.34); |
| I-121 | 8.439 (9.38); 7.968 (3.40); 7.573 (0.47); 7.556 (1.00); 7.552 (0.92); 7.539 (0.72); 7.535 (1.91); 7.531 (0.72); 7.518 (0.95); 7.514 (1.13); 7.497 (0.51); 7.216 (0.35); 7.212 (0.47); 7.203 (2.85); 7.191 (0.64); 7.183 (4.34); 7.174 (0.65); 7.170 (0.50); 7.162 (2.44); 7.153 (0.39); 7.042 (2.42); 7.023 (2.92); 6.998 (3.17); 6.854 (1.86); 6.835 (1.56); 5.742 (0.62); 5.397 (8.36); 4.162 (1.83); 4.129 (1.91); 4.058 (0.42); 4.040 (1.21); 4.022 (1.21); 4.004 (0.41); 3.341 (0.60); 3.332 (1.03); 3.322 (1.17); 3.293 (382.66); 3.269 (2.79); 2.981 (1.27); 2.952 (2.34); 2.923 (1.31); 2.891 (0.38); 2.673 (0.37); 2.669 (0.50); 2.664 (0.36); 2.538 (1.51); 2.522 (1.80); 2.509 (28.22); 2.504 (55.78); 2.499 (74.64); 2.495 (52.46); 2.490 (24.47); 2.331 (0.36); 2.326 (0.49); 2.322 (0.36); 2.230 (15.00); 2.102 (14.86); 2.067 (2.25); 2.058 (1.53); 2.032 (1.76); 1.986 (5.40); 1.908 (1.26); 1.676 (0.58); 1.666 (0.68); 1.645 (1.41); 1.636 (1.53); 1.614 (1.41); 1.605 (1.30); 1.584 (0.54); 1.575 (0.43); 1.193 (1.52); 1.175 (2.98); 1.158 (1.49); −0.000 (4.09); |
| I-122 | 8.122 (9.67); 7.959 (3.40); 7.307 (2.35); 7.304 (3.14); 7.286 (4.76); 7.236 (2.79); 7.218 (4.85); 7.198 (2.42); 7.134 (1.01); 7.131 (1.68); 7.128 (0.98); 7.113 (2.32); 7.098 (0.58); 7.095 (0.88); 7.041 (2.35); 7.022 (2.84); 6.995 (3.14); 6.853 (1.80); 6.834 (1.49); 5.742 (9.55); 5.100 (0.51); 5.085 (0.99); 5.074 (0.86); 5.058 (0.63); 4.139 (1.61); 4.106 (1.70); 4.040 (1.23); 4.022 (1.23); 3.293 (278.64); 3.269 (1.73); 3.260 (1.03); 3.249 (1.01); 3.240 (1.42); 3.230 (0.87); 3.221 (0.57); 3.211 (0.71); 2.970 (1.23); 2.941 (2.26); 2.912 (1.26); 2.871 (0.57); 2.863 (0.55); 2.842 (1.03); 2.833 (0.91); 2.814 (0.66); 2.805 (0.56); 2.538 (1.01); 2.521 (1.27); 2.508 (21.20); 2.503 (42.12); 2.499 (56.59); 2.494 (40.09); 2.490 (19.01); 2.228 (14.49); 2.101 (15.00); 2.066 (0.68); 2.012 (1.49); 1.986 (7.05); 1.907 (1.02); 1.865 (0.84); 1.858 (0.86); 1.827 (1.68); 1.764 (0.74); 1.734 (0.85); 1.720 (0.80); 1.689 (0.96); 1.681 (0.78); 1.657 (0.92); 1.649 (0.77); 1.627 (0.78); 1.598 (1.41); 1.568 (1.48); 1.538 (1.22); 1.520 (1.79); 1.492 (1.06); 1.398 (0.69); 1.367 (0.52); 1.193 (1.51); 1.175 (2.96); 1.157 (1.48); −0.000 (3.14); |
| I-123 | 8.123 (9.43); 7.958 (3.36); 7.307 (2.35); 7.304 (3.10); 7.286 (4.70); 7.236 (2.78); 7.218 (4.80); 7.198 (2.40); 7.131 (1.63); 7.128 (0.99); 7.113 (2.28); 7.095 (0.86); 7.041 (2.36); 7.022 (2.86); 6.994 (3.11); 6.852 (1.80); 6.833 (1.50); 5.742 (8.26); 5.084 (0.97); 5.073 (0.85); |

| Ex. | NMR Data |
|---|---|
| | 5.058 (0.64); 4.138 (1.61); 4.105 (1.69); 4.040 (0.94); 4.022 (0.94); 3.337 (0.59); 3.292 (641.54); 3.250 (1.25); 3.240 (1.53); 3.231 (0.96); 3.222 (0.65); 3.211 (0.75); 2.971 (1.26); 2.941 (2.26); 2.912 (1.25); 2.871 (0.56); 2.841 (1.05); 2.834 (0.93); 2.814 (0.64); 2.672 (0.66); 2.668 (0.86); 2.664 (0.62); 2.538 (2.42); 2.521 (3.18); 2.508 (49.05); 2.503 (96.66); 2.499 (129.40); 2.494 (91.33); 2.490 (42.99); 2.330 (0.64); 2.326 (0.85); 2.321 (0.62); 2.228 (14.61); 2.101 (15.00); 2.067 (1.31); 2.017 (1.44); 2.011 (1.49); 1.986 (5.79); 1.907 (1.53); 1.864 (0.87); 1.858 (0.87); 1.827 (1.66); 1.767 (0.74); 1.734 (0.84); 1.689 (0.98); 1.681 (0.80); 1.656 (0.92); 1.648 (0.75); 1.627 (0.81); 1.618 (0.65); 1.597 (1.42); 1.567 (1.46); 1.536 (1.22); 1.519 (1.77); 1.492 (1.04); 1.398 (0.80); 1.193 (1.15); 1.175 (2.32); 1.157 (1.14); −0.000 (6.78); |
| I-124 | 8.142 (15.00); 7.677 (2.49); 7.345 (2.01); 7.341 (2.51); 7.323 (3.68); 7.255 (2.63); 7.239 (3.19); 7.235 (2.97); 7.226 (1.61); 7.218 (1.70); 7.211 (1.77); 7.202 (4.09); 7.196 (6.40); 7.187 (2.69); 7.179 (5.49); 7.166 (2.41); 7.154 (1.76); 7.143 (2.64); 7.131 (2.58); 7.119 (1.90); 7.107 (1.83); 7.002 (1.63); 6.991 (1.40); 6.982 (2.03); 6.200 (1.83); 6.189 (3.84); 6.177 (1.99); 5.444 (9.38); 4.779 (2.62); 4.745 (2.68); 4.069 (2.15); 4.051 (2.18); 3.431 (1.39); 3.420 (2.55); 3.410 (1.41); 3.392 (1.50); 3.353 (2.44); 3.347 (2.43); 3.323 (3.29); 3.318 (4.14); 3.289 (2.49); 3.283 (2.38); 2.889 (2.77); 2.815 (1.61); 2.807 (1.54); 2.205 (2.39); 2.198 (2.43); 2.173 (3.11); 2.165 (2.99); 2.127 (143.78); 2.106 (5.22); 2.095 (5.33); 2.085 (3.39); 2.075 (2.42); 2.015 (1.52); 2.006 (1.57); 1.993 (1.84); 1.970 (11.21); 1.962 (3.86); 1.955 (6.55); 1.950 (49.40); 1.944 (93.24); 1.937 (129.60); 1.931 (88.28); 1.925 (44.59); 1.893 (2.55); 1.882 (2.61); 1.872 (1.79); 1.863 (3.51); 1.859 (2.91); 1.853 (3.84); 1.830 (2.53); 1.824 (2.32); 1.820 (2.15); 1.277 (2.68); 1.221 (2.77); 1.204 (5.43); 1.186 (2.69); 0.008 (1.56); −0.000 (33.31); |
| I-125 | 8.134 (15.00); 7.498 (5.10); 7.493 (5.12); 7.342 (2.08); 7.338 (2.77); 7.320 (3.84); 7.253 (2.73); 7.237 (3.13); 7.234 (2.72); 7.194 (6.10); 7.177 (4.65); 7.164 (4.54); 7.144 (5.00); 7.037 (3.76); 7.031 (3.46); 7.016 (2.70); 7.011 (2.54); 6.812 (2.52); 6.195 (1.96); 6.184 (4.15); 6.173 (2.11); 4.155 (3.49); 4.122 (3.63); 4.069 (2.40); 4.051 (2.44); 3.323 (1.32); 3.304 (1.45); 3.294 (2.73); 3.284 (1.59); 3.265 (1.43); 3.073 (2.52); 3.067 (2.54); 3.038 (4.46); 3.009 (2.45); 3.003 (2.30); 2.930 (1.37); 2.900 (1.48); 2.887 (3.01); 2.828 (1.37); 2.813 (1.61); 2.805 (1.57); 2.791 (1.43); 2.203 (1.90); 2.190 (32.05); 2.145 (3.30); 2.125 (166.53); 2.105 (6.60); 2.092 (5.81); 2.082 (3.44); 2.072 (2.41); 2.024 (1.28); 2.011 (1.45); 2.002 (1.49); 1.989 (1.81); 1.970 (11.70); 1.962 (3.65); 1.955 (7.09); 1.950 (46.23); 1.944 (88.28); 1.937 (126.10); 1.931 (86.45); 1.925 (43.80); 1.890 (1.48); 1.883 (1.67); 1.878 (1.60); 1.869 (1.65); 1.861 (1.28); 1.850 (1.36); 1.806 (1.49); 1.796 (1.53); 1.776 (3.22); 1.773 (3.20); 1.766 (4.22); 1.743 (2.87); 1.733 (2.54); 1.221 (3.05); 1.204 (5.95); 1.186 (2.96); 0.008 (1.60); −0.000 (35.11); |
| I-126 | 8.568 (7.50); 8.113 (2.92); 7.319 (1.11); 7.315 (1.32); 7.297 (2.09); 7.280 (0.59); 7.277 (0.60); 7.262 (1.71); 7.243 (1.61); 7.240 (1.33); 7.201 (1.66); 7.189 (2.29); 7.185 (2.14); 7.171 (1.29); 7.054 (2.05); 7.035 (2.57); 7.019 (2.63); 6.871 (1.56); 6.852 (1.32); 6.154 (1.00); 6.142 (2.09); 6.131 (1.01); 5.742 (15.00); 4.071 (1.35); 4.040 (1.88); 4.022 (1.06); 3.289 (114.88); 3.265 (3.76); 3.233 (1.69); 3.205 (0.89); 3.198 (0.79); 2.894 (0.60); 2.880 (0.32); 2.864 (0.61); 2.851 (1.19); 2.838 (0.55); 2.796 (0.52); 2.782 (0.65); 2.774 (0.65); 2.759 (0.65); 2.739 (0.32); 2.732 (0.37); 2.717 (0.31); 2.521 (0.86); 2.508 (14.93); 2.503 (30.10); 2.499 (40.71); 2.494 (28.98); 2.490 (13.70); 2.285 (0.37); 2.274 (0.38); 2.239 (12.70); 2.218 (0.70); 2.209 (0.52); 2.149 (1.68); 2.109 (13.41); 2.076 (0.73); 2.065 (1.19); 2.053 (1.81); 2.041 (2.08); 2.031 (1.06); 2.015 (0.32); 1.993 (0.35); 1.986 (3.14); 1.975 (0.57); 1.962 (0.64); 1.952 (0.65); 1.940 (0.64); 1.929 (0.40); 1.901 (0.77); 1.858 (0.63); 1.845 (0.85); 1.832 (0.66); 1.825 (0.46); 1.816 (0.42); 1.810 (0.41); 1.193 (0.76); 1.175 (1.51); 1.157 (0.74); −0.000 (4.10); |
| I-127 | 8.584 (6.52); 8.577 (0.52); 7.311 (1.18); 7.307 (1.37); 7.299 (0.47); 7.290 (2.17); 7.281 (0.71); 7.277 (0.70); 7.262 (1.91); 7.244 (1.76); 7.240 (1.42); 7.201 (1.68); 7.189 (2.70); 7.169 (1.49); 6.491 (3.89); 6.156 (0.96); 6.145 (1.91); 6.134 (0.93); 5.743 (9.24); 5.415 (0.72); 5.372 (1.79); 5.288 (1.67); 5.246 (0.67); 4.311 (0.57); 4.279 (0.64); 4.040 (1.24); 4.022 (1.24); 3.931 (0.55); 3.898 (0.62); 3.479 (0.45); 3.449 (0.77); 3.420 (0.47); 3.321 (0.52); 3.289 (329.26); 3.271 (7.96); 3.180 (0.69); 3.172 (0.67); 3.060 (0.79); 2.891 (0.69); 2.862 (0.64); 2.849 (1.21); 2.836 (0.57); 2.794 (0.56); 2.780 (0.73); 2.772 (0.68); 2.757 (0.72); 2.673 (0.46); 2.668 (0.63); 2.664 (0.44); 2.538 (0.67); 2.521 (2.22); 2.516 (3.45); 2.508 (34.02); 2.503 (67.93); 2.499 (91.69); 2.494 (64.68); 2.490 (30.04); 2.330 (0.47); 2.326 (0.61); 2.321 (0.46); 2.216 (15.00); 2.197 (1.54); 2.169 (1.31); 2.073 (0.75); 2.067 (1.08); 2.062 (1.31); 2.050 (2.13); 2.039 (2.28); 1.986 (5.69); 1.977 (0.49); 1.968 (0.57); 1.955 (0.65); 1.944 (0.65); 1.932 (0.67); 1.855 (0.66); 1.842 (0.90); 1.829 (0.68); 1.822 (0.54); 1.193 (1.54); 1.175 (3.06); 1.157 (1.48); −0.000 (4.58); |
| I-128 | 8.578 (9.40); 7.459 (7.40); 7.453 (4.53); 7.437 (5.99); 7.391 (1.12); 7.382 (1.16); 7.368 (1.58); 7.362 (2.95); 7.356 (2.51); 7.341 (1.86); 7.334 (1.68); 7.314 (1.62); 7.310 (1.97); 7.292 (3.01); 7.282 (0.97); 7.264 (2.50); 7.245 (2.35); 7.242 (1.96); 7.203 (2.38); 7.191 (3.30); 7.187 (3.13); 7.173 (1.93); 7.135 (1.58); 7.131 (2.13); 7.122 (2.87); 7.114 (2.15); 7.109 (2.05); 7.047 (1.34); 7.034 (0.97); 6.157 (1.32); 6.146 (2.73); 6.135 (1.32); 5.742 (15.00); 5.034 (3.70); 5.020 (3.95); 4.549 (0.98); 4.040 (1.27); 4.022 (1.58); 3.933 (3.06); 3.905 (2.83); 3.290 (275.53); 3.266 (6.59); 2.852 (1.63); 2.782 (0.99); 2.760 (1.12); 2.673 (0.98); 2.659 (0.97); 2.522 (1.71); 2.517 (2.68); 2.508 (28.34); 2.504 (57.02); 2.499 (77.21); 2.494 (54.56); 2.490 (25.55); 2.185 (0.98); 2.146 (1.60); 2.112 (0.99); 2.064 (1.73); 2.051 (2.62); 2.040 (2.91); 2.025 (1.62); 1.986 (4.34); 1.906 (1.01); 1.900 (1.22); 1.895 (1.15); 1.893 (1.14); 1.880 (1.51); 1.874 (1.54); 1.870 (1.67); 1.864 (0.98); 1.858 (1.52); 1.846 (1.33); 1.833 (1.13); 1.678 (1.18); 1.671 (1.22); 1.654 (1.11); 1.193 (1.06); 1.175 (2.15); 1.157 (1.03); −0.000 (3.31); |
| I-129 | 8.515 (5.39); 7.912 (2.05); 7.803 (1.02); 7.704 (1.29); 7.701 (1.34); 7.684 (1.46); 7.681 (1.46); 7.599 (0.96); 7.595 (1.02); 7.580 (1.29); 7.577 (1.31); 7.467 (0.73); 7.464 (0.75); 7.448 (1.50); 7.445 (1.47); 7.429 (0.81); 7.426 (0.78); 7.356 (0.81); 7.352 (0.84); 7.337 (1.15); 7.333 (1.17); 7.318 (0.55); 7.313 (0.53); 5.743 (6.89); 4.138 (1.09); 4.104 (1.15); 4.040 (0.65); 4.022 (0.65); 3.351 (0.37); 3.341 (0.30); 3.332 (0.50); 3.323 (0.88); 3.313 (0.77); 3.288 (119.84); 3.003 (0.76); 2.974 (1.41); 2.945 (0.77); 2.538 (1.88); 2.521 (0.89); 2.508 (15.29); 2.504 (30.69); 2.499 (41.49); 2.494 (29.64); 2.490 (14.09); 2.359 (0.44); 2.268 (1.20); 2.261 (8.33); 2.220 (12.31); 2.148 (0.43); 2.108 (1.48); 2.102 (10.51); 2.084 (1.02); 2.067 (0.85); 2.052 (15.00); 1.986 (2.84); 1.687 (0.34); 1.677 (0.39); 1.656 (0.85); 1.647 (0.91); 1.625 (0.86); 1.617 (0.80); 1.595 (0.32); 1.406 (0.39); 1.193 (0.81); 1.175 (1.56); 1.157 (0.78); 0.008 (0.31); −0.000 (7.87); |
| I-130 | 8.195 (0.82); 8.122 (2.48); 7.306 (0.60); 7.303 (0.80); 7.285 (1.21); 7.247 (0.39); 7.236 (0.81); 7.228 (0.49); 7.217 (1.29); 7.198 (0.62); 7.130 (0.42); 7.112 (0.59); 7.053 (0.39); 7.032 (0.52); 7.026 (0.42); 7.005 (0.50); 5.743 (0.36); 4.136 (0.42); 4.104 (0.44); 3.287 (86.69); 3.263 (0.35); 3.234 (0.34); 2.976 (0.32); 2.946 (0.58); 2.918 (0.32); 2.538 (0.91); 2.521 (0.58); 2.508 (9.07); 2.503 (17.98); 2.499 (24.14); 2.494 (17.17); 2.490 (8.05); 2.242 (3.44); 2.013 (0.37); 1.986 (1.05); 1.907 (0.40); 1.826 (0.43); 1.596 (0.35); 1.567 (0.37); 1.519 (0.45); 1.399 (15.00); 1.175 (0.36); −0.000 (1.38); |
| I-131 | 8.418 (4.55); 8.126 (11.45); 7.934 (3.43); 7.929 (3.43); 7.701 (2.50); 7.680 (3.02); 7.476 (1.99); 7.471 (1.99); 7.455 (1.67); 7.451 (1.65); 7.305 (2.83); 7.301 (3.79); 7.284 (5.75); 7.234 (3.38); 7.215 (5.84); 7.196 (2.95); 7.129 (2.00); 7.126 (1.21); 7.110 (2.85); 7.092 (1.04); 5.111 (0.53); 5.100 (0.62); 5.085 (1.17); 5.074 (1.05); 5.059 (0.79); 4.150 (1.93); 4.115 (2.05); 3.568 (15.00); 3.329 (0.71); 3.288 (914.49); 3.240 (1.49); 3.047 (1.52); 3.017 (2.75); 2.988 (1.55); 2.984 (1.32); 2.869 (0.71); 2.860 (0.70); 2.839 (1.29); 2.832 (1.14); 2.812 (0.81); 2.803 (0.72); 2.673 (0.98); 2.668 (1.35); 2.664 (0.94); 2.538 (7.36); 2.521 (4.33); 2.508 (75.42); 2.503 (150.61); 2.499 (202.57); 2.494 (144.57); 2.490 (68.71); 2.335 (0.63); 2.330 (1.12); 2.326 (1.49); 2.321 (1.04); 2.125 (1.15); 2.115 (1.20); 2.103 (1.00); 2.067 (0.67); 2.048 (2.62); 2.042 (1.86); 2.016 (2.13); 1.986 (0.67); 1.864 (1.01); 1.858 (1.02); 1.826 (2.10); 1.764 (1.01); 1.733 (1.07); 1.687 (1.37); 1.679 (1.44); 1.646 (2.39); 1.615 (1.92); 1.586 (0.71); 1.517 (2.13); 1.490 (1.29); 1.399 (7.35); 1.383 (0.59); 1.367 (0.69); 1.237 (0.58); −0.000 (6.91); |
| I-132 | 8.120 (5.39); 7.591 (2.03); 7.475 (1.71); 7.470 (1.70); 7.303 (1.35); 7.300 (1.78); 7.282 (2.72); 7.233 (1.62); 7.215 (2.78); 7.195 (1.38); 7.127 (0.96); 7.124 (0.58); 7.114 (0.52); 7.109 (1.33); 7.094 (0.33); 7.091 (0.50); 6.871 (1.46); 6.851 (2.59); 6.805 (1.15); 6.801 (1.12); 6.784 (0.63); 6.780 (0.62); 5.084 (0.56); 5.073 (0.49); 5.059 (0.35); 4.093 (0.93); 4.059 (0.98); 3.763 (14.12); 3.568 (15.00); 3.288 (239.12); 3.260 (0.80); 3.249 (0.55); 3.240 (0.63); 3.230 (0.85); 3.220 (0.51); 3.211 (0.35); 3.201 (0.44); 2.989 (0.63); 2.983 (0.71); 2.954 (1.29); 2.925 (0.73); 2.869 (0.33); 2.860 (0.31); 2.838 (0.60); 2.831 (0.54); 2.811 (0.39); 2.803 (0.33); 2.668 (0.37); 2.538 (2.01); 2.521 (1.37); 2.508 (20.95); 2.503 (41.27); 2.499 (55.16); 2.494 (39.14); 2.490 (18.44); 2.325 (0.38); 2.205 (9.57); 2.113 (0.55); 2.103 (0.46); 2.048 (0.31); 2.020 (0.83); 2.014 (0.85); 1.986 (1.02); 1.856 (0.48); 1.824 (0.96); 1.762 (0.44); 1.731 (0.49); 1.685 (0.52); 1.677 (0.42); 1.652 (0.53); 1.645 (0.61); 1.612 (0.85); 1.577 (0.78); 1.540 (0.63); 1.528 (0.58); 1.517 (1.01); 1.490 (0.61); 1.399 (2.88); 1.364 (0.31); −0.000 (2.38); |

| Ex. | NMR Data |
|---|---|
| I-133 | 8.125 (8.60); 8.092 (3.07); 7.325 (2.93); 7.319 (3.07); 7.306 (2.08); 7.302 (2.79); 7.284 (4.17); 7.235 (2.44); 7.216 (4.28); 7.196 (2.64); 7.193 (2.47); 7.172 (2.71); 7.130 (1.49); 7.127 (0.93); 7.112 (2.04); 7.094 (0.79); 7.076 (2.07); 7.071 (1.96); 7.056 (1.47); 7.050 (1.41); 5.084 (0.89); 5.073 (0.76); 5.058 (0.56); 4.137 (1.40); 4.103 (1.49); 3.289 (637.08); 3.260 (1.98); 3.250 (1.91); 3.240 (1.18); 3.230 (0.78); 3.221 (0.90); 3.211 (0.56); 2.999 (1.16); 2.969 (2.02); 2.941 (1.12); 2.869 (0.51); 2.839 (0.92); 2.832 (0.83); 2.812 (0.59); 2.803 (0.50); 2.673 (0.62); 2.668 (0.86); 2.663 (0.62); 2.538 (4.70); 2.521 (2.58); 2.508 (47.72); 2.503 (96.15); 2.499 (130.08); 2.494 (93.40); 2.490 (44.63); 2.330 (0.70); 2.326 (0.92); 2.321 (0.67); 2.145 (15.00); 2.126 (0.92); 2.115 (0.92); 2.105 (0.75); 2.048 (0.78); 2.031 (1.29); 2.025 (1.31); 1.998 (1.54); 1.986 (1.96); 1.858 (0.73); 1.826 (1.50); 1.765 (0.68); 1.733 (0.77); 1.719 (0.71); 1.688 (0.80); 1.679 (0.64); 1.654 (0.91); 1.646 (0.96); 1.613 (1.39); 1.583 (1.28); 1.543 (0.86); 1.518 (1.54); 1.491 (0.93); 1.399 (4.23); 1.175 (0.60); −0.000 (5.15); |
| I-134 | 8.122 (6.98); 8.104 (2.73); 7.316 (2.32); 7.311 (2.62); 7.306 (4.50); 7.302 (2.72); 7.286 (5.87); 7.235 (2.11); 7.216 (3.63); 7.197 (1.82); 7.129 (1.26); 7.111 (1.74); 7.093 (0.66); 6.955 (1.25); 6.951 (1.24); 6.935 (1.11); 6.931 (1.09); 5.110 (0.34); 5.099 (0.38); 5.083 (0.76); 5.073 (0.64); 5.058 (0.47); 5.046 (0.32); 4.135 (1.20); 4.102 (1.29); 3.567 (15.00); 3.287 (490.18); 3.252 (1.64); 3.243 (0.99); 3.232 (0.67); 3.224 (0.78); 3.002 (0.96); 2.973 (1.74); 2.944 (1.00); 2.870 (0.43); 2.861 (0.41); 2.840 (0.80); 2.833 (0.70); 2.813 (0.51); 2.804 (0.43); 2.672 (0.59); 2.668 (0.78); 2.663 (0.56); 2.538 (4.23); 2.521 (2.55); 2.508 (44.52); 2.503 (88.96); 2.499 (120.03); 2.494 (85.92); 2.490 (41.22); 2.335 (0.37); 2.330 (0.63); 2.326 (0.83); 2.321 (0.61); 2.264 (12.39); 2.115 (0.74); 2.104 (0.66); 2.048 (0.63); 2.019 (1.14); 1.992 (1.32); 1.986 (1.52); 1.858 (0.63); 1.826 (1.29); 1.765 (0.58); 1.731 (0.66); 1.688 (0.70); 1.680 (0.57); 1.656 (0.89); 1.648 (0.92); 1.617 (1.25); 1.587 (1.06); 1.540 (0.66); 1.518 (1.33); 1.491 (0.81); 1.399 (2.75); 1.374 (0.35); 1.366 (0.43); −0.000 (4.23); |
| I-135 | 8.512 (9.04); 7.975 (3.47); 7.613 (1.54); 7.607 (1.06); 7.599 (1.59); 7.589 (1.97); 7.540 (1.55); 7.534 (1.19); 7.531 (1.19); 7.526 (0.97); 7.521 (1.29); 7.516 (2.35); 7.443 (0.34); 7.437 (0.71); 7.425 (2.68); 7.419 (3.97); 7.411 (4.75); 7.401 (2.76); 7.397 (2.30); 7.384 (0.50); 7.044 (2.43); 7.025 (2.95); 7.003 (3.32); 6.856 (1.90); 6.837 (3.00); 5.743 (5.00); 5.411 (12.22); 4.172 (1.89); 4.139 (1.96); 4.058 (0.56); 4.040 (1.68); 4.022 (1.69); 4.004 (0.56); 3.361 (0.39); 3.352 (0.68); 3.342 (0.52); 3.332 (0.89); 3.323 (1.50); 3.313 (1.14); 3.289 (125.26); 2.996 (1.31); 2.967 (2.42); 2.958 (1.91); 2.939 (1.32); 2.538 (1.35); 2.521 (0.92); 2.508 (13.89); 2.504 (27.45); 2.499 (36.64); 2.494 (26.07); 2.490 (12.26); 2.286 (0.44); 2.232 (15.00); 2.108 (14.99); 2.085 (1.58); 2.079 (1.62); 2.067 (1.05); 2.052 (1.81); 2.049 (1.83); 1.986 (7.46); 1.698 (0.56); 1.688 (0.68); 1.667 (1.42); 1.658 (1.56); 1.636 (1.44); 1.628 (1.30); 1.606 (0.53); 1.597 (0.43); 1.237 (0.32); 1.193 (2.03); 1.175 (4.06); 1.158 (1.96); −0.000 (3.11); |
| I-136 | 8.507 (9.48); 8.314 (0.32); 8.103 (0.32); 8.087 (0.33); 7.976 (3.52); 7.942 (2.37); 7.939 (2.38); 7.922 (2.51); 7.919 (2.41); 7.555 (1.50); 7.551 (1.60); 7.536 (2.40); 7.532 (2.31); 7.476 (1.51); 7.473 (1.50); 7.457 (2.49); 7.454 (2.40); 7.438 (1.14); 7.435 (1.08); 7.165 (1.22); 7.161 (1.25); 7.146 (2.00); 7.142 (1.97); 7.127 (1.08); 7.123 (1.01); 7.044 (2.44); 7.025 (2.94); 7.003 (3.31); 6.856 (1.90); 6.837 (1.59); 6.590 (0.37); 6.574 (0.36); 5.742 (12.57); 5.301 (11.40); 4.174 (1.86); 4.140 (1.95); 4.040 (0.43); 4.022 (0.44); 3.364 (0.34); 3.355 (0.67); 3.345 (0.51); 3.335 (0.82); 3.326 (1.45); 3.316 (1.09); 3.289 (166.79); 3.004 (1.13); 2.999 (1.31); 2.969 (2.38); 2.945 (5.26); 2.668 (0.31); 2.538 (1.71); 2.521 (1.14); 2.508 (17.72); 2.503 (35.03); 2.499 (46.82); 2.494 (33.21); 2.490 (15.62); 2.326 (0.32); 2.286 (0.51); 2.232 (15.00); 2.109 (15.00); 2.089 (1.63); 2.083 (1.63); 2.067 (1.45); 2.056 (1.80); 2.049 (1.80); 1.986 (1.95); 1.701 (0.57); 1.691 (0.68); 1.670 (1.41); 1.661 (1.54); 1.639 (1.43); 1.631 (1.31); 1.609 (0.55); 1.599 (0.44); 1.193 (0.53); 1.175 (1.06); 1.157 (0.51); −0.000 (6.32); |
| I-137 | 8.422 (8.73); 8.314 (0.42); 7.968 (3.42); 7.589 (3.76); 7.586 (3.99); 7.567 (7.88); 7.505 (3.57); 7.487 (2.62); 7.483 (2.21); 7.465 (1.58); 7.041 (2.35); 7.022 (2.85); 6.998 (3.21); 6.853 (1.84); 6.835 (1.55); 5.743 (12.06); 5.530 (12.99); 4.165 (1.87); 4.131 (1.91); 4.040 (0.59); 4.022 (0.59); 3.343 (0.38); 3.333 (0.65); 3.324 (0.59); 3.314 (1.07); 3.287 (167.35); 3.028 (0.94); 2.983 (1.15); 2.979 (1.30); 2.949 (2.34); 2.920 (1.27); 2.668 (0.35); 2.538 (1.81); 2.521 (1.16); 2.508 (19.55); 2.504 (39.08); 2.499 (52.80); 2.494 (37.83); 2.490 (18.14); 2.326 (0.37); 2.286 (0.71); 2.230 (15.00); 2.120 (1.00); 2.102 (14.59); 2.067 (1.84); 2.059 (1.56); 2.049 (0.92); 2.032 (1.76); 1.986 (2.62); 1.676 (0.56); 1.666 (0.65); 1.645 (1.38); 1.636 (1.51); 1.614 (1.40); 1.605 (1.30); 1.584 (0.55); 1.575 (0.44); 1.193 (0.71); 1.175 (1.41); 1.158 (0.71); −0.000 (5.41); |
| I-138 | 8.343 (5.64); 7.971 (2.05); 7.361 (0.57); 7.344 (0.70); 7.340 (1.25); 7.323 (1.25); 7.319 (0.80); 7.302 (0.66); 7.043 (1.43); 7.024 (1.73); 6.999 (1.92); 6.911 (1.60); 6.890 (1.45); 6.855 (1.12); 6.832 (1.57); 6.809 (0.86); 6.805 (0.93); 6.784 (0.74); 6.431 (0.35); 6.413 (1.07); 6.397 (1.07); 6.380 (0.34); 5.743 (3.05); 4.162 (1.11); 4.129 (1.14); 4.040 (0.85); 4.022 (0.80); 3.860 (15.00); 3.333 (0.65); 3.287 (276.11); 2.994 (0.77); 2.964 (1.39); 2.936 (0.77); 2.672 (0.36); 2.668 (0.48); 2.663 (0.35); 2.538 (2.67); 2.521 (1.82); 2.508 (26.61); 2.503 (52.24); 2.499 (69.52); 2.494 (49.14); 2.490 (22.93); 2.330 (0.34); 2.326 (0.45); 2.321 (0.31); 2.231 (8.68); 2.106 (8.77); 2.067 (1.35); 2.058 (0.90); 2.049 (0.67); 2.033 (1.03); 1.986 (3.43); 1.678 (0.35); 1.669 (0.42); 1.647 (5.47); 1.630 (4.98); 1.617 (0.88); 1.608 (0.76); 1.587 (0.30); 1.237 (0.52); 1.193 (0.96); 1.175 (1.90); 1.157 (0.94); −0.000 (5.49); |
| I-139 | 8.679 (5.60); 8.627 (9.22); 8.580 (3.98); 8.567 (4.06); 8.106 (0.37); 8.089 (0.39); 7.981 (3.33); 7.591 (2.81); 7.590 (2.76); 7.578 (2.72); 7.046 (2.33); 7.027 (2.84); 7.004 (3.13); 6.858 (1.77); 6.839 (1.48); 6.603 (0.38); 6.587 (0.30); 5.743 (4.12); 5.450 (10.67); 4.179 (1.83); 4.145 (1.90); 4.040 (0.70); 4.022 (0.72); 3.381 (0.46); 3.371 (0.76); 3.361 (0.64); 3.352 (0.98); 3.342 (1.62); 3.333 (1.13); 3.286 (466.24); 3.015 (1.11); 3.010 (1.28); 2.981 (2.30); 2.953 (6.23); 2.677 (0.35); 2.672 (0.65); 2.668 (0.87); 2.663 (0.63); 2.538 (4.96); 2.521 (3.49); 2.508 (48.75); 2.503 (95.63); 2.499 (127.26); 2.494 (89.58); 2.490 (41.56); 2.335 (0.31); 2.330 (0.61); 2.326 (0.82); 2.321 (0.59); 2.233 (14.08); 2.111 (15.00); 2.067 (3.13); 2.049 (0.76); 1.986 (3.13); 1.714 (0.54); 1.704 (0.65); 1.683 (1.36); 1.674 (1.47); 1.652 (1.39); 1.644 (1.27); 1.623 (0.51); 1.613 (0.42); 1.193 (0.88); 1.175 (1.71); 1.157 (0.87); 0.008 (0.50); −0.000 (11.00); −0.008 (0.35); |
| I-140 | 8.483 (9.47); 7.971 (3.44); 7.581 (0.87); 7.577 (0.93); 7.563 (1.73); 7.558 (1.84); 7.543 (0.98); 7.539 (1.00); 7.474 (0.47); 7.469 (0.48); 7.460 (0.55); 7.455 (1.12); 7.440 (1.00); 7.435 (1.26); 7.430 (0.71); 7.421 (0.69); 7.416 (0.60); 7.283 (1.45); 7.269 (1.63); 7.267 (1.95); 7.259 (1.77); 7.256 (1.67); 7.251 (2.89); 7.248 (2.33); 7.239 (1.16); 7.236 (1.26); 7.232 (1.43); 7.229 (1.10); 7.043 (2.45); 7.024 (2.95); 7.001 (3.24); 6.855 (1.88); 6.836 (1.58); 5.743 (4.60); 5.385 (9.04); 4.167 (1.88); 4.134 (1.96); 4.040 (0.62); 4.022 (0.62); 3.351 (0.40); 3.342 (0.72); 3.332 (0.61); 3.322 (1.03); 3.313 (1.86); 3.288 (237.25); 2.995 (1.15); 2.990 (1.32); 2.965 (3.60); 2.932 (1.34); 2.927 (1.12); 2.775 (0.65); 2.668 (0.43); 2.538 (2.45); 2.521 (1.59); 2.508 (24.66); 2.503 (48.75); 2.499 (65.21); 2.494 (46.16); 2.490 (21.61); 2.330 (0.36); 2.326 (0.45); 2.286 (0.37); 2.231 (14.95); 2.105 (15.00); 2.067 (2.16); 2.043 (1.80); 1.986 (2.79); 1.688 (0.58); 1.678 (0.68); 1.657 (1.43); 1.648 (1.55); 1.626 (1.44); 1.618 (1.31); 1.596 (0.55); 1.587 (0.45); 1.237 (0.50); 1.193 (0.77); 1.175 (1.54); 1.157 (0.77); −0.000 (7.31); |
| I-141 | 8.861 (8.05); 7.990 (3.16); 7.597 (1.60); 7.595 (1.66); 7.577 (1.82); 7.575 (1.78); 7.388 (1.58); 7.386 (1.56); 7.369 (1.97); 7.218 (2.12); 7.199 (3.27); 7.179 (1.60); 7.049 (2.17); 7.029 (2.66); 7.012 (2.95); 6.859 (1.68); 6.839 (1.39); 5.742 (3.25); 4.201 (1.65); 4.167 (1.74); 4.058 (0.76); 4.040 (2.27); 4.022 (2.31); 4.004 (0.78); 3.413 (0.53); 3.404 (0.77); 3.394 (0.73); 3.384 (1.11); 3.375 (1.90); 3.364 (0.45); 3.355 (0.63); 3.346 (0.40); 3.290 (238.65); 3.023 (1.17); 2.994 (2.12); 2.964 (1.17); 2.668 (0.35); 2.538 (1.86); 2.521 (1.22); 2.508 (19.58); 2.503 (38.78); 2.499 (51.97); 2.494 (37.00); 2.490 (17.52); 2.326 (0.36); 2.235 (13.17); 2.206 (15.00); 2.136 (1.58); 2.119 (14.23); 2.067 (0.54); 1.986 (10.10); 1.749 (0.49); 1.739 (0.59); 1.718 (1.24); 1.709 (1.37); 1.687 (1.29); 1.679 (1.20); 1.658 (0.51); 1.648 (0.40); 1.237 (0.38); 1.193 (2.73); 1.175 (5.46); 1.157 (2.65); −0.000 (5.43); |
| I-142 | 8.794 (5.58); 7.989 (2.21); 7.319 (0.78); 7.315 (0.99); 7.300 (2.21); 7.295 (2.27); 7.283 (1.58); 7.263 (2.85); 7.243 (1.59); 7.230 (2.03); 7.225 (1.92); 7.209 (0.92); 7.205 (0.73); 7.048 (1.53); 7.029 (1.87); 7.013 (2.05); 6.858 (1.17); 6.839 (0.95); 5.743 (5.57); 4.200 (1.17); 4.167 (1.22); 4.057 (0.35); 4.040 (1.01); 4.022 (1.04); 4.004 (0.35); 3.800 (15.00); 3.407 (0.38); 3.387 (0.46); 3.378 (0.81); 3.369 (0.49); 3.359 (0.35); 3.349 (0.50); 3.339 (0.32); 3.286 (201.83); 3.021 (0.82); 2.991 (1.79); 2.963 (0.83); 2.668 (0.38); 2.538 (1.64); 2.521 (1.42); 2.507 (21.49); 2.503 (42.51); 2.499 (56.90); 2.494 (40.48); 2.489 (19.08); 2.325 (0.37); 2.235 (9.09); 2.119 (9.73); 1.986 (4.47); 1.744 (0.35); 1.735 (0.41); 1.712 (0.88); 1.705 (0.96); 1.683 (0.89); 1.675 (0.81); 1.652 (0.33); 1.193 (1.23); 1.175 (2.44); 1.157 (1.21); 1.044 (0.40); 1.029 (0.38); −0.000 (3.22); |
| I-143 | 8.863 (7.89); 7.990 (3.08); 7.467 (1.41); 7.464 (1.50); 7.447 (1.76); 7.444 (1.79); 7.359 (1.26); 7.358 (1.28); 7.340 (2.11); 7.288 (2.50); 7.269 (3.28); 7.249 (1.31); 7.048 (2.11); 7.029 (2.60); 7.013 (2.88); 6.858 (1.63); 6.840 (1.36); 5.742 (1.92); 4.201 (1.64); 4.167 (1.72); |

| Ex. | NMR Data |
|---|---|
| | 4.058 (0.45); 4.040 (1.34); 4.022 (1.34); 4.004 (0.46); 3.413 (0.54); 3.404 (0.38); 3.394 (0.65); 3.384 (1.11); 3.375 (0.66); 3.365 (0.45); 3.356 (0.63); 3.346 (0.38); 3.290 (157.62); 3.023 (1.14); 2.994 (2.08); 2.964 (1.15); 2.538 (1.07); 2.521 (0.92); 2.508 (14.06); 2.503 (27.78); 2.499 (37.08); 2.494 (26.42); 2.490 (12.49); 2.235 (12.81); 2.204 (15.00); 2.134 (1.60); 2.119 (13.82); 1.986 (5.97); 1.749 (0.49); 1.739 (0.57); 1.718 (1.22); 1.709 (1.35); 1.687 (1.26); 1.679 (1.17); 1.658 (0.48); 1.648 (0.39); 1.193 (1.61); 1.175 (3.22); 1.157 (1.56); −0.000 (1.18); |
| I-144 | 8.916 (8.28); 7.990 (3.29); 7.821 (8.83); 7.801 (9.56); 7.283 (2.59); 7.263 (4.24); 7.243 (2.28); 7.048 (2.24); 7.029 (2.77); 7.014 (3.03); 6.858 (1.71); 6.856 (1.69); 6.839 (1.44); 5.743 (1.38); 4.202 (1.72); 4.169 (1.81); 3.420 (0.55); 3.411 (0.43); 3.401 (0.67); 3.391 (1.16); 3.382 (0.70); 3.372 (0.46); 3.363 (0.66); 3.353 (0.37); 3.286 (185.24); 3.021 (1.22); 2.992 (2.20); 2.963 (1.22); 2.668 (0.39); 2.538 (1.67); 2.521 (1.49); 2.508 (21.68); 2.503 (42.79); 2.499 (57.19); 2.494 (40.70); 2.490 (19.17); 2.325 (0.38); 2.235 (13.46); 2.140 (1.60); 2.120 (15.00); 1.986 (0.33); 1.750 (0.50); 1.740 (0.60); 1.719 (1.30); 1.710 (1.40); 1.688 (1.32); 1.680 (1.22); 1.658 (0.50); 1.649 (0.40); −0.000 (5.08); |
| I-145 | 8.796 (5.52); 7.988 (2.14); 7.353 (0.55); 7.337 (0.67); 7.332 (1.21); 7.315 (1.22); 7.310 (0.75); 7.294 (0.67); 7.064 (1.46); 7.047 (1.97); 7.043 (1.56); 7.028 (2.48); 7.012 (2.14); 7.006 (1.34); 7.003 (1.55); 6.982 (0.73); 6.979 (0.66); 6.858 (1.14); 6.839 (0.94); 5.742 (0.55); 4.197 (1.13); 4.163 (1.19); 3.820 (15.00); 3.406 (0.37); 3.387 (0.45); 3.377 (0.76); 3.368 (0.45); 3.358 (0.32); 3.348 (0.48); 3.339 (0.30); 3.288 (263.50); 3.020 (0.79); 2.991 (1.45); 2.962 (0.81); 2.672 (0.30); 2.668 (0.41); 2.538 (1.77); 2.521 (1.41); 2.508 (23.71); 2.503 (47.25); 2.499 (63.43); 2.494 (45.27); 2.490 (21.44); 2.330 (0.33); 2.326 (0.41); 2.234 (8.84); 2.118 (9.58); 2.102 (1.22); 2.067 (0.32); 1.986 (0.71); 1.743 (0.35); 1.733 (0.39); 1.711 (0.84); 1.702 (0.93); 1.680 (0.87); 1.673 (0.79); 1.651 (0.35); 1.175 (0.37); −0.000 (2.36); |
| I-146 | 8.803 (8.64); 7.990 (3.39); 7.785 (2.23); 7.781 (2.30); 7.765 (2.43); 7.761 (2.38); 7.523 (0.85); 7.519 (0.83); 7.502 (2.03); 7.499 (1.80); 7.484 (2.02); 7.481 (1.92); 7.459 (2.91); 7.455 (3.31); 7.439 (1.59); 7.434 (1.31); 7.319 (1.50); 7.315 (1.40); 7.301 (1.78); 7.299 (1.85); 7.296 (1.76); 7.281 (1.23); 7.277 (1.08); 7.048 (2.34); 7.029 (2.86); 7.012 (3.14); 6.858 (1.81); 6.839 (1.50); 5.742 (10.21); 4.198 (1.80); 4.165 (1.87); 4.057 (0.32); 4.040 (0.95); 4.022 (0.97); 4.004 (0.33); 3.421 (0.32); 3.412 (0.59); 3.402 (0.45); 3.392 (0.71); 3.383 (1.24); 3.373 (0.74); 3.364 (0.50); 3.354 (0.72); 3.345 (0.42); 3.289 (127.02); 3.029 (1.09); 3.024 (1.24); 2.994 (2.28); 2.966 (1.25); 2.538 (1.49); 2.521 (0.99); 2.508 (14.70); 2.503 (28.86); 2.499 (38.41); 2.494 (27.13); 2.490 (12.63); 2.235 (14.04); 2.119 (15.00); 2.105 (1.91); 2.097 (1.95); 1.986 (4.18); 1.907 (0.30); 1.746 (0.54); 1.736 (0.63); 1.714 (1.34); 1.706 (1.48); 1.684 (1.38); 1.676 (1.26); 1.654 (0.53); 1.645 (0.42); 1.237 (0.74); 1.193 (1.16); 1.175 (2.29); 1.157 (1.14); −0.000 (2.85); |
| I-147 | 8.804 (8.81); 7.988 (3.32); 7.472 (0.92); 7.467 (1.01); 7.457 (0.97); 7.452 (2.35); 7.448 (2.14); 7.437 (1.67); 7.432 (2.78); 7.428 (1.87); 7.411 (1.48); 7.406 (1.90); 7.401 (0.82); 7.393 (0.83); 7.387 (1.40); 7.383 (1.01); 7.374 (1.21); 7.370 (1.06); 7.362 (0.51); 7.354 (0.75); 7.349 (0.42); 7.324 (1.30); 7.322 (1.29); 7.319 (1.41); 7.304 (1.68); 7.299 (1.67); 7.284 (0.65); 7.281 (0.63); 7.048 (2.31); 7.029 (2.84); 7.011 (3.07); 6.858 (1.77); 6.839 (1.46); 5.743 (6.54); 4.196 (1.79); 4.162 (1.87); 4.040 (1.00); 4.022 (1.00); 3.410 (0.68); 3.401 (0.52); 3.391 (0.83); 3.381 (1.33); 3.372 (0.84); 3.362 (0.66); 3.353 (0.87); 3.344 (0.64); 3.288 (406.51); 3.022 (1.24); 2.993 (2.25); 2.964 (1.24); 2.672 (0.49); 2.668 (0.66); 2.663 (0.49); 2.538 (3.74); 2.521 (2.68); 2.508 (36.53); 2.503 (70.91); 2.499 (93.62); 2.494 (65.50); 2.490 (30.13); 2.330 (0.44); 2.326 (0.59); 2.321 (0.42); 2.234 (13.93); 2.118 (15.00); 2.100 (1.85); 2.048 (0.44); 1.986 (4.38); 1.744 (0.54); 1.734 (0.63); 1.713 (1.36); 1.704 (1.45); 1.682 (1.38); 1.674 (1.24); 1.653 (0.52); 1.237 (0.61); 1.193 (1.20); 1.175 (2.42); 1.157 (1.19); −0.000 (3.75); |
| I-148 | 8.806 (8.68); 7.990 (3.37); 7.649 (2.49); 7.630 (2.45); 7.481 (0.46); 7.473 (4.66); 7.471 (4.97); 7.461 (5.50); 7.458 (2.99); 7.437 (0.31); 7.405 (0.31); 7.395 (1.67); 7.385 (1.72); 7.375 (1.59); 7.373 (1.25); 7.366 (1.27); 7.362 (1.11); 7.353 (0.91); 7.048 (2.33); 7.029 (2.85); 7.012 (3.12); 6.858 (1.79); 6.839 (1.48); 5.743 (4.09); 4.198 (1.78); 4.164 (1.87); 4.057 (0.46); 4.040 (1.27); 4.022 (1.27); 4.004 (0.73); 3.421 (0.31); 3.411 (0.60); 3.402 (0.43); 3.392 (0.71); 3.383 (1.23); 3.373 (0.72); 3.364 (0.50); 3.354 (0.71); 3.344 (0.43); 3.288 (199.49); 3.023 (1.25); 2.993 (2.28); 2.965 (1.26); 2.668 (0.34); 2.538 (1.92); 2.521 (1.26); 2.508 (19.08); 2.503 (37.77); 2.499 (50.48); 2.494 (35.81); 2.490 (16.76); 2.325 (0.34); 2.234 (13.99); 2.118 (15.00); 2.104 (1.91); 2.097 (1.86); 1.986 (9.73); 1.745 (0.53); 1.735 (0.64); 1.714 (1.35); 1.705 (1.46); 1.683 (1.37); 1.675 (1.25); 1.654 (0.53); 1.644 (0.42); 1.398 (0.46); 1.237 (0.37); 1.193 (2.68); 1.175 (5.33); 1.157 (2.62); −0.000 (2.11); |
| I-149 | 8.913 (8.35); 7.988 (3.26); 7.539 (0.98); 7.535 (1.44); 7.531 (1.01); 7.520 (1.44); 7.515 (2.31); 7.512 (2.27); 7.508 (1.01); 7.491 (1.97); 7.487 (1.39); 7.467 (2.01); 7.463 (3.04); 7.448 (2.04); 7.443 (1.45); 7.429 (1.48); 7.422 (0.59); 7.408 (0.47); 7.048 (2.29); 7.028 (2.81); 7.012 (3.07); 6.858 (1.76); 6.839 (1.46); 5.743 (6.50); 4.198 (1.78); 4.164 (1.86); 4.057 (0.46); 4.040 (1.27); 4.022 (1.30); 4.004 (0.45); 3.430 (0.37); 3.421 (0.65); 3.411 (0.49); 3.401 (0.75); 3.392 (1.30); 3.383 (0.81); 3.373 (0.61); 3.364 (0.82); 3.353 (0.55); 3.342 (0.43); 3.286 (415.52); 3.258 (0.40); 3.021 (1.27); 2.992 (2.24); 2.963 (1.23); 2.677 (0.33); 2.672 (0.61); 2.668 (0.79); 2.663 (0.58); 2.659 (0.32); 2.538 (4.51); 2.521 (3.11); 2.508 (44.37); 2.503 (87.00); 2.499 (116.18); 2.494 (82.14); 2.490 (38.32); 2.330 (0.56); 2.326 (0.74); 2.321 (0.53); 2.286 (0.43); 2.234 (13.95); 2.133 (1.72); 2.118 (15.00); 2.049 (0.54); 1.986 (5.55); 1.748 (0.55); 1.739 (0.65); 1.717 (1.35); 1.709 (1.43); 1.686 (1.33); 1.678 (1.21); 1.657 (0.49); 1.648 (0.42); 1.399 (1.96); 1.193 (1.57); 1.175 (3.04); 1.157 (1.56); −0.000 (6.26); |
| I-150 | 8.906 (8.67); 8.314 (0.42); 7.988 (3.24); 7.484 (0.32); 7.469 (0.72); 7.465 (0.53); 7.460 (0.57); 7.453 (0.52); 7.447 (1.39); 7.442 (0.74); 7.434 (0.54); 7.426 (1.37); 7.411 (0.62); 7.379 (0.41); 7.374 (0.78); 7.367 (3.00); 7.357 (0.55); 7.347 (4.19); 7.335 (0.49); 7.327 (1.61); 7.324 (1.29); 7.319 (0.45); 7.047 (2.31); 7.028 (2.86); 7.011 (3.09); 6.858 (1.78); 6.839 (1.48); 5.743 (7.03); 4.197 (1.79); 4.163 (1.87); 4.058 (0.34); 4.040 (1.00); 4.022 (1.02); 4.004 (0.36); 3.428 (0.34); 3.419 (0.62); 3.410 (0.45); 3.400 (0.73); 3.391 (1.24); 3.381 (0.75); 3.371 (0.51); 3.362 (0.74); 3.353 (0.48); 3.285 (293.64); 3.021 (1.29); 2.991 (2.26); 2.963 (1.23); 2.672 (0.48); 2.668 (0.66); 2.663 (0.46); 2.538 (3.76); 2.521 (2.55); 2.508 (36.11); 2.503 (70.91); 2.499 (94.74); 2.494 (66.89); 2.490 (31.23); 2.330 (0.44); 2.326 (0.62); 2.321 (0.44); 2.286 (0.69); 2.234 (14.24); 2.118 (15.00); 2.049 (0.46); 1.986 (4.44); 1.747 (0.57); 1.737 (0.69); 1.717 (1.36); 1.708 (1.46); 1.686 (1.34); 1.678 (1.23); 1.656 (0.52); 1.646 (0.43); 1.399 (2.01); 1.193 (1.24); 1.175 (2.45); 1.157 (1.25); 0.008 (0.32); −0.000 (6.98); |
| I-151 | 8.920 (8.70); 7.989 (3.27); 7.677 (7.48); 7.657 (9.48); 7.442 (3.03); 7.422 (3.43); 7.421 (3.12); 7.401 (2.20); 7.048 (2.26); 7.029 (2.78); 7.013 (3.04); 6.858 (1.73); 6.839 (1.42); 5.743 (6.63); 4.201 (1.72); 4.168 (1.82); 4.058 (0.46); 4.040 (1.34); 4.022 (1.38); 4.004 (0.47); 3.421 (0.55); 3.412 (0.41); 3.401 (0.66); 3.392 (1.19); 3.382 (0.67); 3.373 (0.44); 3.364 (0.65); 3.355 (0.35); 3.314 (0.41); 3.286 (170.97); 3.021 (1.22); 2.991 (2.21); 2.963 (1.21); 2.668 (0.39); 2.538 (2.28); 2.521 (1.36); 2.508 (22.16); 2.503 (43.96); 2.499 (58.73); 2.494 (41.56); 2.490 (19.42); 2.330 (0.31); 2.326 (0.39); 2.235 (13.60); 2.138 (1.59); 2.119 (15.00); 2.049 (0.30); 1.986 (6.07); 1.749 (0.52); 1.740 (0.61); 1.718 (1.30); 1.710 (1.42); 1.688 (1.33); 1.680 (1.21); 1.658 (0.50); 1.648 (0.41); 1.399 (1.86); 1.193 (1.68); 1.175 (3.34); 1.157 (1.64); −0.000 (4.05); |
| I-152 | 8.817 (8.39); 7.988 (3.34); 7.819 (1.85); 7.813 (1.85); 7.794 (1.87); 7.788 (1.87); 7.546 (1.04); 7.543 (1.08); 7.540 (1.05); 7.524 (1.76); 7.521 (1.96); 7.518 (1.86); 7.480 (2.37); 7.459 (2.96); 7.438 (2.31); 7.028 (2.81); 7.010 (3.08); 6.858 (1.78); 6.839 (1.47); 5.742 (6.17); 4.193 (1.77); 4.160 (1.84); 4.058 (0.48); 4.040 (1.42); 4.022 (1.45); 4.004 (0.49); 3.417 (0.37); 3.408 (0.63); 3.398 (0.47); 3.388 (0.78); 3.379 (1.26); 3.369 (0.79); 3.360 (0.60); 3.350 (0.82); 3.341 (0.63); 3.296 (236.06); 3.273 (0.48); 3.020 (1.22); 2.991 (2.24); 2.962 (1.23); 2.539 (1.37); 2.522 (0.98); 2.509 (14.01); 2.504 (27.22); 2.500 (35.97); 2.495 (25.26); 2.491 (11.69); 2.234 (13.85); 2.117 (15.00); 2.096 (1.87); 1.986 (6.33); 1.740 (0.54); 1.730 (0.61); 1.709 (1.32); 1.701 (1.41); 1.678 (1.35); 1.670 (1.20); 1.648 (0.52); 1.639 (0.39); 1.398 (0.72); 1.237 (0.64); 1.193 (1.72); 1.175 (3.40); 1.158 (1.67); −0.000 (1.38); |
| I-153 | 9.588 (0.60); 8.518 (7.54); 8.314 (1.62); 7.996 (0.76); 7.977 (2.92); 7.584 (0.96); 7.579 (0.81); 7.564 (1.52); 7.560 (1.57); 7.545 (0.85); 7.541 (0.83); 7.404 (0.47); 7.399 (1.02); 7.392 (0.62); 7.385 (0.80); 7.379 (1.10); 7.374 (0.63); 7.365 (0.63); 7.361 (0.56); 7.259 (1.49); 7.250 (1.31); 7.247 (1.47); 7.242 (2.16); 7.229 (1.09); 7.223 (2.24); 7.202 (0.96); 7.200 (0.85); 7.155 (0.46); 7.135 (0.56); 7.045 (2.12); 7.026 (2.54); 7.006 (3.27); 6.856 (1.86); 6.837 (1.55); 6.257 (0.54); 6.240 (1.77); 6.224 (1.79); 6.207 (0.54); 5.743 (3.31); 4.174 (1.62); 4.141 (1.64); 4.058 (0.43); 4.040 (1.27); 4.022 (1.28); 4.005 (0.44); 3.351 (0.65); 3.341 (0.50); 3.332 (0.75); 3.322 (1.25); 3.312 (1.02); 3.290 (128.58); 3.018 (0.52); 3.003 (0.99); 2.998 (1.14); 2.969 (1.99); 2.940 (1.11); 2.538 (1.15); 2.522 (0.83); 2.508 (12.76); 2.504 (24.96); |

| Ex. | NMR Data |
|---|---|
| | 2.499 (33.15); 2.495 (23.45); 2.490 (11.00); 2.286 (2.70); 2.233 (15.00); 2.121 (3.72); 2.110 (12.65); 2.074 (1.39); 2.067 (1.02); 2.049 (1.60); 1.986 (5.64); 1.690 (0.53); 1.682 (0.55); 1.655 (1.21); 1.630 (8.79); 1.614 (7.98); 1.193 (1.54); 1.175 (3.03); 1.158 (1.49); −0.000 (2.56); |
| I-154 | 8.799 (9.09); 7.991 (3.42); 7.950 (2.36); 7.947 (2.40); 7.931 (2.52); 7.927 (2.39); 7.519 (1.09); 7.515 (1.08); 7.498 (2.00); 7.496 (1.86); 7.480 (1.64); 7.476 (1.55); 7.379 (2.69); 7.375 (2.83); 7.359 (2.14); 7.355 (1.96); 7.144 (1.47); 7.140 (1.44); 7.125 (2.16); 7.121 (2.07); 7.106 (1.31); 7.102 (1.21); 7.049 (2.36); 7.030 (2.88); 7.014 (3.10); 6.859 (1.81); 6.840 (1.51); 5.742 (0.97); 4.198 (1.78); 4.165 (1.86); 3.423 (0.32); 3.413 (0.58); 3.404 (0.44); 3.394 (0.73); 3.385 (1.21); 3.375 (0.74); 3.365 (0.51); 3.356 (0.73); 3.346 (0.45); 3.288 (251.80); 3.032 (1.06); 3.026 (1.24); 2.997 (2.25); 2.968 (1.25); 2.672 (0.31); 2.668 (0.40); 2.537 (2.33); 2.521 (1.63); 2.507 (22.89); 2.503 (44.58); 2.498 (59.09); 2.494 (41.30); 2.489 (19.01); 2.325 (0.39); 2.235 (13.99); 2.119 (15.00); 2.048 (0.30); 1.985 (0.87); 1.748 (0.53); 1.739 (0.64); 1.717 (1.34); 1.709 (1.47); 1.687 (1.38); 1.679 (1.28); 1.657 (0.54); 1.648 (0.43); 1.399 (1.26); 1.237 (0.69); 1.175 (0.49); −0.000 (2.77); |
| I-155 | 8.425 (9.08); 8.314 (0.36); 7.968 (3.46); 7.595 (2.09); 7.575 (2.71); 7.476 (1.00); 7.461 (1.17); 7.455 (1.93); 7.440 (1.98); 7.435 (1.27); 7.420 (1.12); 7.384 (1.44); 7.381 (1.44); 7.360 (2.24); 7.339 (0.94); 7.336 (0.87); 7.042 (2.38); 7.022 (2.89); 7.000 (3.22); 6.854 (1.87); 6.835 (1.57); 5.743 (8.83); 5.435 (7.14); 5.431 (7.07); 4.165 (1.88); 4.131 (1.93); 4.040 (0.43); 4.022 (0.44); 3.342 (0.39); 3.333 (0.70); 3.323 (0.63); 3.313 (1.15); 3.290 (114.47); 2.981 (1.31); 2.951 (4.15); 2.923 (1.30); 2.539 (1.16); 2.522 (0.79); 2.508 (12.58); 2.504 (24.72); 2.499 (32.93); 2.495 (23.37); 2.490 (11.01); 2.286 (0.60); 2.230 (15.00); 2.121 (0.89); 2.102 (14.73); 2.068 (1.71); 2.060 (1.56); 2.033 (1.77); 1.986 (1.91); 1.678 (0.56); 1.668 (0.66); 1.646 (1.40); 1.638 (1.51); 1.616 (1.42); 1.608 (1.30); 1.586 (0.54); 1.576 (0.43); 1.193 (0.53); 1.176 (1.03); 1.158 (0.52); −0.000 (3.91); |
| I-156 | 8.467 (8.72); 8.314 (0.69); 7.994 (0.36); 7.974 (3.36); 7.492 (4.88); 7.491 (4.84); 7.472 (8.28); 7.371 (3.20); 7.352 (2.73); 7.349 (2.43); 7.330 (1.82); 7.043 (2.34); 7.024 (2.78); 6.997 (3.14); 6.855 (1.87); 6.836 (1.57); 6.579 (0.75); 6.562 (2.76); 6.544 (2.76); 6.527 (0.76); 5.743 (4.32); 4.159 (1.80); 4.126 (1.76); 4.058 (0.64); 4.040 (1.90); 4.022 (1.93); 4.004 (0.64); 3.350 (0.47); 3.341 (0.78); 3.332 (0.73); 3.322 (1.18); 3.312 (2.25); 3.287 (385.62); 3.002 (1.30); 2.973 (2.33); 2.947 (1.82); 2.673 (0.51); 2.668 (0.68); 2.664 (0.50); 2.538 (3.75); 2.521 (2.56); 2.508 (39.36); 2.503 (77.85); 2.499 (104.15); 2.494 (74.30); 2.490 (35.30); 2.330 (0.52); 2.326 (0.71); 2.321 (0.51); 2.286 (1.18); 2.231 (15.00); 2.119 (1.72); 2.106 (14.36); 2.067 (2.07); 2.049 (1.14); 2.038 (1.70); 1.986 (8.44); 1.734 (10.96); 1.717 (10.95); 1.683 (0.62); 1.674 (0.50); 1.652 (1.41); 1.622 (1.33); 1.600 (0.40); 1.592 (0.48); 1.580 (0.48); 1.193 (2.28); 1.175 (4.58); 1.157 (2.24); −0.000 (5.84); |
| I-157 | 8.364 (9.15); 7.975 (3.49); 7.487 (5.98); 7.467 (8.51); 7.331 (2.95); 7.312 (2.94); 7.310 (2.71); 7.291 (1.90); 7.047 (2.44); 7.028 (2.94); 7.006 (3.37); 6.858 (1.90); 6.839 (1.58); 5.742 (6.86); 4.506 (2.79); 4.489 (6.42); 4.472 (2.96); 4.161 (1.91); 4.127 (1.97); 4.058 (0.31); 4.040 (0.92); 4.022 (0.93); 4.004 (0.32); 3.369 (2.83); 3.352 (5.94); 3.335 (3.38); 3.293 (377.10); 3.012 (1.16); 3.006 (1.31); 2.977 (2.41); 2.948 (1.32); 2.673 (0.35); 2.669 (0.48); 2.664 (0.35); 2.539 (1.25); 2.522 (1.61); 2.509 (26.57); 2.504 (52.84); 2.499 (70.91); 2.495 (50.64); 2.490 (24.01); 2.331 (0.35); 2.326 (0.49); 2.322 (0.35); 2.286 (0.48); 2.234 (15.00); 2.112 (14.99); 2.075 (1.60); 2.067 (2.10); 2.049 (1.46); 2.043 (1.81); 1.986 (4.06); 1.692 (0.58); 1.682 (0.68); 1.661 (1.40); 1.653 (1.54); 1.630 (1.44); 1.622 (1.30); 1.601 (0.55); 1.591 (0.45); 1.193 (1.13); 1.175 (2.25); 1.158 (1.11); −0.000 (3.76); |
| I-158 | 9.013 (2.58); 8.131 (7.64); 7.309 (1.84); 7.306 (2.46); 7.288 (3.75); 7.239 (2.22); 7.220 (3.79); 7.201 (1.89); 7.133 (1.35); 7.130 (0.81); 7.115 (1.83); 7.096 (0.73); 7.094 (0.51); 7.084 (1.75); 7.065 (2.24); 6.952 (1.46); 6.933 (1.11); 6.859 (2.48); 5.098 (0.41); 5.084 (0.77); 5.072 (0.68); 5.058 (0.50); 4.766 (1.26); 4.732 (1.33); 3.568 (0.50); 3.395 (0.43); 3.376 (0.57); 3.366 (0.95); 3.356 (0.66); 3.347 (0.54); 3.338 (0.81); 3.289 (625.35); 3.236 (2.21); 3.208 (1.23); 2.875 (0.46); 2.866 (0.44); 2.845 (0.85); 2.837 (0.76); 2.817 (0.55); 2.809 (0.46); 2.672 (0.62); 2.668 (0.87); 2.663 (0.63); 2.538 (3.30); 2.521 (3.08); 2.508 (50.11); 2.503 (99.13); 2.499 (132.67); 2.494 (94.37); 2.490 (44.64); 2.335 (0.39); 2.330 (0.71); 2.326 (0.93); 2.321 (0.69); 2.286 (10.25); 2.107 (11.05); 2.067 (1.39); 2.048 (1.49); 2.027 (1.34); 1.864 (0.68); 1.829 (1.37); 1.766 (0.62); 1.723 (0.76); 1.713 (0.48); 1.702 (0.61); 1.693 (1.05); 1.684 (1.10); 1.672 (1.22); 1.662 (1.27); 1.650 (1.17); 1.642 (1.11); 1.620 (0.49); 1.612 (0.43); 1.522 (1.45); 1.496 (0.88); 1.399 (15.00); 1.370 (0.45); 0.008 (0.50); −0.000 (10.70); −0.008 (0.41); |
| I-159 | 9.114 (1.61); 8.134 (4.68); 7.308 (1.16); 7.305 (1.54); 7.287 (2.33); 7.244 (0.94); 7.238 (1.50); 7.222 (2.86); 7.221 (2.85); 7.205 (1.97); 7.200 (2.50); 7.185 (0.50); 7.179 (0.62); 7.133 (0.97); 7.126 (1.78); 7.120 (1.71); 7.115 (1.26); 7.100 (0.32); 7.096 (0.45); 5.084 (0.48); 5.074 (0.44); 5.059 (0.33); 4.766 (0.74); 4.732 (0.76); 3.388 (0.33); 3.378 (0.56); 3.368 (0.36); 3.350 (0.36); 3.286 (235.97); 3.238 (0.81); 2.844 (0.51); 2.836 (0.45); 2.817 (0.33); 2.672 (0.34); 2.668 (0.46); 2.663 (0.32); 2.538 (1.75); 2.521 (1.68); 2.508 (26.34); 2.503 (51.96); 2.499 (69.35); 2.494 (49.16); 2.490 (23.15); 2.330 (0.37); 2.325 (0.52); 2.322 (0.48); 2.137 (7.82); 2.108 (0.50); 2.075 (0.75); 2.067 (0.61); 2.048 (1.14); 1.865 (0.42); 1.830 (0.88); 1.767 (0.41); 1.723 (0.69); 1.692 (1.03); 1.661 (0.93); 1.633 (0.32); 1.522 (0.90); 1.494 (0.54); 1.399 (15.00); 1.369 (0.31); 0.008 (0.32); −0.000 (6.74); |
| I-160 | 8.313 (1.02); 8.205 (8.88); 7.963 (3.24); 7.432 (0.81); 7.417 (0.94); 7.412 (0.95); 7.406 (0.91); 7.401 (0.95); 7.386 (0.83); 7.381 (0.81); 7.265 (1.50); 7.259 (0.78); 7.244 (1.11); 7.238 (1.45); 7.217 (0.90); 7.167 (0.96); 7.156 (1.24); 7.146 (0.99); 7.043 (2.24); 7.024 (2.66); 6.996 (2.94); 6.855 (1.80); 6.835 (1.48); 5.742 (7.47); 5.045 (0.99); 5.034 (0.78); 4.148 (1.81); 4.116 (1.71); 4.040 (1.07); 4.022 (1.08); 3.294 (1637.23); 3.255 (2.58); 3.247 (1.46); 3.237 (0.95); 3.227 (0.96); 2.979 (1.18); 2.948 (2.13); 2.920 (1.27); 2.872 (1.04); 2.673 (1.32); 2.668 (1.76); 2.664 (1.28); 2.538 (8.17); 2.522 (6.65); 2.508 (97.46); 2.504 (191.69); 2.499 (256.32); 2.495 (181.69); 2.490 (85.90); 2.331 (1.29); 2.326 (1.66); 2.322 (1.25); 2.286 (1.68); 2.229 (1.82); 2.120 (2.94); 2.103 (13.95); 2.067 (0.79); 2.049 (1.48); 2.027 (1.39); 2.000 (1.63); 1.994 (1.65); 1.986 (5.39); 1.846 (0.86); 1.819 (1.58); 1.754 (0.91); 1.747 (0.91); 1.720 (1.63); 1.689 (0.86); 1.616 (1.25); 1.608 (1.36); 1.586 (1.32); 1.579 (1.28); 1.546 (0.76); 1.519 (1.22); 1.507 (1.33); 1.193 (1.44); 1.175 (2.53); 1.157 (1.29); −0.000 (4.49); |
| I-161 | 8.436 (10.39); 8.114 (3.20); 7.551 (0.82); 7.535 (0.88); 7.530 (2.02); 7.515 (2.07); 7.510 (1.47); 7.494 (1.42); 7.442 (2.65); 7.421 (1.65); 7.355 (1.22); 7.352 (1.20); 7.328 (4.50); 7.323 (3.44); 7.310 (1.00); 7.307 (0.95); 7.194 (2.06); 7.173 (2.85); 7.080 (2.25); 7.074 (2.16); 7.060 (1.61); 7.054 (1.56); 5.747 (6.92); 5.446 (6.56); 5.442 (6.75); 4.164 (1.56); 4.130 (1.63); 4.040 (0.47); 4.022 (0.47); 3.352 (0.36); 3.342 (0.72); 3.332 (0.70); 3.306 (207.42); 3.284 (0.97); 3.275 (0.38); 3.013 (0.90); 3.007 (1.10); 2.977 (1.98); 2.949 (1.09); 2.944 (0.93); 2.540 (0.42); 2.523 (0.72); 2.519 (1.06); 2.510 (14.17); 2.506 (28.15); 2.501 (38.46); 2.497 (26.45); 2.492 (12.50); 2.146 (16.00); 2.077 (1.21); 2.070 (1.68); 2.046 (1.46); 2.040 (1.38); 1.987 (1.21); 1.909 (0.50); 1.690 (0.47); 1.680 (0.60); 1.658 (1.19); 1.650 (1.33); 1.628 (1.20); 1.620 (1.10); 1.598 (0.45); 1.589 (0.36); 1.236 (0.92); 1.193 (0.61); 1.175 (1.21); 1.158 (0.60); −0.000 (3.79); |
| I-162 | 8.432 (6.28); 7.613 (2.13); 7.550 (0.52); 7.534 (0.56); 7.529 (1.27); 7.514 (1.31); 7.509 (0.93); 7.493 (0.90); 7.469 (1.73); 7.464 (1.76); 7.440 (1.71); 7.420 (1.06); 7.354 (0.78); 7.351 (0.74); 7.330 (1.34); 7.309 (0.62); 7.307 (0.57); 6.869 (1.54); 6.848 (2.91); 6.809 (1.17); 6.808 (1.18); 6.804 (1.19); 6.787 (0.61); 6.783 (0.61); 5.747 (5.52); 5.444 (4.28); 5.439 (4.33); 4.121 (1.01); 4.087 (1.06); 3.758 (16.00); 3.321 (1.06); 3.302 (248.55); 3.264 (0.47); 2.995 (0.61); 2.989 (0.72); 2.960 (1.29); 2.931 (0.74); 2.925 (0.60); 2.669 (0.36); 2.539 (0.53); 2.523 (0.98); 2.518 (1.51); 2.509 (19.61); 2.505 (38.48); 2.500 (51.91); 2.496 (35.49); 2.491 (16.59); 2.327 (0.34); 2.207 (10.22); 2.070 (1.10); 2.060 (0.83); 2.050 (0.47); 2.034 (0.95); 1.987 (0.74); 1.673 (0.37); 1.652 (0.77); 1.643 (0.86); 1.621 (0.78); 1.613 (0.73); 1.175 (0.42); −0.000 (4.52); |
| I-163 | 8.447 (10.06); 8.115 (3.24); 7.575 (0.43); 7.558 (0.92); 7.553 (0.85); 7.541 (0.59); 7.537 (1.82); 7.532 (0.71); 7.520 (0.85); 7.516 (1.09); 7.499 (0.48); 7.330 (3.13); 7.324 (3.36); 7.215 (0.41); 7.206 (2.69); 7.194 (2.52); 7.185 (4.10); 7.174 (3.28); 7.165 (2.41); 7.156 (0.39); 7.081 (2.24); 7.075 (2.18); 7.060 (1.59); 7.055 (1.57); 5.748 (0.82); 5.397 (7.52); 4.165 (1.60); 4.131 (1.68); 3.352 (0.32); 3.342 (0.66); 3.332 (0.66); 3.295 (0.84); 3.285 (0.84); 3.276 (0.37); 3.014 (0.93); 3.009 (1.14); 2.979 (2.04); 2.951 (1.12); 2.945 (0.97); 2.524 (0.43); 2.520 (0.63); 2.511 (8.61); 2.506 (17.36); 2.502 (23.97); 2.497 (16.91); 2.493 (8.25); 2.147 (16.00); 2.078 (1.24); 2.071 (1.56); 2.046 (1.50); 2.040 (1.44); 1.988 (0.34); 1.691 (0.47); 1.681 (0.56); 1.660 (1.18); 1.651 (1.33); 1.629 (1.22); 1.621 (1.14); 1.599 (0.46); 1.590 (0.38); −0.000 (1.55); |
| I-164 | 8.443 (6.32); 7.614 (2.10); 7.556 (0.61); 7.552 (0.55); 7.539 (0.39); 7.535 (1.16); 7.531 (0.41); 7.518 (0.55); 7.514 (0.68); 7.471 (1.72); 7.466 (1.74); 7.204 (1.72); 7.184 (2.55); 7.176 (0.35); 7.164 (1.46); 6.870 (1.54); 6.850 (2.90); 6.810 (1.16); 6.808 (1.16); 6.804 (1.18); |

| Ex. | NMR Data |
|---|---|
| | 6.789 (0.60); 6.787 (0.61); 6.784 (0.61); 5.748 (4.08); 5.394 (4.79); 4.121 (1.02); 4.087 (1.06); 3.760 (16.00); 3.304 (166.71); 3.284 (0.74); 3.274 (0.35); 3.264 (0.40); 2.997 (0.60); 2.991 (0.73); 2.961 (1.27); 2.933 (0.72); 2.928 (0.60); 2.540 (0.33); 2.523 (0.62); 2.518 (0.95); 2.510 (12.11); 2.505 (23.72); 2.501 (31.99); 2.496 (21.83); 2.492 (10.14); 2.207 (10.16); 2.070 (1.01); 2.060 (0.82); 2.034 (0.94); 2.029 (0.90); 1.987 (1.37); 1.674 (0.36); 1.653 (0.76); 1.644 (0.85); 1.622 (0.79); 1.614 (0.71); 1.193 (0.39); 1.175 (0.76); 1.157 (0.38); −0.000 (2.56); |
| I-165 | 8.631 (8.18); 8.624 (0.59); 7.576 (0.44); 7.560 (0.90); 7.555 (0.82); 7.539 (1.74); 7.522 (0.86); 7.518 (1.01); 7.501 (0.45); 7.216 (0.42); 7.207 (2.65); 7.187 (3.95); 7.179 (0.59); 7.167 (2.23); 6.493 (3.95); 5.747 (7.53); 5.418 (7.70); 5.372 (2.00); 5.289 (1.91); 5.247 (0.78); 5.183 (0.73); 4.308 (0.60); 4.276 (0.68); 4.022 (0.44); 3.921 (0.59); 3.892 (0.68); 3.568 (1.60); 3.470 (0.61); 3.455 (0.56); 3.437 (1.20); 3.420 (0.80); 3.410 (0.70); 3.372 (0.58); 3.305 (1677.54); 3.282 (7.60); 3.261 (0.44); 3.046 (0.71); 3.015 (0.39); 2.674 (1.47); 2.669 (2.00); 2.664 (1.38); 2.660 (0.75); 2.539 (2.83); 2.523 (5.77); 2.518 (8.63); 2.509 (107.78); 2.505 (210.41); 2.500 (282.72); 2.496 (192.97); 2.491 (90.13); 2.336 (0.66); 2.332 (1.41); 2.327 (1.86); 2.322 (1.35); 2.264 (0.94); 2.213 (16.00); 2.195 (1.53); 2.185 (0.88); 2.179 (0.87); 2.160 (1.26); 2.132 (0.75); 2.069 (1.97); 2.049 (0.59); 1.987 (1.67); 1.398 (0.47); 1.237 (0.56); 1.193 (0.50); 1.175 (0.92); 1.157 (0.51); 1.093 (0.66); 0.008 (0.44); −0.000 (12.60); |
| I-166 | 8.620 (8.22); 8.246 (3.25); 7.576 (0.41); 7.559 (0.88); 7.555 (0.81); 7.542 (0.57); 7.538 (1.71); 7.534 (0.62); 7.521 (0.82); 7.517 (1.00); 7.500 (0.45); 7.351 (3.03); 7.345 (3.15); 7.215 (0.43); 7.206 (4.14); 7.194 (0.61); 7.185 (4.70); 7.166 (2.23); 7.156 (0.34); 7.097 (2.19); 7.091 (2.09); 7.077 (1.51); 7.071 (1.48); 5.747 (0.34); 5.418 (7.20); 4.075 (1.41); 4.040 (1.48); 3.308 (355.53); 3.285 (1.39); 3.275 (1.03); 3.269 (1.01); 3.239 (1.65); 3.213 (0.87); 3.204 (0.78); 2.670 (0.38); 2.540 (0.51); 2.523 (1.05); 2.519 (1.60); 2.510 (20.89); 2.505 (41.08); 2.501 (55.48); 2.497 (38.22); 2.492 (17.96); 2.328 (0.39); 2.281 (0.33); 2.256 (0.64); 2.247 (0.55); 2.228 (0.57); 2.216 (0.48); 2.165 (1.86); 2.147 (16.00); 2.132 (2.43); 2.070 (0.32); −0.000 (1.85); |
| I-167 | 8.588 (8.85); 8.259 (3.14); 7.363 (2.96); 7.357 (3.09); 7.213 (1.99); 7.192 (2.77); 7.099 (2.20); 7.094 (2.06); 7.079 (1.54); 7.073 (1.50); 5.747 (0.49); 4.938 (0.58); 4.926 (0.70); 4.917 (1.15); 4.907 (0.73); 4.894 (0.58); 4.089 (1.35); 4.055 (1.43); 3.568 (0.54); 3.305 (731.69); 3.266 (1.34); 3.259 (1.80); 3.232 (0.86); 3.224 (0.76); 2.674 (0.61); 2.669 (0.83); 2.665 (0.60); 2.539 (1.18); 2.523 (2.39); 2.518 (3.53); 2.509 (44.88); 2.505 (88.53); 2.500 (120.50); 2.496 (82.43); 2.491 (38.66); 2.332 (0.62); 2.327 (0.90); 2.322 (0.62); 2.277 (0.62); 2.248 (0.57); 2.186 (1.91); 2.170 (16.00); 2.148 (2.34); 2.069 (1.63); 1.892 (0.96); 1.871 (1.03); 1.863 (1.06); 1.745 (0.85); 1.737 (0.93); 1.728 (0.97); 1.722 (1.03); 1.713 (1.05); 1.565 (0.52); 1.541 (1.62); 1.532 (1.04); 1.525 (1.24); 1.517 (1.87); 1.509 (1.32); 1.495 (0.87); 1.487 (0.72); 1.438 (0.57); 1.421 (0.68); 1.414 (1.29); 1.406 (0.92); 1.398 (1.73); 1.389 (1.13); 1.381 (1.15); 1.356 (0.59); 1.336 (0.48); 1.311 (0.56); 1.306 (0.55); −0.000 (9.72); |
| I-168 | 8.631 (13.75); 7.577 (0.66); 7.561 (1.42); 7.556 (1.24); 7.544 (0.91); 7.540 (2.74); 7.535 (0.97); 7.523 (1.27); 7.518 (1.63); 7.502 (0.73); 7.308 (2.11); 7.217 (0.61); 7.208 (4.05); 7.200 (0.63); 7.196 (0.77); 7.188 (6.02); 7.175 (5.29); 7.167 (3.82); 7.161 (2.72); 7.042 (2.40); 7.025 (5.94); 6.906 (4.42); 6.889 (2.79); 5.746 (16.00); 5.518 (1.04); 5.476 (2.95); 5.421 (11.25); 5.411 (3.50); 5.368 (1.03); 4.293 (0.86); 4.260 (0.93); 4.039 (0.77); 4.022 (0.79); 3.930 (0.78); 3.896 (0.90); 3.470 (0.65); 3.440 (1.16); 3.411 (0.65); 3.314 (1183.89); 3.081 (0.54); 3.073 (0.62); 3.045 (1.00); 3.019 (0.53); 3.012 (0.52); 2.675 (0.62); 2.670 (0.86); 2.665 (0.63); 2.540 (1.19); 2.523 (2.27); 2.519 (3.44); 2.510 (45.59); 2.506 (89.89); 2.501 (122.58); 2.497 (83.59); 2.492 (39.32); 2.376 (0.45); 2.337 (0.54); 2.332 (0.83); 2.328 (0.97); 2.323 (0.70); 2.212 (0.66); 2.176 (1.23); 2.154 (1.89); 2.125 (1.14); 2.069 (1.26); 2.050 (0.50); 1.987 (3.69); 1.398 (0.47); 1.193 (1.08); 1.175 (2.11); 1.157 (1.06); −0.000 (0.60); |
| I-169 | 8.581 (5.54); 7.813 (2.38); 7.419 (1.83); 7.414 (1.88); 6.891 (1.44); 6.879 (0.43); 6.870 (3.18); 6.859 (0.49); 6.840 (1.34); 6.836 (1.34); 6.819 (0.59); 6.816 (0.61); 5.747 (8.68); 4.933 (0.43); 4.920 (0.51); 4.911 (0.83); 4.901 (0.52); 4.888 (0.41); 4.053 (0.99); 4.019 (1.03); 3.819 (2.51); 3.781 (16.00); 3.299 (151.19); 3.276 (0.60); 3.262 (0.68); 3.255 (0.76); 3.226 (1.25); 3.198 (0.69); 3.191 (0.60); 2.522 (0.97); 2.517 (1.45); 2.509 (17.49); 2.504 (34.29); 2.500 (46.28); 2.495 (32.40); 2.491 (15.62); 2.275 (0.49); 2.246 (0.44); 2.233 (0.50); 2.218 (11.25); 2.181 (0.52); 2.171 (0.49); 2.153 (1.17); 2.121 (1.22); 2.087 (0.36); 2.070 (1.57); 1.892 (0.72); 1.871 (0.79); 1.864 (0.81); 1.743 (0.65); 1.736 (0.70); 1.721 (0.77); 1.713 (0.80); 1.565 (0.39); 1.556 (0.53); 1.541 (1.07); 1.533 (1.43); 1.517 (0.97); 1.509 (1.43); 1.502 (0.92); 1.486 (0.55); 1.479 (0.44); 1.433 (0.42); 1.417 (0.52); 1.409 (0.97); 1.398 (2.48); 1.384 (0.83); 1.376 (0.84); 1.351 (0.42); 1.304 (0.43); 1.298 (0.42); −0.000 (5.76); |
| I-170 | 8.596 (8.47); 6.500 (4.04); 5.748 (10.39); 5.430 (0.81); 5.387 (2.04); 5.301 (2.00); 5.259 (0.81); 4.936 (0.63); 4.924 (0.75); 4.914 (1.20); 4.904 (0.78); 4.891 (0.62); 4.319 (0.61); 4.285 (0.69); 3.944 (0.57); 3.909 (0.63); 3.488 (0.52); 3.459 (0.83); 3.428 (0.49); 3.296 (932.40); 3.272 (3.62); 3.067 (0.76); 2.678 (0.98); 2.673 (1.89); 2.668 (2.56); 2.664 (1.83); 2.659 (0.88); 2.539 (3.05); 2.522 (9.02); 2.517 (14.10); 2.508 (144.39); 2.504 (273.40); 2.499 (360.52); 2.495 (244.38); 2.490 (112.92); 2.335 (0.97); 2.331 (1.88); 2.326 (2.49); 2.322 (1.80); 2.317 (0.85); 2.225 (16.00); 2.202 (1.37); 2.175 (1.45); 2.146 (0.83); 2.069 (5.30); 1.897 (1.14); 1.873 (1.22); 1.867 (1.23); 1.748 (1.01); 1.737 (1.05); 1.716 (1.24); 1.564 (0.65); 1.558 (0.85); 1.541 (1.56); 1.534 (1.89); 1.510 (1.99); 1.487 (0.79); 1.479 (0.64); 1.436 (0.63); 1.411 (1.41); 1.403 (1.04); 1.387 (1.24); 1.379 (1.24); 1.361 (0.49); 1.354 (0.64); 1.331 (0.56); 1.306 (0.67); 1.275 (0.56); 1.236 (0.64); 0.008 (1.38); −0.000 (36.06); −0.009 (1.16); |
| I-171 | 8.616 (9.60); 8.122 (3.70); 7.577 (0.48); 7.560 (1.05); 7.556 (0.95); 7.543 (0.70); 7.539 (2.03); 7.535 (0.77); 7.522 (0.96); 7.518 (1.21); 7.501 (0.54); 7.216 (0.46); 7.207 (3.05); 7.195 (0.61); 7.187 (4.57); 7.179 (0.72); 7.167 (2.60); 7.157 (0.45); 7.052 (2.44); 7.033 (3.00); 7.013 (3.21); 6.872 (1.81); 6.869 (1.78); 6.852 (1.50); 5.747 (14.39); 5.419 (8.61); 4.068 (1.71); 4.057 (1.25); 4.039 (1.91); 4.034 (1.79); 4.022 (1.46); 3.298 (338.12); 3.275 (1.34); 3.256 (1.07); 3.250 (1.05); 3.220 (1.98); 3.194 (1.06); 3.186 (0.94); 2.673 (0.56); 2.669 (0.76); 2.664 (0.56); 2.539 (2.80); 2.522 (2.17); 2.517 (3.29); 2.509 (41.01); 2.504 (80.68); 2.500 (109.29); 2.495 (75.81); 2.491 (36.26); 2.331 (0.56); 2.326 (0.79); 2.322 (0.55); 2.270 (0.39); 2.257 (0.54); 2.238 (15.15); 2.205 (0.76); 2.194 (0.62); 2.168 (0.33); 2.143 (2.17); 2.099 (16.00); 2.070 (1.27); 1.987 (2.94); 1.398 (3.25); 1.193 (0.82); 1.175 (1.62); 1.157 (0.81); −0.000 (5.46); |
| I-172 | 8.586 (8.69); 8.134 (3.34); 7.061 (2.22); 7.042 (2.72); 7.026 (2.94); 6.874 (1.64); 6.871 (1.63); 6.855 (1.37); 5.747 (11.02); 4.941 (0.63); 4.929 (0.78); 4.919 (1.27); 4.909 (0.82); 4.896 (0.63); 4.083 (1.55); 4.048 (1.61); 3.297 (365.38); 3.273 (2.20); 3.240 (1.89); 3.213 (1.02); 3.205 (0.91); 2.673 (0.69); 2.668 (0.96); 2.664 (0.69); 2.539 (1.02); 2.522 (2.78); 2.517 (4.25); 2.508 (51.73); 2.504 (101.30); 2.499 (136.63); 2.495 (94.99); 2.490 (45.45); 2.331 (0.69); 2.326 (0.96); 2.322 (0.71); 2.242 (13.99); 2.216 (0.64); 2.162 (1.84); 2.125 (16.00); 2.069 (0.69); 1.907 (0.98); 1.892 (1.12); 1.870 (1.22); 1.862 (1.24); 1.747 (1.00); 1.738 (1.07); 1.730 (1.12); 1.722 (1.21); 1.715 (1.22); 1.577 (0.54); 1.569 (0.59); 1.553 (1.44); 1.546 (1.84); 1.530 (1.45); 1.522 (2.07); 1.500 (1.10); 1.491 (0.84); 1.440 (0.65); 1.424 (0.80); 1.416 (1.45); 1.408 (1.09); 1.398 (3.41); 1.391 (1.38); 1.383 (1.31); 1.367 (0.51); 1.359 (0.68); 1.353 (0.51); 1.339 (0.56); 1.315 (0.66); 1.309 (0.65); 1.285 (0.53); −0.000 (13.51); |
| I-173 | 8.615 (5.63); 7.806 (2.25); 7.558 (0.62); 7.554 (0.55); 7.542 (0.40); 7.537 (1.19); 7.533 (0.44); 7.521 (0.57); 7.516 (0.70); 7.396 (1.78); 7.391 (1.72); 7.206 (1.78); 7.194 (0.34); 7.186 (2.63); 7.177 (0.38); 7.165 (1.53); 6.867 (0.80); 6.847 (3.68); 6.839 (1.81); 6.834 (1.67); 6.817 (0.37); 6.813 (0.39); 5.747 (2.90); 5.415 (4.95); 4.039 (0.95); 4.003 (1.00); 3.742 (16.00); 3.303 (239.83); 3.279 (3.48); 3.242 (0.61); 3.234 (0.69); 3.206 (1.19); 3.178 (0.66); 3.172 (0.58); 2.669 (0.40); 2.539 (0.45); 2.523 (1.18); 2.518 (1.74); 2.509 (21.25); 2.505 (41.84); 2.500 (56.79); 2.496 (39.18); 2.491 (18.71); 2.327 (0.39); 2.257 (0.46); 2.215 (11.30); 2.162 (0.48); 2.151 (0.48); 2.134 (1.17); 2.102 (1.18); 2.070 (0.88); 1.987 (0.39); 1.398 (0.46); −0.000 (2.71); |
| I-175 | 8.362 (16.00); 7.577 (0.81); 7.560 (1.80); 7.556 (1.72); 7.543 (1.31); 7.539 (3.53); 7.535 (1.40); 7.522 (1.78); 7.518 (2.08); 7.501 (0.94); 7.300 (2.96); 7.213 (0.87); 7.204 (5.37); 7.195 (1.06); 7.192 (1.26); 7.184 (8.49); 7.176 (1.74); 7.166 (8.92); 7.155 (4.97); 7.033 (3.37); 7.018 (8.50); 6.898 (7.22); 6.883 (4.20); 5.748 (10.45); 5.431 (1.37); 5.417 (15.88); 5.390 (5.65); 5.361 (8.04); 5.320 (1.08); 4.340 (1.45); 4.306 (1.52); 3.969 (1.35); 3.934 (1.49); 3.421 (1.08); 3.412 (0.90); 3.402 (1.46); 3.393 (2.34); 3.384 (1.49); 3.374 (1.05); 3.365 (1.34); 3.355 (0.77); 3.307 (111.47); 3.284 (2.88); 3.261 (2.01); 3.231 (1.20); 2.865 (1.01); 2.854 (0.85); 2.836 (1.79); 2.808 (1.02); 2.525 (0.79); 2.512 (14.06); 2.507 (26.94); 2.503 (35.76); 2.499 (25.34); 2.494 (12.47); 2.134 (1.29); 2.099 (2.61); 2.072 (1.28); 2.063 (1.51); 1.989 (3.02); |

| Ex. | NMR Data |
|---|---|
| | 1.803 (1.42); 1.780 (1.33); 1.773 (1.23); 1.590 (1.19); 1.580 (1.25); 1.559 (1.17); 1.551 (1.12); 1.397 (0.81); 1.194 (0.85); 1.177 (1.63); 1.159 (0.81); −0.000 (4.38); |
| I-176 | 8.746 (16.00); 7.549 (1.87); 7.545 (2.63); 7.542 (1.95); 7.530 (2.88); 7.525 (5.13); 7.522 (4.32); 7.503 (4.16); 7.499 (2.72); 7.480 (7.69); 7.475 (3.08); 7.465 (4.38); 7.461 (2.94); 7.446 (2.95); 7.440 (1.18); 7.425 (0.95); 7.315 (3.00); 7.182 (6.83); 7.164 (3.30); 7.048 (3.31); 7.028 (7.55); 6.908 (6.52); 6.892 (3.72); 5.748 (10.49); 5.462 (1.18); 5.419 (5.16); 5.383 (5.08); 5.340 (1.19); 4.386 (1.45); 4.352 (1.55); 4.041 (1.61); 4.023 (2.34); 4.014 (1.40); 4.005 (1.52); 3.979 (1.50); 3.534 (1.05); 3.524 (0.75); 3.514 (1.28); 3.505 (2.23); 3.496 (1.30); 3.486 (0.83); 3.477 (1.18); 3.468 (0.61); 3.330 (1.30); 3.306 (128.39); 3.282 (3.26); 3.271 (1.34); 2.904 (0.99); 2.873 (1.80); 2.846 (1.02); 2.524 (0.91); 2.511 (16.46); 2.507 (31.32); 2.502 (41.31); 2.498 (29.07); 2.494 (14.15); 2.207 (1.30); 2.171 (2.65); 2.136 (1.54); 1.988 (6.67); 1.882 (1.18); 1.874 (1.25); 1.851 (1.19); 1.843 (1.12); 1.667 (1.19); 1.658 (1.30); 1.636 (1.20); 1.628 (1.15); 1.194 (1.91); 1.176 (3.75); 1.158 (1.82); −0.000 (5.53); |
| I-177 | 8.378 (8.39); 7.299 (1.51); 7.288 (0.48); 7.235 (1.53); 7.217 (2.06); 7.191 (1.38); 7.173 (2.48); 7.166 (3.92); 7.154 (2.99); 7.120 (2.01); 7.101 (2.58); 7.082 (0.95); 7.033 (1.72); 7.018 (4.82); 6.898 (3.98); 6.882 (2.34); 5.747 (5.98); 5.434 (0.55); 5.392 (2.81); 5.360 (14.06); 5.319 (0.59); 4.344 (0.73); 4.312 (0.76); 4.040 (0.42); 4.022 (0.44); 3.971 (0.68); 3.937 (0.74); 3.425 (0.56); 3.415 (0.43); 3.405 (0.78); 3.396 (1.26); 3.387 (0.79); 3.377 (0.61); 3.368 (0.75); 3.359 (0.44); 3.303 (99.52); 3.280 (2.35); 3.262 (1.05); 3.233 (0.63); 3.143 (0.37); 3.038 (0.44); 2.865 (0.50); 2.851 (0.57); 2.835 (0.90); 2.808 (0.51); 2.523 (0.79); 2.509 (12.59); 2.505 (23.77); 2.500 (31.24); 2.496 (21.75); 2.492 (10.49); 2.270 (15.51); 2.226 (16.00); 2.141 (0.68); 2.103 (1.35); 2.069 (1.16); 1.987 (1.98); 1.843 (0.36); 1.833 (0.39); 1.811 (0.73); 1.804 (0.80); 1.781 (0.73); 1.624 (0.37); 1.614 (0.38); 1.592 (0.63); 1.583 (0.64); 1.562 (0.58); 1.553 (0.55); 1.193 (0.56); 1.175 (1.08); 1.158 (0.54); −0.000 (3.14); |
| I-178 | 8.259 (7.95); 6.986 (1.60); 6.896 (3.35); 6.877 (1.80); 6.832 (2.76); 6.806 (1.67); 6.786 (3.82); 6.695 (1.84); 5.260 (0.80); 5.232 (2.78); 5.202 (2.76); 5.174 (0.81); 5.058 (1.28); 4.946 (0.64); 4.939 (1.05); 4.933 (0.65); 4.473 (0.61); 4.451 (0.63); 3.882 (0.62); 3.600 (16.00); 3.349 (0.61); 3.336 (0.65); 3.330 (1.25); 3.324 (0.67); 3.311 (0.66); 3.281 (0.65); 3.277 (0.87); 3.274 (0.63); 3.021 (0.73); 2.848 (0.76); 2.844 (0.78); 2.167 (1.87); 2.087 (0.69); 1.950 (4.42); 1.946 (8.58); 1.942 (12.67); 1.938 (8.65); 1.933 (4.40); 1.917 (0.73); 1.906 (0.84); 1.903 (0.80); 1.896 (0.85); 1.893 (0.86); 1.887 (0.89); 1.881 (0.74); 1.861 (0.59); 1.854 (0.62); 1.764 (0.83); 1.758 (0.83); 1.752 (0.95); 1.747 (0.90); 1.742 (0.97); 1.737 (0.71); 1.694 (0.60); 1.564 (1.09); 1.559 (1.46); 1.554 (0.98); 1.549 (1.10); 1.543 (1.60); 1.539 (1.21); 1.528 (0.73); 1.522 (0.60); 1.457 (0.61); 1.447 (0.83); 1.441 (1.48); 1.435 (1.13); 1.430 (0.70); 1.425 (1.26); 1.419 (1.33); 1.402 (0.60); 1.354 (0.60); −0.000 (1.52); |

Intensity of sharp signals correlates with the height of the signals in a printed example of a NMR spectrum in cm and shows the real relations of signal intensities. From broad signals several peaks or the middle of the signal and their relative intisity in comparison to the most intensive signal in the spectrum can be shown The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-d6 and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical 1H-NMR interpretation.

USE EXAMPLES

Example A

Phytophthora Test (Tomato)/Protective

Solvent: 49 parts by weight of N,N-dimethylformamide
Emulsifier: 1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young tomato plants are sprayed with the preparation of active compound at the stated application rate. 1 day after the treatment, the plants are inoculated with a spore suspension of *Phytophthora infestans* and then remain at 100% relative humidity and 22° C. for 24 h. The plants are then placed in a climatized cabin at about 96% relative atmospheric humidity and a temperature of about 20° C.

Evaluation is carried out 7 days after the inoculation. 0% means an efficacy which corresponds to that of the control, whereas an efficacy of 100% means that no infection is observed.

In this test, the compounds (I-2), (I-12), (I-13), (I-14), (I-15), (I-16), (I-17), (I-18), (I-19), (I-20), (I-25), (I-26), (I-27), (I-31), (I-32), (I-34), (I-35), (I-36), (I-41), (I-42), (I-43), (I-44), (I-45), (I-46), (I-48), (I-49), (I-51), (I-52), (I-53), (I-54), (I-55), (I-57), (I-58), (I-59), (I-61), (I-62), (I-63), (I-64), (I-65), (I-68), (I-71), (I-72), (I-73), (I-74), (I-78), (I-79), (I-80), (I-91), (I-96), (I-111), (I-112), (I-120), (I-121), (I-122), (I-123), (I-125), (I-126), (I-127), (I-135), (I-137), (I-138), (I-140), (I-141), (I-142), (I-143), (I-144), (I-145), (I-149), (I-150), (I-151), (I-152), (I-153), (I-155), (I-156), (I-157), (I-161), (I-162), (I-163), (I-164), (I-167), (I-168), (I-169), (I-170), (I-171), (I-172) and (I-173) according to the invention show, at an active compound concentration of 500 ppm, an efficacy of 70% or more.

Example B

Plasmopara Test (Grapevine)/Protective

Solvent: 24.5 parts by weight of acetone
24.5 parts by weight of dimethylacetamide
1 part by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the stated application rate. After the spray coating has dried on, the plants are inoculated with an aqueous spore suspension of *Plasmopara viticola* and then remain in an incubation cabin at about 20° C. and 100% relative atmospheric humidity for 1 day. The plants are then placed in a greenhouse at about 21° C. and about 90% atmospheric humidity for 4 days. The plants are then moistened and placed in an incubation cabin for 1 day.

Evaluation is carried out 6 days after the inoculation. 0% means an efficacy which corresponds to that of the control, whereas an efficacy of 100% means that no infection is observed.

In this test, the compounds (I-12), (I-13), (I-14), (I-15), (I-16), (I-17), (I-18), (I-19), (I-20), (I-25), (I-26), (I-41), (I-42), (I-43), (I-46), (I-48), (I-51), (I-52), (I-53), (I-54), (I-59), (I-61), (I-62), (I-63), (I-64), (I-68), (I-69), (I-71) and (I-72) according to the invention show, at an active compound concentration of 100 ppm, an efficacy of 70% or more.

The invention claimed is:
1. A compound of formula (I)

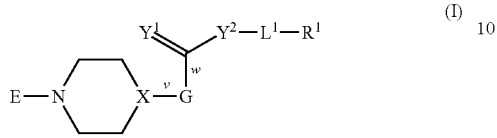

in which:
E represents

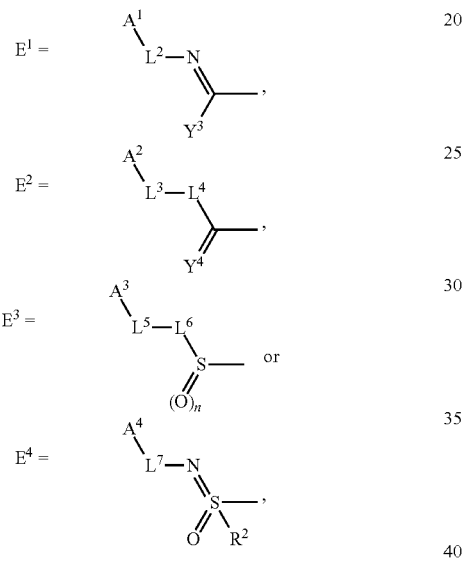

$A^1$, $A^2$, $A^3$, $A^4$ represent cyano, $C_1$-$C_8$-alkyl, $C_1$-$C_8$-haloalkyl, $C_3$-$C_8$-cycloalkyl, $C_5$-$C_8$-cycloalkenyl, $C_3$-$C_8$-halocycloalkyl, $C_4$-$C_{10}$-cycloalkylalkyl, $C_4$-$C_{10}$-halocycloalkylalkyl, $C_4$-$C_{10}$-alkylcycloalkyl, $C_5$-$C_{10}$-alkylcycloalkylalkyl, $C_2$-$C_8$-alkenyl, $C_2$-$C_8$-haloalkenyl, $C_2$-$C_8$-alkynyl, $C_2$-$C_8$-haloalkynyl, $C_2$-$C_8$-alkoxyalkyl, $C_2$-$C_8$-haloalkoxyalkyl, $C_4$-$C_{10}$-cycloalkoxyalkyl, $C_3$-$C_{10}$-alkoxyalkoxyalkyl, $C_2$-$C_8$-alkylthioalkyl, $C_2$-$C_8$-haloalkylthioalkyl, $C_2$-$C_8$-alkylsulphinylalkyl, $C_2$-$C_8$-alkylsulphonylalkyl, $C_2$-$C_8$-alkoxycarbonyl, $C_3$-$C_8$-alkoxycarbonylalkyl, $C_3$-$C_8$-haloalkoxycarbonylalkyl, $C_2$-$C_8$-alkylaminoalkyl, $C_3$-$C_{10}$-dialkylaminoalkyl, $C_2$-$C_8$-haloalkylaminoalkyl, $C_4$-$C_{10}$-cycloalkylaminoalkyl, $C_1$-$C_8$-alkoxy, $C_1$-$C_8$-haloalkoxy, $C_3$-$C_8$-cycloalkoxy, $C_3$-$C_8$-halocycloalkoxy, $C_4$-$C_{10}$-cycloalkylalkoxy, $C_2$-$C_8$-alkenyloxy, $C_2$-$C_8$-haloalkenyloxy, $C_2$-$C_8$-alkynyloxy, $C_2$-$C_8$-haloalkynyloxy, $C_2$-$C_8$-alkoxyalkoxy, $C_2$-$C_8$-alkylcarbonyloxy, $C_2$-$C_8$-haloalkylcarbonyloxy, $C_1$-$C_8$-alkylthio, $C_1$-$C_8$-haloalkylthio, $C_3$-$C_8$-cycloalkylthio, tri($C_1$-$C_4$-alkyl)silyl, $C_1$-$C_8$-alkylamino, $C_2$-$C_8$-dialkylamino, $C_1$-$C_8$-haloalkylamino, $C_2$-$C_8$-halodialkylamino, $C_3$-$C_8$-cycloalkylamino, $C_2$-$C_8$-alkylcarbonylamino, $C_2$-$C_8$-haloalkylcarbonylamino, $C_1$-$C_8$-alkylsulphonylamino or $C_1$-$C_8$-haloalkylsulphonylamino, or $A^1$, $A^2$, $A^3$, $A^4$ represent phenyl which may contain up to three substituents, where the substituents independently of one another are selected from the list below:
halogen, cyano, hydroxyl, SH, amino, nitro, $C_1$-$C_6$-alkyl, $C_2$-$C_6$-alkenyl, $C_2$-$C_6$-alkynyl, $C_3$-$C_{10}$-cycloalkyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, $C_2$-$C_8$-dialkylamino, $C_3$-$C_6$-cycloalkylamino, $C_4$-$C_{10}$-cycloalkylalkoxy, $C_2$-$C_4$-alkoxyalkyl, $C_2$-$C_6$-alkoxyalkoxy, $C_1$-$C_4$-hydroxyalkyl, $C_2$-$C_4$-alkylcarbonyl, $C_2$-$C_6$-alkoxycarbonyl, $C_2$-$C_6$-alkylcarbonyloxy, $C_2$-$C_6$-alkylcarbonylthio, $C_2$-$C_6$-alkylaminocarbonyl, $C_3$-$C_8$-dialkylaminocarbonyl, tri($C_1$-$C_4$alkyl)silyl, C(=O)H, $CR^3$=$NOR^4$, phenyl or benzyl or $A^1$, $A^2$, $A^3$, $A^4$ represent a heteroaromatic radical selected from the group below: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, pyrimidin-4-yl and pyrimidin-5-yl which may contain up to three substituents, where the substituents independently of one another are selected from the list below:
substituents at carbon may be chosen from: halogen, cyano, hydroxyl, SH, amino, nitro, $C_1$-$C_6$-alkyl, $C_2$-$C_6$-alkenyl, $C_2$-$C_6$-alkynyl, $C_3$-$C_{10}$-cycloalkyl, $C_4$-$C_{10}$-cycloalkylalkyl, $C_4$-$C_{10}$-alkylcycloalkyl, $C_5$-$C_{10}$-alkylcycloalkylalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphinyl, $C_1$-$C_4$-alkylsulphonyl, $C_1$-$C_4$-haloalkylthio, $C_1$-$C_4$-haloalkylsulphinyl, $C_1$-$C_4$-haloalkylsulphonyl, $C_1$-$C_4$-alkylamino, $C_2$-$C_6$-dialkylamino, $C_3$-$C_6$-cycloalkylamino, $C_4$-$C_{10}$-cycloalkylalkoxy, $C_2$-$C_4$-alkoxyalkyl, $C_2$-$C_6$-alkoxyalkoxy, $C_1$-$C_4$-hydroxyalkyl, $C_2$-$C_4$-alkylcarbonyl, $C_2$-$C_6$-alkoxycarbonyl, $C_2$-$C_6$-alkylcarbonyloxy, $C_2$-$C_6$-alkylcarbonylthio, $C_2$-$C_6$-alkylaminocarbonyl, $C_3$-$C_8$-dialkylaminocarbonyl, tri($C_1$-$C_4$-alkyl)silyl, C(=O)H, $CR^3$=$NOR^4$, phenyl and benzyl, and
substituents at nitrogen may be chosen from:
$C_1$-$C_6$-alkyl, $C_2$-$C_6$-alkenyl, $C_2$-$C_6$-alkynyl, $C_3$-$C_6$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkylsulfonyl, C(=O)H, C(=O)Me, C(=O)OMe and $C_2$-$C_4$-alkoxyalkyl, $L^1$ represents $(C(R^{15})_2)_p$,
p represents 0, 1 or 2,
$L^2$, $L^5$, $L^7$ represent a direct bond, C(=O) or S(=O)$_2$,
$L^3$ represents a direct bond,
$L^4$ represents oxygen, $CHR^5$, $NR^6$ or C(=O),
$L^6$ represents $CHR^5$ or $NR^6$,
$L^8$ represents a direct bond, —O—, —C(=O), —S(O)$_m$, —$CHR^{16}$ or —$NR^{17}$,
m represents 0, 1 or 2, $Y^1, Y^2, Y^4$ independently of one another represent sulphur or oxygen, $Y^3$ represents $OR^7$, $SR^8$, $NR^9R^{10}$ or $R^{11}$, n represents 0, 1 or 2, X represents $CR^{12}$ or nitrogen, G represents $G^1 =$ 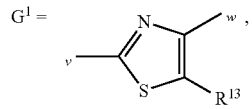

$G^2 =$ 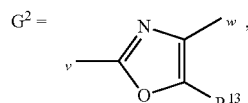

$G^3 =$ 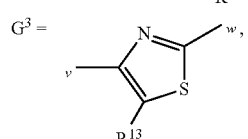

$G^4 =$ 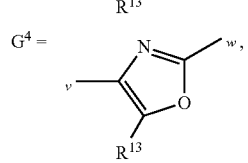

$G^5 =$ 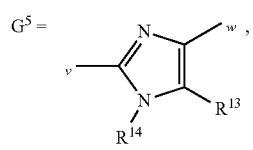

$G^6 =$ 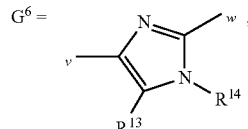

$G^7 =$ 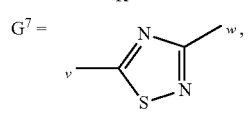

$G^8 =$ 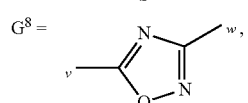

$G^9 =$ 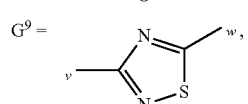

$G^{10} =$ 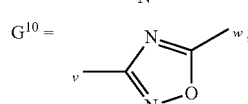

$G^{11} =$ 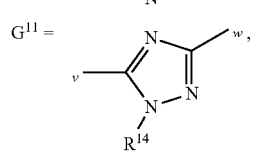

$G^{12} =$ 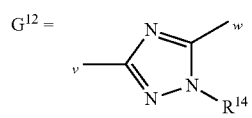

-continued $G^{13} =$ 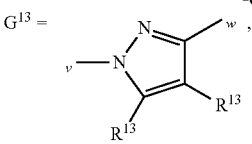

$G^{14} =$ 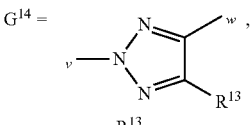

$G^{15} =$ 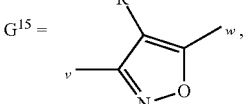

$G^{16} =$ 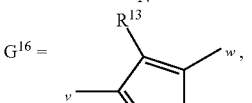

$G^{17} =$ 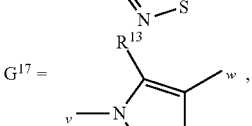

$G^{18} =$ 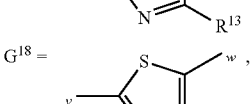

$G^{19} =$ 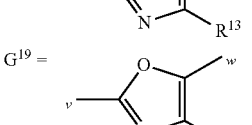 or $G^{20} =$ 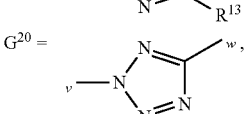

where the bond identified by "v" is attached directly to X and where the bond identified by "w" is attached directly to $C(=Y^1)y^2L^1R^1$, $R^1$ represents $C_3$-$C_6$-alkyl, $C_3$-$C_6$-haloalkyl, $C_2$-$C_6$-alkenyl, $C_2$-$C_6$-alkynyl, $C_3$-$C_8$-alkoxyalkyl or $C_5$-$C_9$-cycloalkoxyalkyl, or $R^1$ represents unsubstituted or substituted $C_3$-$C_{10}$-cycloalkyl, where the substituents independently of one another are selected from the list below:

cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, phenoxy, hydroxyl, oxo, $C_2$-$C_6$-alkoxycarbonyl, $C_1$-$C_6$-alkylcarbonyloxy, $C_1$-$C_6$-alkylcarbonyl, $C_1$-$C_6$-alkoxy, $C_1$-$C_2$-haloalkoxy, $C_2$-$C_6$-alkenyloxy, $C_2$-$C_6$-alkynyloxy, $C_1$-$C_6$-alkylthio, $C_1$-$C_6$-haloalkylthio and -Q, or $R^1$ represents unsubstituted or substituted $C_5$-$C_{10}$-cycloalkenyl, where the substituents independently of one another are selected from the list below:

cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, phenyl, hydroxyl, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio and $C_1$-$C_6$-haloalkylthio, or $R^1$ represents unsubstituted or substituted phenyl, where the substituents independently of one another are selected from the list below:

halogen, cyano, hydroxyl, SH, amino, nitro, C(=O)H, C(=O)OH, CONR$^3$R$^4$, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_8$-cycloalkyl, C$_3$-C$_8$-halocycloalkyl, C$_4$-C$_{10}$-alkylcycloalkylalkyl, C$_3$-C$_8$-cycloalkenyl, C$_3$-C$_8$-halocycloalkenyl, C$_2$-C$_6$-alkoxyalkyl, C$_4$-C$_{10}$-cycloalkoxyalkyl, C$_3$-C$_8$-alkoxyalkoxyalkyl, C$_2$-C$_6$-alkylthioalkyl, C$_2$-C$_6$-alkylsulphinylalkyl, C$_2$-C$_6$-alkylsulphonylalkyl, C$_2$-C$_6$-alkylaminoalkyl, C$_3$-C$_8$-dialkylaminoalkyl, C$_2$-C$_6$-haloalkylaminoalkyl, C$_4$-C$_{10}$-cycloalkylaminoalkyl, C$_2$-C$_6$-alkylcarbonyl, C$_2$-C$_6$-haloalkylcarbonyl, C$_4$-C$_8$-cycloalkylcarbonyl, C$_2$-C$_6$-alkoxycarbonyl, C$_4$-C$_8$-cycloalkoxycarbonyl, C$_5$-C$_{10}$-cycloalkylalkoxycarbonyl, C$_2$-C$_6$-alkylaminocarbonyl, C$_3$-C$_8$-dialkylaminocarbonyl, C$_4$-C$_8$-cycloalkylaminocarbonyl, C$_2$-C$_6$-haloalkoxyalkyl, C$_1$-C$_6$-hydroxyalkyl, C$_1$-C$_6$-alkoxy, C$_1$-C$_6$-haloalkoxy, C$_3$-C$_8$-cycloalkoxy, C$_3$-C$_8$-halocycloalkoxy, C$_4$-C$_{10}$-cycloalkylalkoxy, C$_2$-C$_6$-alkenyloxy, C$_2$-C$_6$-haloalkenyloxy, C$_2$-C$_6$-alkynyloxy, C$_2$-C$_6$-haloalkynyloxy, C$_2$-C$_6$-alkoxyalkoxy, C$_2$-C$_6$-alkylcarbonyloxy, C$_2$-C$_6$-haloalkylcarbonyloxy, C$_4$-C$_8$-cycloalkylcarbonyloxy, C$_3$-C$_6$-alkylcarbonylalkoxy, C$_1$-C$_6$-alkylthio, C$_1$-C$_6$-haloalkylthio, C$_3$-C$_6$-cycloalkylthio, C$_1$-C$_6$-haloalkylsulphinyl, C$_1$-C$_6$-alkylsulphonyl, C$_1$-C$_6$-haloalkylsulphonyl, C$_3$-C$_8$-cycloalkylsulphonyl, tri(C$_1$-C$_4$-alkyl)silyl, C$_1$-C$_6$-alkylsulphonylamino, C$_1$-C$_6$-haloalkylsulphonylamino and -L$^8$Q, or R represents saturated or partially or fully unsaturated unsubstituted or substituted naphthyl or indenyl, where the substituents independently of one another are selected from the list below:
cyano, nitro, halogen, C$_1$-C$_6$-alkyl, C$_1$-C$_4$-haloalkyl, C$_3$-C$_6$-cycloalkyl, C$_2$-C$_6$-alkenyl, C$_2$-C$_6$-haloalkenyl, C$_2$-C$_6$-alkynyl, C$_2$-C$_6$-haloalkynyl, tri(C$_1$-C$_4$-alkyl)silyl, benzyl, phenyl, hydroxyl, SH, C$_1$-C$_6$-alkoxy, C$_1$-C$_6$-haloalkoxy, C$_2$-C$_6$-alkenyloxy, C$_2$-C$_6$-alkynyloxy, C$_1$-C$_6$-alkylthio and C$_1$-C$_6$-haloalkylthio, or R$^1$ represents an unsubstituted or substituted 5- or 6-membered heteroaryl radical where L$^1$ is attached to a carbon of the heteroaryl radical and where the substituents independently of one another are selected from the list below:
substituents at carbon may be chosen from: halogen, cyano, hydroxyl, SH, amino, nitro, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_6$-C$_{14}$-cycloalkylcycloalkyl, C$_5$-C$_{10}$-alkylcycloalkylalkyl, C$_2$-C$_4$-alkoxyalkyl, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl, C$_1$-C$_4$-hydroxyalkyl, C$_1$-C$_4$-alkoxy, C$_1$-C$_4$-haloalkoxy, C$_2$-C$_6$-alkylcarbonyloxy, C$_2$-C$_6$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkyl-sulphonyl, C$_1$-C$_4$-haloalkylsulphonyl, tri(C$_1$-C$_4$-alkyl)silyl and -L$^8$Q, and
substituents at nitrogen may be chosen from: C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_1$-C$_4$-alkylsulphonyl, C(=O)H, C(=O)Me, C(=O)OMe, benzyl and phenyl, or R$^1$ represents benzo-fused unsubstituted or substituted 5- or 6-membered heteroaryl where L$^1$ is attached to a carbon of the heteroaryl radical and where the substituents independently of one another are selected from the list below:
substituents at carbon may be chosen from: halogen, cyano, hydroxyl, SH, amino, nitro, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_6$-C$_{14}$-cycloalkylcycloalkyl, C$_5$-C$_{10}$-alkylcycloalkylalkyl, C$_2$-C$_4$-alkoxyalkyl, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl, C$_1$-C$_4$-hydroxyalkyl, C$_1$-C$_4$-alkoxy, C$_1$-C$_4$-haloalkoxy, C$_2$-C$_6$-alkylcarbonyloxy, C$_2$-C$_6$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkylsulphonyl, C$_1$-C$_4$-haloalkylsulphonyl, tri(C$_1$-C$_4$-alkyl)silyl and phenyl, and
substituents at nitrogen may be chosen from: C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_1$-C$_4$-alkylsulphonyl, C(=O)H, C(=O)Me, C(=O)OMe, benzyl and phenyl, or R$^1$ represents unsubstituted or substituted C$_5$-C$_{15}$-heterocyclyl where L$^1$ is attached to a carbon of the heterocyclyl radical and possible substituents independently of one another are selected from the list below:
substituents at carbon may be chosen from: halogen, cyano, hydroxyl, SH, amino, nitro, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_6$-C$_{14}$-cycloalkylcycloalkyl, C$_5$-C$_{10}$-alkylcycloalkylalkyl, C$_2$-C$_4$-alkoxyalkyl, C$_2$-C$_4$-alkylcarbonyl, C$_2$-C$_6$-alkoxycarbonyl, C$_2$-C$_6$-alkylaminocarbonyl, C$_3$-C$_8$-dialkylaminocarbonyl, C$_1$-C$_4$-hydroxyalkyl, C$_1$-C$_4$-alkoxy, C$_1$-C$_4$-haloalkoxy, C$_2$-C$_6$-alkylcarbonyloxy, C$_2$-C$_6$-alkylcarbonylthio, C$_1$-C$_4$-alkylthio, C$_1$-C$_4$-haloalkylthio, C$_1$-C$_4$-alkylsulphinyl, C$_1$-C$_4$-haloalkylsulphinyl, C$_1$-C$_4$-alkylsulphonyl, C$_1$-C$_4$-haloalkylsulphonyl, tri(C$_1$-C$_4$-alkyl)silyl and phenyl, and
substituents at nitrogen may be chosen from: C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_1$-C$_4$-alkylsulphonyl, C(=O)H, C(=O)Me, C(=O)OMe, benzyl and phenyl, Q represents phenyl which may contain up to two substituents, where the substituents independently of one another are selected from the list below:
halogen, cyano, hydroxyl, SH, amino, nitro, NR$^3$R$^4$, C$_1$-C$_6$-alkyl, C$_2$-C$_6$-alkenyl, C$_2$-C$_6$-alkynyl, C$_1$-C$_6$-haloalkyl, C$_2$-C$_6$-haloalkenyl, C$_2$-C$_6$-haloalkynyl, C$_3$-C$_6$-cycloalkyl, C$_3$-C$_6$-halocycloalkyl, C$_4$-C$_{10}$-alkylcycloalkyl, C$_4$-C$_{10}$-cycloalkylalkyl, C$_6$-C$_{14}$-cycloalkylcycloalkyl, C$_5$-C$_{10}$-alkylcycloalkylalkyl, C$_2$-C$_4$-alkoxyalkyl, C$_2$-C$_4$-alkylcarbonyl, C$_2$-C$_6$- alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl and phenyl, or Q represents a 5- or 6-membered heteroaryl radical which may contain up to two substituents, where the substituents independently of one another are selected from the list below:

substituents at carbon may be chosen from: halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl and phenyl, and substituents at nitrogen may be chosen from: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_1$-$C_4$-alkylsulphonyl, C(=O)H, C(=O)Me, C(=O)OMe and phenyl, $R^2$ represents $C_1$-$C_4$-alkyl, $C_1$-$C_4$-haloalkyl or $C_2$-$C_4$-alkoxyalkyl, $R^3$, $R^4$ independently of one another represent hydrogen, $C_1$-$C_4$-alkyl, $C_2$-$C_6$-alkenyl, $C_2$-$C_6$-alkynyl, $C_1$-$C_3$-haloalkyl, $C_3$-$C_6$-cycloalkyl, benzyl or phenyl, $R^5$ represents hydrogen, halogen, cyano, hydroxyl, C(=O)H, OC(=O)H, OC(=O)Me, $C_1$-$C_4$-alkyl, $C_2$-$C_4$-alkenyl, $C_1$-$C_4$-alkynyl, $C_1$-$C_4$-haloalkyl, $C_2$-$C_4$-haloalkenyl, $C_2$-$C_4$-haloalkynyl, $C_2$-$C_4$-alkoxyalkyl, $C_2$-$C_4$-alkylthioalkyl, $C_2$-$C_4$-alkylsulphinylalkyl, $C_2$-$C_4$-alkylsulphonylalkyl, $C_2$-$C_4$-alkylcarbonyl, $C_2$-$C_4$-haloalkylcarbonyl, $C_2$-$C_5$-alkoxycarbonyl, $C_3$-$C_5$-alkoxycarbonylalkyl, $C_2$-$C_5$-alkylaminocarbonyl, $C_3$-$C_5$-dialkylaminocarbonyl, $C_1$-$C_4$-alkoxy, $C_1$-$C_4$-haloalkoxy, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl or $C_1$-$C_4$-haloalkylsulphonyl, $R^6$ represents hydrogen, C(=O)H, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_4$-haloalkynyl, $C_2$-$C_4$-alkoxyalkyl, $C_2$-$C_4$-alkylthioalkyl, $C_2$-$C_4$-alkylsulphinylalkyl, $C_2$-$C_4$-alkylsulphonylalkyl, $C_2$-$C_4$-alkylcarbonyl, $C_2$-$C_4$-haloalkylcarbonyl, $C_2$-$C_5$-alkoxycarbonyl, $C_3$-$C_5$-alkoxycarbonylalkyl, $C_2$-$C_5$-alkylaminocarbonyl, $C_3$-$C_5$-dialkylaminocarbonyl, $C_1$-$C_4$-alkylsulphonyl or $C_1$-$C_4$-haloalkylsulphonyl, $R^7$, $R^8$ independently of one another are selected from the list below:

$C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_3$-$C_6$-cycloalkyl, $C_3$-$C_6$-halocycloalkyl, $C_4$-$C_8$-alkylcycloalkyl, $C_4$-$C_8$-cycloalkylalkyl, $C_4$-$C_8$-halocycloalkylalkyl, $C_5$-$C_8$-alkylcycloalkylalkyl, $C_2$-$C_6$-alkoxyalkyl, $C_4$-$C_8$-cycloalkoxyalkyl, $C_3$-$C_6$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_6$-dialkylaminoalkyl, $C_2$-$C_6$-haloalkylaminoalkyl, $C_4$-$C_8$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxylcarbonyl, $C_2$-$C_6$-alkylaminocarbonyl, $C_3$-$C_8$-dialkylaminocarbonyl, tri($C_1$-$C_4$-alkyl)silyl or $C_4$-$C_8$-cycloalkylaminocarbonyl, $R^9$ represents hydrogen, cyano, hydroxyl, amino, $C_1$-$C_6$-alkyl, $C_3$-$C_6$-alkenyl, $C_3$-$C_6$-alkynyl, $C_1$-$C_6$-haloalkyl, $C_3$-$C_6$-haloalkenyl, $C_3$-$C_6$-haloalkynyl, $C_3$-$C_6$-cycloalkyl, $C_4$-$C_8$-cycloalkylalkyl, $C_2$-$C_6$-alkoxyalkyl, $C_1$-$C_6$-alkoxy, $C_1$-$C_6$-haloalkoxy, $C_1$-$C_6$-alkylsulphonyl, $C_1$-$C_6$-haloalkylsulphonyl, $C_2$-$C_6$-alkylcarbonyl, $C_2$-$C_6$-haloalkylcarbonyl, $C_1$-$C_6$-alkylamino, $C_2$-$C_8$-dialkylamino, $C_1$-$C_6$-haloalkylamino and $C_2$-$C_8$-halodialkylamino, $R^{10}$ represents hydrogen, $C_1$-$C_6$-alkyl, $C_2$-$C_6$-alkenyl, $C_2$-$C_6$-alkynyl, $C_1$-$C_6$-haloalkyl or $C_3$-$C_6$-cycloalkyl, or $R^9$, $R^{10}$ together form a —(CH$_2$)$_4$—, —(CH$_2$)$_5$—, —(CH$_2$)$_2$S(CH$_2$)$_2$—, —(CH$_2$)$_2$S(=O)(CH$_2$)$_2$—, —(CH$_2$)$_2$S(=O)$_2$(CH$_2$)$_2$—, —(CH$_2$)$_2$NR$^3$(CH$_2$)$_2$— or —(CH$_2$)$_2$O(CH$_2$)$_2$— radical, $R^{11}$ represents hydrogen, halogen, cyano, $C_1$-$C_4$-alkyl, $C_1$-$C_4$-haloalkyl, $C_2$-$C_4$-alkoxylalkyl, $C_2$-$C_4$-alkylcarbonyl, $C_2$-$C_4$-alkoxycarbonyl, $C_2$-$C_3$-alkylaminocarbonyl or $C_3$-$C_6$-dialkylaminocarbonyl, $R^{12}$ represents hydrogen, halogen, cyano, hydroxyl, OC(=O)Me, OC(=O)H, C(=O)H, C(=O)OH, C(=O)OMe, C(=O)Me, $C_1$-$C_4$-alkyl, $C_2$-$C_4$-alkenyl, $C_2$-$C_4$-alkynyl, $C_1$-$C_4$-haloalkyl, $C_1$-$C_4$-alkoxy or $C_1$-$C_4$-haloalkoxy, $R^{13}$ represents hydrogen, $C_1$-$C_3$-alkyl, $C_1$-$C_3$-haloalkyl or halogen, $R^{14}$ represents hydrogen or $C_1$-$C_3$-alkyl, C(=O)H, C(=O)Me or C(=O)OMe, $R^{14}$ represents hydrogen or $C_1$-$C_3$-alkyl, C(=O)H, C(=O)Me or C(=O)OMe, $R^{15}$ are identical or different and independently of one another represent hydrogen, halogen, $C_1$-$C_4$-alkyl, $C_2$-$C_4$-alkenyl, $C_2$-$C_4$-alkynyl, $C_1$-$C_4$-alkoxy, oxo, $C_3$-$C_6$-cycloalkyl, $C_1$-$C_4$-haloalkyl or phenyl $R^{16}$ represents hydrogen, $C_1$-$C_4$-alkyl or $C_1$-$C_4$-haloalkyl, and $R^{17}$ represents hydrogen, $C_1$-$C_6$-alkyl, $C_1$-$C_6$ haloalkyl, $C_3$-$C_8$-cycloalkyl, $C_2$-$C_6$-alkylcarbonyl, $C_2$-$C_6$-haloalkylcarbonyl, $C_2$-$C_6$-alkoxycarbonyl or $C_2$-$C_6$-haloalkoxycarbonyl, and agrochemically active salts thereof, except for the following compounds:

a) compounds in which
   $A^2$ represents pyrazol-1-yl,
   X represents CH, and
   G represents $G^1$, b) compounds in which
   X represents nitrogen, and
   G represents $G^{13}$, $G^{14}$, $G^{17}$ or $G^{20}$, and c) compounds in which
   $Y^4$ represents sulphur, and
   $L^4$ represents C(=O).

2. The compound of formula (I) according to claim 1, in which:

E represents $E^1$, $E^2$ or $E^3$, $A^1$, $A^2$ represent cyano, $C_1$-$C_8$-alkyl, $C_1$-$C_8$-haloalkyl, $C_2$-$C_8$-alkenyl, $C_2$-$C_8$-haloalkenyl, $C_2$-$C_8$-alkynyl, $C_2$-$C_8$-haloalkynyl, $C_3$-$C_8$-cycloalkyl, $C_4$-$C_8$-halocycloalkylalkyl, $C_2$-$C_8$-alkoxyalkyl, $C_2$-$C_8$-haloalkoxyalkyl, $C_2$-$C_8$-alkylthioalkyl, $C_2$-$C_8$-haloalkylthioalkyl, $C_2$-$C_8$-alkylsulphinylalkyl, $C_2$-$C_8$-alkylsulphonylalkyl, $C_3$-$C_8$-alkoxycarbonylalkyl, $C_3$-$C_8$-haloalkoxycarbonylalkyl, $C_2$-$C_8$-alkylaminoalkyl, $C_3$-$C_{10}$-dialkylaminoalkyl, $C_1$-$C_8$-alkoxy, $C_1$-$C_8$-haloalkoxy, $C_2$-$C_8$-alkylcarbonyloxy, $C_2$-$C_8$-haloalkylcarbonyloxy, $C_1$-$C_8$-alkylthio, $C_1$-$C_8$-haloalkylthio, tri($C_1$-$C_4$-alkyl)-silyl, $C_1$-$C_8$-alkylamino or $C_2$-$C_8$-dialkylamino, $A^1$, $A^2$, $A^3$ represent phenyl which may contain up to two substituents, where the substituents independently of one another are selected from the list below:
  halogen, cyano, hydroxyl, amino, nitro, $C_1$-$C_6$-alkyl, $C_2$-$C_6$-alkenyl, $C_2$-$C_6$-alkynyl, $C_3$-$C_{10}$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_2$-$C_4$-alkoxyalkyl, $C_1$-$C_4$-hydroxyalkyl, $C_2$-$C_4$-alkylcarbonyl, $C_2$-$C_6$-alkoxycarbonyl, $C_2$-$C_6$-alkylcarbonyloxy, and C(=O)H or $CR^3$=$NOR^4$, or $A^1$, $A^2$, $A^3$ represent a heteroaromatic radical selected from the group below: furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol 3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,3-triazol-1-yl, 1,2,4-triazol-1-yl, pyridin-2-yl, pyridin-3-yl, pyridin-4-yl, pyridazin-3-yl, pyridazin-4-yl, pyrimidin-2-yl, and pyrimidin-4-yl or pyrimidin-5-yl which may contain up to two substituents, where the substituents independently of one another are selected from the list below:
  substituents at carbon may be chosen from: halogen, cyano, hydroxyl, amino, nitro, $C_1$-$C_6$-alkyl, $C_2$-$C_6$-alkenyl, $C_2$-$C_6$-alkynyl, $C_3$-$C_{10}$-cycloalkyl, $C_1$-$C_6$-haloalkyl, $C_2$-$C_6$-haloalkenyl, $C_2$-$C_6$-haloalkynyl, $C_3$-$C_6$-halocycloalkyl, $C_1$-$C_4$-alkoxy, $C_1$-$C_4$-haloalkoxy, $C_1$-$C_4$-alkylthio, $C_1$-$C_4$-alkylsulphonyl, $C_1$-$C_4$-haloalkylthio, $C_1$-$C_4$-haloalkylsulphonyl, $C_2$-$C_4$-alkoxyalkyl, $C_1$-$C_4$-hydroxyalkyl, $C_2$-$C_4$-alkylcarbonyl, $C_2$-$C_6$-alkoxycarbonyl, $C_2$-$C_6$-alkylcarbonyloxy, C(=O)H, $CR^3$=$NOR^4$ and phenyl, and
  substituents at nitrogen may be chosen from: $C_1$-$C_6$-alkyl, $C_1$-$C_4$-haloalkyl, $C_2$-$C_6$-alkenyl, $C_2$-$C_6$-haloalkenyl, $C_2$-$C_6$-alkynyl and $C_2$-$C_6$-haloalkynyl, $L^1$ represents a direct bond, —$CH_2$— or —$CH(CH_3)$—,
$L^2$ represents a direct bond,
$L^3$ represents a direct bond,
$L^4$ represents oxygen, $CHR^5$, $NR^6$,
$L^5$ represents a direct bond,
$L^6$ represents $CHR^5$, $NR^6$,
$L^8$ represents a direct bond, —O—,
$Y^1$ represents oxygen, sulphur,
$Y^2$ represents oxygen, sulphur,
$Y^3$ represents $OR^7$, $SR^8$,
$Y^4$ represents oxygen, sulphur,
X represents CH, CF, N,
G represents $G^1$, $G^2$, $G^3$, $G^{13}$, $G^{14}$ or $G^{18}$
$R^1$ represents $C_3$-$C_6$-alkyl, $C_3$-$C_6$-haloalkyl, $C_2$-$C_6$-alkenyl or $C_2$-$C_6$-alkynyl, or
$R^1$ represents unsubstituted or substituted $C_3$-$C_{10}$-cycloalkyl, where the substituents independently of one another are selected from the list below:
  cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl) silyl, phenyl, hydroxyl, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio and $C_1$-$C_6$-haloalkylthio, or $R^1$ represents unsubstituted or substituted $C_5$-$C_{10}$-cycloalkenyl, where the substituents independently of one another are selected from the list below:
  cyano, halogen, $C_1$-$C_6$-alkyl, $C_1$-$C_6$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl) silyl, phenyl, hydroxyl, oxo, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio and $C_1$-$C_6$-haloalkylthio, or $R^1$ represents unsubstituted or substituted phenyl, where the substituents independently of one another are selected from the list below:
  halogen, cyano, hydroxyl, SH, amino, nitro, C(=O)H, C(=O)OH, $CONR^3R^4$, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_8$-cycloalkyl, $C_3$-$C_8$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_4$-$C_{10}$-halocycloalkylalkyl, $C_5$-$C_{10}$-alkylcycloalkylalkyl, $C_3$-$C_8$-cycloalkenyl, $C_3$-$C_8$-halocycloalkenyl, $C_2$-$C_6$-alkoxyalkyl, $C_4$-$C_{10}$-cycloalkoxyalkyl, $C_3$-$C_8$-alkoxyalkoxyalkyl, $C_2$-$C_6$-alkylthioalkyl, $C_2$-$C_6$-alkylsulphinylalkyl, $C_2$-$C_6$-alkylsulphonylalkyl, $C_2$-$C_6$-alkylaminoalkyl, $C_3$-$C_8$-dialkylaminoalkyl, $C_2$-$C_6$-haloalkylaminoalkyl, $C_4$-$C_{10}$-cycloalkylaminoalkyl, $C_2$-$C_6$-alkylcarbonyl, $C_2$-$C_6$-haloalkylcarbonyl, $C_4$-$C_8$-cycloalkylcarbonyl, $C_2$-$C_6$-alkoxycarbonyl, $C_4$-$C_8$-cycloalkoxycarbonyl, $C_5$-$C_{10}$-cycloalkylalkoxycarbonyl, $C_2$-$C_6$-alkylaminocarbonyl, $C_3$-$C_8$-dialkylaminocarbonyl, $C_4$-$C_8$-cycloalkylaminocarbonyl, $C_2$-$C_6$-haloalkoxyalkyl, $C_1$-$C_6$-hydroxyalkyl, $C_1$-$C_6$-alkoxy, $C_1$-$C_6$-haloalkoxy, $C_3$-$C_8$-cycloalkoxy, $C_3$-$C_8$-halocycloalkoxy, $C_4$-$C_{10}$-cycloalkylalkoxy, $C_2$-$C_6$-alkenyloxy, $C_2$-$C_6$-haloalkenyloxy, $C_2$-$C_6$-alkynyloxy, $C_2$-$C_6$-haloalkynyloxy, $C_2$-$C_6$-alkoxyalkoxy, $C_2$-$C_6$-alkylcarbonyloxy, $C_2$-$C_6$-haloalkylcarbonyloxy, $C_4$-$C_8$-cycloalkylcarbonyloxy, $C_3$-$C_6$-alkylcarbonylalkoxy, $C_1$-$C_6$-alkylthio, $C_1$-$C_6$-haloalkylthio, $C_3$-$C_6$-cycloalkylthio, $C_1$-$C_6$-alkylsulphinyl, $C_1$-$C_6$-haloalkylsulphinyl, $C_1$-$C_6$-alkylsulphonyl, $C_1$-$C_6$-haloalkylsulphonyl, $C_3$-$C_8$-cycloalkylsulphonyl, tri($C_1$-$C_4$-alkyl)silyl, $C_1$-$C_6$-alkylsulphonylamino, $C_1$-$C_6$-haloalkylsulphonylamino and -$L^8Q$, or $R^1$ represents saturated or partially or fully unsaturated unsubstituted or substituted naphthyl or indenyl, where the substituents independently of one another are selected from the list below:
  cyano, nitro, halogen, $C_1$-$C_6$-alkyl, $C_1$-$C_4$-haloalkyl, $C_3$-$C_6$-cycloalkyl, $C_2$-$C_6$-alkenyl, $C_2$-$C_6$-haloalkenyl, $C_2$-$C_6$-alkynyl, $C_2$-$C_6$-haloalkynyl, tri($C_1$-$C_4$-alkyl)silyl, benzyl, phenyl, hydroxyl, SH, $C_1$-$C_6$-alkoxy, $C_1$-$C_6$-haloalkoxy, $C_2$-$C_6$-alkenyloxy, $C_2$-$C_6$-alkynyloxy, $C_1$-$C_6$-alkylthio and $C_1$-$C_6$-haloalkylthio, or $R^1$ represents an unsubstituted or substituted 5- or 6-membered heteroaryl radical where $L^1$ is attached to a carbon of the heteroaryl radical and where the substituents independently of one another are selected from the list below:
  substituents at carbon may be chosen from: halogen, cyano, hydroxyl, SH, amino, nitro, $NR^3R^4$, $C_1$-$C_6$- alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl and -$L^8$Q, and substituents at nitrogen may be chosen from: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl and phenyl, or $R^1$ represents benzo-fused unsubstituted or substituted 5- or 6-membered heteroaryl where $L^1$ is attached to a carbon of the heteroaryl radical and where the substituents independently of one another are selected from the list below:

substituents at carbon may be chosen from: halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl and phenyl, and substituents at nitrogen may be chosen from: $C_1$-$C_6$-alkyl, $C_2$-$C_6$-alkenyl, $C_2C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl and phenyl, or $R^1$ represents unsubstituted or substituted $C_5$-$C_{15}$-heterocyclyl where $L^1$ is attached to a carbon of the heterocyclyl radical and where possible substituents independently of one another are selected from the list below:

substituents at carbon may be chosen from: halogen, cyano, hydroxyl, SH, amino, nitro, $NR^3R^4$, $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$ -halocycloalkyl, $C_4$-$C_{10}$-alkylcycloalkyl, $C_4$-$C_{10}$-cycloalkylalkyl, $C_6$-$C_{14}$-cycloalkylcycloalkyl, $C_5$-$C_{10}$-alkylcycloalkylalkyl, $C_2$-$C_4$-alkoxyalkyl, $C_2$-$C_4$-alkylcarbonyl, $C_2$-$C_6$-alkoxycarbonyl, $C_2$-$C_6$-alkylaminocarbonyl, $C_3$-$C_8$-dialkylaminocarbonyl, $C_1$-$C_4$-hydroxyalkyl, $C_1$-$C_4$-alkoxy, $C_1$-$C_4$-haloalkoxy, $C_2$-$C_6$-alkylcarbonyloxy, $C_2$-$C_6$-alkylcarbonylthio, $C_1$-$C_4$-alkylthio, $C_1$-$C_4$-haloalkylthio, $C_1$-$C_4$-alkylsulphinyl, $C_1$-$C_4$-haloalkylsulphinyl, $C_1$-$C_4$-alkylsulphonyl, $C_1$-$C_4$-haloalkylsulphonyl, tri($C_1$-$C_4$-alkyl)silyl and phenyl, and substituents at nitrogen may be chosen from: $C_1$-$C_6$-alkyl, $C_2$-$C_6$-alkenyl, $C_2$-$C_6$-alkynyl, $C_1$-$C_6$-haloalkyl, $C_2$-$C_6$-haloalkenyl, $C_2$-$C_6$-haloalkynyl, $C_3$-$C_6$-cycloalkyl, $C_3$-$C_6$-halocycloalkyl, $C_4$-$C_{10}$-alkylcycloalkyl, $C_4$-$C_{10}$-cycloalkylalkyl and phenyl, Q represents phenyl which may contain up to two substituents, where the substituents independently of one another are selected from the list below:

halogen, cyano, hydroxyl, SH, nitro, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio and phenyl, or Q represents furan-2-yl, furan-3-yl, thiophen-2-yl, thiophen-3-yl, isoxazol-3-yl, isoxazol-4-yl, isoxazol-5-yl, pyrrol-1-yl, pyrrol-2-yl, pyrrol-3-yl, oxazol-2-yl, oxazol-4-yl, oxazol-5-yl, thiazol-2-yl, thiazol-4-yl, thiazol-5-yl, isothiazol-3-yl, isothiazol-4-yl, isothiazol-5-yl, pyrazol-1-yl, pyrazol-3-yl, pyrazol-4-yl, imidazol-1-yl, imidazol-2-yl, imidazol-4-yl, 1,2,4-oxadiazol-3-yl, 1,2,4-oxadiazol-5-yl, 1,3,4-oxadiazol-2-yl, tetrazol-5-yl, 1,2,4-thiadiazol-3-yl, 1,2,4-thiadiazol-5-yl, 1,3,4-thiadiazol-2-yl, 1,2,3-triazol-2-yl, 1,2,3-triazol-4-yl, 1,2,4-triazol-1-yl, 1,2,4-triazol-3-yl, 1,2,4-triazol-4-yl, tetrazol-5-yl, pyridin-2-yl, pyridin-3-yl, pyridin-4-yl, pyridazin-3-yl, pyridazin-4-yl, pyrimidin-2-yl, pyrimidin-4-yl, pyrimidin-5-yl, pyrazin-2-yl, 1,3,5-triazin-2-yl and 1,2,4-triazin-3-yl which may contain up to two substituents, where the substituents independently of one another are selected from the list below:

substituents at carbon may be chosen from: halogen, cyano, hydroxyl, SH, nitro, $C_1$-$C_6$-alkyl, $C_1$-$C_6$-haloalkyl, $C_3$-$C_6$-cycloalkyl, $C_1$-$C_4$-alkoxy, $C_1$-$C_4$-haloalkoxy, $C_1$-$C_4$-alkylthio, $C_1$-$C_4$-haloalkylthio and phenyl, and substituents at nitrogen may be chosen from: $C_1$-$C_6$-alkyl, $C_2$-$C_6$-alkenyl, $C_2$-$C_6$-alkynyl, $C_3$-$C_6$-cycloalkyl and phenyl, $R^3$, $R^4$ independently of one another represent hydrogen, or $R^3$, $R^4$ independently of one another represent methyl, ethyl, propyl, isopropyl, butyl, isobutyl or tert-butyl, $R^5$ represents hydrogen, or $R^5$ represents methyl, ethyl, propyl, isopropyl, butyl, isobutyl or tert-butyl, $R^6$ represents hydrogen, $R^6$ represents methyl, ethyl, propyl, isopropyl, butyl, isobutyl or tert-butyl, $R^7$ represents methyl, ethyl, propyl, isopropyl, butyl, isobutyl or tert-butyl, $R^8$ represents methyl, ethyl, propyl, isopropyl, butyl, isobutyl or tert-butyl, and $R^{13}$ represents hydrogen, and agrochemically active salts thereof.

3. A method for controlling phytopathogenic harmful fungi, comprising contacting one or more compounds of formula (I) according to claim 1 with the phytopathogenic harmful fungi, their habitat, or combinations thereof.

4. A composition for controlling phytopathogenic harmful fungi comprising at least one compound of formula (I) according to claim 1 and one or more extenders, surfactants, and combinations thereof.

5. The method of claim 3, wherein said compound is a heteroarylpiperidine or -piperazine derivative.

6. A process for preparing compositions for controlling phytopathogenic harmful fungi, comprising mixing a heteroarylpiperidine and-piperazine derivative of formula (I) according to claim 1 with one or more extenders, surfactants, and combinations thereof.

7. The compound of formula (I) according to claim 1, in which:

$L^1$ represents a direct bond, —$CH_2$—, or —$CH(CH_3)$—,
$Y^1$ represents oxygen or sulphur,
$Y^2$ represents oxygen or sulphur,
X represents CH, CF, or nitrogen,
CF represents $G^1$, $G^2$, $G^3$, $G^{13}$, $G^{14}$, or $G^{18}$, and
$R^{13}$ represents hydrogen.

8. The compound of formula (I) according to claim 7, in which:

$L^1$ represents a direct bond or —$CH_2$—,
$Y^1$ represents oxygen,
Y2 represents oxygen,
X represents CH, and
G represents $G^1$ or $G^{18}$.

* * * * *